(12) United States Patent
DeFrees et al.

(10) Patent No.: US 8,198,045 B2
(45) Date of Patent: Jun. 12, 2012

(54) EXPRESSION OF O-GLYCOSYLATED THERAPEUTIC PROTEINS IN PROKARYOTIC MICROORGANISMS

(75) Inventors: Shawn DeFrees, North Wales, PA (US); Marc F. Schwartz, West Windsor, NJ (US); Karl Johnson, Hatboro, PA (US)

(73) Assignee: BioGeneriX AG, Ulm (DE)

( * ) Notice: Subject to any disclaimer, the term of this patent is extended or adjusted under 35 U.S.C. 154(b) by 392 days.

(21) Appl. No.: 12/297,488

(22) PCT Filed: Apr. 19, 2007

(86) PCT No.: PCT/US2007/009782
§ 371 (c)(1),
(2), (4) Date: May 17, 2009

(87) PCT Pub. No.: WO2007/120932
PCT Pub. Date: Oct. 25, 2007

(65) Prior Publication Data
US 2009/0311744 A1    Dec. 17, 2009

Related U.S. Application Data

(60) Provisional application No. 60/793,531, filed on Apr. 19, 2006, provisional application No. 60/842,926, filed on Sep. 6, 2006.

(51) Int. Cl.
C12P 21/06 (2006.01)
C12P 19/04 (2006.01)
C12N 9/10 (2006.01)
C12N 1/20 (2006.01)
C12N 15/00 (2006.01)
C07H 21/04 (2006.01)

(52) U.S. Cl. .... 435/69.1; 435/101; 435/193; 435/252.3; 435/320.1; 536/23.2

(58) Field of Classification Search .................. None
See application file for complete search history.

(56) References Cited

U.S. PATENT DOCUMENTS

2003/0059915 A1    3/2003  Canfield et al.
2004/0142856 A1*   7/2004  DeFrees et al. ............. 514/8

FOREIGN PATENT DOCUMENTS
WO   97/43405 A1    11/1997
WO   2006/010143 A2    1/2006

OTHER PUBLICATIONS

Sorensen et al. Microb Cell Fact. 2005; 4: 1-8.*
Rousseau et al. Genomics. May 2004;83(5):936-9.*
Ten Hagen et al. Glycobiology. Jan. 2003;13(1):1R-16R. Epub Nov. 1, 2002.*
Marcos et al. Cancer Res. Oct. 1, 2004;64(19):7050-7.*
Xia et al. J Cell Biol. Feb. 2, 2004;164(3):451-9. Epub Jan. 26, 2004.*
Daude et al. Biochem Mol Med. Oct. 1995; 56(1): 1-7; Abstract.*
Hollingsworth et al. Nat Rev Cancer. Jan. 2004;4(1):45-60.*
Jeanneau et al. J Biol Chem. Apr. 2, 2004;279(14):13461-8. Epub Jan. 13, 2004.*
Dolby, Nichol et al.; "Design and expression of a synthetic mucin gene fragment in *Escherichia coli*"; Protein Expr Purif.; Feb. 15, 1999; pp. 146-154; vol. 15; No. 1.
Freire, Teresa et al.; "Enzymatic large-scale synthesis of MUC6-Tn glycoconjugates for antitumor vaccination"; Glycobiology; Jan. 31, 2006; pp. 390-401; vol. 16; No. 5.
Xiong, Sheng et al.; "Solubility of disulfide-bonded proteins in the cytoplasm of *Escherichia coli* and its "oxidizing" mutant"; World J. Gastroenterol.; Feb. 21, 2005; pp. 1077-1082; vol. 11; No. 7.
Defrees et al., "In Vitro O-Glycosylation of *E. coli*-Produced Therapeutic Proteins Using Recombinant Glycosyltransferases," *Glycobiology*, 14(11): 1086 (2004).
Defrees et al., "GlycoPEGylation of Recombinant Therapeutic Proteins Produced in *Escherichia coli*," *Glycobiology*, 16(9): 833-843 (2006).
European Patent Office, Supplemental European Search Report in European Patent Application 07775963 (Jan. 25, 2012).
Sewell et al., "The ST6GaINAc-I Sialyltransferase Localizes Throughout the Golgi and is Responsible for the Synthesis of the Tumor-Associated Sialyl-Tn-*O*-Glycan in Human Breast Cancer," *J. Biol. Chem.*, 281(6): 3586-3594 (2006).

* cited by examiner

*Primary Examiner* — Christian Fronda
(74) *Attorney, Agent, or Firm* — Leydig, Voit & Mayer, Ltd.

(57) ABSTRACT

The invention relates to methods of producing an O-glycosylated soluble therapeutic protein in a prokaryotic microorganism by co-expressing the therapeutic protein and a heterologous glycosyltransferase that transfers a sugar moiety to an amino acid acceptor on the therapeutic protein.

19 Claims, 36 Drawing Sheets

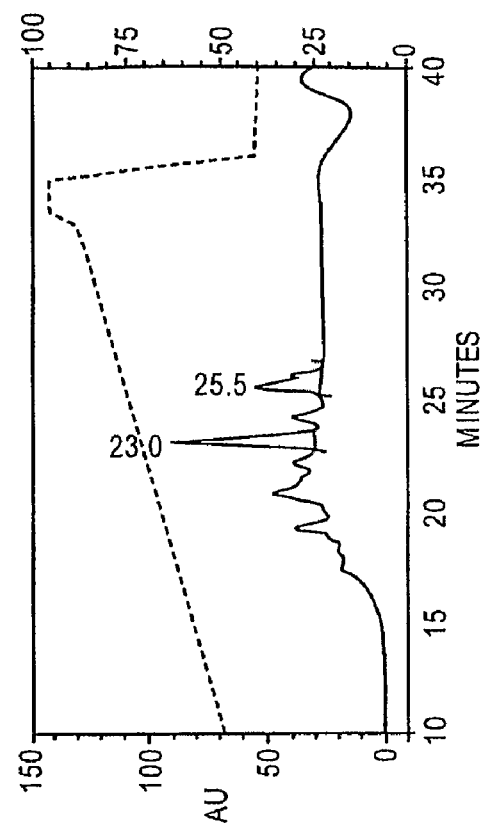
FIG. 4A
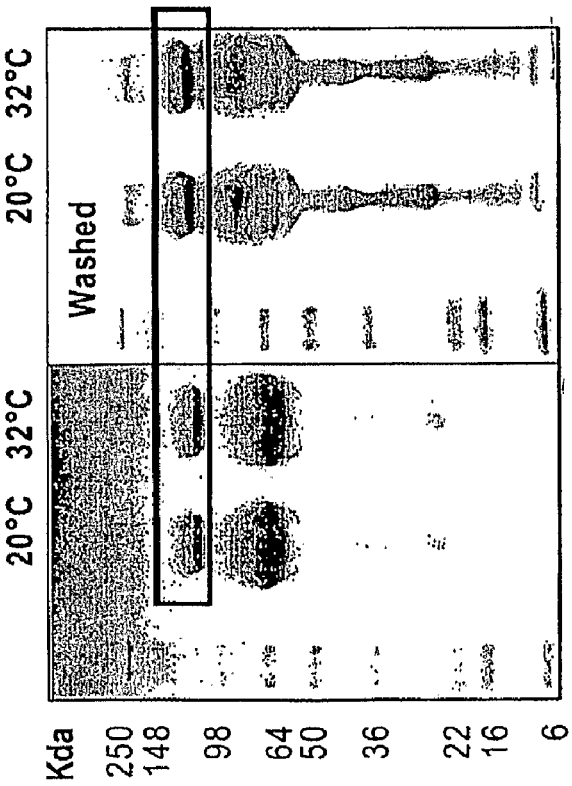
FIG. 4C
FIG. 4B

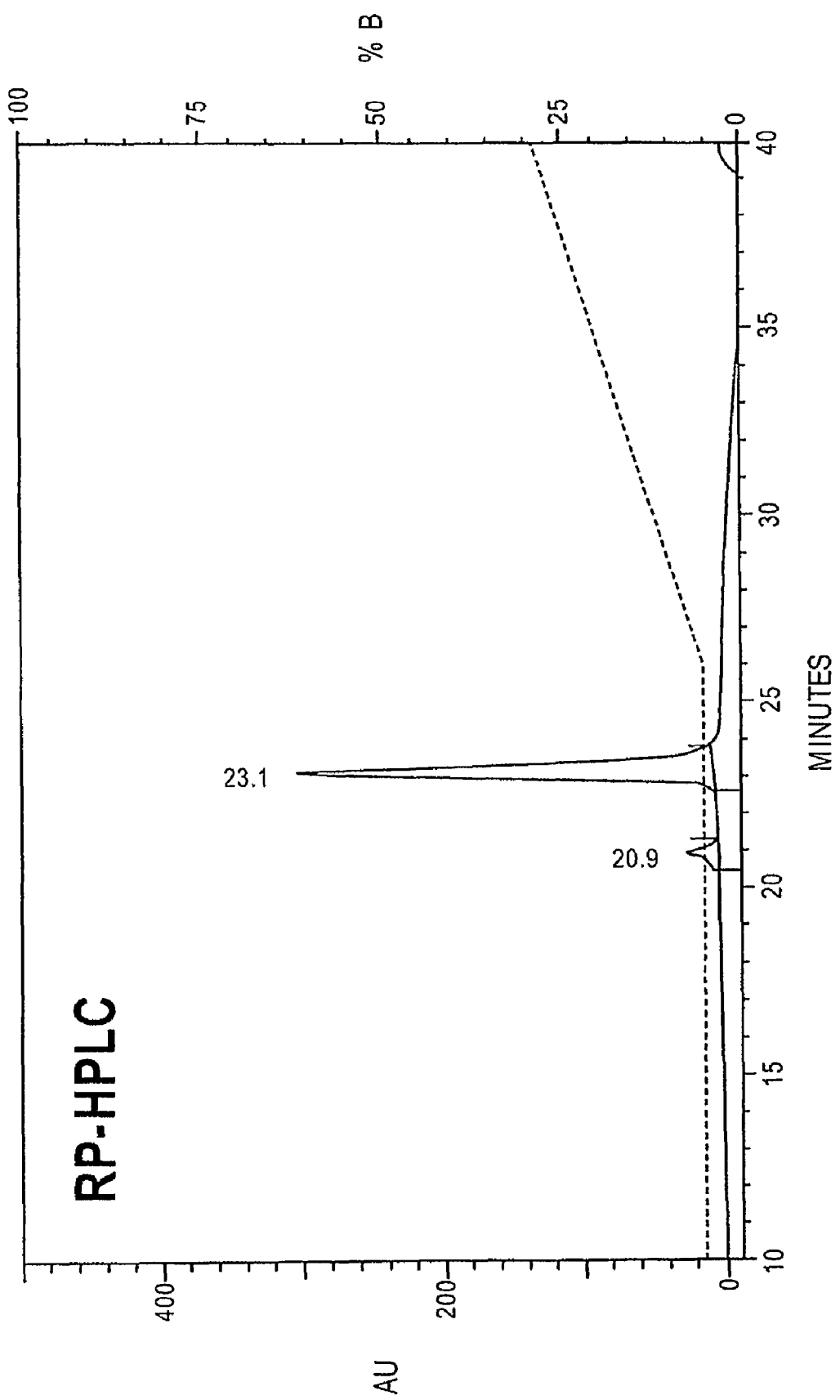

| Epimerase | GalNAcT2 | Total hGH | Conversion Yield | hGH-GalNAc |
|---|---|---|---|---|
| GalE | GalNAcT2 Δ51 Δ445 | 9.6 mg/L | 38.5% | 3.7 mg/L |
| | | 10.2 mg/L | 41.2% | 4.2 mg/L |
| GNE | | 13.5 mg/L | 38.5% | 5.2 mg/L |
| | | 9.3 mg/L | 31.2% | 2.9 mg/L |

FIG. 8

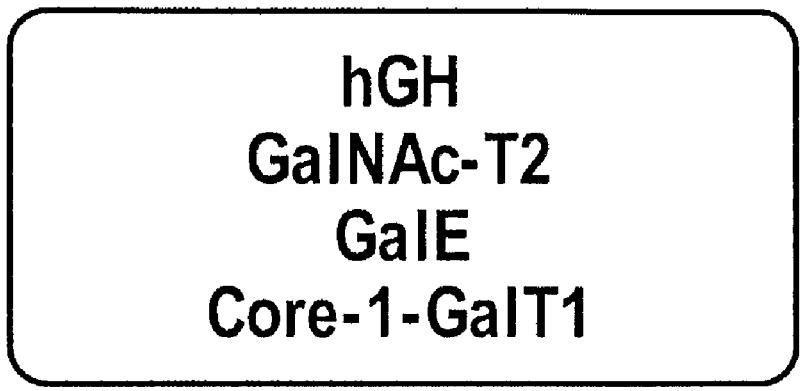
*E. coli*
hGH
GalNAc-T2
GalE
Core-1-GalT1
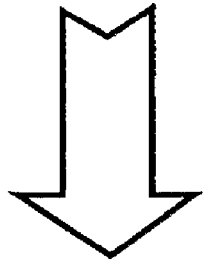
hGH-GalNAc-Gal
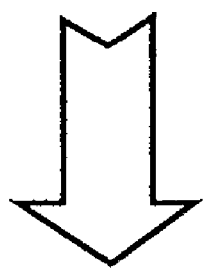
MBP-ST3Gal1
hGH-GalNAc-Gal-SA-PEG
FIG. 10

|  | hGH mg/L | hGH-GalNAc | hGH-GalNAc mg/L |
|---|---|---|---|
| Cassette 1 | 59.2 | 30.4 % | 18.0 |
| Cassette 2 | 49.5 | 30.1 % | 14.9 |

FIG. 11

*Core 1*
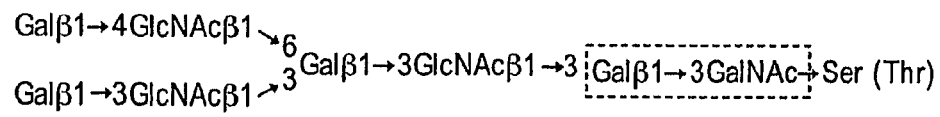
*Core 2*
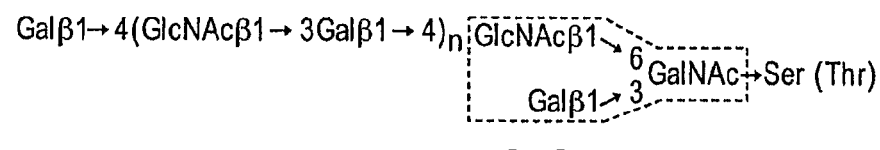
n = 0 ~ 2
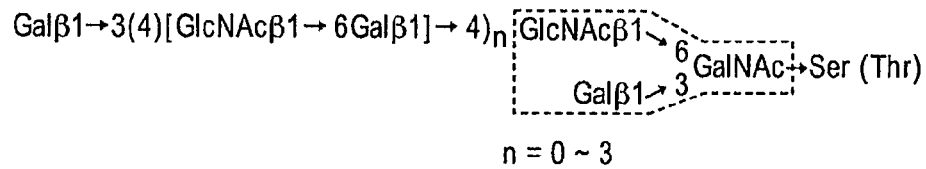
n = 0 ~ 3
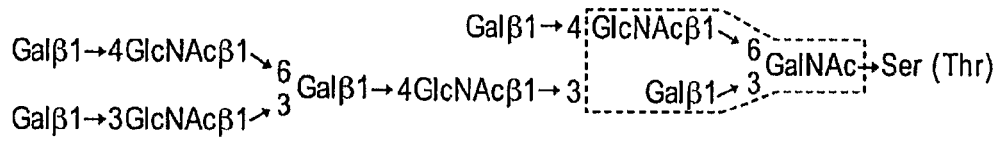
*Core 3*
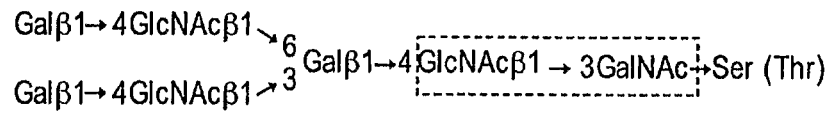
*Core 4*
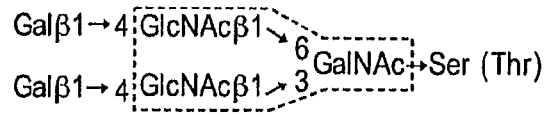
FIG. 16

GlycosylTransferase Family 27

| BACTERIA | Protein | Organism | GenBank/GenPept | UniProt | PDB/3D |
|---|---|---|---|---|---|
| CHY_2609 | | Carboxydothermus hydrogenoformans Z-2901 | CP000141 | | CHY_2609 |
| CHY_2608 | | Carboxydothermus hydrogenoformans Z-2901 | CP000141 | | CHY_2608 |
| EUKARYOTA | | | | | |
| Unknown(protein for MGC:133911) | | Bos taurus | BC111260 | AAI11261.1 | |
| GALNT6 | | Bos taurus | BT020728 | AAX08745.1 | |
| Polypeptide GalNAc transferase T1 | | Bos taurus | L07780 | AAA30532.1 | Q07537 |
| | | | L17437 | AAA68489.1 | |
| | | | | AAE24810 | |
| | | | | AAE24816 | |
| ZK688.8 (gly3) | | Caenorhabditis elegans | NM_177519 | NP_803485.1 | |
| | | | L16621 | AAA28224.3 | P34678 |
| | | | AF031833 | AAC13669.1 | Q9U003 |
| | | | NM_066321 | NP_498722.1 | |
| Y46H3A.6 (gly-7) | | Caenorhabditis elegans | AF031841 | AAC13677.1 | O61397 |
| | | | AC006774 | AAF60620.1 | |
| | | | NM_071111 | NP_503512.1 | |
| Y39E4B.12 (gly-5) | | Caenorhabditis elegans | AF031835 | AAC13671.1 | O61391 |
| | | | AF031836 | AAC13672.1 | O61392 |
| | | | AF031837 | AAC13673.1 | O61393 |
| | | | AL110487 | CAB54435.1 | Q9U2I8 |
| | | | AL110487 | CAC42368.1 | Q95ZJ2 |
| | | | AL110487 | CAC42369.1 | Q95ZJ1 |
| | | | NM_067320 | NP_499721.3 | |
| | | | NM_067321 | NP_499722.2 | |
| | | | NM_171894 | NP_741277.1 | |
| Y75B8A.9 | | Caenorhabditis elegans | AL033514 | CAA22098.1 | Q9XW72 |
| | | | AL033514 | CAE47472.1 | |
| | | | NM_067181 | NP_499582.1 | |
| Y66A7A.6 (gly-8) | | Caenorhabditis elegans | AF031842 | AAC13678.1 | O45293 |
| | | | AL032622 | CAA21500.1 | |
| | | | AL590342 | CAC35860.1 | |
| | | | NM_067103 | NP_499504.1 | |
| Y45F10D.3 | | Caenorhabditis elegans | AL021492 | CAA16378.1 | O45947 |

FIG. 18

| Protein | Organism | GenBank/GenPept | UniPort | PDB/3D |
|---|---|---|---|---|
| H38K22.5 (gly-6) | Caenorhabditis elegans | AL021492 | | |
| | | NM_070255 | | |
| | | AF031838 | CAJ76949.1 | |
| | | AF031839 | NP_502656.1 | |
| | | AF031840 | AAC13674.1 | O61394 |
| | | AL024499 | AAC13675.1 | O61395 |
| | | AL024499 | AAC13676.1 | O61396 |
| | | AL024499 | CAA19707.1 | |
| | | NM_065469 | CAC42317.1 | |
| | | NM_065470 | CAC42318.1 | |
| | | NM_065471 | NP_497870.2 | |
| | | | NP_497871.2 | |
| | | | NP_497872.2 | |
| Y116F11B.12 (gly-4) | Caenorhabditis elegans | AF031834 | AAC13670.1 | O61390 |
| | | AL132943 | CAB81983.1 | Q8I136 |
| | | AL132943 | CAB81985.3 | |
| | | AL132943 | CAC14394.1 | |
| | | NM_075449 | NP_507850.1 | |
| GLY9 (Y47D3A.23) | Caenorhabditis elegans | AF031843 | AAC13679.1 | O61398 |
| | | AL117202 | CAB57897.1 | Q9U2C4 |
| | | AL117202 | CAI46621.1 | |
| | | NM_067050 | NP_499451.1 | |
| Polypeptide GalNAc transferase T2 (ppGalNAc-T2; 1MB.187) | Cryptosporidium parvum | AY466374 | AAR23115.1 | Q7YYJ5 |
| UDP-GalNAc:polypeptide N-acetylgalactosaminyltransferase T1 | Cryptosporidium parvum | BX538351 | CAD98487.1 | |
| UDP-GalNAc:polypeptide N-acetylgalactosaminyltransferase T3 | Cryptosporidium parvum | AY424893 | AAQ95174.1 | |
| UDP-GalNAc:polypeptide N-acetylgalactosaminyltransferase T4 | Cryptosporidium parvum | AY424894 | AAQ95175.1 | |
| | | AY424895 | AAQ95176.1 | |
| Unknown (protein for MGC:112011) (fragment) | Danio rerio | BC095642 | AAH95642.1 | |
| CH211-147C14.1-001 | Danio rerio | CR626885 | CAI11605.1 | |
| CH211-214J24.2-001 (fragment) | Danio rerio | BX323558 | CAI11790.1 | |
| Unknown (protein for MGC:113219) | Danio rerio | BC090692 | AAH90692.1 | |
| MGC:77836 | Danio rerio | BC067340 | AAH67340.1 | |
| CH211-147C1.1-001 | Danio rerio | CR626885 | CAI20718.1 | |

FIG. 18 (cont.)

| Protein | Organism | GenBank/GenPept | UniPort | PDB/3D |
|---|---|---|---|---|
| CH211-214J24.3-001 (fragment) | Danio rerio | BX323558 | | |
| CG7579 | Drosophila melanogaster | AE003530 | Q8VUT5 | |
| | | AF326979 | Q8IA41 | |
| | | NM_140542 | | |
| polypeptide N-acetylgalactosaminyltransferase T3 (CG4445) | Drosophila melanogaster | AF145655 | Q9Y117 | |
| | | AE003842 | | |
| | | NM_136412 | | |
| CG30463 | Drosophila melanogaster | AE003806 | Q9V7T0 | |
| | | AE003806 | Q8MRC9 | |
| | | AY121661 | | |
| | | NM_166188 | | |
| | | NM_166189 | | |
| polypeptide N-acetylgalactosaminyltransferase T6 (CG2103) | Drosophila melanogaster | AE003476 | Q95R40 | |
| | | AE003476 | Q9VZX5 | |
| | | AY061629 | | |
| | | AY268067 | | |
| | | NM_139492 | | |
| | | NM_167966 | | |
| polypeptide N-acetylgalactosaminyltransferase T5 (CG31651) | Drosophila melanogaster | AE003608 | Q9VMU3 | |
| | | AY060338 | Q95T43 | |
| | | AY268066 | | |
| | | NM_135062 | | |
| polypeptide N-acetylgalactosaminyltransferase T4 (CG31956) | Drosophila melanogaster | AE003579 | Q8IQ11 | |
| | | AF324752 | Q8IA42 | |
| | | AY268065 | | |
| | | NM_164539 | | |
| CG7304 | Drosophila melanogaster | AE003530 | Q9VUT4 | |
| | | AF324750 | Q8IA44 | |
| | | AE003530 | | |
| | | NM_140541 | | |

FIG. 18 (cont.)

| Protein | Organism | GenBank/GenPept | UniPort | PDB/3D |
|---|---|---|---|---|
| polypeptide N-acetylgalactosaminyltransferase T8 (CG7297) | Drosophila melanogaster | AE003530<br>AY070966<br>NM_140543 | Q9VUT6 | |
| polypeptide N-acetylgalactosaminyltransferase T1 (CG8182) | Drosophila melanogaster | AE003810<br>AF218236<br>AY113411<br>AE003810<br>AY268063<br>NM_137199<br>NM_166099 | Q9V7C8 | |
| polypeptide N-acetylgalactosaminyltransferase T7 (CG6394) | Drosophila melanogaster | AE003509<br>AF493067<br>AE003509<br>AY268068<br>BT016123<br>NM_133073<br>NM_167623 | Q9VWT6<br>Q8MV48 | |
| polypeptide N-acetylgalactosaminyltransferase T2 (CG3254) | Drosophila melanogaster | AE003580<br>AE003580<br>BT010030<br>AY268064<br>AE003580<br>NM_134929 | Q9VQQ2<br>Q7YU21 | |
| CG10000 | Drosophila melanogaster | AE003766<br>AE003766<br>AY113484 | Q9VAT9<br>Q8MYY6 | |

FIG. 18 (cont.)

| Protein | Organism | GenBank/GenPept | UniPort | PDB/3D |
|---|---|---|---|---|
| polypeptide N-acetylgalactosaminyltransferase T35A (CG7480) | Drosophila melanogaster | NM_143373 | | |
| | | AE003409 | Q9V3C9 | |
| | | AE003643 | Q9G5E4 | |
| | | AF158747 | Q8MVS5 | |
| | | AF478697 | Q8MVS4 | |
| | | AF478698 | Q8MVS3 | |
| | | AF478699 | | |
| | | NM_143812 | | |
| CG31776 | Drosophila melanogaster | AE003579 | Q9VQR4 | |
| | | AE003579 | Q8IA43 | |
| | | AF324751 | | |
| | | BT022827 | | |
| | | NM_164538 | | |
| N-acetylgalactosaminytransferase (ppGalNAc-T1) | Echinococcus granulosus | AY353720 | | |
| RCJMB04_17f16 | Gallus gallus | AJ720423 | | |
| RCJMB04_1b1 | Gallus gallus | AJ851373 | | |
| GALNT16 | Homo sapiens | BC036812 | Q8N428 | |
| | | BC098578 | Q9ULT9 | |
| | | AB032956 | | |
| | | AB078143 | | |
| | | AJ505951 | | |
| | | CQ816250 | | |
| | | XM_031104 | | |
| FLJ12691 | Homo sapiens | BC006269 | Q9H9J8 | |
| | | BC006269 | | |
| | | BC010659 | | |
| | | AK022753 | | |
| | | AK024039 | | |
| | | AX262414 | | |
| | | AX882259 | | |
| | | NM_024572 | | |

FIG. 18 (cont.)

| Protein | Organism | GenBank/GenPept | UniPort | PDB/3D cryst |
|---|---|---|---|---|
| UDP-GalNAc:polypeptide N-acetylgalactosaminyltransferase (GalNAc-T10) | Homo sapiens | Y09324 | Q8IVI4 | |
| UDP-GalNAc:polypeptide N-acetylgalactosaminyltransferase GalNT11 (FLJ21634) | Homo sapiens | AC006017 | Q8NCW6 | |
| | | BC059377 | Q9UDR8 | |
| | | AK025287 | Q9H6Z5 | |
| | | AK026056 | Q9H6C2 | |
| | | Y12434 | | |
| | | AX461608 | | |
| | | NM_022087 | | |
| UDP-GalNAc:polypeptide-N-acetylgalactosaminyltransferase T6 (GalNAc-T6) | Homo sapiens | BC035822 | Q9UIV5 | |
| | | BC114505 | Q9H6G2 | |
| | | AK025961 | Q8NCL4 | |
| | | AK074658 | | |
| | | Y08565 | | |
| | | CQ782628 | | |
| | | NM_007210 | | |
| UDP-GalNAc:polypeptide N-acetylgalactosaminyltransferase 5 (GALNT5) | Homo sapiens | AF154107 | Q9UGK7 | |
| | | AY277591 | Q9UHL6 | |
| | | AJ245539 | Q7Z7M9 | |
| | | AJ505956 | | |
| | | NM_014568 | | |
| | | XM_050509 | | |
| Unknown (protein for MGC:26636) | Homo sapiens | BC022021 | Q7Z4T8 | |
| | | AF440400 | Q8WW05 | |
| | | AF440404 | Q8NCV4 | |
| | | AC099345 | | |
| | | AC074257 | | |

FIG. 18 (cont.)

| Protein | Organism | GenBank/GenPept | UniPort | PDB/3D |
|---|---|---|---|---|
| polypeptide GalNAc transferase 8 (GalNAc-T8) | Homo sapiens | NM_145292<br>AJ505959<br>NM_017417<br>BC013945 | | |
| | | AAX04410.1<br>ABA67768.1<br>NP_660335.1<br>CAD44539.1<br>NP_059113 | | |
| UDP-GalNAc polypeptide N-acetylgalactosaminyltransferase 12 | Homo sapiens | AK024865<br>AB078146<br>AB040673<br>AJ132365<br>AJ505963 | | |
| | | AAH13945.1<br>ABA38425.1<br>BAB15027.1<br>BAC07181.1<br>BAD93346.1<br>CAC80100.2<br>CAD44541.1 | Q96CT9<br>Q9H771<br>Q8NG54<br>Q8IXK2 | |
| UDP-GalNAc polypeptide N-acetylgalactosaminyltransferase T2 (GalNAc-T2; GalNT2) | Homo sapiens | CQ816242<br>AL136084<br>NM_024642<br>BC041120 | | |
| | | CAG32962.1<br>CAI17042.1<br>NP_078918<br>AAH41120.1 | Q10471 | 2FFU |
| | | X85019<br>AL117349<br>AL117349<br>AL117349<br>NM_004481 | | 2FFV |
| | | CAA59381.1<br>CAC00565.2<br>CAI22902.1<br>CAI23447.1<br>NP_004472.1<br>AAE72285.1 | | |
| UDP-N-acetyl-D-galactosamine:polypeptide N-acetylgalactosaminyltransferase 7 (GALNT7) | Homo sapiens | BC014789<br>BC030625<br>AY035399<br>AY358443 | Q96DJ5 | |
| | | AAE73125.1<br>AAH14789.1<br>AAH30625.1<br>AAK63127.1<br>AAQ88808.1 | Q96C46<br>Q8N3T1 | |

FIG. 18 (cont.)

| Protein | Organism | GenBank/GenPept | UniPort | PDB/3D |
|---|---|---|---|---|
| | | | ABA31473.1 | |
| | | | ABA36473.1 | |
| | | | ABA38055.1 | |
| | | | ABA68732.1 | |
| | | | ABA69735.1 | |
| | | | ABA70117.1 | |
| | | | ABA70240.1 | |
| | | | ABC04061.1 | |
| | | | ABC16096.1 | |
| | | | ABE23551.1 | |
| | | | ABE26114.1 | |
| | | | ABE26387.1 | |
| | | | BAD29961.1 | |
| | | | CAD38585.1 | |
| | | | CAG32963.1 | |
| | | | NP_473451.2 | |
| pp-GalNAc-transferase 17 (GALNT17) | Homo sapiens | AB078149 | AAH44793.1 | |
| | | AL831925 | AAH47551.1 | |
| | | CQ816244 | CAF25036.1 | |
| | | NM_054110 | | |
| | | BC044793 | | |
| | | BC047551 | | |
| | | AJ626725 | | |
| GalNAc-transferase 18 (GALNT18) aka GalNAc-T15 | Homo sapiens | BC037341 | AAH37341.3 | |
| | | BC060864 | AAH60864.1 | |
| | | | ABE14321.1 | |
| | | AB078147 | BAD93179.1 | |
| | | AJ626724 | CAF25035.1 | |
| | | NM_198516 | NP_940918.1 | |
| polypeptide N-acetylgalactosaminyltransferase 10 (GalNT10) | Homo sapiens | BC007224 | AAH07224.2 | Q9H8E1 |
| | | BC050333 | AAH50333.1 | Q8TEJ2 |
| | | BC072450 | AAH72450.1 | Q96IV2 |
| | | BC098444 | AAH98444.1 | Q86VP8 |

FIG. 18 (cont.)

| Protein | Organism | GenBank/GenPept | UniProt | PDB/3D |
|---|---|---|---|---|
| | | AAP65370.1 | Q86SR1 | |
| | | AAP65371.1 | Q9Y4M4 | |
| | | AAP65372.1 | Q8IXJ2 | |
| | | AAP65373.1 | | |
| | | AAP65374.1 | | |
| | | AAP65376.1 | | |
| | | AAP65377.1 | | |
| | | AAP65378.1 | | |
| | | AAP65379.1 | | |
| | | ABA33146.1 | | |
| | | ABA33147.1 | | |
| | | ABA33148.1 | | |
| | | ABA33149.1 | | |
| | | ABA33150.1 | | |
| | | ABA33151.1 | | |
| | | ABA33152.1 | | |
| | | ABA33153.1 | | |
| | | ABA33154.1 | | |
| | | ABA33155.1 | | |
| | AK023782 | BAB14676.1 | | |
| | AK074132 | BAB84958.1 | | |
| | AB078145 | BAC56890.1 | | |
| | AL096739 | CAB46378.1 | | |
| | AJ505950 | CAD44532.1 | | |
| | AX880860 | CAE91109.1 | | |
| | NM_017540 | NP_060010.2 | | |
| | NM_198321 | NP_938080.1 | | |
| polypeptide N-acetylgalactosaminyltransferase 9 (GalNAc-T9) | Homo sapiens | BC069354 | AAH69354.1 | Q8NFR1 |
| | | BC093817 | AAH93817.1 | Q9HCQ5 |
| | | BC093819 | AAH93819.1 | |
| | | AF458594 | AAM49722.1 | |

| Protein | Organism | GenBank/GenPept | UniPort | PDB/3D |
|---|---|---|---|---|
| GalNAc-T15 UDP-GalNAc:polypeptide N-acetylgalactosaminyltransferase 7 | | AB040672 AAT18857.1 | | |
| | | AJ505960 ABE14200.1 | | |
| | | NM_021808 BAB13699.2 | | |
| | | CQ816248 CAD44540.1 | | |
| | Homo sapiens | BC035303 NP_068580.1 | Q9UJ28 | |
| | Homo sapiens | BC046129 CAG32965.1 | Q7Z5W7 | |
| | | BC047468 AAH35303.1 | Q86SF2 | |
| | | AC105285 AAH46129.1 | | |
| | | | AAH47468.1 | |
| | | | AAY41020.1 | |

| Protein | Organism | GenBank/GenPept | UniPort | PDB/3D |
|---|---|---|---|---|
| polypeptide N-acetylgalactosaminyltransferase 14 (GalNAc-T14) | Homo sapiens | AJ002744<br>AX136283<br>AJ505958<br>CS051319<br>NM_017423<br>AY358758<br>AAU97249<br>AC009301 | CAB60270.1<br>CAC39783.1<br>CAD44538.1<br>CAI72154.1<br>NP_059119.1<br>AAQ89118.1<br>AAU97249.1<br>AAX88899.1<br>ABA66763.1 | | |
| | | AK091313<br>AB078144<br>AX405663<br>AJ505966<br>AX881147<br>BC056246 | BAC03634.1<br>BAC56889.1<br>CAD34770.1<br>CAD44543.1<br>CAE91230.1<br>AAH56246.1 | | |
| UDP-GalNAc:polypeptide-N-acetylgalactosaminyltransferase T3 (GALNAc-T3;GALNT3) | Homo sapiens | AC009495<br>X92689<br>AJ505954 | AAY14678.1<br>CAA63371.1<br>CAD44536.1 | Q14435 | |
| pp-GalNAc-transferase 20 (GALNT20) | Homo sapiens | NM_004482<br>BC067524<br>BC067525<br>BC069624<br>BC069628<br>BC069636<br>BC069645<br>BC069997<br>AF410457 | NP_004473.1<br>AAH67524.1<br>AAH67525.1<br>AAH69624.1<br>AAH69628.1<br>AAH69636.1<br>AAH69645.1<br>AAH69997.1<br>AAM62306.1<br>ABA66799.1 | Q8NFV9 | |
| | | AB078148 | BAD93180.1 | | |

FIG. 18 (cont.)

| Protein | Organism | GenBank/GenPept | UniPort | PDB/3D |
|---|---|---|---|---|
| UDP-GalNAc:polypeptide-N-acetylgalactosaminyltransferase T1 (GalNAc-T1;GALNT1) | Homo sapiens | AJ626726<br>NM_022479<br>U41514 | CAF25037.1<br>NP_071924.1<br>AAC50327.1 | Q10472 | |
| UDP-GalNAc:polypeptide-N-acetylgalactosaminyltransferase T4 (GalNAc-T4;GALNT4) | Homo sapiens | BC047746<br>X85018<br>AJ505952<br>NM_020474<br>BC036390 | AAH47746.1<br>CAA59380.1<br>CAD44535.1<br>NP_065207.2<br>AAH36390.1 | Q86TJ7<br><br><br><br>O00208 | |
| Polypeptide GalNAc transferase T13 (contains KIAA1918) | Homo sapiens | Y08564<br>NM_003774<br>BC101031<br>BC101033<br>AB078142<br>AJ505991<br>CQ816246<br>NM_052917 | AAN94203.1<br>AAN94205.1<br>CAA69875.1<br>NP_003765.1<br>AAI01032.1<br>AAI01034.1<br>BAC54545.1<br>CAD44533.2<br>CAG32964.1<br>NP_443149.1 | Q8N4A0 | |
| ORF (fragment)<br>-unnamed protein product (fragment)<br>UDP-GalNAc: polypeptide N-acetylgalactosaminyltransferase<br>ORF | Macaca fascicularis<br>Macaca fascicularis<br>Macaca fascicularis<br>Macaca fascicularis | AB050513<br>AB172088<br>AB050509<br>AB069985<br>AB070020<br>AB070053 | BAB17281.1<br>BAE89150.1<br>BAB17277.1<br>BAB62930.1<br>BAB62965.1<br>BAB62998.1 | Q9GLZ7<br>Q9GM01<br>Q95JX4<br>Q95K42<br>Q95K07 | |
| ORF (fragment)<br>ORF (fragment)<br>UDP-GalNAc:polypeptide-N-acetylgalactosaminyltransferase 16 | Macaca fascicularis<br>Macaca fascicularis<br>Mus musculus | AB168494<br>AB169420<br>AB045325 | BAE00614.1<br>BAE01503.1<br>BAA97985.1 | Q9JJ61 | |

FIG. 18 (cont.)

| Protein | Organism | GenBank/GenPept | UniPort | PDB/3D |
|---|---|---|---|---|
| (ppGalNAc-T16) | | AK173105 | | |
| | | AB175683 | | |
| | | AK138883 | | |
| UDP-GalNAc:polypeptide -N-acetylgalactosaminyltransferase 14 (pp-GalNAc-T14) | Mus musculus | AK002747 | Q8BTI6 | |
| | | AK078292 | Q9DCJ2 | |
| | | AK090146 | Q8BVG5 | |
| | | AB175681 | | |
| UDP-GalNAc:polypeptide -N-acetylgalactosaminyltransferase 7 | Mus musculus | BC007484 | Q8BZW0 | |
| | | BC049907 | Q91VW6 | |
| | | BC052461 | Q80VA0 | |
| | | AF349573 | Q99MD7 | |
| | | AK033427 | Q8BZ70 | |
| | | AK036523 | | |
| | | AK151424 | | |
| | | AK151753 | | |
| | | AK152205 | | |
| | | AK153143 | | |
| | | NM_144731 | | |
| UDP-GalNAc:polypeptide -N-acetylgalactosaminyltransferase 12 (pp-GalNAc-T12) | Mus musculus | BC056425 | Q8BGT9 | |
| | | AK033638 | | |
| | | AK042133 | | |
| | | AB175680 | | |
| | | AK156751 | | |
| | | NM_172693 | | |
| Polypeptide GalNAc transferase T3 (GALNT3) | Mus musculus | U70538 | P70419 | |
| | | BC043331 | Q80V55 | |

FIG. 18 (cont.)

| Protein | Organism | GenBank/GenPept | UniProt | PDB/3D |
|---|---|---|---|---|
| UDP-GalNAc:polypeptide-N-acetylgalactosaminyltransferase t1 (GalNAc-T1;ppGalNAcTase-1;Galnt1) | Mus musculus | AK135489<br>BAE22551.1<br>NM_015736 NP_056551.1<br>U73820 AAB58477.1 | O08912 | 1XHB |
| pp-GalNAc-T17 | Mus musculus | BC056215 AAH56215.1<br>BC090962 AAH90962.1<br>AK148550 BAE28617.1<br>NM_013814 NP_038842.2<br>BC052469 AAH52469.1<br>AF467979 AAM62404.1<br>AK035817 BAC29197.1<br>AK048758 BAC33446.1<br>AK048758 BAC33446.2<br>AK051281 BAC34591.1<br>AK051281 BAC34591.2<br>AK081B48 BAC38348.1<br>AK087726 BAC39982.1<br>AB175684 BAD91810.1<br>NM_145218 NP_660253.2 | Q7ND1<br>Q8BZC8<br>Q7TT15<br>Q8K483<br>Q8BKN7<br>Q8BX73<br>Q8BU49 | |
| Polypeptide GalNAc transferase T4 | Mus musculus | U73819 AAB53301.1<br>BC057882 AAH57882.1<br>ABA38430.1<br>AK033494 BAC28317.1<br>AK148036 BAE28303.1<br>AK153253 BAE31844.1<br>NM_015737 NP_056552.1 | O08832 | |
| ppGalNTase-T5 | Mus musculus | AK029323 BAC26396.1 | Q8C102 | |

| Protein | Organism | GenBank/GenPept | UniPort | PDB/3D |
|---|---|---|---|---|
| ORF | Mus musculus | NM_172855 | | |
| | | BC024988 | Q8K1B9 | |
| | | AB175685 AAH24988.1 | | |
| | | BAD91811.1 | | |
| Unknown (protein for MGC:63144) (fragment) | Mus musculus | NM_173739 NP_776100.2 | Q7TQL0 | |
| | | BC054061 AAH54061.1 | | |
| | | AK171529 BAE42509.1 | | |
| | | NM_198306 NP_938048.1 | | |
| GALNT10;GALNT9 | Mus musculus | BC016585 AAH16585.1 | Q91YJ6 | |
| | | BC060617 AAH60617.1 | Q8BZU8 | |
| | | AK033515 BAC28334.1 | | |
| | | AK131155 BAD21405.1 | | |
| | | AK159088 BAE34806.1 | | |
| | | AK159362 BAE35020.1 | | |
| | | AK172609 BAF43090.1 | | |
| | | AL662868 CAI24136.1 | | |
| | | AL662868 CAI24137.1 | | |
| | | AL662868 CAI24811.1 | | |
| | | NM_134189 NP_598950.1 | | |
| unnamed protein product (fragment) | Mus musculus | AK080614 BAC37957.1 | Q8BJR4 | |
| UDP-GalNAc:polypeptide-N-acetylgalactosaminyltransferase 15 (pp-GalNAc-T15) | Mus musculus | NM_175032 NP_778197.1 | Q9D2N8 | |
| | | AK019470 BAB31741.1 | | |
| polypeptide GalNAc transferase-T2 | Mus musculus | AB175682 BAD52070.1 | Q922K5 | |
| | | BC007172 AAH07172.1 | Q7TSI5 | |
| | | BC053063 AAH53063.1 | Q99ME1 | |
| | | BC059818 AAH59818.1 | Q8BL27 | |
| | | AF348988 AAK37548.1 | | |
| | | AK046567 BAC32790.1 | | |
| | | AK145122 BAE26246.1 | | |
| | | AK151536 BAE30483.1 | | |
| | | NM_139272 NP_844678.1 | | |

| Protein | Organism | GenBank/GenPept | UniPort | PDB/3D |
|---|---|---|---|---|
| UDP-GalNAc:polypeptide -GalNAc-transferase (GaLnt13) | Mus musculus | AK038387<br>AK045417<br>AB082928<br>NM_173030 | Q8BYT3<br>Q8BLE4 | |
| Polypeptide GalNAc transferase T6 | Mus musculus | AK028506<br>AK049222<br>AK155008<br>AK159721<br>AJ133523<br>NM_172451 | Q8CED2<br>Q8C7U7<br>Q9QZ16 | |
| 1700021B12Rik | Mus musculus | BC049554<br>BC100447<br>AK005605<br>AK016415<br>NM_026449 | Q8IOS4<br>Q9CW06<br>Q9D4M9 | |
| A630038F14<br>UDP-GalNAc:polypeptide N-acetylgalactosaminyltransferase GalNT11 | Mus musculus<br>Mus musculus | AK041791<br>BC011428<br>BC021504<br>BC034184<br>BC034185<br>BC036143<br>BC036145<br>AF495528<br>AK088014<br>AK161524<br>Y12435 | Q8BY62<br>Q921L8<br>Q8K032<br>Q8BU26 | |
| DKFZp469B1122<br>DKFZp469L0611<br>Polypeptide GalNAc transferase T6 | Pongo pygmaeus<br>Pongo pygmaeus<br>Rattus norvegicus | CR857160<br>CR857560<br>AF076167 | Q9R0C5 | |

FIG. 18 (cont.)

| Protein | Organism | GenBank/GenPept | UniPort | PDB/3D |
|---|---|---|---|---|
| N-acetylgalactosaminyltransferase T5 (Galnt5) | Rattus norvegicus | NM_022926<br>AF049344<br>NM_031796 | O88422 | |
| UDP-GalNAc polypeptide N-acetylgalactosaminyltransferase-3 (GalNAc-T3) | Rattus norvegicus | BC101886 | | |
| Polypeptide GalNAc transferase T1 | Rattus norvegicus | AB040674<br>U35890 | Q10473 | |
| Polypeptide GalNAc transferase T13 | Rattus norvegicus | NM_024373<br>AY371923<br>NM_199106 | | |
| Unknown (protein for MGC:93899) | Rattus norvegicus | BC078995 | | |
| Unknown (protein for IMAGE:7317097) (fragment) | Rattus norvegicus | BC091351 | | |
| UDP-GalNAc:polypeptide N-acetylgalactosaminyltransferase T9 | Rattus norvegicus | AF241241<br>NM_130742 | Q925R7 | |
| UDP-GalNAc polypeptide N-acetylgalactosaminyltransferase-4 (GalNAc-T4) | Rattus norvegicus | BC105818 | | |
| Unknown (protein for MGC:94136)<br>pt-GalNAc-T<br>ORF | Rattus norvegicus<br>Rattus norvegicus<br>Rattus norvegicus | AB040675<br>BC079128<br>AB040671<br>BC062004<br>NM_199393 | | |
| ORF<br>SJCHGC07375 (fragment)<br>SJCHGC03147 (fragment)<br>Polypeptide GalNAc transferase T1<br>UDP-GalNAc:polypeptide N-acetylgalactosaminyltransferase T1 (ppGalNAc-T1) | Schistosoma japonicum<br>Schistosoma japonicum<br>Schistosoma japonicum<br>Sus scrofa<br>Toxoplasma gondii RH | AY814498<br>AY811519<br>AY810748<br>D85389<br>AF234624 | Q29121<br>Q8MM26 | |

FIG. 18 (cont.)

| Protein | Organism | GenBank/GenPept | UniPort | PDB/3D |
|---|---|---|---|---|
| UDP-GalNAc:polypeptide N-acetylgalactosaminyltransferase T4 (ppGalNAc-T4) (fragment) | Toxoplasma gondii RH | AF321881<br>AY424889 | AAM81087.1<br>AAQ95170.1 | |
| UDP-GalNAc:polypeptide N-acetylgalactosaminyltransferase T3 (ppGalNAc-T3) | Toxoplasma gondii RH | AY160970 | AAO20278.1 | |
| UDP-GalNAc:polypeptide N-acetylgalactosaminyltransferase T5 (ppGalNAc-T5) (fragment) | Toxoplasma gondii RH | AY424892<br>AYA424890 | AAQ95173.1<br>AAQ95171.1 | |
| UDP-GalNAc:polypeptide N-acetylgalactosaminyltransferase T2 (ppGalNAc-T2) | Toxoplasma gondii RH | AY136814 | AAM95450.1 | |
| Unknown (protein for MGC:81150) | Xenopus laevis | AY424891 | AAQ95172.1 | |
| Unknown (protein for MGC:78803) | Xenopus laevis | BC071009 | AAH71009.1 | |
| Unknown (protein for MGC:81846) | Xenopus laevis | BC070527 | AAH70527.1 | |
| ORF | Xenopus laevis | BC080006 | AAH80006.1 | |
| Unknown (protein for MGC:83963) | Xenopus laevis | BC060419 | AAH60419.1 | |
| Unknown (protein for MGC:130697) | Xenopus laevis | BC074234 | AAH74234.1 | |
| MGC:76103 | Xenopus tropicalis | BC110706 | AAI10707.1 | |
| TGas006c10.1-001 (probable fragment) | Xenopus tropicalis | BC067317 | AAH67317.1 | |
| Unknown (protein for MGC:79650) | Xenopus tropicalis | CR855751 | CAJ81616.1 | |
| Unknown (protein for MGC:75106) | Xenopus tropicalis | BC075106 | AAH75106.1 | |
| Unknown (protein for MGC:69370) | Xenopus tropicalis | BC090583 | AAH90583.1 | |
| TGas07lo13.1-001 | Xenopus tropicalis | CR942331 | CAJ83416.1 | |
| UNCLASSIFIED | | | | |
| Sequence 7 from patent US 6939698 (fragment) | Unknown. | | AT18860.1<br>ABA38429.1 | |

FIG. 18 (cont.)

EXPRESSION OF O-GLYCOSYLATED THERAPEUTIC PROTEINS IN PROKARYOTIC MICROORGANISMS

CROSS-REFERENCES TO RELATED APPLICATIONS

This application is a U.S. National Phase Application under 35 U.S.C. §371 of International Application No. PCT/US2007/009782, filed on Apr. 19, 2007, which claims the benefit of U.S. Provisional Application No. 60/793,531, filed Apr. 19, 2006 and U.S. Provisional Application No. 60/842,926, filed Sep. 6, 2006; both of which are herein incorporated by reference for all purposes.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 327,462 bytes ASCII (Text) file named "SequenceListing" created Oct. 6, 2011.

FIELD OF THE INVENTION

The invention relates to methods of producing an O-glycosylated soluble therapeutic protein in a prokaryotic microorganism by expressing the therapeutic protein and at least one heterologous glycosyltransferase that transfers a sugar moiety to an amino acid acceptor on the therapeutic protein. The therapeutic protein and the heterologous glycosyltransferase can be expressed in separate microorganisms and combined after cell lysis or the therapeutic protein and the heterologous glycosyltransferase can be expressed in the same microorganism.

BACKGROUND OF THE INVENTION

One of the most efficient hosts for production of recombinant proteins are prokaryotic host cells. Many therapeutic proteins are being used to treat humans and other higher mammals. Yet in spite of the need for efficient and economic methods to produce such proteins, therapeutic proteins are produced in costly eukaryotic cell systems, e.g., mammalian tissue culture cells, such as CHO cells; insect cells, and yeast cells. The main obstacles to use of prokaryotic production systems are production of insoluble therapeutic proteins in many prokaryotic cells, e.g., *E. coli*, and failure of prokaryotic cells to provide appropriate post-translation modification of eukaryotic proteins, e.g., glycosylation of eukaryotic proteins. Thus, at present production of therapeutic proteins in prokaryotic hosts must include labor intensive and expensive steps of refolding misfolded proteins, purification of refolded therapeutic proteins and purification of refolded glycosyltransferases. The present invention solves these and other needs.

BRIEF SUMMARY OF THE INVENTION

In one aspect the present invention provides a method of producing an O-glycosylated soluble therapeutic protein in a prokaryotic microorganism by expressing a soluble therapeutic protein and a heterologous soluble active nucleotide sugar:polypeptide glycosyltransferase protein in the prokaryotic microorganism, and growing the microorganism under conditions that allow intracellular transfer of a first sugar moiety from a first donor substrate to an amino acid acceptor substrate on the therapeutic protein catalyzed by the heterologous soluble active nucleotide sugar:polypeptide glycosyltransferase protein, to produce the O-glycosylated soluble therapeutic protein.

In one embodiment, the prokaryotic microorganism has an intracellular oxidizing environment. Examples of prokaryotic microorganisms include, e.g., *E. coli* and *Pseudomonas bacterium*. In one embodiment, the prokaryotic microorganism is genetically modified to have the intracellular oxidizing environment. Genetic manipulation of *E. coli*, by mutating an endogenous reductase nucleic acid is known to affect the redox state of the cell and produce an intracellular oxidizing environment.

In one embodiment, the heterologous soluble active nucleotide sugar:polypeptide glycosyltransferase is a soluble active eukaryotic N-acetylgalactosaminyl transferase (GalNAcT) protein.

In another embodiment, the method has an additional step of expressing a first heterologous soluble active glycosyltransferase in the prokaryotic microorganism and allowing it to catalyze intracellular transfer of a sugar moiety from a donor substrate to O-linked sugar on the therapeutic protein. Exemplary heterologous soluble active glycosyltransferase proteins include, e.g., a eukaryotic core I galactosyltransferase (Core 1 GalT1) protein and a ST6 GalNAc 1 protein. In a further embodiment, the method has an additional step of expressing a second heterologous soluble active glycosyltransferase in the prokaryotic microorganism and allowing it to catalyze intracellular transfer of a sugar moiety from a donor substrate to a second acceptor substrate, e.g., part of the O-linked glycan, on the therapeutic protein. Exemplary second heterologous soluble active glycosyltransferase protein include, e.g., a eukaryotic α(2,3)sialyltransferase (ST3Gal1) protein, and a bacterial α(2,3)sialyltransferase protein.

In another embodiment, the microorganism is grown in a medium that comprises a precursor of the donor substrate, e.g., GalNAc, GlcNAc, glucose, or sialic acid. The growth medium can be a rich medium, e.g., LB, or a minimal medium used for growth of microorganisms. The microorganism, e.g., *E. coli*, can also by genetically modified to enhance production of the donor substrate. Examples of such genetic modifications are included herein.

In still another embodiment, the N-glycosylated soluble therapeutic protein is isolated from the microorganism. The N-glycosylated soluble therapeutic protein can be produced on a commercial scale. The N-glycosylated therapeutic protein can be further modified in vitro by, e.g., addition of a PEG moiety.

In another embodiment, the prokaryotic microorganism also expresses an accessory enzyme that has a role in synthesis of any donor substrate needed. The accessory enzyme can be e.g., a UDP-glucose 4' epimerase protein, a UDP-GlcNAc 4' epimerase protein or a dual function UDP-glucose 4' epimerase protein/UDP-GlcNAc 4' epimerase protein.

In another aspect the invention provides a prokaryotic microorganism that expresses both the O-glycosylated soluble therapeutic protein and the heterologous soluble active nucleotide sugar:polypeptide glycosyltransferase. In some embodiments, both the O-glycosylated soluble therapeutic protein and the heterologous soluble active nucleotide sugar:polypeptide glycosyltransferase are expressed in the intracellular space of the microorganism. In one embodiment, the heterologous soluble active nucleotide sugar:polypeptide glycosyltransferase is expressed in the intracellular space and glycosylates a therapeutic protein in the intracellular space. The O-glycosylated therapeutic protein is then transported through the bacterial membrane to the periplasm where refolding occurs. In some embodiments, the prokaryotic microorganism has an intracellular oxidizing environment.

BRIEF DESCRIPTION OF THE DRAWINGS

FIG. 3 provides analysis of a hGH GlycoPEGylation reaction utilizing crude lysates of hGH, GalNAcT2 Δ51 Δ445, GalE, MBP-Core-1-GalT1 and MBP-ST3Gal1 produced in trxB, gor, supp E. coli. hGH-GalNAc-Gal was prepared as described in FIGS. 1-2 was subsequently glycoPEGylated after addition of reaction substrates and a crude cell lysate from a trxB, gor, supp E. coli strain that expressed MBP-ST3Gal1 protein.

FIG. 5 shows the results of reverse phase HPLC (RP-HPLC) analysis of hGH-GalNAc-Gal-SA-cys-PEG-40 kDa after purification by Q-sepharose fast flow chromatography followed by size exclusion chromatography.

FIG. 7 demonstrates in vivo glycosylation of hGH by GalNAc-T2 Δ51 Δ445 co-expressed in a trxB, gor, supp E. coli strain. Epimerases GalE or GNE were also expressed in the cells, in order to compare their in vivo activities. FIG. 7 shows the results of the co-expression as analyzed by RP-HPLC.

FIG. 8 summarizes the expression levels and percent yield of hGH and hGH-GalNAc in crude lysates produced by the coexpression of hGH with GalNAcT2 and GalE or GNE.

FIG. 10 shows a reaction scheme for production of glycosylated hGH using a single fermentation. The hGH protein is coexpressed in a trxB, gor, supp E. coli strain with, here, GalE, GalNAc-T2 Δ445, and Core-1-Gal-T1. After fermentation, the cells are lysed and, if desired, mixed with an ST3Gal1 protein and CMP-sialic acid-cys-PEG-40 kDa to form the hGH-GalNAc-Gal-SA-cys-PEG-40 kDa product.

FIG. 11 shows the yields of bacterially produced hGH and hGH-GalNAc. The yields of hGH and glycosylated hGH in crude lysate for two polycistronic expression cassettes expressing hGH, GalNAcT2 Δ53 Δ445, Core-1-GalT1 Δ50, and GNE in trxB, gor, supp E. coli were determined by RP-HPLC and LC/MS and compared.

FIG. 14 provides an analysis of the progression of glycosylation in vivo when produced from a polycistronic expression cassette in trxB gor supp mutant *E. coli*. hGH was coexpressed with glycosyltransferases and accessory enzymes in trxB, gor, supp *E. coli* using a polycistronic expression cassette. Glycosylation of hGH in cell lysate at each timepoint was monitored by LC/MS.

FIG. 16 provides examples of some naturally-occurring O-glycan structures.

FIG. 18 provides a list of exemplary nucleotide sugar: polypeptide glycosyltransferase proteins from CAZy family 27.

DEFINITIONS

Figure 1:
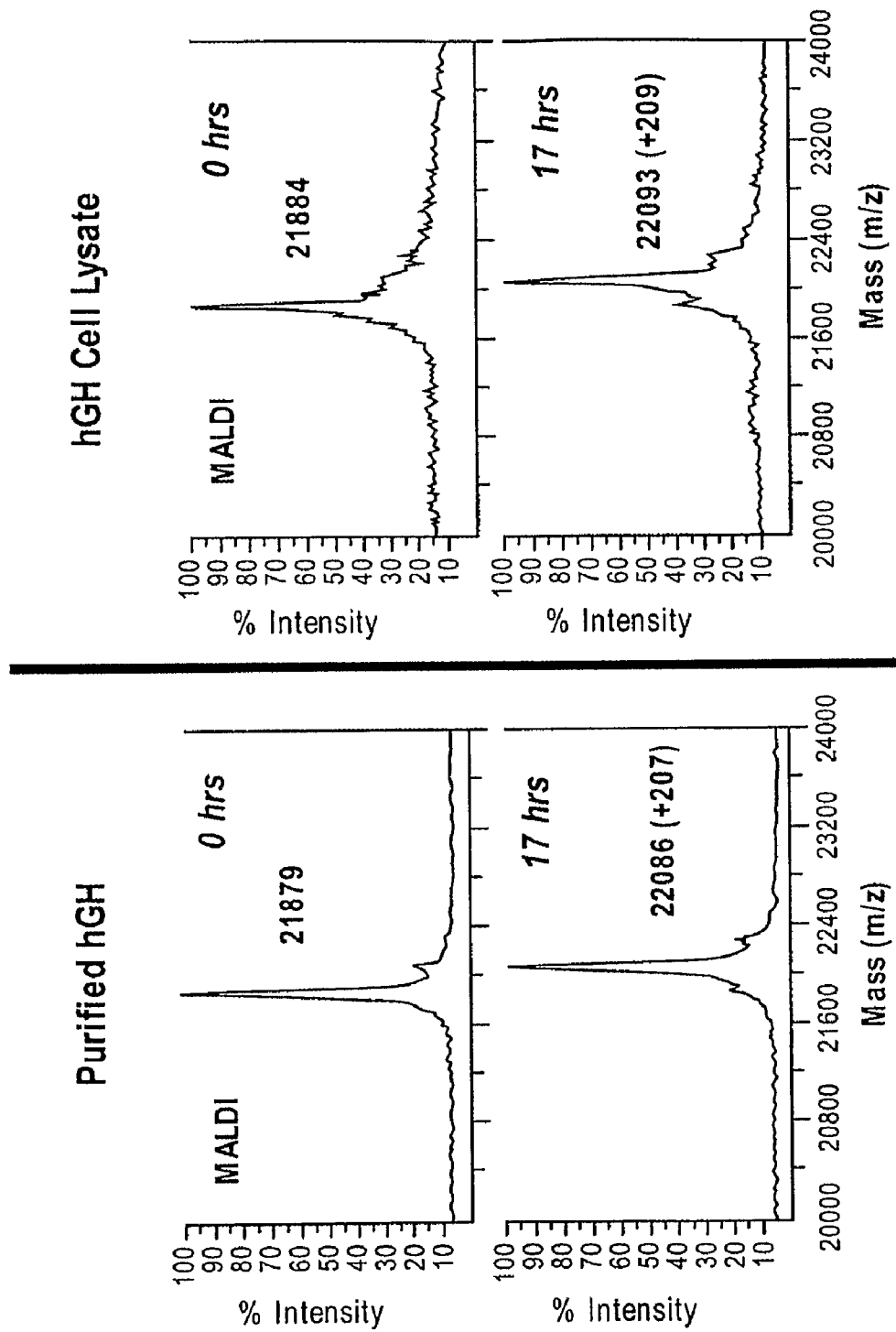
FIG. 1 demonstrates glycosylation of mutant human growth hormone (hGH) either as purified material (left) or in a crude cell lysate containing soluble hGH (right). hGH was produced in a trxB, gor, supp E. coli strain. GalNAc was transferred to the hGH protein after addition of reaction substrates and a crude cell lysate from a trxB, gor, supp E. coli strain that expressed human GalNAc-T2 Δ51 Δ445 protein and an epimerase protein, GalE. Reaction products were analyzed by MALDI TOF mass spectrometry and compared to unglycosylated hGH. The expected mass due to addition of GalNAc (expected +203.2, observed +207 or +209) to hGH from either source was observed.

The recombinant glycosyltransferase proteins produced by the methods of the invention are useful for transferring a saccharide from a donor substrate to an acceptor substrate. The addition generally takes place at the non-reducing end of an oligosaccharide or carbohydrate moiety on a biomolecule. Biomolecules as defined here include, but are not limited to, biologically significant molecules such as carbohydrates, proteins (e.g., glycoproteins), and lipids (e.g., glycolipids, phospholipids, sphingolipids and gangliosides).

The following abbreviations are used herein:
Ara=arabinosyl;
Fru=fructosyl;
Fuc=fucosyl;
Gal=galactosyl;
GalNAc=N-acetylgalactosylamino;
Glc=glucosyl;
GlcNAc=N-acetylglucosylamino;
Man=mannosyl; and
NeuAc=sialyl(N-acetylneuraminyl)
FT or FucT=fucosyltransferase*
ST=sialyltransferase*
GalT=galactosyltransferase*

Arabic or Roman numerals are used interchangeably herein according to the naming convention used in the art to indicate the identity of a specific glycosyltransferase (e.g., FTVII and FT7 refer to the same fucosyltransferase).

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

The term "sialic acid" refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O-$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

An "acceptor substrate" for a glycosyltransferase is an oligosaccharide moiety that can act as an acceptor for a particular glycosyltransferase. When the acceptor substrate is contacted with the corresponding glycosyltransferase and sugar donor substrate, and other necessary reaction mixture components, and the reaction mixture is incubated for a sufficient period of time, the glycosyltransferase transfers sugar residues from the sugar donor substrate to the acceptor substrate. The acceptor substrate will often vary for different types of a particular glycosyltransferase. For example, the acceptor substrate for a mammalian galactoside 2-L-fucosyl-transferase ($\alpha$1,2-fucosyltransferase) will include a Gal$\beta$1,4-GlcNAc-R at a non-reducing terminus of an oligosaccharide; this fucosyltransferase attaches a fucose residue to the Gal via an $\alpha$1,2 linkage. Terminal Gal$\beta$1,4-GlcNAc-R and Gal$\beta$1,3-GlcNAc-R and sialylated analogs thereof are acceptor substrates for $\alpha$1,3 and $\alpha$1,4-fucosyltransferases, respectively. These enzymes, however, attach the fucose residue to the GlcNAc residue of the acceptor substrate. Accordingly, the term "acceptor substrate" is taken in context with the particular glycosyltransferase of interest for a particular application. Acceptor substrates for additional glycosyltransferases, are described herein. Acceptor substrates also include e.g., glycolipids, peptides, proteins, glycopeptides, glycoproteins and therapeutic proteins.

An "amino acid acceptor substrate" is an amino acid in a protein or peptide that is conjugated to a sugar moiety in a reaction catalyzed by a nucleotide sugar:polypeptide glycosyltransferase protein. Amino acid acceptor substrates for nucleotide sugar:polypeptide glycosyltransferase protein include, e.g., threonine, serine, hydroxyproline, tyrosine, or other hydroxy-containing amino acids.

A "donor substrate" for glycosyltransferases is an activated nucleotide sugar. Such activated sugars generally consist of uridine, guanosine, and cytidine monophosphate derivatives of the sugars (UMP, GMP and CMP, respectively) or diphosphate derivatives of the sugars (UDP, GDP and CDP, respectively) in which the nucleoside monophosphate or diphosphate serves as a leaving group. For example, a donor substrate for fucosyltransferases is GDP-fucose. Donor substrates for sialyltransferases, for example, are activated sugar nucleotides comprising the desired sialic acid. For instance, in the case of NeuAc, the activated sugar is CMP-NeuAc. Other donor substrates include e.g., GDP mannose, UDP-galactose, UDP-N-acetylgalactosamine, CMP-NeuAc-PEG (also referred to as CMP-sialic acid-PEG), UDP-N-acetyl-glucosamine, UDP-glucose, UDP-glucorionic acid, and UDP-xylose. Sugars include, e.g., NeuAc, mannose, galactose, N-acetylgalactosamine, N-acetylglucosamine, glucose, glucorionic acid, and xylose. Bacterial, plant, and fungal systems can sometimes use other activated nucleotide sugars.

A "method of remodeling a protein, a peptide, a glycoprotein, or a glycopeptide" as used herein, refers to addition of a sugar residue to a protein, a peptide, a glycoprotein, or a glycopeptide using a glycosyltransferase. In a preferred embodiment, the sugar residue is covalently attached to a PEG molecule.

A "glycosyltransferase" as used herein refers to an enzyme that catalyzes transfer of a sugar residue from a donor substrate, i.e., from an activated nucleotide sugar, to an acceptor substrate, e.g., an oligosaccharide, a glycolipid, a peptide, a protein, a glycopeptide, or a glycoprotein. In preferred embodiments, a glycosyltransferase transfers a sugar from a donor substrate, i.e., a nucleotide sugar, to a peptide, a protein, a glycopeptide, or a glycoprotein. In another preferred embodiment, a eukaryotic glycosyltransferase is a type II transmembrane glycosyltransferase. Unmodified type II transmembrane glycosyltransferases typically include an amino terminal cytoplasmic domain, a signal-anchor or transmembrane domain, a stem region, and a catalytic domain. See, e.g., Paulson and Colley, *J. Biol. Chem.* 264:17615-17618 (1989). Many unmodified type II transmembrane glycosyltransferases are associated with cellular membranes and, therefore, fractionate with insoluble material when expressed in eukaryotic cells. Removal of the amino terminal cytoplasmic domain, signal-anchor or transmembrane domain, and the stem region of a eukaryotic glycosyltransferase results in an active, soluble enzyme that does not associate with the membrane fraction of a eukaryotic cell. See, e.g., Paulson et al., U.S. Pat. No. 5,032,519, filed Oct. 24, 1989; which is herein incorporated by reference for all purposes. A glycosyltransferase can be derived from an eukaryotic organism, e.g., a unicellular or multicellular eukaryotic organism, a plant, an invertebrate animal, such as *Drosophila* or *C. elegans*, a vertebrate animal, an amphibian or reptile, a mammal, a rodent, a primate, a human, a rabbit, a rat, a mouse, a cow, or a pig and so on. Examples of many eukaryotic glycosyltransferases are at, e.g., See, e.g., U.S. Provisional Application No. 60/665,396, filed Mar. 24, 2005; U.S. Provisional Application No. 60/668,899, filed Apr. 5, 2005; U.S. Provisional Application No. 60/732,409, filed Oct. 31, 2005; and International Application PCT/US06/11065, filed Mar. 24, 2006; each of which are herein incorporated by reference for all purposes. Prokaryotic glycosyltransferases can also be used in the methods of the invention.

A "sialyltransferase" as used herein, refers to an enzyme that catalyzes the transfer of a sialic acid moiety from a CMP-sialic acid donor to an acceptor molecule. Eukaryotic sialyltransferases can also be recognized by the presence of conserved structural motifs, e.g., a sialyl motif L and a sialyl motif S as described in Tsuji, *J. Biochem.* 120:1-13 (1996), which is herein incorporated by reference for all purposes. Additional sialyltransferase motifs, e.g., the very small (VS) motif and motif III, are described in Patel and Balaji, *Glycobiology*, 16:108-116 (2006), e-published Oct. 5, 2005, which is herein incorporated by reference for all purposes. Sialyltransferases include enzymes that form a variety of linkages including α2→3, α2→6, α2→8. Sialyltransferases transfer the sialic acid moiety to different acceptor sugars on an acceptor molecule, e.g., galactose, GalNAc, and another sialic acid molecule. Eukaryotic sialyltransferases that catalyze specific reaction, i.e., that are members of the ST3 Gal, ST6Gal, ST6GalNAc, or ST8Sia families can be identified by the presence of amino acid residues conserved within those families. Such family-based conserved amino acid residues are disclosed at Patel and Balaji, *Glycobiology*, 16:108-116 (2006), e-published Oct. 5, 2005, which is herein incorporated by reference for all purposes. Prokaryotic sialyltransferases are known and can also be used in the disclosed methods.

An α(2,3)sialyltransferase is a sialyltransferase that transfers sialic acid to an acceptor substrate by forming an α(2,3) linkage. One example of a eukaryotic α(2,3)sialyltransferase is the ST3Gal3 protein. This enzyme catalyzes the transfer of sialic acid to the Gal of a Galβ1,3GlcNAc, Galβ1,3GalNAc or Galβ1,4GlcNAc glycoside (see, e.g., Wen et al. (1992) *J.* *Biol. Chem.* 267: 21011; Van den Eijnden et al. (1991) *J. Biol. Chem.* 256: 3159). The sialic acid is linked to a Gal with the formation of an α-linkage between the two saccharides. Bonding (linkage) between the saccharides is between the 2-position of NeuAc and the 3-position of Gal. Like other eukaryotic glycosyltransferases, ST3Gal3 enzymes have a transmembrane domain, a stem region, and a catalytic domain. This particular enzyme can be isolated from rat liver (Weinstein et al. (1982) *J. Biol. Chem.* 257: 13845); the human cDNA (Sasaki et al. (1993) *J. Biol. Chem.* 268: 22782-22787; Kitagawa & Paulson (1994) *J. Biol. Chem.* 269: 1394-1401) and genomic (Kitagawa et al. (1996) *J. Biol. Chem.* 271: 931-938) DNA sequences are known, facilitating production of this enzyme by recombinant expression. Rat ST3Gal3 has been cloned and the sequence is known. See, e.g., Wen et al., *J. Biol. Chem.* 267:21011-21019 (1992) and Accession number M97754, each of which are herein incorporated by reference. Prokaryotic α(2,3) sialyltransferases are also known e.g., enzymes from *Neiserria* species and CstI, CstII, and CstIII enzymes from Campylobacter, and can be used in the methods of the invention.

A "eukaryotic α-N-acetylgalactosaminide α-2,6-sialyltransferase I (ST6GalNAcT1 or ST6GalNAc-1) (SEQ ID NOs: 59 and 60) as used herein, refers to an α(2,6)sialyltransferase isolated from a eukaryotic organism. The enzyme catalyzes the transfer of sialic acid from a CMP-sialic acid donor to an acceptor molecule. The transfer is an α2,6-linkage to N-acetylgalactosamine-O-Thr/Ser. Like other eukaryotic glycosyltransferases, ST6GalNAcT1 enzymes have a transmembrane domain, a stem region, and a catalytic domain. A number of ST6GalNAcT1 enzymes have been isolated and characterized, e.g., the full length mouse sequence, Kurosawa et al., *J. Biochem.* 127:845-854 (2000) and accession number JC7248, each of which are herein incorporated by reference. Prokaryotic sialyltransferases that catalyze α-2,6 linkages are also known and can be used in the methods of the invention.

A "eukaryotic Gal β1,3GalNAc α2,3-sialyltransferase (ST3GalI or ST3Gal-1)" as used herein, refers to a Gal β1,3GalNAc α2,3-sialyltransferase isolated from a eukaryotic organism. The enzyme catalyzes the transfer of sialic acid from a CMP-sialic acid donor to an acceptor molecule. The transfer is an α2,3-linkage to N-acetylgalactosamine-O-Thr/Ser. Like other eukaryotic glycosyltransferases, ST3GalI enzymes have a transmembrane domain, a stem region, and a catalytic domain. A number of ST3GalI enzymes have been isolated and characterized, e.g., the full length porcine sequence, Gillespie et al., *J. Biol. Chem.* 267:21004-21010 (1992) and accession number A45073, each of which are herein incorporated by reference.

Other sialyltransferases that can be used in the present invention include, e.g., "eukaryotic beta galactoside alpha 2,6-sialyltransferase (ST6Gal I) proteins.

Eukaryotic sialyltransferase proteins used in the invention also include alpha 2,8 sialyltransferase proteins, e.g., ST8Sia I, ST8Sia II, ST8Sia III, and ST8Sia IV.

Prokaryotic α(2,3) sialyltransferases are also known, e.g., enzymes from *Neisseria* species and CstI, CstII, and CstIII enzymes from *Campylobacter*, and can be used in the methods of the invention. Exemplary *Neisseria* sialyltransferase are disclosed at, e.g., U.S. Pat. No. 6,096,529, issued Aug. 1, 2000; which is herein incorporated by reference for all purposes. Exemplary *Campylobacter* sialyltransferase are disclosed at, e.g., U.S. Pat. No. 6,689,604, issued Feb. 10, 2004, U.S. Pat. No. 6,503,744, issued Jan. 7, 2003, and U.S. Pat. No. 6,699,705, issued Mar. 2, 2004; each of which is herein incorporated by reference for all purposes. Other exemplary bacterial sialyltransferases are disclosed at International Application PCT/CA2005/001432, filed Sep. 16, 2005; which is herein incorporated by reference for all purposes. Prokaryotic α(2,6)sialyltransferases are also known and can be used in the methods of the invention. One example of a prokaryotic α(2,6)sialyltransferase is from *Photobacterium*. See, e.g., Yamamoto et al., *J. Biochem.* 120:104-110 (1996).

A "eukaryotic N-acetylglucosaminyltransferase" as used herein, refers to an N-acetylglucosaminyltransferase derived from a eukaryotic organism. The enzyme catalyzes the transfer of N-acetylglucosamine (GlcNAc) from a UDP-GlcNAc donor to an acceptor molecule. Like other eukaryotic glycosyltransferases, N-acetylglucosaminyltransferase has a transmembrane domain, a stem region, and a catalytic domain.

A "β-1,2-N-eukaryotic N-acetylglucosaminyltransferase I (GnTI or GNTI)" as used herein, refers to a β-1,2-N-acetylglucosaminyltransferase I derived from a eukaryotic organism. Like other eukaryotic glycosyltransferases, GnTI has a transmembrane domain, a stem region, and a catalytic domain. Eukaryotic GnT1 proteins include, e.g., human, accession number NP_002397; Chinese hamster, accession number AAK61868; rabbit, accession number AAA31493; rat, accession number NP_110488; golden hamster, accession number AAD04130; mouse, accession number P27808; zebrafish, accession number AAH58297; *Xenopus*, accession number CAC51119; *Drosophila*, accession number NP-525117; *Anopheles*, accession number XP_315359; *C. elegans*, accession number NP_497719; *Physcomitrella patens*, accession number CAD22107; *Solanum tuberosum*, accession number CAC80697; *Nicotiana tabacum*, accession number CAC80702; *Oryza sativa*, accession number CAD30022; *Nicotiana benthamiana*, accession number CAC82507; and *Arabidopsis thaliana*, accession number NP_195537, each of which are herein incorporated by reference. Other eukaryotic N-acetylglucosaminyltransferase proteins that can be used in the present invention are include, e.g., BGnT-1, GnT-II, GnT-III, GnT-IV (e.g., GnT-IVa and GnT-IVb), GnT-V, GnT-VI, and GnT-IVH.

Other eukaryotic N-acetylglucosaminyltransferase proteins can be produced using the methods of the present invention and include, e.g., maniac fringe protein, and MGNT1 proteins.

A "nucleotide sugar:polypeptide glycosyltransferase protein" as used herein, refers to a glycosyltransferase protein that catalyzes the transfer of a sugar moiety from a donor substrate to an amino acid acceptor. The amino acid acceptor is an amino acid that includes a hydroxyl group, e.g., threonine, serine, hydroxyproline, tyrosine, or other hydroxy-containing amino acids. For eukaryotic nucleotide sugar:polypeptide glycosyltransferase proteins, the amino acid acceptor is typically a serine or threonine residues. For prokaryotic nucleotide sugar:polypeptide glycosyltransferase proteins, more variability is seen in the amino acid acceptor; the most commonly used amino acid residues are threonine, serine, and tyrosine. Eukaryotic nucleotide sugar:polypeptide glycosyltransferase proteins include the GalNAcT proteins described below. Some examples of nucleotide sugar:polypeptide glycosyltransferase proteins are disclosed at, e.g., CAZy family 27 (FIG. 18).

A "eukaryotic N-acetylgalactosaminyltransferase (GalNAcT)" as used herein, refers to an N-acetylgalactosaminyltransferase isolated from a eukaryotic organism. The enzyme catalyzes the transfer of N-acetylgalactosamine (GalNAc) from a UDP-GalNAc donor to an acceptor molecule. Like other eukaryotic glycosyltransferases, GalNAcT enzymes have a transmembrane domain, a stem region, and a catalytic domain. A number of GalNAcT enzymes have been isolated and characterized, e.g., GalNAcT1, accession number X85018; GalNAcT2, accession number X85019 (both described in White et al., *J. Biol. Chem.* 270:24156-24165 (1995)); and GalNAcT3, accession number X92689 (described in Bennett et al., *J. Biol. Chem.* 271:17006-17012 (1996), each of which are herein incorporated by reference). At present eukaryotic 20 GalNacT proteins, i.e., GalNAcT1-20) are known and can be used in the methods of the invention.

A "eukaryotic galactosyltransferase as used herein, refers to a galactosyltransferase derived from a eukaryotic organism. The enzyme catalyzes the transfer of galactose from a UDP-Gal donor to an acceptor molecule. Like other eukaryotic glycosyltransferases, galactosyltransferases have a transmembrane domain, a stem region, and a catalytic domain.

A "eukaryotic β-1,4-galactosyltransferase (GalT1) as used herein, refers to a β-1,4-galactosyltransferase derived from a eukaryotic organism. The enzyme catalyzes the transfer of galactose from a UDP-Gal donor to an acceptor molecule. Like other eukaryotic glycosyltransferases, GalT1 enzymes have a transmembrane domain, a stem region, and a catalytic domain. A number of GalT1 enzymes have been isolated and characterized, e.g., the full length bovine sequence, D'Agostaro et al., *Eur. J. Biochem.* 183:211-217 (1989) and accession number CAA32695, each of which are herein incorporated by reference.

A "eukaryotic core I galactosyltransferase (Core 1 GalT1 or Core-1-Gal-T1)" (SEQ ID NOs: 47-49) as used herein refers to a protein with Core 1 β1,3-Galactosyltransferase activity. Like other eukaryotic glycosyltransferases, Core 1 GalT1 enzymes have a transmembrane domain, a stem region, and a catalytic domain. A number of Core 1 GalT1 enzymes have been isolated and characterized, e.g., the *Drosophila* and human sequences. The human protein is characterized in Ju et al., *J. Biol. Chem.* 277 (1), 178-186 (2002), which is herein incorporated by reference for all purposes.

A "β-1,3-galactosyl-O-glycosyl-glycoprotein beta-1,6-N-acetylglucosaminyltransferase (Core 2 GlcNAcT or Core-2-GlcNAcT)" as used herein refers to a protein with Core 2 β1,6-GlcNActransferase activity. Like other eukaryotic glycosyltransferases, Core 2 GlcNAcT enzymes have a transmembrane domain, a stem region, and a catalytic domain. A number of Core 2 GlcNAcT enzymes have been isolated and characterized and are disclosed at, e.g., CAZy family 14. The CAZy family 14 includes examples of prokaryotic proteins with Core 2 β1,6-GlcNActransferase activity. Such prokaryotic proteins can also be used in the invention.

A "eukaryotic fucosyltransferase" as used herein, refers to a fucosyltransferase derived from a eukaryotic organism. The enzyme catalyzes the transfer of fucose from a UDP-fucose donor to an acceptor molecule. Like other eukaryotic glycosyltransferases, fucosyltransferases have a transmembrane domain, a stem region, and a catalytic domain.

Other eukaryotic glycosyltransferase proteins that can be used in the present invention include, e.g., dolichyl-phosphate mannosyltransferase polypeptide 1, or Dpm1, alpha-1,6-mannosyltransferase, alpha-1,3-mannosyltransferase, and beta-1,4-mannosyltransferase proteins.

Many prokaryotic glycosyltransferases are also known, e.g., galactosyltransferases, GalNAc transferases, GlcNAc transferases, mannosyltransferases, glucosyltransferases, xylosyltransferases, and fucosyltransferases, and can be used in the methods of the invention.

A "therapeutic protein" as used herein, refers a protein, peptide, glycoprotein or glycopeptide that is administered to a subject to treat disease or dysfunction or to improve health of the subject. In a preferred embodiment the subject is a human. In a further preferred embodiment, the therapeutic protein is a human protein. A soluble therapeutic protein refers to a therapeutic protein that is soluble in an aqueous solution. In some embodiments the soluble therapeutic protein is soluble in an intracellular compartment of a prokaryotic cell. Most of the therapeutic protein or a fraction of the expressed therapeutic protein can be soluble in the intracellular compartment of a prokaryotic cell. In another embodiment the soluble therapeutic protein is an active protein, e.g., has enzymatic activity, binding activity, or ability to elicit an immune response in a mammal, e.g., a human. In an additional embodiment, the therapeutic protein is glycosylated or otherwise modified by one or more glycosyltransferases produced in a microorganism that has an oxidizing intracellular environment. In another embodiment, the therapeutic protein is produced in a microorganism that has an oxidizing intracellular environment and is glycosylated by one or more heterologous, e.g., eukaryotic, glycosyltransferases produced the same microorganism. In one embodiment, a therapeutic protein is one of the following: FGF-20 (SEQ ID NO: 1), FGF-21 (SEQ ID NO: 2), NT-3 (SEQ ID NOs: 4 and 5), or glucocerebrosidase (SEQ ID NO: 3). In another embodiment, a therapeutic protein is one of the following: human FGF-20, human FGF-21, human NT-3 or human glucocerebrosidase. Therapeutic proteins are not limited to those listed above, and can include, e.g., proteins listed in Table 1.

An "O-glycosylated therapeutic protein" or an "O-glycosylated soluble therapeutic protein" as used herein refer to a therapeutic protein that has been modified to include at least one sugar residue conjugated to a hydroxyl group on an amino acid of the therapeutic protein.

An "unpaired cysteine residue" as used herein, refers to a cysteine residue, which in a correctly folded protein (i.e., a protein with biological activity), does not form a disulfide bind with another cysteine residue.

A "redox couple" refers to mixtures of reduced and oxidized thiol reagents and include reduced and oxidized glutathione (GSH/GSSG), cysteine/cystine, cysteamine/cystamine, DTT/GSSG, and DTE/GSSG. (See, e.g., Clark, *Cur. Op. Biotech.* 12:202-207 (2001)).

The term "oxidant" or "oxidizing agent" refers to a compound which oxidizes molecules in its environment, i.e., which changes the molecules in its environment to become more oxidized and more oxidizing. An oxidant acts by accepting electrons, thereby becoming itself reduced after having oxidized a substrate. Thus, an oxidant is an agent which accepts electrons.

The term "oxidizing conditions" or "oxidizing environment" refers to a condition or an environment in which a substrate is more likely to become oxidized than reduced. For example, the periplasm of a wild type *E. coli* cell constitutes an oxidizing environment, whereas the cytoplasm of a wild type *E. coli* cell is a reducing environment. In an oxidizing environment, there is a greater likelihood that disulfide bonds will form.

An enzyme in an "oxidized state" refers to an enzyme that has fewer electrons than its reduced form.

The term "reductant" or "reducing agent" refers to a compound which reduces molecules in its environment, i.e., which changes molecules in its environment to become more reduced and more reducing. A reducing agent acts by donating electrons, thereby becoming itself oxidized after having reduced a substrate. Thus, a reducing agent is an agent which donates electrons. Examples of reducing agents include dithiothreitol (DTT), mercaptoethanol, cysteine, thioglycolate, cysteamine, glutathione, and sodium borohydride.

The term "reductase" refers to a thioredoxin reductase, glutathione or glutathione reductase (also referred to as "oxidoreductases") or any other enzyme that can reduce members of the thioredoxin or glutaredoxin systems.

The term "reductase pathways" refers to the systems in cells which maintain the environment in reducing conditions, and includes the glutaredoxin system and the thioredoxin system.

The term "reducing conditions" or "reducing environment" refers to a condition or an environment in which a substrate is more likely to become reduced than oxidized. For example, the cytoplasm of a eukaryotic cell constitutes a reducing environment.

"Disulfide bond formation" or "disulfide bond oxidation", used interchangeably herein, refers to the process of forming a covalent bond between two cysteines present in one or two polypeptides. Oxidation of disulfide bonds can be mediated by thiol-disulfide exchange between the active site cysteines of enzymes and cysteines in the target protein. Disulfide bond formation can be catalyzed by enzymes which are referred to as catalysts of disulfide bond formation or can be catalyzed by chemical means, e.g., an intracellular environment.

An enzyme in a "reduced state", has more electrons than its oxidized form.

"Disulfide bond reduction" refers to the process of cleaving a disulfide bond, thereby resulting in two thiol groups. Reduction of disulfide bonds is mediated by thiol-disulfide exchange between the active site cysteines of enzymes and cysteines in the target protein.

The term "disulfide bond isomerization" refers to an exchange of disulfide bonds between different cysteines, i.e., the shuffling of disulfide bonds. Isomerization of disulfide bonds is mediated by thiol-disulfide exchange between the active site cysteines of enzymes and cysteines in the target protein and catalyzed by isomerases. In *E. coli*, isomerization is catalyzed by DsbC (SEQ ID NO: 18) or DsbG (SEQ ID NO: 20) a periplasmic disulfide bond oxidoreductase.

A "catalyst of disulfide bond formation" is an agent which stimulates disulfide bond formation. Such an agent must be in an oxidized state to be active.

A "catalyst of disulfide bond isomerization", also referred to as an "disulfide bond isomerase" is an agent which stimulates disulfide bond isomerization. Such an agent must be in a reduced form to be active.

The term "contacting" is used herein interchangeably with the following: combined with, added to, mixed with, passed over, incubated with, flowed over, etc.

"Chaperone proteins" are proteins that are known to promote proper folding of newly synthesized proteins. Chaperone proteins include, e.g., trigger factor; members of the Hsp70 chaperone family, e.g. DnaK (SEQ ID NO: 8); members of the Hsp100 chaperone family, e.g. ClpB (SEQ ID NO: 9), and members of the Hsp60 chaperone family, e.g. GroEL (SEQ ID NO: 10). See, e.g., Sorensen and Mortensen, *BioMed Central*, microbialcellfactories.com/content/4/1/1. Chaperones are also known that allow protein folding at 4° C., e.g., Cpn60 (SEQ ID NO: 12) and Cpn 10 (SEQ ID NO: 11) from *Oleispira antartica* RB8$^T$. See, e.g., Id. and Ferrer et al., *Nat. Biotechnol.* 21:1266-1267 (2003).

"Protein disulfide isomerases" or "PDI proteins" can make or shuffle disulfide bonds. PDI proteins are described e.g., in Georgiou et al. U.S. Pat. No. 6,027,888, which is herein incorporated by reference for all purposes. PDI proteins are derived from eukaryotic and prokaryotic organisms. Eukaryotic PDI proteins include those of the Interpro family IPR005792 Protein disulphide isomerase. Exemplary eukaryotic PDI proteins include PDI proteins from e.g., rat liver PDI (SEQ ID NO: 13), Ero1p (SEQ ID NO: 14) and Pdi1p (SEQ ID NO: 15) proteins from *Sacchromyces*.

Prokaryotic proteins include e.g., DsbC from *E. coli*. See, e.g., Frand et al., *Trends in Cell Biol.* 10:203-210 (2000).

Other prokaryotic proteins that act to maintain the redox state of protein disulfide bonds include, e.g., DsbB (SEQ ID NO: 16), DsbA (SEQ ID NO: 17), DsbC (SEQ ID NO: 18), DsbD (SEQ ID NO: 19), and DsbG (SEQ ID NO: 20) from *E. coli*. These proteins are well known in the art and are described in, e.g., Beckwith et al. U.S. Pat. No. 6,872,563, which is herein incorporated by reference for all purposes.

The term "PEG" refers to poly(ethylene glycol). PEG is an exemplary polymer that has been conjugated to peptides. The use of PEG to derivatize peptide therapeutics has been demonstrated to reduce the immunogenicity of the peptides and prolong the clearance time from the circulation. For example, U.S. Pat. No. 4,179,337 (Davis et al.) concerns non-immunogenic peptides, such as enzymes and peptide hormones coupled to polyethylene glycol (PEG) or polypropylene glycol. Between 10 and 100 moles of polymer are used per mole peptide and at least 15% of the physiological activity is maintained.

The term "specific activity" as used herein refers to the catalytic activity of an enzyme, e.g., a recombinant glycosyltransferase of the present invention, and may be expressed in activity units. As used herein, one activity unit catalyzes the formation of 1 µmol of product per minute at a given temperature (e.g., at 37° C.) and pH value (e.g., at pH 7.5). Thus, 10 units of an enzyme is a catalytic amount of that enzyme where 10 µmol of substrate are converted to 10 µmol of product in one minute at a temperature of, e.g., 37° C. and a pH value of, e.g., 7.5.

"N-linked" oligosaccharides are those oligosaccharides that are linked to a peptide backbone through asparagine, by way of an asparagine-N-acetylglucosamine linkage. N-linked oligosaccharides are also called "N-glycans." Naturally occurring N-linked oligosaccharides have a common pentasaccharide core of $Man_3GlcNAc_2$. They differ in the presence of, and in the number of branches (also called antennae) of peripheral sugars such as N-acetylglucosamine, galactose, N-acetylgalactosamine, fucose and sialic acid. Optionally, this structure may also contain a core fucose molecule and/or a xylose molecule. Using the soluble eukaryotic glycosyltransferases produced by the methods of the invention, oligosaccharides can be produced that mimic natural N-linked structures or that are designed by the user. Soluble eukaryotic glycosyltransferases that generate N-linked oligosaccharides include, e.g., GnT1, GalT1, and ST3Gal3 (SEQ ID NOs: 75 and 76) enzymes.

"O-linked" oligosaccharides are those oligosaccharides that are linked to a peptide backbone through threonine, serine, hydroxyproline, tyrosine, or other hydroxy-containing amino acids. Using the soluble eukaryotic glycosyltransferases produced by the methods of the invention, oligosaccharides can be produced that mimic natural O-linked structures or that are designed by the user. In one embodiment of the invention, soluble eukaryotic glycosyltransferases that generate O-linked oligosaccharides are expressed in one or more microorganisms that have an oxidizing, intracellular environment. Soluble eukaryotic glycosyltransferases that generate O-linked oligosaccharides include, e.g., GalNAc-T2 (SEQ ID NOs: 21-23), Cor-1-Gal-T1 (SEQ ID NOs: 36-40), ST6GalNAc-1 (SEQ ID NOs: 61-71), and ST3Gal-1 (SEQ ID NOs: 50-54) enzymes.

A "substantially uniform glycoform" or a "substantially uniform glycosylation pattern," when referring to a glycoprotein species, refers to the percentage of acceptor substrates that are glycosylated by the glycosyltransferase of interest (e.g., fucosyltransferase). It will be understood by one of skill in the art, that the starting material may contain glycosylated acceptor substrates. Thus, the calculated amount of glycosylation will include acceptor substrates that are glycosylated by the methods of the invention, as well as those acceptor substrates already glycosylated in the starting material.

The term "biological activity" refers to, e.g., an enzymatic activity of a protein. For example, biological activity of a sialyltransferase refers to the activity of transferring a sialic acid moiety from a donor molecule to an acceptor molecule. Biological activity of a GalNAcT2 refers to the activity of transferring an N-acetylgalactosamine moiety from a donor molecule to an acceptor molecule. For GalNAcT2 proteins, an acceptor molecule can be a protein, a peptide, a glycoprotein, or a glycopeptide. Biological activity of a GnT1 protein refers to the activity of transferring a N-acetylglucosamine moiety from a donor molecule to an acceptor molecule. Biological activity of a galactosyltransferase refers to the activity of transferring a galactose moiety from a donor molecule to an acceptor molecule. Other biological activities include binding by e.g., a hormone or receptor, induction of a second messenger system by e.g., a cytokine, and ability to elicit an immune response.

"Commercial scale" refers to gram scale production of a glycosylated product in a single reaction. In preferred embodiments, commercial scale refers to production of at least about 0.2, 0.5, 1, 2, 5, 10, 15, 25, 50, 75, 80, 90 or 100, 125, 150, 175, 200, 500 or 1000 grams a glycosylated product in a single reaction. Commercial scale production of a soluble, active O-glycosylated therapeutic protein refers to gram scale production of a soluble, active O-glycosylated therapeutic protein.

The term "substantially" in the above definitions of "substantially uniform" generally means at least about 60%, at least about 70%, at least about 80%, or more preferably at least about 90%, and still more preferably at least about 95% of the acceptor substrates for a particular glycosyltransferase are glycosylated.

The term "amino acid" refers to naturally occurring and unnatural amino acids, e.g., synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Protein", "polypeptide", or "peptide" refer to a polymer in which the monomers are amino acids and are joined together through amide bonds, alternatively referred to as a polypeptide. When the amino acids are α-amino acids, either the L-optical isomer or the D-optical isomer can be used. Additionally, unnatural amino acids, for example, β-alanine, phenylglycine and homoarginine are also included. Amino acids that are not gene-encoded may also be used in the present invention. Furthermore, amino acids that have been modified to include reactive groups may also be used in the invention. All of the amino acids used in the present invention may be either the D- or L-isomer. The L-isomers are generally preferred. In addition, other peptidomimetics are also useful in the present invention. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques. A "recombinant protein" is one which has been produced by a recombinant cell. In preferred embodiments, a recombinant eukaryotic glycosyltransferase is produced by a recombinant bacterial cell.

A "fusion protein" refers to a protein comprising amino acid sequences that are in addition to, in place of, less than, and/or different from the amino acid sequences encoding the original or native full-length protein or subsequences thereof. More than one additional domain can be added to a glycosyltransferase as described herein, e.g., an accessory domain and an epitope tag or purification tag, or multiple epitope tags or purification tags.

Components of fusion proteins include "accessory enzymes" and/or "purification tags." An "accessory enzyme" as referred to herein, is an enzyme that is involved in catalyzing a reaction that, for example, forms a substrate for a glycosyltransferase. An accessory enzyme can, for example, catalyze the formation of a nucleotide sugar that is used as a donor moiety by a glycosyltransferase. An accessory enzyme can also be one that is used in the generation of a nucleotide triphosphate required for formation of a nucleotide sugar, or in the generation of the sugar which is incorporated into the nucleotide sugar. Examples of accessory enzymes, and fusion of accessory enzymes are disclosed, e.g., in PCT application CA98/01180, filed on Dec. 15, 1998.

The recombinant proteins of the invention can be constructed and expressed as a fusion protein with a molecular "purification tag" at one end, which facilitates purification of the protein. Such tags can also be used for immobilization of a protein of interest during the glycosylation reaction. Suitable tags include "epitope tags," which are a protein sequence that is specifically recognized by an antibody. Epitope tags are generally incorporated into fusion proteins to enable the use of a readily available antibody to unambiguously detect or isolate the fusion protein. A "FLAG tag" is a commonly used epitope tag, specifically recognized by a monoclonal anti-FLAG antibody, consisting of the sequence Asp-TyrLysAspAspAspAspLys (SEQ ID NO: 82) or a substantially identical variant thereof. Other epitope tags that can be used in the invention include, e.g., myc tag, AU1, AU5, DDDDK (EC5) (SEQ ID NO: 83), E tag, E2 tag, Glu-Glu, a 6 residue peptide, EYMPME (SEQ ID NO: 84), derived from the Polyoma middle T protein, HA, HSV, IRS, KT3, S tage, S1 tag, T7 tag, V5 tag, VSV-G, β-galactosidase, Gal4, green fluorescent protein (GFP), luciferase, protein C, protein A, cellulose binding protein, GST (glutathione S-transferase), a step-tag, Nus-S, PPI-ases, Pfg 27, calmodulin binding protein, dsb A and fragments thereof, and granzyme B. Epitope peptides and antibodies that bind specifically to epitope sequences are commercially available from, e.g., Covance Research Products, Inc.; Bethyl Laboratories, Inc.; Abcam Ltd.; and Novus Biologicals, Inc.

Other suitable purification tags are known to those of skill in the art, and include, for example, an affinity tag such as a hexahistidine peptide or other poly-histidine peptides, which will bind to metal ions such as nickel or cobalt ions. Proteins comprising purification tags can be purified using a binding partner that binds the purification tag, e.g., antibodies to the purification tag, nickel or cobalt ions or resins, and amylose, maltose, or a cyclodextrin. Purification tags also include starch binding domains, E. coli thioredoxin domains (vectors and antibodies commercially available from e.g., Santa Cruz Biotechnology, Inc. and Alpha Diagnostic International, Inc.), and the carboxy-terminal half of the SUMO protein (vectors and antibodies commercially available from e.g., Life Sensors Inc.). Starch binding domains, such as a maltose binding domain from E. coli and SBD (starch binding domain) from an amylase of A. niger, are described in WO 99/15636, herein incorporated by reference. Affinity purification of a fusion protein comprising a starch binding domain using a betacyclodextrin (BCD)-derivatized resin is described in U.S. Ser. No. 60/468,374, filed May 5, 2003, herein incorporated by reference in its entirety.

Recombinant proteins can also include a self-cleaving protein tag, such as an "intein". Inteins facilitate removal of, e.g., a purification or epitope tag. Inteins and kits for their use are commercially available, e.g., from New England Biolabs.

The term "functional domain" with reference to glycosyltransferases, refers to a domain of the glycosyltransferase that confers or modulates an activity of the enzyme, e.g., acceptor substrate specificity, catalytic activity, binding affinity, localization within the Golgi apparatus, anchoring to a cell membrane, or other biological or biochemical activity. Examples of functional domains of glycosyltransferases include, but are not limited to, the catalytic domain, stem region, signal-anchor or transmembrane domain, and amino-terminal cytoplasmic tail.

The terms "expression level" or "level of expression" with reference to a protein refers to the amount of a protein produced by a cell. The amount of protein produced by a cell can be measured by the assays and activity units described herein or known to one skilled in the art. One skilled in the art would know how to measure and describe the amount of protein produced by a cell using a variety of assays and units, respectively. Thus, the quantitation and quantitative description of the level of expression of a protein, e.g., a glycosyltransferase, is not limited to the assays used to measure the activity or the units used to describe the activity, respectively. The amount of protein produced by a cell can be determined by standard known assays, for example, the protein assay by Bradford (1976), the bicinchoninic acid protein assay kit from Pierce (Rockford, Ill.), or as described in U.S. Pat. No. 5,641,668. Another method of determining protein expression is to analyze a lysate or other sample containing the protein using gel electrophoresis, e.g., SDS-PAGE, followed by a visualization step. Visualization steps include protein dyes and stains, e.g., Comassie or silver stain, or immunoassays, such as western blot analysis using an antibody that will specifically bind to the protein of interest. Antibodies can be directed against the glycosyltransferase or against a purification or epitope tag covalently bound to the protein.

The term "enzymatic activity" refers to an activity of an enzyme and may be measured by the assays and units described herein or known to one skilled in the art. Examples of an activity of a glycosyltransferase include, but are not limited to, those associated with the functional domains of the enzyme, e.g., acceptor substrate specificity, catalytic activity, binding affinity, localization within the Golgi apparatus, anchoring to a cell membrane, or other biological or biochemical activity.

A "stem region" with reference to glycosyltransferases refers to a protein domain, or a subsequence thereof, which in the native glycosyltransferases is located adjacent to the signal anchor or transmembrane domain, between the membrane region and the shortest catalytic domain, and has been reported to function as a retention signal to maintain the glycosyltransferase in the Golgi apparatus and as a site of proteolytic cleavage. Stem regions generally start with the first hydrophilic amino acid following the hydrophobic transmembrane domain and end at the catalytic domain, or in some cases the first cysteine residue following the transmembrane domain. Exemplary stem regions include, but are not limited to, the stem region of fucosyltransferase VI, amino acid residues 40-54; the stem region of mammalian GnT1, amino acid residues from about 36 to about 103 (see, e.g., the human enzyme); the stem region of mammalian GalT1, amino acid residues from about 71 to about 129 (see e.g., the bovine enzyme); the stem region of mammalian ST3GalIII, amino acid residues from about 29 to about 84 (see, e.g., the rat enzyme); the stem region of invertebrate Core-1-Gal-T1, amino acid residues from about 36 to about 102 (see e.g., the *Drosophila* enzyme); the stem region of mammalian Core-1-Gal-T1, amino acid residues from about 32 to about 90 (see e.g., the human enzyme); the stem region of mammalian ST3Gal1, amino acid residues from about 28 to about 61 (see e.g., the porcine enzyme) or for the human enzyme amino acid residues from about 18 to about 58; the stem region of mammalian ST6GalNAc-1, amino acid residues from about 30 to about 207 (see e.g., the murine enzyme), amino acids 35-278 for the human enzyme or amino acids 37-253 for the chicken enzyme; the stem region of mammalian GalNAc-T2, amino acid residues from about 71 to about 129 (see e.g., the rat enzyme).

A "catalytic domain" refers to a protein domain, or a subsequence thereof, that catalyzes an enzymatic reaction performed by the enzyme. For example, a catalytic domain of a sialyltransferase will include a subsequence of the sialyltransferase sufficient to transfer a sialic acid residue from a donor to an acceptor saccharide. A catalytic domain can include an entire enzyme, a subsequence thereof, or can include additional amino acid sequences that are not attached to the enzyme, or a subsequence thereof, as found in nature. An exemplary catalytic region is, but is not limited to, the catalytic domain of fucosyltransferase VII, amino acid residues 39-342; the catalytic domain of mammalian GnT1, amino acid residues from about 104 to about 445 (see, e.g., the human enzyme); the catalytic domain of mammalian GalT1, amino acid residues from about 130 to about 402 (see e.g., the bovine enzyme); and the catalytic domain of mammalian ST3Gal3, amino acid residues from about 85 to about 374 (see, e.g., the rat enzyme). Catalytic domains and truncation mutants of GalNAc-T2 proteins are described in U.S. Ser. No. 60/576,530 filed Jun. 3, 2004; and U.S. provisional patent application Ser. No. 60/598,584, filed Aug. 3, 2004; both of which are herein incorporated by reference for all purposes. Catalytic domains can also be identified by alignment with known glycosyltransferases.

A "subsequence" refers to a sequence of nucleic acids or amino acids that comprise a part of a longer sequence of nucleic acids or amino acids (e.g., protein) respectively.

A "glycosyltransferase truncation" or a "truncated glycosyltransferase" or grammatical variants, refer to a glycosyltransferase that has fewer amino acid residues than a naturally occurring glycosyltransferase, but that retains enzymatic activity. Truncated glycosyltransferases include, e.g., truncated GnT1 enzymes, truncated GalT1 enzymes, truncated ST3GalIII (SEQ ID NOs: 77 and 78) enzymes, truncated GalNAc-T2 (SEQ ID NOs: 24-35) enzymes, truncated Core 1 GalT1 (SEQ ID NOs: 41-46) enzymes, amino acid residues from about 32 to about 90 (see e.g., the human enzyme); truncated ST3Gal1 (SEQ ID NOs: 55-58) enzymes, truncated ST6GalNAc-1 (SEQ ID NOs: 72-74) enzymes, and truncated GalNAc-T2 enzymes. Any number of amino acid residues can be deleted so long as the enzyme retains activity. In some embodiments, domains or portions of domains can be deleted, e.g., a signal-anchor domain can be deleted leaving a truncation comprising a stem region and a catalytic domain; a signal-anchor domain and a portion of a stem region can be deleted leaving a truncation comprising the remaining stem region and a catalytic domain; or a signal-anchor domain and a stem region can be deleted leaving a truncation comprising a catalytic domain. Glycosyltransferase truncations can also occur at the C-terminus of the protein. For example, some GalNAcT enzymes have a C-terminal lectin domain that can be deleted without diminishing enzymatic activity.

The term "nucleic acid" refers to a deoxyribonucleotide or ribonucleotide polymer in either single- or double-stranded form, and unless otherwise limited, encompasses known analogues of natural nucleotides that hybridize to nucleic acids in a manner similar to naturally occurring nucleotides. Unless otherwise indicated, a particular nucleic acid sequence includes the complementary sequence thereof.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals. Typically, the recombinant expression cassette includes a nucleic acid to be transcribed (e.g., a nucleic acid encoding a desired polypeptide), and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette. In preferred embodiments, a recombinant expression cassette encoding an amino acid sequence comprising a eukaryotic glycosyltransferase is expressed in a bacterial host cell.

A "heterologous sequence" or a "heterologous nucleic acid", as used herein, is one that originates from a source foreign to the particular host cell, or, if from the same source, is modified from its original form. Thus, a heterologous glycoprotein gene in a eukaryotic host cell includes a glycoprotein-encoding gene that is endogenous to the particular host cell that has been modified. Modification of the heterologous sequence may occur, e.g., by treating the DNA with a restriction enzyme to generate a DNA fragment that is capable of being operably linked to the promoter. Techniques such as site-directed mutagenesis are also useful for modifying a heterologous sequence.

The term "isolated" refers to material that is substantially or essentially free from components which interfere with the activity of an enzyme. For a saccharide, protein, or nucleic acid of the invention, the term "isolated" refers to material that is substantially or essentially free from components which normally accompany the material as found in its native state. Typically, an isolated saccharide, protein, or nucleic acid of the invention is at least about 80% pure, usually at least about 90%, and preferably at least about 95% pure as measured by band intensity on a silver stained gel or other method for determining purity. Purity or homogeneity can be indicated by a number of means well known in the art. For example, a protein or nucleic acid in a sample can be resolved by polyacrylamide gel electrophoresis, and then the protein or nucleic acid can be visualized by staining. For certain purposes high resolution of the protein or nucleic acid may be desirable and HPLC or a similar means for purification, for example, may be utilized.

The term "operably linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

The terms "identical" or percent "identity," in the context of two or more nucleic acids or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or proteins, refers to two or more sequences or subsequences that have at least greater than about 60% nucleic acid or amino acid sequence identity, 65%, 70%, 75%, 80%, 85%, 90%, preferably 91%, 92%, 93%, 94%, 95%, 96%, 97%, 98% or 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al, eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschuel et al. (1977) *Nucleic Acids Res.* 25: 3389-3402, respectively. Software for performing BLAST analyses is publicly available through the National Center for Biotechnology Information (ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or proteins are substantially identical is that the protein encoded by the first nucleic acid is immunologically cross reactive with the protein encoded by the second nucleic acid, as described below. Thus, a protein is typically substantially identical to a second protein, for example, where the two peptides differ only by conservative substitutions. Another indication that two nucleic acid sequences are substantially identical is that the two molecules hybridize to each other under stringent conditions, as described below.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA.

The term "stringent conditions" refers to conditions under which a probe will hybridize to its target subsequence, but to no other sequences. Stringent conditions are sequence-dependent and will be different in different circumstances. Longer sequences hybridize specifically at higher temperatures. Generally, stringent conditions are selected to be about 15° C. lower than the thermal melting point (Tm) for the specific sequence at a defined ionic strength and pH. The Tm is the temperature (under defined ionic strength, pH, and nucleic acid concentration) at which 50% of the probes complementary to the target sequence hybridize to the target sequence at equilibrium. (As the target sequences are generally present in excess, at Tm, 50% of the probes are occupied at equilibrium). Typically, stringent conditions will be those in which the salt concentration is less than about 1.0 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is typically at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32-48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90-95° C. for 30-120 sec, an annealing phase lasting 30-120 sec, and an extension phase of about 72° C. for 1-2 min. Protocols and guidelines for low and high stringency amplification reactions are available, e.g., in Innis, et al. (1990) *PCR Protocols: A Guide to Methods and Applications* Academic Press, N.Y.

The phrases "specifically binds to a protein" or "specifically immunoreactive with", when referring to an antibody refers to a binding reaction which is determinative of the presence of the protein in the presence of a heterogeneous population of proteins and other biologics. Thus, under designated immunoassay conditions, the specified antibodies bind preferentially to a particular protein and do not bind in a significant amount to other proteins present in the sample. Specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

"Conservatively modified variations" of a particular polynucleotide sequence refers to those polynucleotides that encode identical or essentially identical amino acid sequences, or where the polynucleotide does not encode an amino acid sequence, to essentially identical sequences. Because of the degeneracy of the genetic code, a large number of functionally identical nucleic acids encode any given protein. For instance, the codons CGU, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every polynucleotide sequence described herein which encodes a protein also describes every possible silent variation, except where otherwise noted. One of skill will recognize that each codon in a nucleic acid (except AUG, which is ordinarily the only codon for methionine, and UGG which is ordinarily the only codon for tryptophan) can be modified to yield a functionally identical molecule by standard techniques. Accordingly, each "silent variation" of a nucleic acid which encodes a protein is implicit in each described sequence.

Furthermore, one of skill will recognize that individual substitutions, deletions or additions which alter, add or delete a single amino acid or a small percentage of amino acids (typically less than 5%, more typically less than 1%) in an encoded sequence are "conservatively modified variations" where the alterations result in the substitution of an amino acid with a chemically similar amino acid. Conservative substitution tables providing functionally similar amino acids are well known in the art.

One of skill will appreciate that many conservative variations of proteins, e.g., glycosyltransferases, and nucleic acid which encode proteins yield essentially identical products. For example, due to the degeneracy of the genetic code, "silent substitutions" (i.e., substitutions of a nucleic acid sequence which do not result in an alteration in an encoded protein) are an implied feature of every nucleic acid sequence which encodes an amino acid. As described herein, sequences are preferably optimized for expression in a particular host cell used to produce the chimeric glycosyltransferases (e.g., yeast, human, and the like). Similarly, "conservative amino acid substitutions," in one or a few amino acids in an amino acid sequence are substituted with different amino acids with highly similar properties (see, the definitions section, supra), are also readily identified as being highly similar to a particular amino acid sequence, or to a particular nucleic acid sequence which encodes an amino acid. Such conservatively substituted variations of any particular sequence are a feature of the present invention. See also, Creighton (1984) *Proteins*, W.H. Freeman and Company. In addition, individual substitutions, deletions or additions which alter, add or delete a single amino acid or a small percentage of amino acids in an encoded sequence are also "conservatively modified variations".

The practice of this invention can involve the construction of recombinant nucleic acids and the expression of genes in host cells, preferably bacterial host cells. Molecular cloning techniques to achieve these ends are known in the art. A wide variety of cloning and in vitro amplification methods suitable for the construction of recombinant nucleic acids such as expression vectors are well known to persons of skill. Examples of these techniques and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); and *Current Protocols in Molecular Biology*, F. M. Ausubel et al., eds., Current Protocols, a joint venture between Greene Publishing Associates, Inc. and John Wiley & Sons, Inc., (1999 Supplement) (Ausubel). Suitable host cells for expression of the recombinant polypeptides are known to those of skill in the art, and include, for example, prokaryotic cells, such as *E. coli*, and eukaryotic cells including insect, mammalian and fungal cells (e.g., *Aspergillus niger*)

Examples of protocols sufficient to direct persons of skill through in vitro amplification methods, including the polymerase chain reaction (PCR) the ligase chain reaction (LCR), Qβ-replicase amplification and other RNA polymerase mediated techniques are found in Berger, Sambrook, and Ausubel, as well as Mullis et al. (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87: 1874; Lomell et al. (1989) *J. Clin. Chem.* 35: 1826; Landegren et al. (1988) *Science* 241: 1077-1080; Van Brunt (1990) *Biotechnology* 8: 291-294; Wu and Wallace (1989) *Gene* 4: 560; and Barringer et al. (1990) *Gene* 89: 117. Improved methods of cloning in vitro amplified nucleic acids are described in Wallace et al., U.S. Pat. No. 5,426,039.

DETAILED DESCRIPTION OF THE INVENTION

I. Introduction

The present invention provides for the first time methods of producing soluble, active O-glycosylated therapeutic proteins in prokaryotes. In some embodiments, the solubility of the therapeutic proteins is improved by expression in prokaryotes that have an intracellular oxidizing environment. The intracellular oxidizing environment enhances disulfide bond formation and permits correct folding of both the therapeutic proteins and heterologous glycosyltransferases. The activity and solubility of those proteins are generally more convenient to measure than protein refolding and disulfide bond formation. Therefore, protein activity and solubility are used as surrogates for determination of correct protein folding. The O-glycosylation is provided by co-expression of a heterologous soluble active nucleotide sugar:polypeptide glycosyltransferase protein that transfers a sugar moiety to an amino acid acceptor on the therapeutic protein. The glycosylation of the therapeutic protein occurs in the cytoplasm of the prokaryote. In preferred embodiments, the amino acid acceptor is a serine or threonine residue. In this way the invention provides an efficient way of reproducing a system of eukaryotic post-translational modification in a prokaryotic cell and of making large amounts of soluble active O-glycosylated therapeutic protein in a prokaryotic cell.

Some therapeutic proteins are soluble in prokaryotic microorganisms that have a reducing environment, as are some glycosyltransferases, e.g., prokaryotic glycosyltransferases, including nucleotide sugar:polypeptide glycosyltransferase proteins. Therefore, in some embodiments the methods of the invention can be performed using prokaryotic host cells that have a reducing environment, e.g., expression of O-therapeutic proteins and heterologous glycosyltransferases that are soluble and active in a reducing environment. One example of a prokaryotic microorganisms that has a reducing environment is an unmodified *E. coli* cell.

The present invention also provides for the first time prokaryotic cells that comprise a soluble, active O-glycosylated therapeutic protein and a heterologous soluble active nucleotide sugar:polypeptide glycosyltransferase protein. The prokaryotic cells can have an intracellular oxidizing environment or an intracellular reducing environment. The heterologous soluble active nucleotide sugar:polypeptide glycosyltransferase protein, any other heterologous glycosyltransferases, and the soluble, active O-glycosylated therapeutic protein are expressed in the cytoplasm of the prokaryotic cell.

II. O-Glycosylation of Proteins

O-glycosylation is the conjugation of a sugar group to protein through an amino acid that has a hydroxyl group. O-glycosylation of proteins occurs in both eukaryotes and prokaryotes.

In eukaryotes O-glycosylation occurs in the endoplasmic reticulum at serine or threonine residues on a protein. Eukaryotic O-glycosylated proteins are found, e.g., within the endoplasmic reticulum, the golgi apparatus, and are frequently secreted out of the cell. Sugars that are transferred to an amino acid O-glycosylation site on eukaryotic proteins include GalNAc, GlcNAc, mannose, xylose, glucose, and fucose. The most commonly added sugar is GalNAc, which forms a mucin type linkage with serine or threonine. GalNAc is transferred to proteins by a family of GalNAc transferases, which includes at least 24 members in human alone. See, e.g., Ten Hagen et al., *Glycobiol.* 13:1R-16R (2003). Additional sugars can be added to the first conjugated sugar by additional heterologous glycosyltransferases.

Prokaryotes, i.e., archaea and bacteria, also have endogenous O-glycosylated proteins which typically are found on the outer layer of the cell, e.g., as part of the S-layer, or on extra cellular proteins, such as flagellin and pillin. See, e.g., Schaffer et al., *Proteomics*, 1:248-261 (2001); Benz and Schmidt, *Mole. Microbiol.* 45:267-276 (2002); and Eichler, *Microbiol.* 149:3347-3351 (2003). A variety of sugars are added to amino acids on prokaryotic proteins through O-linkages, e.g., GalNAc, GlcNAc, mannose, xylose, glucose, and fucose. Additional sugars can be added to the first conjugated sugar by additional heterologous glycosyltransferases.

It can be useful for those of skill to determine the composition of an oligosaccharide added to a protein in an O-linkage and/or to determine the amino acid site of O-linkage on a particular protein. For example, one of skill can determine the composition and/or amino acid site of an O-linked oligosaccharide on a naturally occurring therapeutic protein, e.g., a hormone or growth factor, before using the disclosed methods. Or one of skill can determine the composition or amino acid site of a soluble, active O-glycosylated therapeutic protein after using the disclosed methods to verify the production of the desired product.

Methods to determine the composition and/or amino acid site of an O-linked oligosaccharide on a protein are known to those of skill in the art. See, e.g., Schaffer et al., *Proteomics*, 1:248-261 (2001). For example, glycoconjugates can be detected on proteins that have been separated by SDS-PAGE, using e.g., the Schiff staining method. Separated proteins can also be transferred to nylon or PVDF membrane and then assayed for the presence of glyconjugates after labeling with digoxigenin. Glycosylation of proteins modifies their behavior on SDS-PAGE. Thus, a protein suspected of being glycosylated can by compared on SDS-PAGE to a non-glycosylated control. Lectins can also be used analyze a protein believed to be glycosylated and to identify conjugated sugar moieties. The identity of an O-linked oligosaccharide moiety can be determined using, e.g., gas chromatography, mass spectrometry techniques (MALDI-MS) or liquid chromatography-electrospray mass spectrometry. See, e.g., Benz and Schmidt, *Mole. Microbiol.* 45:267-276 (2002).

Once a site for glycosylation and composition of the glycoconjugate have been determined for a particular therapeutic protein, the appropriate heterologous glycosyltransferase(s) and prokaryotic cells can be selected for use in producing a soluble, active O-linked therapeutic protein. In preferred embodiments, the therapeutic protein and heterologous glycosyltransferase(s) are expressed in the cytoplasm of the prokaryotic cell and the O-linked glycosylation of the therapeutic protein occurs in the cytoplasm of the prokaryotic cell.

In a further preferred embodiment, the therapeutic protein and heterologous glycosyltransferase(s) are expressed in the cytoplasm of the prokaryotic cell and the therapeutic protein is glycosylated in the cytoplasm and then transported to the periplasm or extracellular where disulfide bonds are formed in the therapeutic protein. In another preferred embodiment, transfer of the therapeutic protein and heterologous glycosyltransferase(s) in the periplasm or outside of the living prokaryotic cell is excluded from the invention.

III. Soluble, Active O-Glycosylated Therapeutic Proteins

Therapeutic proteins are typically recombinant eukaryotic protein that are administered to a subject, e.g., a higher mammal and preferably a human, to treat a disease or to alleviate symptoms of a disease. Other uses for therapeutic proteins include, e.g., use as a vaccine, that is eliciting an immune response in a subject. Therapeutic proteins are not typically produced commercially in prokaryotes such as bacteria. Reasons include, e.g., inefficient production because of expression in inclusion bodies (insoluble protein) or production of proteins that are not glycosylated or that are not correctly glycosylated. The methods of the invention overcome these problems, first by enhancing the solubility of the therapeutic protein expressed in the prokaryote and second by allowing glycosylation of the therapeutic protein with in the prokaryotic cell. Therapeutic proteins include the proteins listed in Table 1, any of which can be O-glycosylated using the methods of disclosed herein.

TABLE 1

Preferred therapeutic proteins

Hormones and Growth Factors

Granulocyte colony stimulating factor (G-CSF)
Granulocyte-macrophage colony stimulating factor (GM-CSF)
TPO
Erythropoietin (EPO)
EPO variants
Follicle Stimulating Hormone (FSH)
Human Growth Hormone (HGH)
Insulin
alpha-TNF
Leptin
Human chorionic gonadotropin
Bone morphogenetic protein 2 (BMP-2)
Bone morphogenetic protein 7 (BMP-7)
Fibroblast growth factor-20 (FGF-7)
Fibroblast growth factor-20 (FGF-20)
Fibroblast growth factor-20 (FGF-21)
Neurotrophin-3

Enzymes and Inhibitors

Tissue-type plasminogen activator (TPA)
TPA variants
Urokinase
Factor VII clotting factor
Factor VIII
Factor IX clotting factor
Factor X
Factor XIII
hrDNase
Glucocerebrosidase (Cerezyme ™)
Hirudin
α1 antitrypsin (α1 protease inhibitor)
Antithrombin III
Acid α-glucosidase (acid maltase)
α galactosidase A
α-L-iduronidase
Urokinase Cytokines and Chimeric Cytokines Interleukin-1 (IL-1), 1B, 2, 3, 4,
Interleukin-21
Interleukin-22

TABLE 1-continued

Preferred therapeutic proteins

Interferon-alpha (IFN-alpha)
Interferon -alpha-2b
Interferon -beta
Interferon -gamma
Interferon -omega Receptors and Chimeric Receptors CD4
Tumor Necrosis Factor receptor (TNF-R)
TNF-R:IgG Fc fusion
Alpha-CD20
PSGL-1
Complement
GlyCAM or its chimera
N-CAM or its chimera Monoclonal Antibodies (Immunoglobulins)

MAb-anti-RSV
MAb-anti-IL-2 receptor
MAb-anti-CEA
MAb-Glycoprotein IIb/IIIa (Reopro ™)
MAb-anti-EGF
MAb-Her-2 (Herceptin ™)
MAb-CD20 (Rituxan ™)
MAb-alpha-CD3
TNF receptor-IgG Fc fusion (Enbrel ™)
MAb-TNFα (Remicade ™)
MAb-CD4
MAb-PSGL-1
Mab-anti F protein of Respiratory Syncytial Virus
Anti-thrombin-III Others Hepatitis B surface antigen (HbsAg)
Chimeric diphtheria toxin-IL-2

Transport Proteins

Transferrin

The amino acid sequences of many potential soluble, active O-glycosylated therapeutic proteins are known to those of skill. The amino acid site and composition of a glycoconjugate can be determined by e.g., repeating all or part of the O-glycosylation pattern of a naturally occurring soluble, active O-glycosylated therapeutic protein. The amino acid site and composition of a glycoconjugate on a naturally occurring soluble, active O-glycosylated therapeutic protein can be determined empirically, as described above. Or those of skill can make use of a previously determined amino acid site and composition of a glycoconjugate on a naturally occurring soluble, active O-glycosylated therapeutic protein. Many are known and have been collected for use by those of skill at e.g., O-GLYCBASE, a database of O-glycosylated proteins. See, e.g., cbs.dtu.dk/databases/OGLYCBASE/.

Other preferred therapeutic proteins that can be produced using the method of the invention are disclosed in Application No. PCT/US02/32263, filed Oct. 9, 2002; Provisional Patent Application No. 60/448,381, filed Feb. 19, 2003; Provisional Patent Application No. 60/438,582, filed Jan. 6, 2003; Provisional Patent Application No. 60/407,527, filed Aug. 28, 2002; Provisional Patent Application No. 60/404,249, filed Aug. 16, 2002; Provisional Patent Application No. 60/396, 594, filed Jul. 17, 2002; Provisional Patent Application No. 60/391,777, filed Jun. 25, 2002; Provisional Patent Application No. 60/387,292, filed Jun. 7, 2002; Provisional Patent Application No. 60/334,301, filed Nov. 28, 2001; Provisional Patent Application No. 60/334,233, filed Nov. 28, 2001; Provisional Patent Application No. 60/344,692, filed Oct. 19, 2001; and Provisional Patent Application No. 60/328,523, filed Oct. 10, 2001; and in the following US Patent Application Publications 20040142856, 20040137557, 20040132640, 20040126838, 20040115168, 20040082026, 20040077836, 20040063911, 20040043446. The preferred therapeutic proteins in the above references are also referred to as preferred peptides for remodeling.

The amino acid sequence of the therapeutic proteins includes an O-linked glycosylation site. The O-linked glycosylation site can be a naturally occurring site, or can result from manipulation to introduce an O-linked glycosylation site into the amino acid sequence. Exemplary proteins with O-linked glycosylation sites include, e.g., granulocyte colony stimulating factor (G-CSF), e.g., 175 (SEQ ID NO: 81) and 178 amino acid wild types (with or without N-terminal methionine residues), interferon (e.g., interferon alpha, e.g., interferon alpha 2b, or interferon alpha 2a), granulocyte macrophage colony stimulating factor (GM-CSF), human growth hormone, interleukin (e.g., interleukin 2), and fibroblast growth factor (FGF). Examples of wild-type and mutant proteins and peptides are found in, e.g., PCT/US2004/014254, filed May 7, 2004; U.S. Provisional Patent Application No. 60/469,114, filed May 9, 2003; U.S. Provisional Patent Application No. 60/494,751, filed Aug. 13, 2003; U.S. Provisional Patent Application No. 60/495,076, filed Aug. 14, 2003; U.S. Provisional Patent Application No. 60/535,290, filed Jan. 8, 2003; PCT/US05/000799, filed Jan. 10, 2005; U.S. Ser. No. 11/033,365 filed Jan. 10, 2005; U.S. Provisional Patent Application No. 60/535,284, filed Jan. 8, 2004; U.S. Provisional Patent Application No. 60/544,411, filed Feb. 12, 2004; U.S. Provisional Patent Application No. 60/546,631, filed Feb. 20, 2004; U.S. Provisional Patent Application No. 60/555,813, filed Mar. 23, 2004; U.S. Provisional Patent Application No. 60/570,891, filed May 12, 2004; PCT/US05/39226, filed Oct. 31, 2005; and U.S. Provisional Patent Application No. 60/623,342, filed Oct. 29, 2004; each of which is herein incorporated by reference for all purposes.

Examples of synthetic O-glycosylation sites that can be inserted into an amino acid sequence are disclosed in U.S. Provisional Patent Application 60/832,461, filed Jul. 21, 2006; which is herein incorporated by reference for all purposes.

The invention also encompasses therapeutic proteins that have been modified to increase resistance to proteases. In one embodiment, the protease resistant therapeutic protein is a human growth hormone protein. Exemplary protease resistant therapeutic proteins are found in e.g., U.S. Provisional Patent Application No. 60/669,736, filed Apr. 8, 2005; U.S. Provisional Patent Application No. 60/710,401, filed Aug. 22, 2005; and U.S. Provisional Patent Application No. 60/720, 030, filed Sep. 23, 2005; each of which is herein incorporated by reference for all purposes.

After expression of the soluble, active O-glycosylated therapeutic protein using the methods of the invention, the soluble, active O-glycosylated therapeutic protein will preferably be an active protein. Those of skill will recognize how to determine the activity of an O-glycosylated therapeutic protein. Enzymatic assays of O-glycosylated enzymes or inhibitors, e.g., clotting factors, can be performed to determine activity. Some O-glycosylated therapeutic protein can be assayed for biological activity. For example, O-glycosylated hormones or growth factors can be assayed for binding to an appropriate receptor or for an appropriate response in a cell based or animal model. O-glycosylated receptor proteins can be assayed for binding to an appropriate ligand or for an appropriate response in a cell based or animal model. O-glycosylated antibodies or immunoglobin proteins can be assayed for binding to an appropriate antigen. O-glycosylated cytokines can be assayed for activity using an appropriate cell based model or animal model. O-glycosylated therapeutic proteins that are vaccines, can be assayed for an ability to elicit an immune response in a model animal or in a human.

In one embodiment, a soluble, active O-glycosylated therapeutic protein made by the methods described herein has activity levels, e.g., U/cell or U/mg protein, up to 1.1, 1.2, 1.5, 2, 3, 5, 10, 15, 20, 50, 100, 500, 1000, or up to 10,000 times greater than activity levels of the same therapeutic protein expressed in a microorganism with a reducing environment. In another embodiment, a soluble, active O-glycosylated therapeutic protein made by the methods described herein has activity levels, e.g., U/cell or U/mg protein, up to 1.1, 1.2, 1.5, 2, 3, 5, 10, 15, 20, 50, 100, 500, 1000, or up to 10,000 times greater than activity levels of the same therapeutic protein expressed in a microorganism without a heterologous glycosyltransferase.

In a preferred embodiment, the soluble, active O-glycosylated therapeutic protein has improved therapeutic properties as compared to, e.g., the therapeutic protein expressed in a prokaryotic or eukaryotic cell without expression of a heterologous glycosyltransferase. Improved therapeutic properties include, e.g., increased bioavailability of the therapeutic protein in a subject, increased half life of the therapeutic protein in a subject, enhanced pharmacokinetics, enhanced pharmacodynamics, improved biodistribution, providing a polyvalent species, improved water solubility, enhanced or diminished lipophilicity, and tissue targeting. Tests for improved therapeutic properties can be performed in e.g., humans and model animal systems, e.g., rodents, cats, dogs, and non-human primates.

In one embodiment, a soluble, active O-glycosylated therapeutic protein made by the methods described herein has improved therapeutic properties, up to 1.1, 1.2, 1.5, 2, 3, 5, 10, 15, 20, 50, 100, 500, 1000, or up to 10,000 times greater than those of the same therapeutic protein expressed in a microorganism with a reducing environment. In another embodiment, a soluble, active O-glycosylated therapeutic protein made by the methods described herein has improved therapeutic properties, up to 1.1, 1.2, 1.5, 2, 3, 5, 10, 15, 20, 50, 100, 500, 1000, or up to 10,000 times greater than those of the same therapeutic protein expressed in a microorganism without a heterologous soluble, active glycosyltransferase.

IV. Soluble, Active Glycosyltransferases

Soluble, active glycosyltransferases are used to conjugate an O-linked sugar or oligosaccharide to a soluble active therapeutic protein of the invention. The conjugation occurs within the cytoplasm of a prokaryote that has an intracellular oxidizing environment. Soluble active glycosyltransferases include, e.g., nucleotide sugar:polypeptide glycosyltransferase proteins and other glycosyltransferases.

At least one heterologous glycosyltransferase is used in the methods of the invention. The total number of glycosyltransferases will depend on the needs of the user. The glycosyltransferase can be a eukaryotic glycosyltransferase or a prokaryotic glycosyltransferase. Active eukaryotic glycosyltransferases can be produced in prokaryotes that have an oxidizing environment. See, e.g., U.S. Provisional Application No. 60/665,396, filed Mar. 24, 2005; U.S. Provisional Application No. 60/668,899, filed Apr. 5, 2005; U.S. Provisional Application No. 60/732,409, filed Oct. 31, 2005; and International Application PCT/US06/11065, filed Mar. 24, 2006; each of which are herein incorporated by reference for all purposes. In prokaryotes that have a reducing environment, e.g., unmodified E. coli species, eukaryotic glycosyltransferases and other heterologous proteins frequently are insoluble and expressed in inclusion bodies. The ability to co-express heterologous soluble, active glycosyltransferases with the therapeutic protein of choice allows the in vivo O-linked glycosylation of the therapeutic protein to occur in the cytoplasm of the prokaryotic host cell.

The first glycosylation step is carried out by a nucleotide sugar:polypeptide glycosyltransferase protein, i.e., a glycosyltransferase protein that transfers a sugar moiety from a donor substrate to an amino acid acceptor on the therapeutic protein. In eukaryotes, commonly used nucleotide sugar:polypeptide glycosyltransferase proteins include GalNAc transferase proteins. These proteins transfer a GalNAc moiety from UDP-GalNAc to a serine or threonine residue on a protein. In one embodiment, a single nucleotide sugar:polypeptide glycosyltransferase protein is used in the invention and a soluble, active O-glycosylated therapeutic protein comprising an O-linked amino acid is produced.

N-acetylgalactosaminyltransferases are of use in practicing the present invention, particularly for binding a GalNAc moiety to an amino acid of the O-linked glycosylation site of the peptide. Suitable N-acetylgalactosaminyltransferases include, but are not limited to, α(1,3)N-acetylgalactosaminyltransferase, β(1,4)N-acetylgalactosaminyltransferases (Nagata et al., *J. Biol. Chem.* 267: 12082-12089 (1992) and Smith et al., *J. Biol Chem.* 269: 15162 (1994)) and polypeptide N-acetylgalactosaminyltransferase (Homa et al., *J. Biol. Chem.* 268: 12609 (1993)).

Production of proteins such as the enzyme GalNAc $T_{1-XX}$ from cloned genes by genetic engineering is well known. See, eg., U.S. Pat. No. 4,761,371. One method involves collection of sufficient samples, then the amino acid sequence of the enzyme is determined by N-terminal sequencing. This information is then used to isolate a cDNA clone encoding a full-length (membrane bound) transferase which upon expression in the insect cell line Sf9 resulted in the synthesis of a fully active enzyme. The acceptor specificity of the enzyme is then determined using a semiquantitative analysis of the amino acids surrounding known glycosylation sites in 16 different proteins followed by in vitro glycosylation studies of synthetic peptides. This work has demonstrated that certain amino acid residues are overrepresented in glycosylated peptide segments and that residues in specific positions surrounding glycosylated serine and threonine residues may have a more marked influence on acceptor efficiency than other amino acid moieties.

The second glycosylation step is carried out by a glycosyltransferase that can transfer a sugar moiety to the amino acid conjugated sugar on the soluble, active O-glycosylated therapeutic protein. In one embodiment the first glycosylation step is performed by a GalNAc transferase protein and a second glycosylation step is performed by a Core 1 Galactose transferase 1 protein (Core 1 Gal T1), which transfers a galactose moiety to the amino acid-conjugated GalNac moiety. Alternatively, the second glycosyltransferase can be a sialyltransferase, e.g., an ST6GalNAc1 protein.

The third glycosylation step is carried out by a glycosyltransferase that can transfer a sugar moiety to the terminal conjugated sugar on the soluble, active O-glycosylated therapeutic protein. For example, if the second glycosylation step was performed by a Core 1 Gal T1 protein, the third glycosylation step can be carried out by, e.g., an ST3Gal1 protein to add a sialic acid moiety to the soluble, active O-glycosylated therapeutic protein. Additional or different steps can be performed as desired by the user.

In some embodiments, eukaryotic glycosyltransferases are used in all or some of the glycosylation steps. Any eukaryotic glycosyltransferase can be used in the methods of the present invention. The eukaryotic glycosyltransferases can be the naturally occurring, unmodified proteins or can be glycosyltransferases that have been modified to enhance catalytic activity, or stability, or other characteristics of the proteins. Modification of eukaryotic glycosyltransferases include e.g., truncation of the protein to remove e.g., the stem region, the signal-anchor domain, or a portion of the stem region or the signal-anchor domain, or removal of both the stem region and the signal-anchor domain; or removal of an unpaired cysteine residue by substitution to another amino acid residue. A glycosyltransferase can also be truncated at the C-terminus to remove a non-catalytic domain or domains. For example, a C-terminal lectin domain can be removed from GalNAcT enzymes without diminishing enzymatic activity. Modified glycosyltransferases are described e.g., in U.S. Ser. No. 60/542,210, filed Feb. 4, 2004; U.S. Ser. No. 60/599,406, filed Aug. 6, 2004; U.S. Ser. No. 60/627,406, filed Nov. 12, 2004; U.S. Ser. No. 60/576,433, filed Jun. 3, 2004; U.S. Ser. No. 60/650,011, filed Feb. 4, 2005; PCT/US05/19583, filed Jun. 3, 2005; U.S. Ser. No. 60/576,530, filed Jun. 3, 2004; U.S. Ser. No. 60/598,584, filed Aug. 3, 2004; PCT/US05/19442, filed Jun. 3, 2005; PCT/US05/03856, filed Feb. 4, 2005; WO 2004/063344; U.S. Provisional Application No. 60/665,396, filed Mar. 24, 2005; U.S. Provisional Application No. 60/668,899, filed Apr. 5, 2005; U.S. Provisional Application No. 60/732,409, filed Oct. 31, 2005; and International Application PCT/US06/11065, filed Mar. 24, 2006; each of which is herein incorporated by reference for all purposes Preferred embodiments of the invention include use of, e.g., a eukaryotic N-acetylglucosaminyltransferase (GnTI or GNTI, GnTII or GNTII, GnTIII or GNTIII, GnTIV or GNTIV, GnTV or GNTV, GnTIV or GNTIV or a Core 2 GalNAcT); a eukaryotic N-acetylgalactosaminyltransferase (GalNAcT, e.g., GalNAcT1, GalNAcT2, or GalNAcT3); any galactosyltransferase, e.g., a eukaryotic β-1,4-galactosyltransferase (GalT1) or a eukaryotic core I galactosyltransferase (Core-1-Gal-T1); any eukaryotic sialyltransferase, e.g., a eukaryotic α(2,3)sialyltransferase (ST3Gal3), or a eukaryotic α-N-acetylgalactosaminyl α-2,6-sialyltransferase I (ST6GalNAc-1), or a eukaryotic gal β1,3GalNAc α2,3-sialyltransferase (ST3Gal-1); and any eukaryotic fucosyltransferase. Many examples of proteins having the above listed activities are known, see, e.g., afmb.cnrs-mrs.fr/CAZY/, in particular Glycosyltransferase Families 2, 4, 6, 7, 10, 1, 12, 13, 14, 15, 16, 17, 18, 21, 22, 23, 24, 25, 26, 27, 28, 29, 31, 32, 34, 37, 38, 41, 42, 49, 52, 54, 65, or 68. Other preferred embodiments include use of prokaryotic glycosyltransferases.

As indicated above, the glycosyltransferases can be modified before production using the disclosed methods. Modifications include, e.g., truncation of the glycosyltransferase to remove all or a portion of a non-catalytic domain, such as a cytoplasmic domain, a signal-anchor domain, a stem region, and or a lectin or ricin domain. Exemplary truncated glycosyltransferase that can be produced in the present invention include, e.g., ST3Gal III (Δ27, Δ28, Δ73, Δ85, Δ86), human GnT1 (Δ103), bovine GalT1 (Δ40, Δ129, Δ70), human GalNAcT2 (Δ51, Δ40, Δ73, Δ94, Δ51Δ445, Δ53, Δ53 Δ445), ST3Gal1 (Δ45), *Drosophila* Core-1-Gal-T1 (Δ31, Δ50), and human ST6GalNAc1 mutants as described in U.S. Provisional Application No. 60/665,396, filed Mar. 24, 2005; U.S. Provisional Application No. 60/668,899, filed Apr. 5, 2005; U.S. Provisional Application No. 60/732,409, filed Oct. 31, 2005; and International Application PCT/US06/11065, filed Mar. 24, 2006; each of which are herein incorporated by reference for all purposes.

In a preferred embodiment, the first glycosylation step is carried out by a eukaryotic GalNAcT protein. Such proteins are exemplified as CAZy family 27, see, e.g. FIG. 18. Gal- NAcT proteins have been aligned and the alignments used to identify domains within the proteins, e.g., transmembrane, stem, catalytic and lectin or ricin domains. See, e.g., Ten Hagen et al. *Glycobiology* 13:1R-16R (2003), which is herein incorporated by reference for all purposes. Such alignments can also be used by those of skill to identify truncations, substitutions and other modifications that can be made while retaining activity of the proteins. See, e.g., Ten Hagen et al., above.

CAZy family 27 also includes bacterial proteins that can be used in the invention, as can eukaryotic or prokaryotic polypeptide:nucleotide sugar transferases that transfer different sugars, e.g., GlcNAc, glucose, fucose, and xylose to an amino acid.

In further embodiments, prokaryotic glycosyltransferases are used to carry out one or more glycosylation steps of the invention. Bacterial glycosyltransferases that can be used in the invention include, e.g., sialyltransferases, galactosyltransferases, fucosyltransferases, and GalNAc transferases. Examples of bacterial glycosyltransferases are disclosed at, e.g., U.S. Pat. No. 6,503,744, issued Jan. 7, 2003; U.S. Pat. No. 6,699,705, issued Mar. 2, 2004; U.S. Pat. No. 6,096,529, issued Aug. 1, 2000; U.S. Pat. No. 6,689,604, issued Feb. 10, 2004; International Application No. PCT/US2005/001614 filed Jan. 21, 2005; International Application No. PCT/CA2005/001432, filed Sep. 16, 2005; U.S. Ser. No. 60/670,608, filed Apr. 11, 2005; and U.S. Ser. No. 60/764,171, filed Jan. 31, 2006.

V. O-Linked Glycan Structures

For a review of O-linked glycan structures, see Schachter and Brockhausen, The Biosynthesis of Branched O-Linked Glycans, 1989, Society for Experimental Biology, pp. 1-26 (Great Britain).

The following are exemplary O-linked glycan structures:

Ser/Thr-α-1-GalNAc[--β-1,6--GlcNAc--β-1,4--Gal--

α2,3-Sia]β-1,3-Gal-β2,3-Sia

Ser/Thr-α-1-GalNAc[--β-1,6--GlcNAc--β-1,4--Gal--

α2,3-Sia]β-1,3-Gal-α2,3-Sia

Ser/Thr-α-1-GalNAc--β-1,3-Gal-α2,3-Sia

Ser/Thr-α-1 -GalNAc--β-1,3-Gal

Ser/Thr-α-1-GalNAc-α2,6-Sia

Ser/Thr-α-1-GalNAc

The O-glycan structure can be made using any appropriate combination(s) of eukaryotic and prokaryotic glycosyltransferases. Examples of naturally-occurring O-glycan structures are provided in FIG. 16. However, those of skill will recognize that alternative O-glycan structures can be made using appropriate glycosyltransferases and activated sugar substrates.

Figure 17:
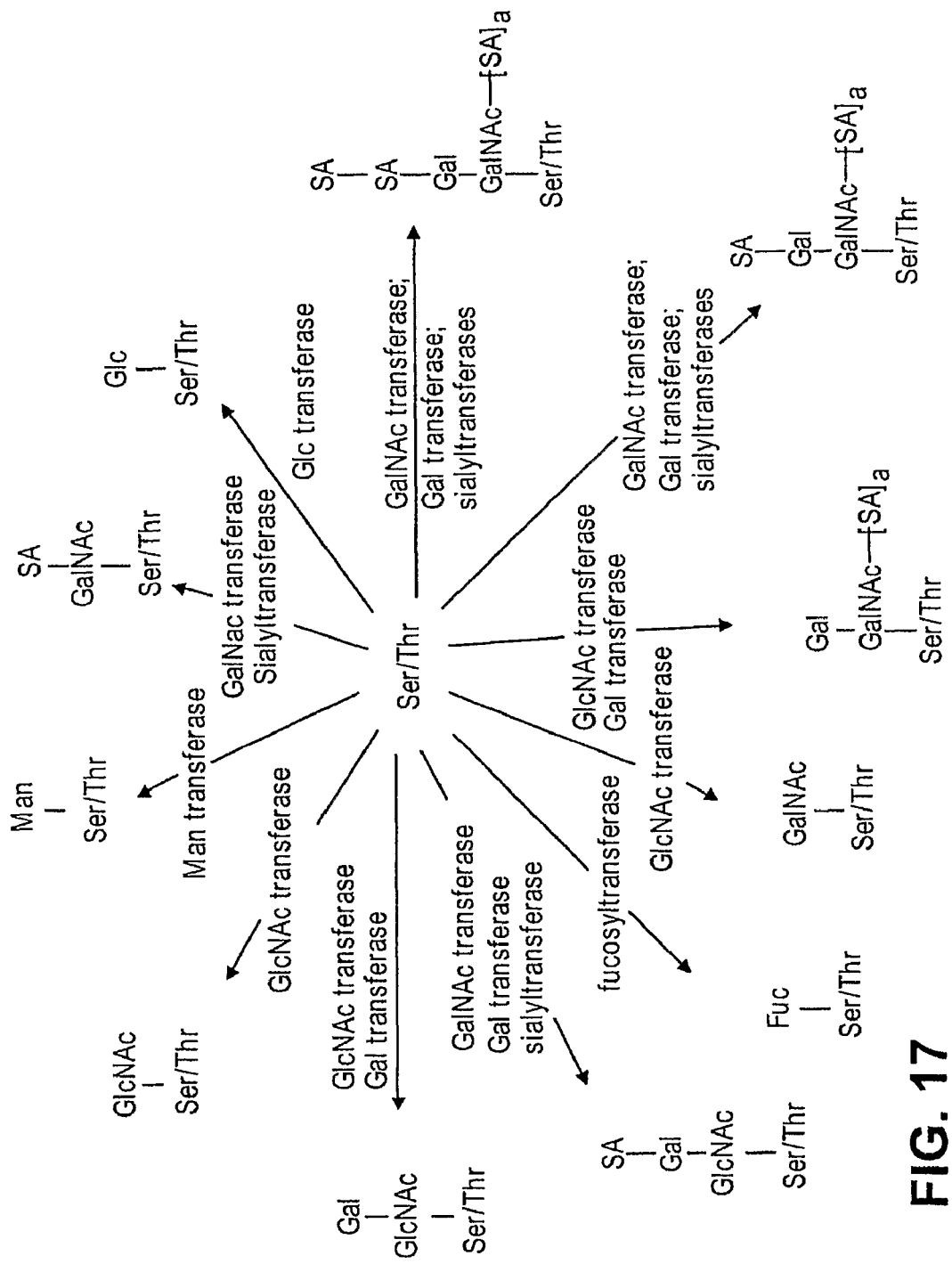
FIG. 17 provides examples of glycosyltransferases that can be used to conjugate sugars to amino acids, e.g., Serine or Threonine. O-glycan structures are also provided.

The identity of the sugar transferred to an amino acid residue is not limited to GalNAc. Other sugars can be transferred to oxygen-containing amino acid residues using appropriate glycosyltransferases, as shown in FIG. 17. Thus, GalNAc is transferred to an amino acid residue by GalNAc transferases; GlcNAc is transferred to an amino acid residue by GlcNAc transferases; fucose is transferred to an amino acid residue by fucosyltransferases; glucose is transferred to an amino acid residue by glucosyltransferases; and mannose is transferred to an amino acid residue by mannosyltransferases.

While FIGS. 16 and 17 demonstrate O-glycosylation on serine or threonine residues, other oxygen-containing amino acid residues can accept sugar molecules, e.g., hydroxyproline. In addition, glucose can be enzymatically conjugated to tryptophan residues.

An example of an O-glycosylation protocol, beginning with transfer of GalNAc to a serine or threonine residue follows. The GalNAc residue is conjugated to the serine or threonine residue by a heterologous GalNAcT protein. Exemplary GalNAcT proteins include eukaryotic GalNAcT1-20 and bacterial enzymes and are listed in FIG. 18.

The galactose residue is conjugated to the GalNAc sugar by a heterologous galactosyltransferase protein. Exemplary galactosyltransferase protein include eukaryotic core 1 Gal T1 proteins and bacterial proteins that conjugate galactose to GalNAc in β-1,3 linkage. Sialic acid residues can be added to the galactose sugar by a sialyltransferase protein with α2,3 activity. Exemplary sialyltransferase proteins include ST3 Gal1, ST3 Gal2 or *Campylobacter* CstI protein.

The GlcNAc residue is conjugated to GalNAc sugar by a heterologous GlcNAcT protein. Exemplary GlcNAcT proteins are disclosed at, e.g., CAZy family 14. The CAZy family 14 includes examples of eukaryotic and prokaryotic proteins with Core 2 β1,6-GlcNAc transferase activity that can be used in the invention. The galactose residue is conjugated to the GlcNAc sugar by a heterologous galactosyltransferase protein specific for a β(1-4) linkage, e.g., a eukaryotic Gal T1 or Gal T7 or a *Neisseria* lgtB protein. Other bacterial proteins are members of CAZy family 82. Sialic acid residues can be added to the galactose sugar by a sialyltransferase protein with α2,3 activity. Exemplary sialyltransferase proteins include ST3 Gal2, ST3 Gal3, ST3 Gal4 or *Campylobacter* CstI protein.

Additional modifications can occur on the terminal sialic acid residues, e.g., addition of sialic acid in an α2,8 linkage. Exemplary proteins include e.g., ST8Sia I, ST8Sia II, ST8Sia III, ST8Sia IV or *Campylobacter* CstII protein. Fucose residues can also be added using, e.g., eukaryotic fucosyltransferases V, VI, VIII, or *Helicobacter* fucosyltransferases.

VI. Intracellular, Oxidizing Environments in Prokaryotes

In preferred embodiments, soluble, active O-glycosylated therapeutic proteins and heterologous soluble, active glycosyltransferases are co-expressed in prokaryotic organisms that have intracellular oxidizing environments.

A. Prokaryotic Microorganisms that have Oxidizing Intracellular Environments

The method of the invention are carried out using prokaryotic microorganisms that have oxidizing intracellular environments. Such microorganisms include prokaryotic microorganisms that have endogenous, intracellular oxidizing environments and prokaryotic microorganisms that are genetically manipulated to have an intracellular oxidizing environment.

Some prokaryotic organisms have endogenous, intracellular oxidizing environments and, thus, promote formation of protein disulfide bonds inside the cell. Oxidizing intracellular compartments in prokaryotic organisms specifically exclude a bacterial periplasmic space. Prokaryotic organisms that have endogenous, intracellular oxidizing environments can be used in to produce soluble, active eukaryotic glycosyltransferases in an intracellular compartment. Prokaryotic organisms with endogenous, intracellular oxidizing environments include members of e.g., *Pseudomonas* species, including *testosteroni, putida, aeruginosa, syringae*, and *fluorescens*; some gram positive bacteria; and some gram negative bacteria. Additional *Pseudomonas* species and strains are described in, e.g., U.S. Patent Application Publication No. US 2005/0186666, published Aug. 25, 2005, which is herein incorporated by reference for all purposes. Gram positive bacteria include, e.g., *Bacillus, Listeria, Staphylococcus, Streptococcus, Enterococcus*, and *Clostridium* species.

Prokaryotic organisms with modification of a redox pathway can also be used in the methods of the invention to produce soluble, active eukaryotic glycosyltransferases or soluble, active therapeutic proteins. Modifications can be performed on prokaryotic organisms that have a reducing environment, e.g., *E. coli* or other gram negative bacteria or some gram positive bacteria. The prokaryotic microorganisms are modified to promote an oxidizing intracellular environment, thereby enhancing intracellular disulfide bond formation and protein refolding of e.g., therapeutic proteins and eukaryotic glycosyltransferases.

Many prokaryotic organisms use two pathways to reduce disulfide bonds that form in some cytoplasmic proteins, including recombinantly expressed proteins. The components of these pathways can be manipulated to promote formation of an intracellular oxidizing environment. The first pathway is the thioredoxin system, which generally includes a thioredoxin reductase and thioredoxin. Thioredoxin reductase maintains thioredoxin in a reduced state. The second pathway is the glutaredoxin system, which generally includes a glutathione oxidoreductase, glutathione, and glutaredoxins. Inactivating mutations of some components of these redox pathways can ultimately increase the formation of disulfide bonds in expressed proteins, and in the case of heterologous proteins expressed in the prokaryotic organism, can increase the solubility and activity of the expressed heterologous proteins. For example, in *E. coli* elimination of thioredoxin reductase activity results in an accumulation of oxidized thioredoxin that act as an oxidase in the intracellular compartment.

Some preferred examples are prokaryotic microorganisms that have reduced or absent reductase activity. For example, the activity of a thioredoxin reductase and/or a glutathione oxidoreductase can be reduced or eliminated to modify the intracellular environment, thereby producing an oxidizing intracellular environment that favors formation of disulfide bonds.

For example, *E. coli* strains that have mutations in both the thioredoxin reductase gene (trxB) and the glutathione oxidoreductase gene (gor) are able to express proteins with higher levels of disulfide bond formation. See, e.g., Prinz et al., *J. Biol Chem.* 272:15661-15667 (1997). These trxB gor double mutants grow very slowly on most growth media, although growth can be enhanced by addition of a reductant, such as DTT. However, the double mutant strains frequently give rise to suppressor mutant strains that retain the trxB gor mutations and that grow faster in medium lacking DTT. One example of a trxB gor suppressor mutation in *E. coli* is a mutation of the gene ahpC, which encodes a catalytic subunit of the alkyl hydroperoxidase, AhpCF. This suppressor mutation adds a triplet to the DNA that encodes the catalytic site of the AhpCF enzyme. Fast growing double mutant *E. coli* strains, e.g., trxB, gor, supp and trxB, gshA, supp strains are disclosed in e.g., U.S. Pat. No. 6,872,563, which is herein incorporated by reference for all purposes. Such manipulated *E. coli* strains, e.g., trxB, gor, supp strains, are commercially available, e.g., under the trade names ORIGAMI™, ORIGAMI 2™, and ROSETTA-GAMI™, from e.g., EMD Biosciences, Inc. Other *E. coli* mutations can result in an oxidizing intracellular environment, e.g., trxb, gshA and trxB, gshA supp strains.

Other manipulations of components of a redox pathway in a microorganism can be used to enhance formation of disulfide bonds in a protein, e.g., a therapeutic protein and a heterologous glycosyltransferase. For example, proteins with oxidizing activity, e.g., *E. coli* thioredoxin proteins in trxB, gor mutant strains, can be overexpressed in the prokaryotic microorganism. Another example is expression or overexpression of thioredoxin mutants that have enhanced oxidizing activity. Examples of such mutants are described in, e.g., Bessette, et al. *PNAS* 96:13703-13708 (1999). Targeted cytoplasmic expression of certain oxidizing enzymes can also be used to enhance formation of intracellular disulfide bonds. For example oxidizing proteins that are typically expressed in the periplasmic space, e.g., DsbC, can be expressed in a bacterial cytoplasm by e.g., deleting a periplasmic targeting sequence or including a cytoplasmic retention sequence. Other oxidizing periplasmic proteins can be expressed in the bacterial cytoplasm to enhance oxidation of cytoplasmic proteins, e.g., by deleting a periplasmic targeting sequence or including a cytoplasmic retention sequence.

Thioredoxin reductase nucleic acids, glutathione oxidoreductase nucleic acids, thioredoxin nucleic acids, glutathione nucleic acids, and nucleic acids encoding other proteins involved in maintenance of an intracellular redox environment can be identified in other bacteria, e.g., *Azotobacter* sp. (e.g., *A. vinelandii*), *Pseudomonas* sp., *Rhizobium* sp., *Erwinia* sp., *Escherichia* sp. (e.g., *E. coli*), *Bacillus, Pseudomonas, Proteus, Salmonella, Serratia, Shigella, Rhizobia, Vitreoscilla, Paracoccus* and *Klebsiella* sp., among many others. Such genes can be identified by sequence analysis and comparison to known thioredoxin reductase genes, glutathione oxidoreductase genes, and genes encoding other proteins involved in maintenance of an intracellular redox environment or to the amino acid sequence of the encoded products. The encoded proteins can be further identified functionally by enzymatic assays or by genetic complementation assays of *E. coli* mutants of an appropriate gene function. The endogenous thioredoxin reductase and glutathione oxidoreductase genes can be e.g., mutated to inactivate the gene product using standard molecular biology techniques and those mutated strains can also be used to express proteins with increased levels of disulfide bond formation, as compared to unmutated strains.

B. Identification of Intracellular, Oxidizing Environments

Protein refolding and protein activity frequently depend on the correct formation of disulfide bonds. Disulfide bonds are reversible thiol-disulfide (SH-SS) exchange reactions that are greatly influenced by the redox state of the environment surrounding the protein. In many cells, including *E. coli* and other prokaryotic organisms, glutathione, a tripeptide containing cysteine, is an important thiol-disulfide redox buffer. The redox state of prokaryotic microorganisms is also affected by other proteins, such as thioredoxins. Reductase proteins, in turn, regulate the redox state of glutathione, glutaredoxins and thioredoxins. In *E. coli* glutathiones, encoded by gshA and gshB, regulates the redox state of glutaredoxins. Reductase proteins include, e.g., thioredoxin reductase and glutathione oxidoreductase. *E. coli* has thioredoxins encoded by trxA and trxC genes, glutaredoxin 1, glutaredoxin 2, and glutaredoxin 3, encoded by grxA, grxB, and grxC genes. Many of the proteins that regulate the oxidation state of a cell, e.g., thioredoxin, glutathione, thioredoxin reductase and glutathione oxidoreductase, comprise an active site $CX_1X_2C$ motif. The proteins also comprise a protein structural motif known as the thioredoxin fold.

One method to identify prokaryotes that have an oxidizing intracellular environment is to measure the ratio of reduced glutathione (GSH) to oxidized glutathione (GSSG). Optimum ratios of GSH/GSSG for protein folding have been determined. In vitro, maximum yields of properly folded protein occur at GSH/GSSG ratios of less than 50, preferably less than 40, more preferably less than 30, still more preferably less than 20, and most preferably less than 10. In mammalian cells, cytoplasmic GSH/GSSG ratios ranged from 30/1 to 100/1, while secretory pathway (where most protein refolding occurs) GSH/GSSG ratios ranged from 1/1 to 3/1. Hwang et al., *Science* 257:1496-1502 (1992). *E. coli* express very few intracellular proteins with disulfide bonds. *E. coli* proteins that have disulfide bonds are secreted into the periplasmic space, which has an oxidizing environment. Typical wild type intracellular *E. coli* GSH/GSSG ratios ranged from 50/1 to 200/1. Hwang et al. supra.

The methods of the invention can by used to produce soluble eukaryotic glycosyltransferases in prokaryotic organisms that have an oxidizing intracellular environment. Microorganisms with an oxidizing intracellular environment typically have GSH/GSSG ratios of less than 50, preferably less than 40, more preferably less than 30, still more preferably less than 20, and most preferably less than 10. Thus, in some embodiments, the microorganisms of the invention will have GSH/GSSG ratios that range, e.g., from 0 to 50, or from 0.1 to 25, or from 0.5 to 10.

Prokaryotic organisms with intracellular environments can be identified by e.g., determining the intracellular GSH/GSSG ratio of the prokaryotic organisms. Assays for total glutathione concentration are commercially available from, e.g., Sigma. Assays for determination of a GSH/GSSG ratio are described, e.g., in Hwang et al., *Science* 257:1496-1502 (1992). Methods to quantify intracellular content of GSH and GSSG by derivitization with N-(1-pyrenyl)maleimide (NPM) followed by quantification using HPLC are described in Ostergaard, et al., *J. Cell Biol.* 166:337-345 (2004).

A number of additional assays are available to those of skill to determine whether a prokaryotic organism has an intracellular, oxidizing environment. Those assays include measurement of glutathione reductase activity and glutathione pool redox state (Tuggle and Fuchs, *J. Bacter.* 162:448-450 (1985)), sensitivity to thiol-specific oxidants in growth medium (Prinz et al., *J. Biol. Chem.* 272:15661-15667 (1997)), transcriptional activation of the OxyR gene in *E. coli* after exposure to hydrogen peroxide or diamide (Bessette et al., *PNAS* 96:13703-13708 (1999), measurement of the redox state of a reporter gene, such as a redox sensitive green fluorescent protein, (rxYFP) (Ostergaard et al., *J. Cell Biol.* 166:337-345 (2004)), detection of glutathione using glutathione sensitive dyes such as monochlorobimane, CellTracker Green CMFDA, o-phthaldialdehyde, and naphthalene-2,3-dicarboxaldehyde from e.g., Molecular Probes, and oxidation of cysteine residue in proteins after exposure of cells to a sulfhydryl-alkylating reagent, such as 4-acetamido-4'-maleimidystibene-2,2-disulfonic acid (Jurado et al., *J. Mol. Biol.* 320:1-10 (2002)).

VII. Enhancement of Protein Solubilization

Reduction of disulfide bonds in heterologously expressed proteins, such as the therapeutic proteins and eukaryotic glycosyltransferase polypeptides used in the methods of the invention, frequently results in protein misfolding and precipitation out of solution. In bacterial cells such as e.g., *E. coli*, misfolded proteins are expressed as insoluble inclusion bodies. Enzymes with correct disulfide bond formation and thus, proper folding are usually soluble. Solubilization of a protein is generally indicated by the presence of the protein in an aqueous fraction after centrifugation at an appropriate speed for an appropriate period. In addition, expression of properly folded proteins results in increased levels of protein activity. Thus, assays of enzyme activity can also be used to determine whether proper protein folding has occurred.

Solubilization of e.g., an O-glycosylated therapeutic protein and glycosyltransferase expressed in a microorganism with an oxidizing environment can be compared to solubilization of a therapeutic polypeptide and glycosyltransferase expressed in a microorganism with a reducing environment, e.g., an *E. coli* strain with a reducing environment. In some embodiments, an O-glycosylated therapeutic protein expressed in a microorganism with an oxidizing environment is expressed in a soluble fraction at levels that are up to 1.1, 1.2, 1.5, 2, 3, 5, 10, 15, 20, 50, 100, 500, 1000, or up to 10,000 times greater than soluble levels of the same therapeutic protein expressed in a microorganism with a reducing environment. In other embodiments, an O-glycosylated therapeutic protein expressed in a microorganism with an oxidizing environment has activity levels, e.g., U/cell or U/mg protein, up to 1.1, 1.2, 1.5, 2, 3, 5, 10, 15, 20, 50, 100, 500, 1000, or up to 10,000 times greater than activity levels of the same therapeutic protein expressed in a microorganism with a reducing environment.

A. Characterization of Protein Solubility

In preferred embodiments, the therapeutic proteins and eukaryotic glycosyltransferases are expressed as soluble proteins intracellularly within a prokaryotic microorganism. Solubility of the therapeutic proteins and eukaryotic glycosyltransferase polypeptides can be determined as disclosed above, by determining protein levels in an aqueous fraction after centrifugation at an appropriate speed for an appropriate period. Protein levels can be determined using methods known to those of skill in the art, e.g., immunoassays or direct comparison of proteins separated by, e.g., SDS-PAGE. Immunoassays can be performed using antibodies specific for the therapeutic protein or eukaryotic glycosyltransferase polypeptide of interest or using antibodies specific for an epitope or purification tag that is covalently linked to the therapeutic protein or the eukaryotic glycosyltransferase polypeptide.

Solubility can also be determined by assaying an activity of the O-glycosylated therapeutic protein in a soluble fraction from a prokaryotic microorganism. In a preferred embodiment, O-glycosylated therapeutic protein activity is measurable in a soluble intracellular fraction from a prokaryotic microorganism.

B. Enhancement of Protein Solubility

Further enhancement of solubility of therapeutic proteins and heterologous glycosyltransferase polypeptides can occur, e.g., by reducing the rate of protein expression or by expressing the protein in combination with, e.g. a chaperone protein.

Enhancing the rate of formation of appropriate disulfide bonds can lead to higher expression of active soluble glycosyltransferases and O-glycosylated therapeutic proteins. Another method to enhance expression of active soluble glycosyltransferases and O-glycosylated therapeutic proteins is to reduce the rate of expression thereby allowing the nascent polypeptide more time to achieve a stable, soluble conformation. The combination of the two methods, as described herein, is a preferred embodiment of the invention. Maximal expression of a heterologous protein generally occurs under optimal growth condition for the host cells. One method to slow the expression of proteins is to slow the growth rate of the cells. In a preferred embodiment, host cells are grown at a temperature below their optimal growth temperature. For example, the optimal growth temperature of *E. coli* is 37° C. Therefore, a temperature less that optimal growth temperature for *E. coli* is less than 37° C., e.g., between 4° C. and 36° C., between 8° C. and 33° C., between 12° C. and 30° C., or between 18° C. and 26° C., or at about 20° C., or at about 24° C.

The temperature used to slow protein production will depend on the optimal growth temperature of the host cells. As an example, *E. coli* and many other bacteria have an optimal growth temperature of 37° C. Thus, a temperature lower than an optimal growth temperature for *E. coli* or for other bacteria that grow optimally at 37° C. could be between 4-35° C., between 12-30° C., or between 15-20° C. In a preferred embodiment the temperature lower than an optimal growth temperature for *E. coli* or for other bacteria that grow optimally at 37° C. is between 18 and 23° C. For cells that grow optimally at 30° C., as do many yeasts, a temperature lower than an optimal growth temperature could be between 10 and 25° C., between 12 and 21° C., or between 15 and 20° C.

Another method to reduce the rate of expression of a heterologous protein is to vary the concentration of a molecule that regulates expression from an inducible promoter. For example, some lacY mutations allow protein expression to be controlled by varying the amount of IPTG, the inducer molecule, in the medium. In preferred embodiments the concentration of IPTG in the medium is less than optimal for, e.g., expression of a protein that does not form inclusion bodies when over expressed in a prokaryotic microorganism.

In some embodiments, an O-glycosylated therapeutic protein is expressed in a microorganism that has an oxidizing environment and that further comprises a heterologous chaperone protein. Chaperone proteins include, e.g., trigger factor; members of the Hsp70 chaperone family, e.g. DnaK; members of the Hsp100 chaperone family, e.g. ClpB, and members of the Hsp60 chaperone family, e.g. GroEL. See, e.g., Sorensen and Mortensen, *BioMed Central*, microbialcellfactories.com/content/4/1/1. Chaperones are also known that allow protein folding at 4° C., e.g., Cpn60 and Cpn 10 from *Oleispira antartica* RB8$^T$. See, e.g., Id. and Ferrer et al., *Nat. Biotechnol.* 21:1266-1267 (2003). Exemplary chaperonin proteins include, those listed in U.S. Provisional Application No. 60/665,396, filed Mar. 24, 2005; U.S. Provisional Application No. 60/668,899, filed Apr. 5, 2005; U.S. Provisional Application No. 60/732,409, filed Oct. 31, 2005; and International Application PCT/US06/11065, filed Mar. 24, 2006; each of which are herein incorporated by reference for all purposes.

Chaperone proteins can by specific for either the therapeutic protein or for a glycosyltransferase used in the methods of the invention. For example, a chaperone protein for a mammalian Core 1 Gal T1 protein has been described and can be used herein the enhance production and in vivo activity of a mammalian Core 1 Gal T1. See, e.g., Ju and Cummings, *Proc. Nat'l. Acad. Sci. USA* 99:16613-16618 (2002); Accession number AA578739 and Accession number NP_067525; each of which are herein incorporated by reference for all purposes.

In other embodiments, a therapeutic protein and a eukaryotic glycosyltransferase polypeptide are expressed in a microorganism that has an oxidizing environment that further comprises a heterologous protein disulfide isomerase (PDI). PDI proteins can make or shuffle disulfide bonds. PDI proteins are described e.g., in Georgiou et al. U.S. Pat. No. 6,027,888, which is herein incorporated by reference for all purposes. PDI proteins include e.g., rat liver PDI, Ero1p and Pdi1p proteins from *Saccharomyces*. Prokaryotic proteins include e.g., DsbC from *E. coli*. See, e.g., Frand et al., *Trends in Cell Biol.* 10:203-210 (2000). In some embodiments, DsbC proteins are expressed in a bacterial cytoplasm by e.g., deleting a periplasmic targeting sequence or including a cytoplasmic retention sequence. Thus, DsbC proteins include truncations or other variants that exhibit disulfide isomerase activity, either intracellularly or in the periplasmic space.

Other prokaryotic proteins that act to maintain the redox state of protein disulfide bonds include, e.g., DsbB, DsbA, DsbC, DsbD, and DsbG from *E. coli*. These proteins are well known in the art and are described in, e.g., Beckwith et al. U.S. Pat. No. 6,872,563, which is herein incorporated by reference for all purposes. In some embodiments, DsbB, DsbA, DsbC, DsbD, and DsbG are expressed in the bacterial cytoplasm to enhance oxidation of cytoplasmic proteins, e.g., by deleting a periplasmic targeting sequence or including a cytoplasmic retention sequence.

In a further embodiment, a therapeutic protein and a eukaryotic glycosyltransferase polypeptide are expressed in a prokaryotic microorganism that has an oxidizing environment and that also comprises a heterologous chaperone protein and/or a heterologous PDI protein and or a protein such as DsbB, DsbA, DsbC, DsbD, and DsbG from *E. coli*.

VIII. Accessory Enzymes and Enhanced Intracellular Synthesis of Donor Substrates Suitable donor substrates used by the heterologous soluble, active glycosyltransferases and methods of the invention include, but are not limited to, UDP-Glc, UDP-GlcNAc, UDP-Gal, UDP-GalNAc, GDP-Man, GDP-Fuc, UDP-GlcUA, UDP-GlcNH$_2$, UDP-GalNH$_2$, and CMP-sialic acid. Guo et al., *Applied Biochem. and Biotech.* 68: 1-20 (1997). As the reactions catalyzed by the heterologous soluble, active glycosyltransferases typically take place within the cell, the present invention also provides methods to enhance the production of donor substrates, e.g., nucleotide sugars, used by the heterologous soluble, active glycosyltransferases.

Intracellular synthesis of donor substrates can be enhanced by expression of an "accessory enzyme." An accessory enzyme is an enzyme that is involved in catalyzing a reaction that, for example, forms a substrate or other reactant for a glycosyltransferase reaction. An accessory enzyme can, e.g., catalyze the formation of a nucleotide sugar that is used as a sugar donor moiety by a glycosyltransferase. An accessory enzyme can also be one that is used in the generation of a nucleotide triphosphate that is required for formation of a nucleotide sugar, or in the generation of the sugar which is incorporated into the nucleotide sugar. The heterologous glycosyltransferases can be used in combination with an appropriate recombinant accessory enzymes, which may or may not be fused to the glycosyltransferase. Examples of heterologous accessory enzyme and glycosyltransferase pairs include, e.g., a galactosyltransferase and an epimerase, e.g., a UDP-glucose 4' epimerase protein, a UDP-GlcNAc 4' epimerase protein or a dual function UDP-glucose 4' epimerase protein/UDP-GlcNAc 4' epimerase protein; or a sialyltransferase and a sialic acid synthetase. Other examples are disclosed in PCT Patent Application PCT/CA98/01180, published as WO99/31224 on Jun. 24, 1999; which is herein incorporated by reference for all purposes.

Sugar nucleotides serve as donors for the in vivo glycosylation of a therapeutic protein. Production of sugar nucleotides can be enhanced to increase intracellular sugar nucleotide pools in a variety of ways. One method to increase production of any sugar nucleotide is to increase expression of the biosynthetic enzymes that make the sugar nucleotide. Expression of single enzymes, multiple enzymes or an entire biosynthetic pathway, e.g., an operon, can be increased. For example the appropriate nucleic acids can be cloned in endogenous operons with endogenous regulatory sequences or can be cloned into synthetic expression cassettes, including polycistronic expression cassettes. Enzymatic syntheses of sugar nucleotides are reviewed in Bulter and Elling, *Glycoconj J* 16:147-159 (1999); some non-limiting in vivo examples follow.

For example, for synthesis of UDP-GlcNAc in *E. coli*, the gene products GlmS, GlmM, and GlmU are required to convert Fructose-6P to UDP-GlcNAc. glmU and glmS are adjacent in the genome, and could be cloned out as a single fragment including regulatory structures, and included in an expression construct or reintroduced into the bacterial genome. The expression construct could be reengineered to also include the glmM gene, thus, adding another pathway gene to a natural operon.

Also to increase UDP-GlcNAc production, expression of the acetyl-CoA synthase (acs) gene can be increased. See, e.g., Lin et al., *Appl Micro Biotech* 71:870-874 (2006). Increased expression of acs boosts the pool of CoA available the acetylation of GlcN-1P by GlmU.

In addition to endogenous genes from the host microorganism, orthologs can be expressed to increase UDP-GlcNAc production. For a list of genes and pathways, see, e.g., Milewski et al. *Yeast* 23:1-14(2006). In particular yeast gene products use different intermediates than the bacterial pathway. For example, yeast acetylate GlcN-6P, then a phospho-GlcNAc mutase converts it to GlcNAc-1P; whereas bacteria first convert Glc6P to Glc1P, and then acetylate it to form GlcNAc-1P.

For synthesis of UDP-Gal, most of the *E. coli* biosynthetic genes occur in a single operon that can be cloned into an expression construct or a host cell genome, in whole or in part. Bacteria typically generate UDP-Gal using two pathways: conversion of UDP-Glc to UDP-Gal by GalE, or from galactose, i.e., Gal - - - galK - - - >Gal-1P - - - galT+UDP-Glc - - - >UDP-Gal+Glc1P. For the second pathway, most of the *E. coli* biosynthetic genes occur in a single operon that can be cloned into an expression construct or a host cell genome, in whole or in part.

An alternative method to synthesize UDP-Gal is by addition and expression of a sucrose synthase gene and feeding of sucrose. See, e.g., Elling et al. Glycobiology 3:349-355 (1993) and Wang et al., *Arch Bioc Biop* 371:70-82(1999). Most *E. coli* K12 strains do not metabolize sucrose. Thus, the reaction is sucrose+UDP - - - Sucrose synthase - - - >UDP-Glc+fructose. An advantage of this approach is that the fructose can be used in the UDP-GlcNAc pathway. Note that while some sucrose enters the cell through other sugar import pathways, addition of natural sucrose transporters to the strain improves import. See, e.g. Jahreis et al. *J. Bact* 184, 5307-5316 (2002). The sucrose transport protein can be manipulated to remove hydrolase activity. If sucrose is phosphorylated on import into the cell, a sucrose-phosphate synthase could also be used; a phosphor-mutase enzyme may be needed to convert sucrose-6P⇌sucrose-1P). See, e.g. Lunn, *Gene* 303:187-196 (2003); and Huynh et al. *Acta Crystal* 61:116-117 (2005).

A number of methods can be used to increase production of UDP-GalNAc. For example, UDP-GlcNAc can be converted to UDP-GalNc using a dual specificity Glc/GlcNAc 4' epimerase, e.g., GNE or GalE. Some bacterial galactose epimerase proteins are not able to convert UDP-Glc. UDP-GlcNAc biosynthetic genes including glmS, glmM, and glmU can also be overexpressed to increase production of UDP-GalNAc.

Mammalian proteins can synthesize UDP-GalNAc directly from GalNAc, UTP, and ATP. See, e.g., Bourgeaux et al. *Bioorg Med Chem Let* 15:5459-5462 (2005), using mammalian GalNAc kinase and UDP-GalNAc pyrophosphorylase (AGX1). A bacterial GlcNAc pyrophosphorylase (GlmU) can also accomplish this last step. See, e.g. Szumilo et al. *JBC* 271:13147-13154(1996).

Some of the sugar kinases make the 6P sugar, not a 1P sugar. In these cases, a phosphor-sugar mutase would be required to transfer the phosphate from the 6 to the 1 position. An example is the endogenous bacterial GlmM, which converts GlcN-6P to GlcN-1P in the UDP-GlcNAc biosynthetic pathway. Addition of a sugar-specific mutase activity that is otherwise lacking in the bacterium may enable certain UDP-sugar synthetic pathways to act on now-available precursors. For example, yeast AGM1, converts GlcNAc-6P to 1P, which could then be converted to UDP-GlcNAc by endogenous bacterial glmU.

For other nucleotide sugars, synthetic genes from other species could be added, for example, from higher eukaryotes or pathogenic bacteria, or specific pathways altered to enhance specific sugar nucleotide production. For example, overexpression of bacterial rcsA and deletion of bacterial wcaJ significantly enhances the production of GDP-fucose, See e.g., Dumon et al. *Glycoconj J* 18, 465-474 (2001). CMP-sialic acid (CMP-NeuAc) can be produced by deleting bacterial nanA, and introducing a CMP-NeuAc synthase (CNS) from, e.g., *Neisseria meningitidis*, see e.g. Priem et al. Glycobiology 12, 235-240 (2002), and Gilbert et al. Biotechnol. Lett. 19, 417-420.

Synthesis of donor substrates can also be enhanced by growth of host prokaryotic microorganisms in medium that includes a donor substrate or a precursor to a donor substrate, e.g., galactose or GalNAc. See, e.g., Priem et al., *Glycobiology* 12:235-240 (2002). The microorganism can be altered to facilitate uptake of precursor molecule from the medium, e.g., by expressing a sugar transport protein. For example, if lactose is used, *E. coli* cells that express the LacY permease can be used.

Synthesis of donor substrates can be enhanced by inhibiting or knocking out pathways that breakdown sugar nucleotide precursors. For example, in *E. coli*, break down of sialic acid can be minimized by using a host strain that lacks aldolase activity, see, e.g., Priem et al. Glycobiology 12, 235-240 (2002). Also in *E. coli*, when lactose is, for example, part of an oligosaccharide on the glycosylated therapeutic protein, lactose breakdown can be minimized by using host cells that are LacZ-. Other examples of enzymes that breakdown sugar precursors and are thus, targets for inhibition or deletion include RfbA and RffH which interfere with UDP-Glc production by siphoning Glc-1P to TDP-Glc. Glc-1P pools decrease after dephosphorylation by agp, thus agp could be targeted. Similarly, manA could be targeted as it interferes with production of UDP-GlcNAc by isomerizing Fruc-6P to man-6P.

Synthesis of donor substrates can also be enhanced by inhibiting or knocking out pathways that breakdown the sugar nucleotide itself. For example, targets include ugd which oxidizes UDP-Glc; glf which converts UDP-Gal to UDP-galactofuranose; and RffE which converts UDP-GlcNAc to UDP-ManNAc.

Additional methods to enhance production of a donor substrate are disclosed in International Application No. PCT/US05/033532, filed Sep. 19, 2005; which is herein incorporated by reference for all purposes.

IX. Conjugation of Modified Sugar Residues

The modified sugars are conjugated to a glycosylated or non-glycosylated peptide or protein using an appropriate enzyme to mediate the conjugation. Preferably, the concentrations of the modified donor sugar(s), enzyme(s) and acceptor peptide(s) or protein(s) are selected such that glycosylation proceeds until the acceptor is consumed. The considerations discussed below, while set forth in the context of a sialyltransferase, are generally applicable to other glycosyltransferase reactions.

The present invention also provides for the industrial-scale production of modified peptides. As used herein, an industrial scale generally produces e.g., at least one microgram, one milligram, or one gram of finished, purified conjugate.

In the discussion that follows, the invention is exemplified by the conjugation of modified sialic acid moieties to a glycosylated peptide. The exemplary modified sialic acid is labeled with PEG. The focus of the following discussion on the use of PEG-modified sialic acid and glycosylated peptides is for clarity of illustration and is not intended to imply that the invention is limited to the conjugation of these two partners. One of skill understands that the discussion is generally applicable to the additions of modified glycosyl moieties other than sialic acid. Moreover, the discussion is equally applicable to the modification of a glycosyl unit with agents other than PEG including other water-soluble polymers, therapeutic moieties, and biomolecules.

An enzymatic approach can be used for the selective introduction of PEGylated or PPGylated carbohydrates onto a peptide or glycopeptide. The method utilizes modified sugars containing PEG, PPG, or a masked reactive functional group, and is combined with the appropriate glycosyltransferase. By selecting the glycosyltransferase that will make the desired carbohydrate linkage and utilizing the modified sugar as the donor substrate, the PEG or PPG can be introduced directly onto the peptide backbone, onto existing sugar residues of a glycopeptide or onto sugar residues that have been added to a peptide.

An acceptor for the sialyltransferase is present on the peptide to be modified by the methods of the present invention either as a naturally occurring structure or one placed there recombinantly, enzymatically or chemically. Suitable acceptors, include, for example, galactosyl acceptors such as Galβ1,4GlcNAc, Galβ1,4GalNAc, Galβ1,3GalNAc, lacto-N-tetraose, Galβ1,3GlcNAc, Galβ1,3Ara, Galβ1,6GlcNAc, Galβ1,4Glc (lactose), GalNAc and sialic acid containing structures, and other acceptors known to those of skill in the art (see, e.g., Paulson et al., *J. Biol. Chem.* 253: 5617-5624 (1978)).

In one embodiment, an acceptor for the sialyltransferase is present on the glycopeptide to be modified upon in vivo synthesis of the glycopeptide. Such glycopeptides can be sialylated using the claimed methods without prior modification of the glycosylation pattern of the glycopeptide. Alternatively, the methods of the invention can be used to sialylate a peptide that does not include a suitable acceptor; one first modifies the peptide to include an acceptor by methods known to those of skill in the art. In an exemplary embodiment, a GalNAc residue is added by the action of a GalNAc transferase.

In an exemplary embodiment, the galactosyl acceptor is assembled by attaching a galactose residue to an appropriate acceptor linked to the peptide, e.g., a GalNAc. The method includes incubating the peptide to be modified with a reaction mixture that contains a suitable amount of a galactosyltransferase (e.g., galβ1,3 or galβ1,4), and a suitable galactosyl donor (e.g., UDP-galactose). The reaction is allowed to proceed substantially to completion or, alternatively, the reaction is terminated when a preselected amount of the galactose residue is added. Other methods of assembling a selected saccharide acceptor will be apparent to those of skill in the art.

Methods for conjugation of modified sugars to peptides or proteins are found e.g., in U.S. Ser. No. 60/328,523 filed Oct. 10, 2001; U.S. Ser. No. 60/387,292, filed Jun. 7, 2002; U.S. Ser. No. 60/391,777 filed Jun. 25, 2002; U.S. Ser. No. 60/404,249 filed Aug. 16, 2002; and PCT/US02/32263; each of which are herein incorporated by reference for all purposes.

X. Expression of Proteins in Prokaryotic Host Cells

Soluble, active O-glycosylated therapeutic proteins and glycosyltransferase polypeptides of the invention can be expressed in a variety of prokaryotic microorganisms with oxidizing intracellular environments, including *E. coli*, and other bacterial hosts, as described above.

Once expressed in a prokaryotic organism that has an oxidizing intracellular environment, the soluble, active O-glycosylated therapeutic proteins and glycosyltransferase polypeptides can be isolated using standard protein purification techniques and used therapeutically or further modified in vitro.

Typically, the polynucleotide that encodes the heterologous polypeptide is placed under the control of a promoter that is functional in the desired prokaryotic organisms that has an oxidizing environment. An extremely wide variety of promoters are well known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Accordingly, the invention provides expression cassettes into which the nucleic acids that encode fusion proteins are incorporated for high level expression in a desired microorganism that has an oxidizing environment.

Examples of expression vectors include, e.g., the pCWin1 vector and pCWin2 vector, both disclosed in WO 2005/067601, which is herein incorporated by reference for all purposes.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the beta-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80:21-25); and the lambda-derived $P_L$ promoter and N-gene ribosome binding site (Shimatake et al., *Nature* (1981) 292: 128). The particular promoter system is not critical to the invention, any available promoter that functions in prokaryotes can be used.

For expression of soluble, active O-glycosylated therapeutic proteins and glycosyltransferase polypeptides in prokaryotic cells other than *E. coli*, a promoter that functions in the particular prokaryotic species is required. Such promoters can be obtained from genes that have been cloned from the species, or heterologous promoters can be used. For example, the hybrid trp-lac promoter functions in *Bacillus* in addition to *E. coli*. Promoters are known for other bacterial species, e.g. *Pseudomonas*. See, e.g. U.S. Patent Application Publication No. US 2005/0186666, published Aug. 25, 2005, which is herein incorporated by reference for all purposes.

A ribosome binding site (RBS) is conveniently included in the expression cassettes of the invention. An RBS in *E. coli*, for example, consists of a nucleotide sequence 3-9 nucleotides in length located 3-11 nucleotides upstream of the initiation codon (Shine and Dalgarno, *Nature* (1975) 254: 34; Steitz, In *Biological regulation and development: Gene expression* (ed. R. F. Goldberger), vol. 1, p. 349, 1979, Plenum Publishing, NY).

Either constitutive or regulated promoters can be used in the present invention. Regulated promoters can be advantageous because the host cells can be grown to high densities before expression of the fusion proteins is induced. High level expression of heterologous proteins slows cell growth in some situations and may not be desired in all situations, see below. An inducible promoter is a promoter that directs expression of a gene where the level of expression is alterable by environmental or developmental factors such as, for example, temperature, pH, anaerobic or aerobic conditions, light, transcription factors and chemicals. Such promoters are referred to herein as "inducible" promoters, which allow one to control the timing of expression of the glycosyltransferase or enzyme involved in nucleotide sugar synthesis. For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol.*; Tabor et al. (1985) *Proc. Nat'l. Acad. Sci. USA* 82: 1074-8). These promoters and their use are discussed in Sambrook et al., supra. A particularly preferred inducible promoter for expression in prokaryotes is a dual promoter that includes a tac promoter component linked to a promoter component obtained from a gene or genes that encode enzymes involved in galactose metabolism (e.g., a promoter from a UDPgalactose 4-epimerase gene (galE)). The dual tac-gal promoter, which is described in PCT Patent Application Publ. No. WO98/2011.

Another inducible promoter is the cspA promoter, which is highly induced at low temperatures in *E. coli*. See, e.g., Sorensen and Mortensen, *BioMed Central*, microbialcellfactories.com/content/4/1/1 and Mujacic et al., *Gene* 238:325-3332 (1999).

A construct that includes a polynucleotide of interest operably linked to gene expression control signals that, when placed in an appropriate host cell, drive expression of the polynucleotide is termed an "expression cassette." Expression cassettes that encode the fusion proteins of the invention are often placed in expression vectors for introduction into the host cell. The vectors typically include, in addition to an expression cassette, a nucleic acid sequence that enables the vector to replicate independently in one or more selected host cells. Generally, this sequence is one that enables the vector to replicate independently of the host chromosomal DNA, and includes origins of replication or autonomously replicating sequences. Such sequences are well known for a variety of bacteria. For instance, the origin of replication from the plasmid pBR322 is suitable for most Gram-negative bacteria. Alternatively, the vector can replicate by becoming integrated into the host cell genomic complement and being replicated as the cell undergoes DNA replication. A preferred expression vector for expression of the enzymes is in bacterial cells is pTGK, which includes a dual tac-gal promoter and is described in PCT Patent Application Publ. N0. WO98/20111. Another useful cloning vector is pCWin2-MBP or a version of pCWin2 with a modified 5' UTR. See, e.g., PCT/US05/00302, filed Jan. 6, 2005, which is herein incorporated by reference for all purposes.

The construction of polynucleotide constructs generally requires the use of vectors able to replicate in bacteria. A plethora of kits are commercially available for the purification of plasmids from bacteria (see, for example, EasyPrepJ, FlexiPrepJ, both from Pharmacia Biotech; StrataCleanJ, from Stratagene; and, QIAexpress Expression System, Qiagen). The isolated and purified plasmids can then be further manipulated to produce other plasmids, and used to transfect cells. Cloning in e.g., *E. coli, Streptomyces* or *Bacillus* is possible.

Selectable markers are often incorporated into the expression vectors used to express the polynucleotides of the invention. These genes can encode a gene product, such as a protein, necessary for the survival or growth of transformed host cells grown in a selective culture medium. Host cells not transformed with the vector containing the selection gene will not survive in the culture medium. Typical selection genes encode proteins that confer resistance to antibiotics or other toxins, such as ampicillin, neomycin, kanamycin, chloramphenicol, or tetracycline. Alternatively, selectable markers may encode proteins that complement auxotrophic deficiencies or supply critical nutrients not available from complex media, e.g., the gene encoding D-alanine racemase for Bacilli. Often, the vector will have one selectable marker that is functional in, e.g., *E. coli*, or other cells in which the vector is replicated prior to being introduced into the host cell. A number of selectable markers are known to those of skill in the art and are described for instance in Sambrook et al., supra. An auxotrophic expression system is known for *Pseudomonas* species. See, e.g., U.S. Patent Application Publication No. US 2005/0186666, published Aug. 25, 2005, which is herein incorporated by reference for all purposes.

Construction of suitable vectors containing one or more of the above listed components employs standard ligation techniques as described in the references cited above. Isolated plasmids or DNA fragments are cleaved, tailored, and religated in the form desired to generate the plasmids required. To confirm correct sequences in plasmids constructed, the plasmids can be analyzed by standard techniques such as by restriction endonuclease digestion, and/or sequence analysis according to known methods. Molecular cloning techniques to achieve these ends are known in the art. A wide variety of cloning and in vitro amplification methods suitable for the construction of recombinant nucleic acids are well-known to persons of skill. Examples of these techniques and instructions sufficient to direct persons of skill through many cloning exercises are found in Berger and Kimmel, *Guide to Molecular Cloning Techniques, Methods in Enzymology*, Volume 152, Academic Press, Inc., San Diego, Calif. (Berger); and Current Protocols in Molecular Biology, F. M. Ausubel et al., eds., *Current Protocols*, a joint venture between Greene Publishing Associates, Inc. and John Wiley & Sons, Inc., (1998 Supplement) (Ausubel).

A variety of common vectors suitable for use as starting materials for constructing the expression vectors of the invention are well known in the art. For cloning in bacteria, common vectors include pBR322 derived vectors such as pBLUESCRIPT™, and λ-phage derived vectors.

The methods for introducing the expression vectors into a chosen prokaryotic microorganism are not particularly critical, and such methods are known to those of skill in the art. For example, the expression vectors can be introduced into prokaryotic cells, including *E. coli*, by calcium chloride transformation, and into eukaryotic cells by calcium phosphate treatment or electroporation. Other transformation methods are also suitable.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297-16302.

The soluble, active O-glycosylated therapeutic proteins and glycosyltransferase polypeptides are preferably expressed intracellularly. Intracellular expression often results in surprisingly high yields. In another embodiment, the soluble, active O-glycosylated therapeutic proteins and glycosyltransferase polypeptides are fused to a subsequence of protein A, a maltose binding protein, a starch binding protein, or bovine serum albumin (BSA), for example, to facilitate purification, secretion, or stability.

The soluble, active O-glycosylated therapeutic proteins and glycosyltransferase polypeptides of the invention can also be further linked to other bacterial proteins. This approach often results in high yields, because normal prokaryotic control sequences direct transcription and translation. In *E. coli*, lacZ fusions are often used to express heterologous proteins. Other examples are discussed below. Suitable vectors are readily available, such as the pUR, pEX, and pMR100 series (see, e.g., Sambrook et al., supra.). For certain applications, it may be desirable to cleave the non-glycosyltransferase amino acids from the fusion protein after purification. This can be accomplished by any of several methods known in the art, including cleavage by cyanogen bromide, a protease, or by Factor $X_a$ (see, e.g., Sambrook et al., supra.; Itakura et al., *Science* (1977) 198: 1056; Goeddel et al., *Proc. Natl. Acad. Sci. USA* (1979) 76: 106; Nagai et al., *Nature* (1984) 309: 810; Sung et al., *Proc. Natl. Acad. Sci. USA* (1986) 83: 561). Cleavage sites can be engineered into the gene for the fusion protein at the desired point of cleavage.

More than one recombinant protein may be expressed in a single host cell by placing multiple transcriptional cassettes in a single expression vector, or by utilizing different selectable markers for each of the expression vectors which are employed in the cloning strategy. For example, multiple proteins can be expressed in a single cell, e.g., accessory enzymes, therapeutic proteins and glycosyltransferases that direct O-linked glycosylation.

A suitable system for obtaining recombinant proteins from *E. coli* which maintains the integrity of their N-termini has been described by Miller et al. *Biotechnology* 7:698-704 (1989). In this system, the gene of interest is produced as a C-terminal fusion to the first 76 residues of the yeast ubiquitin gene containing a peptidase cleavage site. Cleavage at the junction of the two moieties results in production of a protein having an intact authentic N-terminal residue.

In some embodiments, multiple heterologous proteins are expressed in a single cell. Many methods are available to those of skill to accomplish this expression. Some non-limiting examples follow.

In some embodiments, multiple heterologous proteins are expressed from a polycistronic expression construct. A polycistronic expression cassette has the following general form [Promoter] {[enhancer/ribosome binding site (RBS)] [open reading frame]}×n [terminator]; where 'n' is the number of open reading frames in the polycistronic expression cassette and can be varied depending on the needs of the user. The [enhancer/RBS] element can also be varied, e.g., either an extended enhancer/RBS combination or a simple RBS. Other elements that can vary within the polycistronic expression cassette include 5' UTRs.

The cellular location of any expression cassette, e.g., independent promoter or polycistronic expression cassette, can be varied. For example, expression cassettes can be either carried on one or multiple plasmids, or integrated into the genome (either directed or random integration, with a selection marker or regenerated into a stable integrant. See, e.g., Link et al. *J. Bact.* 179:6228-6237 (1997); Muyrers et al., *TIBS* 26:325-331 (2001); and Court et al., *Annu. Rev. Genet.* 36:361-388 (2002). Integrated expression cassettes can be regulated by constructed promoters (e.g. lac, pho, tac, T7, etc, taken from a plasmid), or by integrating a polycistronic array behind an endogenous (natural) genomic promoter. Genomic promoters can be regulated (e.g. integrate into the galE locus, and use the endogenous gal promoter) or constitutive (integrate behind a constitutive promoter; or screen for random integrants that express the enzymes). In one embodiment, all heterologous glycosyltransferase, accessory enzyme, and therapeutic protein nucleic acid are expressed from plasmid constructs. In another embodiment, either all heterologous glycosyltransferase and accessory enzyme nucleic acid or a therapeutic protein nucleic acid are integrated into a bacterial genome and the other is expressed from a plasmid construct. In yet another embodiment, all heterologous glycosyltransferase, accessory enzyme, and therapeutic protein nucleid acid are integrated into the bacterial genome.

Expression of heterologous proteins can be regulated in a temporal fashion, using e.g., different inducible promoters to turn expression of specific genes on and off as desired by the user. For example, expression of the nucleic acid could be induced prior to the production of the glycosyltransferases. Alternately, the cell could be prepared with prior induction of glycosyltransferases followed by the expression of the therapeutic protein.

XI. Purification and In Vitro Modification of Soluble O-Glycosylated Therapeutic Proteins The soluble, active O-glycosylated therapeutic proteins and glycosyltransferase polypeptides of the present invention are preferably expressed as intracellular proteins and can be used in this form, in the methods of the present invention. For example, permeabilized cells or a crude cellular extract containing the expressed intracellular s soluble, active O-glycosylated therapeutic proteins and glycosyltransferase polypeptides can used in the methods of the present invention or to e.g., assay the activity of the soluble, active O-glycosylated therapeutic proteins and/or glycosyltransferase polypeptides.

Alternatively, the soluble, active O-glycosylated therapeutic protein can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification.*, Academic Press, Inc. N.Y. (1990)). Substantially pure compositions of at least about 70, 75, 80, 85, 90% homogeneity are preferred, and 92, 95, 98 to 99% or more homogeneity are most preferred. The purified proteins may also be used, e.g., as immunogens for antibody production.

To facilitate purification and expression of the soluble, active O-glycosylated therapeutic protein of the invention, the nucleic acids that encode the proteins can also include a coding sequence for an epitope or "tag" for which an affinity binding reagent is available, i.e. a purification tag. Examples of suitable epitopes include the myc and V-5 reporter genes; expression vectors useful for recombinant production of fusion proteins having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the glycosyltransferases of the invention, and corresponding detection systems are known to those of skill in the art, and several are commercially available (e.g., FLAG" (Kodak, Rochester N.Y.). Another example of a suitable tag is a polyhistidine sequence, which is capable of binding to metal chelate affinity ligands. Typically, six adjacent histidines (SEQ ID NO: 85) are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, NY; commercially available from Qiagen (Santa Clarita, Calif.)). Other purification or epitope tags include, e.g., AU1, AU5, DDDDK (EC5) (SEQ ID NO: 83), E tag, E2 tag, Glu-Glu, a 6 residue peptide, EYMPME (SEQ ID NO: 84), derived from the Polyoma middle T protein, HA, HSV, IRS, KT3, S tage, 51 tag, T7 tag, V5 tag, VSV-G, β-galactosidase, Gal4, green fluorescent protein (GFP), luciferase, protein C, protein A, cellulose binding protein, GST (glutathione S-transferase), a step-tag, Nus-S, PPI-ases, Pfg 27, calmodulin binding protein, dsb A and fragments thereof, and granzyme B. Epitope peptides and antibodies that bind specifically to epitope sequences are commercially available from, e.g., Covance Research Products, Inc.; Bethyl Laboratories, Inc.; Abcam Ltd.; and Novus Biologicals, Inc.

Purification tags also include maltose binding domains and starch binding domains. Proteins comprising purification tags can be purified using a binding partner that binds the purification tag, e.g., antibodies to the purification tag, nickel or cobalt ions or resins, and amylose, maltose, or a cyclodextrin. Purification tags also include starch binding domains, *E. coli* thioredoxin domains (vectors and antibodies commercially available from e.g., Santa Cruz Biotechnology, Inc. and Alpha Diagnostic International, Inc.), and the carboxy-terminal half of the SUMO protein (vectors and antibodies commercially available from e.g., Life Sensors Inc.). Starch binding domains, such as a maltose binding domain from *E. coli* and SBD (starch binding domain) from an amylase of *A. niger*, are described in WO 99/15636, herein incorporated by reference. Affinity purification of a fusion protein comprising a starch binding domain using a betacyclodextrin (BCD)-derivatized resin is described in WO 2005/014779, published Feb. 17, 2005, herein incorporated by reference in its entirety. In some embodiments, a soluble, active O-glycosylated therapeutic protein comprises more than one purification or epitope tag.

Other haptens that are suitable for use as tags are known to those of skill in the art and are described, for example, in the Handbook of Fluorescent Probes and Research Chemicals (6th Ed., Molecular Probes, Inc., Eugene Oreg.). For example, dinitrophenol (DNP), digoxigenin, barbiturates (see, e.g., U.S. Pat. No. 5,414,085), and several types of fluorophores are useful as haptens, as are derivatives of these compounds. Kits are commercially available for linking haptens and other moieties to proteins and other molecules. For example, where the hapten includes a thiol, a heterobifunctional linker such as SMCC can be used to attach the tag to lysine residues present on the capture reagent.

One of skill would recognize that modifications can be made to the catalytic or functional domains of the soluble, active eukaryotic glycosyltransferase polypeptide without diminishing their biological function. Some modifications may be made to facilitate the cloning, expression, or incorporation of the catalytic domain into a fusion protein. Such modifications are well known to those of skill in the art and include, for example, the addition of codons at either terminus of the polynucleotide that encodes the catalytic domain to provide, for example, a methionine added at the amino terminus to provide an initiation site, or additional amino acids (e.g., poly His) placed on either terminus to create conveniently located restriction enzyme sites or termination codons or purification sequences.

XII. Production of Soluble, Active, O-Glycosylated Therapeutic Proteins

Production of soluble, active O-glycosylated therapeutic protein in microorganisms that have oxidizing environments provides a bacterial system with many of the characteristics of, e.g., protein production in Chinese hamster ovary cells. One difference is that the bacterial cells can be grown on standard microbial media, e.g., a minimal, defined medium or a rich medium such as LB.

Production of soluble, active O-glycosylated therapeutic protein in microorganisms that have oxidizing environments provides efficiency by eliminating one or more time-consuming production steps, such as solubilization, denaturation, and refolding of the O-glycosylated therapeutic protein and/or the enzymes used for glycosylation.

Production of soluble, active O-glycosylated therapeutic protein in microorganisms that have oxidizing environments provides flexibility when designing a protein production protocol. For example, glycosyltransferases can be individually produced in a microorganism that has an oxidizing environment and then stored until needed. If desired, the microorganisms can also produce protein(s) involved in production of a nucleotide sugar that is a substrate for the glycosyltransferase. Similarly, therapeutic proteins can be individually produced in a microorganism that has an oxidizing environment. Lysates containing an appropriate glycosyltransferase, including a nucleotide sugar:polypeptide glycosyltransferase protein, can be mixed with a lysate containing the soluble therapeutic protein under conditions that promote O-glycosylation of the therapeutic protein. The glycosyltransferases can be added sequentially to the therapeutic protein or can be added as a mixture of glycosyltransferases. With the availability of multiple lysates containing glycosyltransferases, the user can select one or more glycosylation patterns for a therapeutic protein for, e.g., simultaneous production and testing. In some embodiments, purified or partially purified glycosyltransferases are used in combination with lysates containing glycosyltransferases and the therapeutic protein of interest. The purified or partially purified glycosyltransferases can be produced in, e.g., a microorganism that has an oxidizing environment; a microorganism that has a reducing environment, such as wild-type *E. coli*; or a eukaryotic expression system, such as yeast, including *Saccharomyces, Schizosaccharomyces*, and *Picchia*, Sf9 cells, and mammalian cells, including CHO cells and NIH3T3 cells.

In another example, appropriate glycosyltransferases, including a nucleotide sugar:polypeptide glycosyltransferase protein, are expressed together in a microorganism that has an oxidizing environment. If desired, the microorganisms can also produce protein(s) involved in production of a nucleotide sugar that is a substrate for the glycosyltransferase(s). Therapeutic proteins of interest are produced individually in a microorganism that has an oxidizing environment. The mixed glycosyltransferase lysate is combined with a lysate containing the soluble therapeutic protein under conditions that promote O-glycosylation of the therapeutic protein. As above, purified or partially purified glycosyltransferases from a variety of sources can also be added to the reaction mixtures.

In another example, one or more glycosyltransferases are expressed together in a prokaryotic microorganism that has an oxidizing environment and other glycosyltransferases are expressed individually in a prokaryotic microorganism that has an oxidizing environment. Therapeutic proteins of interest are produced individually in a microorganism that has an oxidizing environment. The appropriate glycosyltransferase lysates are combined with the lysate containing the soluble therapeutic protein under conditions that promote O-glycosylation of the therapeutic protein. As above, purified or partially purified glycosyltransferases from a variety of sources can also be added to the reaction mixtures.

In another example, appropriate glycosyltransferases, including a nucleotide sugar:polypeptide glycosyltransferase protein and a therapeutic protein, are expressed together in a microorganism that has an oxidizing environment. If desired, the microorganism can also produce protein(s) involved in production of a nucleotide sugar that is a substrate for the glycosyltransferase(s). The soluble therapeutic protein is O-glycosylated within the microorganism and harvested from a cell lysate by the user. In a further embodiment, the cell lysate is combined with additional sugar precursors to enhance production of O-glycosylated therapeutic protein.

Any of the O-glycosylation reactions described above can be further enhanced by addition of a nucleotide sugar donor substrate to the reaction mix containing cell lysates or cell lysates and purified or partially purified glycosyltransferases.

Any of the O-glycosylation reactions described above can be further enhanced by addition of a modified nucleotide sugar donor substrate to the reaction mix containing cell lysates or cell lysates and purified or partially purified glycosyltransferases. Methods for conjugation of modified sugars to peptides or proteins are found e.g., in U.S. Ser. No. 60/328, 523 filed Oct. 10, 2001; U.S. Ser. No. 60/387,292, filed Jun. 7, 2002; U.S. Ser. No. 60/391,777 filed Jun. 25, 2002; U.S. Ser. No. 60/404,249 filed Aug. 16, 2002; and PCT/US02/32263; each of which are herein incorporated by reference for all purposes. Preferred modified sugars include, e.g., CMP-sialic acid PEG.

It must be noted that as used herein and in the appended claims, the singular forms "a", "and", and "the" include plural referents unless the context clearly dictates otherwise. Thus, for example, reference to "a cell" includes a plurality of such cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. Citations are incorporated herein by reference.

EXAMPLES

Example 1

Production of Glycosylated and GlycoPEGylated Human Growth Hormone using Mixtures of Crude Lysate and/or Purified Reagents Storage of Cell Pellets. Unlysed cell pellets from trxb gor supp mutant *E. coli* fermentation harvests of hGH (SEQ ID NO: 7), MBP-GalNAcT2, MBP-Core-1-GalT1, MBP-ST3Gal1, and GalNAcT2 coexpressed with GalE were stored at −80° C.

Cell Lysate of hGH. A human growth hormone mutant (hGH P254; T135INT, Y43A, Y144A, F140A, K141N (SEQ ID NO: 7) was expressed in a trxB, gor, supp *E. coli* strain using a pCWin2-derived vector with an alternate 5' UTR. Cell pellet was resuspended in 50 mM Tris-HCl, 20 mM NaCl, 0.02% $NaN_3$, pH 7.4. Upon resuspension, the cells were homogenized with three passes over a microfluidizer set at 16,000-18,000 PSI. The cell homogenate was immediately centrifuged at 12000×G for 50 minutes on a centrifuge equipped with a fixed angle rotor at 4° C. The supernatant was filtered using a 0.2 micron cellulose acetate filter. The filtered homogenate was stored only briefly at 4° C. prior to enzymatic reaction.

Cell Lysate of MBP-GalNAcT2 and MBP-Core-1-GalT1. Cell pellet from a trxB, gor, supp *E. coli* culture expressing MBP-GalNAcT2 (SEQ ID NO:28) or MBP-Core-1-GalT1 (SEQ ID NO:46) was resuspended in 50 mM Tris-HCl, 20 mM NaCl, 5 mM EDTA, 0.02% $NaN_3$, pH 7.4. Upon resuspension, the cells were homogenized with three passes over a microfluidizer set at 16,000-18,000 PSI. The cell homogenate was immediately centrifuged at 12000×G for 30 minutes on a centrifuge equipped with a fixed angle rotor at 4° C. The supernatant was filtered using 0.2 micron cellulose acetate filters. A portion of the filtered homogenate was concentrated and buffer exchanged with 50 mM Tris-HCl, 20 mM NaCl, 0.02% $NaN_3$, pH 7.4 in a 5 kDa MWCO centrifugal filter. The concentrated lysate was stored briefly at 4° C. prior to enzymatic reaction. On a second occasion, the concentrated lysate of MBP-Core-1-GalT1 was mixed 1:1 with glycerol and stored at −20° C. prior to enzymatic reactions.

Cell Lysate Containing GalNAcT2 and GalE, or MBP-ST3Gal1. Cultures of trxB, gor, supp *E. coli* co-expressing GalNAcT2 (SEQ ID NO:27) with GalE, (SEQ ID NO:79) or expressing MBP-ST3 Gal1 (SEQ ID NO:57) were prepared and resuspended in 50 mM Tris-HCl, 20 mM NaCl, 0.02% $NaN_3$, pH 7.4. Cells were homogenized with three passes over a microfluidizer set at 16,000-18,000 PSI. The cell homogenate was immediately centrifuged at 12000-19000×G for 20-50 minutes on a centrifuge equipped with a fixed angle rotor at 4° C. The supernatant was filtered using a 0.2 micron cellulose acetate filter. The filtrate was concentrated in a 5 kDa MWCO centrifugal filter, mixed 1:1 with glycerol and stored at −20° C. prior to enzymatic reaction.

Figure 2:
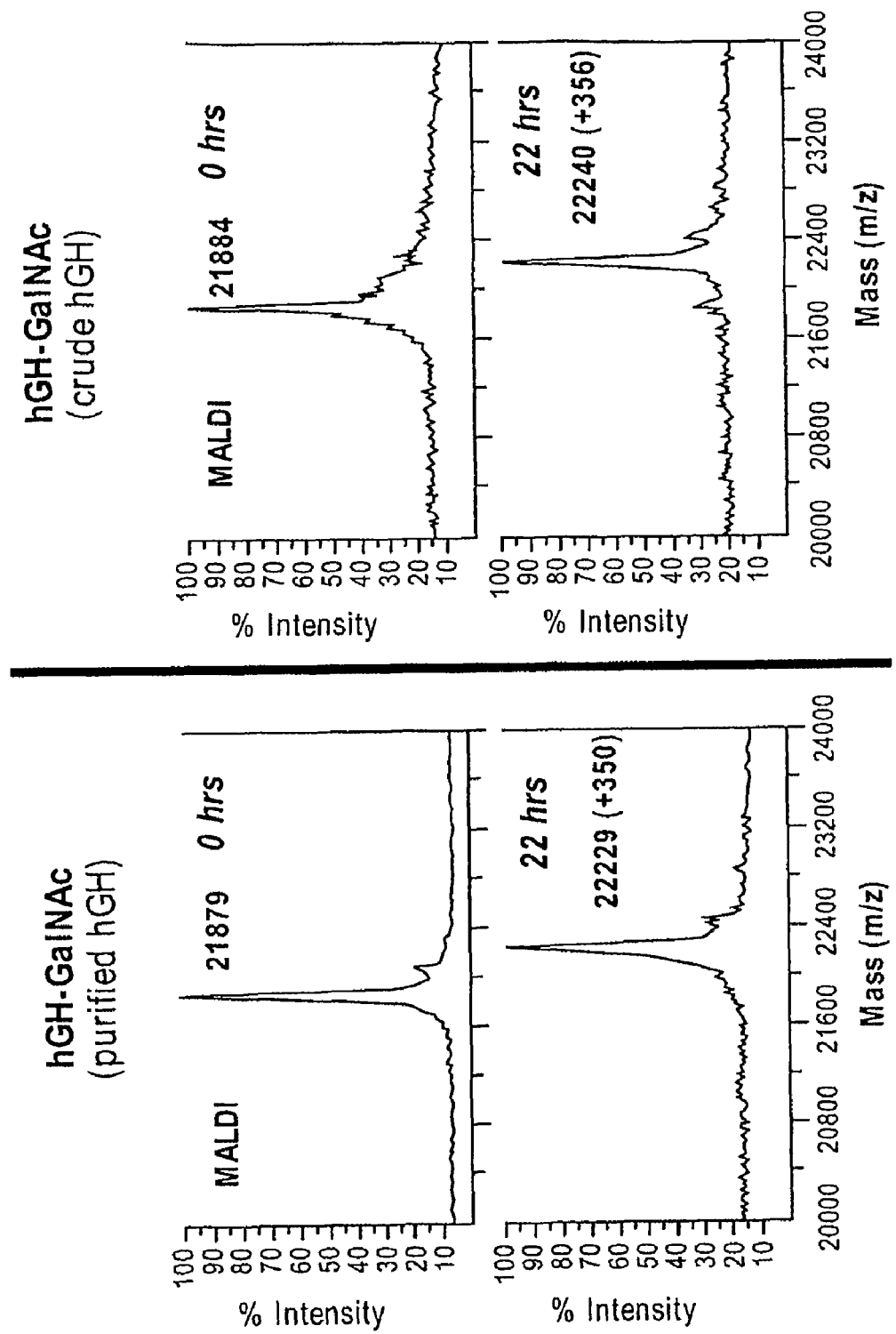
FIG. 2 demonstrates further glycosylation of hGH-GalNAc. The starting material originated from purified hGH (left) or a crude cell lysate containing hGH (right). hGH was produced in a trxB, gor, supp E. coli strain. GalNAc was first transferred to hGH as described in FIG. 1. Galactose was transferred to the hGH-GalNAc protein after addition of reaction substrates and a crude cell lysate from a trxB, gor, supp E. coli strain that expressed MBP-Core-1-GalT1 protein. Reaction products were analyzed by MALDI TOF mass spectrometry and compared to unglycosylated hGH. The expected mass due to addition of GalNAc-Gal (expected +365.6, observed +350 or +356) to hGH was observed.
Figure 3B:
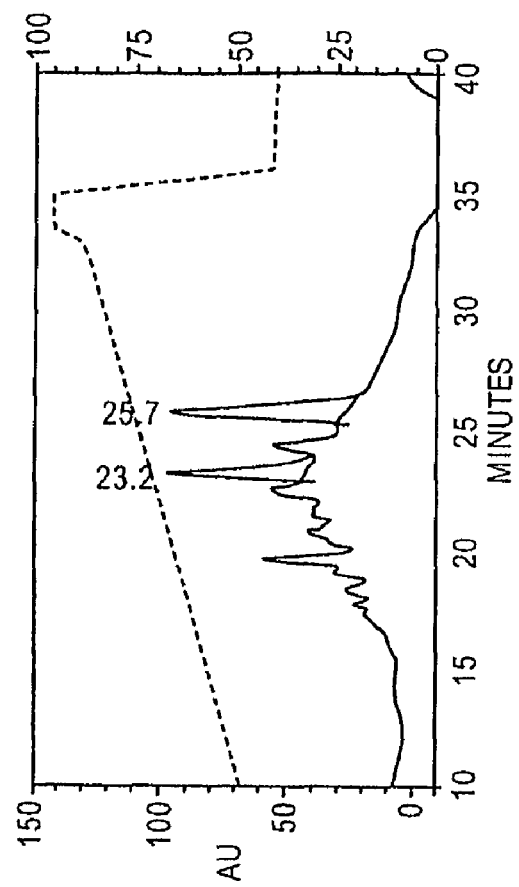
FIG. 3B provides RP-HPLC analysis of the GlycoPEGylation reaction at 62 hours. The retention time of the product hGH-GalNAc-Gal-SA-cys-PEG-40 kDa is 23.2 minutes. The retention time of the hGH starting material is 25.7 minutes. Zorbax 300SB-C3 150×2.1 mm, 5 micron column.
Figure 3A:
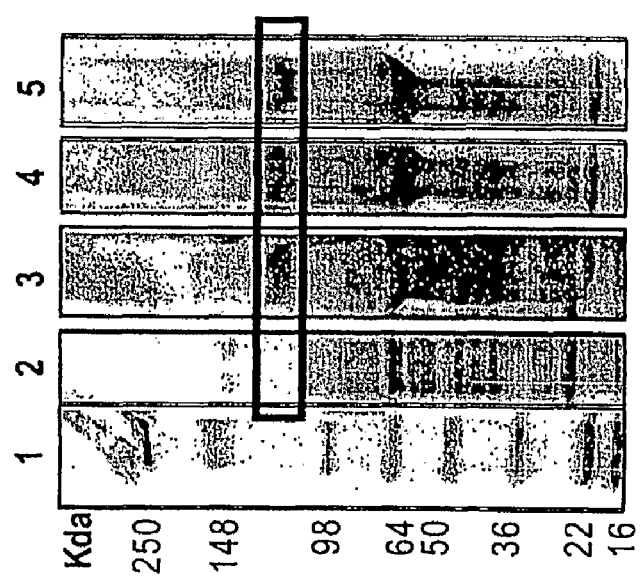
FIG. 3A is a SDS-PAGE analysis; colloidal blue stain. Lane 1: molecular weight markers; Lane 2: GlycoPEGylation reaction at 0 min; Lane 3: GlycoPEGylation reaction at 19 hours; Lane 4: GlycoPEGylation reaction at 46 hours; Lane 5: GlycoPEGylation reaction at 62 hours. The hGH-GalNAc-Gal-SA-cys-PEG-40 kDa product, boxed, is observed in Lanes 3, 4 and 5. The unmodified hGH band is observed in Lanes 2, 3, 4 and 5 at the 22 kDa band.

Preparation of hGH-GalNAc-Gal-SA-Cys-PEG-40 kDa using *E. coli* lysates of hGH, GalNAcT2 with GalE. MBP-Core-1-GalT1 and MBP-ST3Gal1. The hGH lysate (SEQ ID NO:7) (200 mcg hGH, 0.025 mL, 9.1 nanomoles) was combined with 50 mM Tris-HCl, 20 mM NaCl, 0.02% $NaN_3$, 0.01% polysorbate 80, pH 7.4 (4.8 mcL) and a solution of UDP-GlcNAc (91 nanomoles, 5.8 mcL in 50 mM Tris-HCl, 20 mM NaCl, 0.02% $NaN_3$, 0.01% polysorbate 80, pH 7.4, 10 mg/mL). A solution of $MnCl_2$ (200 mM $MnCl_2$ in water, 4 mcL) was added to the hGH lysate solution. The crude GalNAcT2/GalE enzyme lysate (0.75 mU GalNAcT2, 2 mcL) was added to the hGH mixture and mixed very gently. The reaction mixture was centrifuged (1 min, 13,000 rpm) to settle particulate matter and the supernatant was removed and incubated at 32° C. with gentle shaking for 17 hours. As shown in FIG. 1, the addition of GalNAc was determined to be complete by MALDI analysis of the reaction mixture. The hGH-GalNAc solution (6.8 nmol, 30 mcL) was combined with a solution of UDP-Gal (34 nmol, 2.1 mcL in 50 mM Tris-HCl, 20 mM NaCl, 0.02% $NaN_3$, 0.01% polysorbate 80, pH 7.4, 10 mg/mL). The MBP-Core-1-GalT1 enzyme lysate (20 mU, 3.75 mcL, 5.4 U/mL) was added to the hGH-GalNAc reaction mixture with gentle mixing. The reaction mixture was centrifuged (1 min, 13,000 rpm) to settle particulate matter and the supernatant was removed and incubated for 22 hrs at 32° C. As shown in FIG. 2, the addition of Gal was determined to be complete by MALDI analysis of the reaction mixture. A solution of CMP-SA-cys-PEG-40 kDa (5.84 nanomoles, 4.56 mcL in 50 mM Tris-HCl, 20 mM NaCl, 0.02% NaN$_3$, 0.01% polysorbate 80, pH 7.4, 1.25 mM) was added the hGH-GalNAc-Gal reaction mixture (15 mcL, 2.92 nanomoles). The MBP-ST3Gal1 lysate (5.9 mU, 4.3 mcL, 1.37 U/mL) and MnCl$_2$ (15 mcL of 200 mM solution in water) were added with gentle mixing. The reaction mixture was incubated at 32° C. for 62 hrs. The reaction was monitored for extent of PEGylation by SDS-PAGE and RP-HPLC (FIG. 3). The hGH-GalNAc-Gal-SA-cys-PEG-40 kDa product was detected by both SDS-PAGE analysis and RP-HPLC analysis.

Figure 4D:
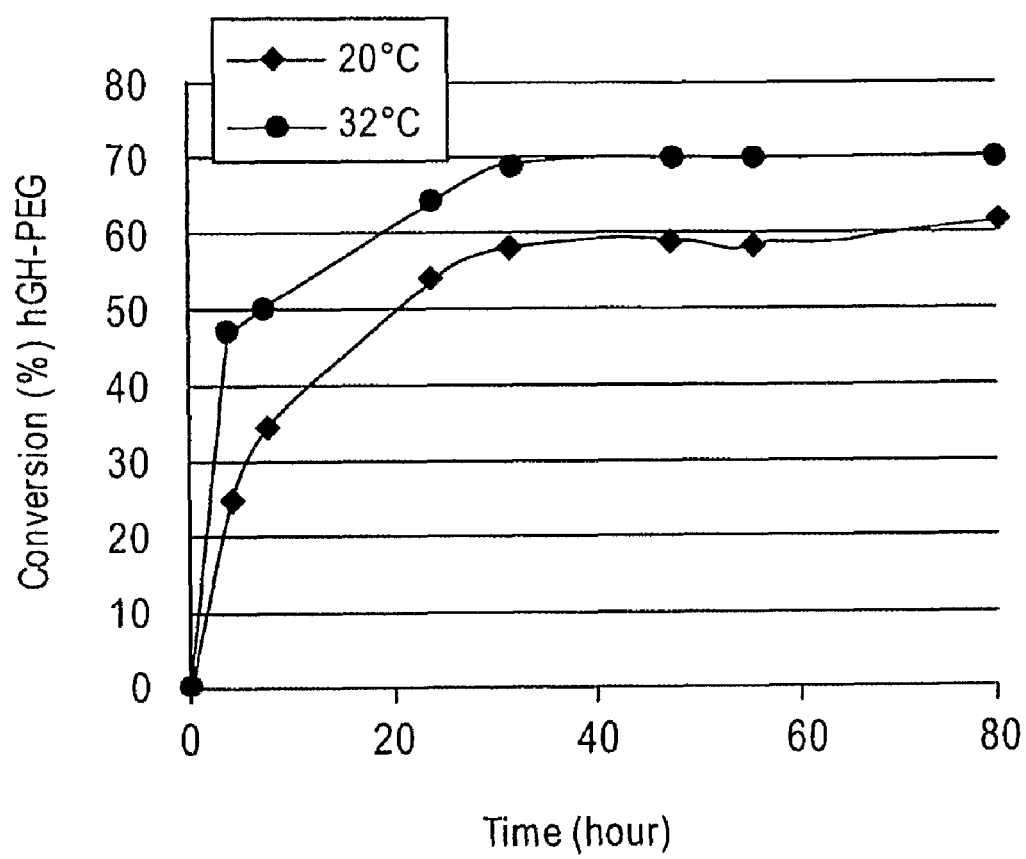
FIG. 4 demonstrates glycoPEGylation of hGH-GalNAc-Gal produced in crude lysates by purified ST3Gal1. The reaction scheme is presented in FIG. 4A. The glycosylated starting material originated from a crude cell lysate of hGH produced in a trxB, gor, supp E. coli strain. hGH-GalNAc-Gal protein prepared using crude lysate mixing (eg FIGS. 1-2) was glycoPEGylated with sialic acid-cys-PEG-40 kDa after addition of reaction substrates and a purified ST3Gal1 protein that was produced in a baculoviral system. Reactions were incubated for up to eighty hours at 20° C. or 32° C. Reaction products were analyzed by SDS-PAGE; the final timepoint is shown in FIG. 4B. The hGH-GalNAc-Gal-SA-cys-PEG-40 kDa product is boxed. RP-HPLC analysis of the final 32° C. glycoPEGylation reaction is shown in FIG. 4C. The retention time of the product hGH-GalNAc-Gal-SA-cys-PEG-40 kDa is 23.0 minutes. The retention time of the hGH starting material is 25.5 minutes. Zorbax 300SB-C3 150×2.1 mm, 5 micron column. A timecourse of hGH glycoPEGylation is provided in FIG. 4D. In the best reaction, up to seventy percent of the starting material was converted to hGH-GalNAc-Gal-SA-cys-PEG-40 kDa.

Preparation of hGH-GalNAc-Gal-SA-Cys-PEG-40 kDa using E. coli lysates of hGH, MBP-GalNAcT2, MBP-Core-1-GalT1 mixed with purified ST3Gal1. The hGH lysate (SEQ. ID NO:7) (22 mg hGH, 2.8 mL, 1 micromole) was diluted with 50 mM Tris-HCl, pH 7.4, 20 mM NaCl, 0.02% NaN$_3$ (0.61 mL). A solution of UDP-GalNAc (3.26 mg, 5 micromoles, 0.33 mL in 50 mM Tris-HCl, pH 7.4, 20 mM NaCl, 0.02% NaN$_3$, 10 mg/mL) was added to the hGH lysate. The resulting solution was adjusted to 0.01% polysorbate-80 (0.04 mL of 1% solution in 50 mM Tris-HCl, pH 7.4, 20 mM NaCl, 0.02% NaN$_3$) and 0.22 mL of a 200 mM MnCl$_2$ solution in water. The crude MBP-GalNAcT2 enzyme lysate (220 mU, 0.44 mL) was added to the hGH mixture, mixed very gently and incubated at room temperature for 16 hours. The addition of GalNAc was determined to be complete by MALDI analysis of the reaction mixture. A solution of UDP-Gal (3.05 mg, 5 micromoles, 0.31 mL in 50 mM Tris-HCl, pH 7.4, 20 mM NaCl, 0.02% NaN$_3$, 10 mg/mL) was added to the hGH-GalNAc solution and the resulting mixture was readjusted to 0.01% polysorbate-80 (0.01 mL of 1% solution in 50 mM Tris-HCl, pH 7.4, 20 mM NaCl, 0.02% NaN$_3$). The MBP-Core-1-GalT1 enzyme lysate (2.8 U, 0.44 mL) was added to the hGH-GalNAc reaction mixture with gentle mixing and the resulting solution was incubated for 24 hrs at room temperature. The addition of Gal was determined to be complete by MALDI analysis of the reaction mixture. A solution of CMP-SA-cys-PEG-40 kDa (27.6 mg, 0.69 micromoles, 0.55 mL in 50 mM Tris-HCl, pH 7.4, 20 mM NaCl, 0.02% NaN$_3$) was added to the hGH-GalNAc-Gal reaction mixture (5 mg, 1.2 mL, 0.23 micromoles). Purified ST3Gal1 enzyme (0.5 U, 0.77 mL) and MnCl$_2$ (0.07 mL of 200 mM solution in water) were added with gentle mixing. The reaction mixture was incubated at 20 and 32° C. for up to 80 hours. The reaction was monitored for extent of PEGylation by SDS-PAGE and RP-HPLC (FIGS. 4A and 4B). The retention time of the product hGH-GalNAc-Gal-SA-cys-PEG-40 kDa is 23.0 minutes. The retention time of the hGH starting material is 25.5 minutes (FIG. 4C). Zorbax 300SB-C3 150×2.1 mm, 5 micron column. Over the course of the incubation, the majority of the unglycosylated hGH starting material was converted to the glycoPEGylated product, with better yield at 32° C. (FIG. 4D).

Purification of hGH-GalNAc-Gal-SA-cys-PEG-40 kDa produced by crude lysate mixing. hGH-GalNAc-Gal-SA-cys-PEG-40 kDa was purified from a crude lysate after glycosylation and glycoPEGylation with the glycosyltransferase-containing lysates from a trxB, gor, supp E. coli strain. The first step was ion exchange chromatography using a strong anion exchanger, e.g., a Q-sepharose fast flow column. The second step was size exclusion chromatography using a Superdex 200 column. A hGH-GalNAc-Gal-SA-cys-PEG-40 kDa-containing fraction was eluted from the size exclusion column. The protein was demonstrated by RP-HPLC to run mostly as a single peak (FIG. 5).

Figure 6:
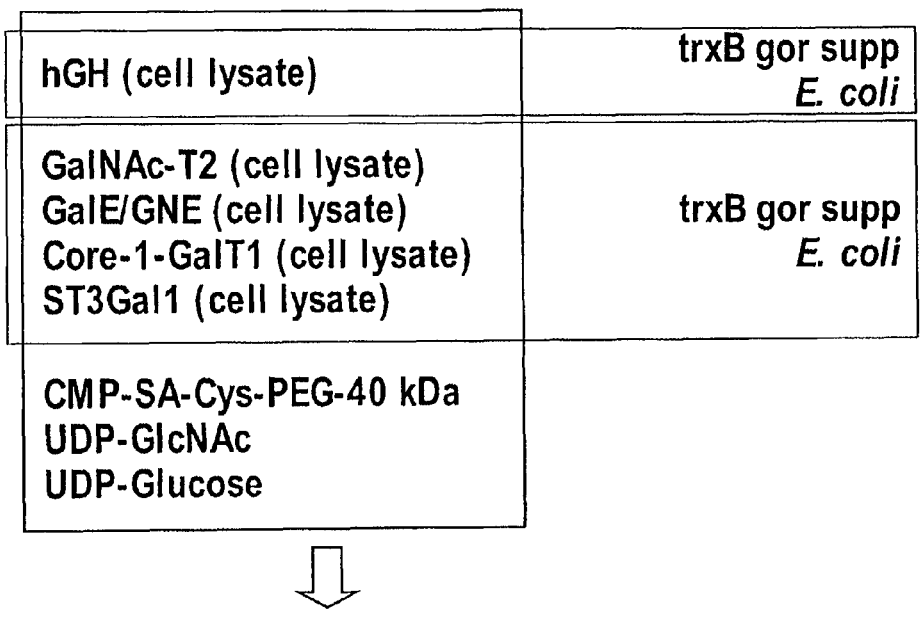
FIG. 6 shows a reaction scheme for production of glycoPEGylated hGH using lysates from two fermentations. Soluble, active hGH protein is expressed at high levels in a trxB, gor, supp E. coli strain. Separately, necessary glycosyltransferases, eg GalNAc-T2 Δ445, Core-1-Gal-T1, ST3Gal1, and accessory enzymes, eg GalE or GNE, are all coexpressed in the same trxB, gor, supp E. coli strain. After fermentation, the hGH cells and enzyme cells are lysed and mixed together in the presence of appropriate reaction substrates to form the glycoPEGylated product.

Production of hGH-GalNAc-Gal-SA-Cys-PEG-40 kDa using mixed E. coli lysates. hGH-GalNAc-Gal-SA-cys-PEG-40 kDa can also be produced in a one pot reaction using the following reagents. GalNAc-T2 (Δ445), GalE or GNE, Core-1-GalT1, and ST3Gal1, which are all co-expressed in a single trxB, gor, supp E. coli cell. The enzymes are expressed from multiple plasmids or are expressed from a single plasmid. Cell lysates containing the co-expressed enzymes are used to glycoPEGylate hGH expressed in trxb, gor, supp E. coli in the presence of the following reaction components: CMP-SA-Cys-PEG-40 kDa, UDP-GlcNAc, and UDP-Glucose. The hGH can be added as part of a cell lysate or can be further purified before addition to the reaction mixture. The reaction scheme is presented in FIG. 6.

Preparation of hGH-GalNAc-Gal-SA-Cys-PEG-40 kDa using purified glycosyltransferases. The hGH (SEQ ID NO:7) from trxb, gor, supp E. coli fermentation lysates was purified by anion exchange chromatography (DEAE) and size exclusion chromatography (Superdex 75). The purified hGH (53.6 mg, 2.4 micromoles) was adjusted to 0.01% Polysorbate 80 in 50 mM Tris-HCl, 20 mM NaCl, 0.02% NaN$_3$, pH 7.4 and concentrated to a volume of 17.8 mL using a centrifugal filter (5 kDa MWCO). The UDP-GalNAc (20 micromoles) was added as a solution in 50 mM Tris, 20 mM NaCl, 0.001% Polysorbate 80, 0.02% NaN$_3$, pH 7.4 (0.1 mL). A solution of MnCl$_2$ (0.1 M MnCl$_2$ in 50 mM Tris-HCl, 20 mM NaCl, 0.02% NaN$_3$, pH 7.4, 12.8 microliters) was added to GalNAcT2 (produced in baculovirus) enzyme (270 mU) and the resulting solution was added to the hGH solution and mixed very gently. The reaction mixture was incubated at room temperature for 17 hours at which time additional GalNAcT2 enzyme (270 mU) and MnCl$_2$ solution (0.1 M MnCl$_2$ in 50 mM Tris-HCl, 20 mM NaCl, 0.02% NaN$_3$, pH 7.4, 12.8 microliters) were added. The addition of GalNAc was determined to be complete by MALDI analysis of the reaction mixture after incubation for a total of 27.5 hours. A solution of MnCl$_2$ (0.1 M MnCl$_2$ in 50 mM Tris-HCl, 20 mM NaCl, 0.02% NaN$_3$, pH 7.4, 19 microliters) was added to Core-1-GalT1 enzyme (produced in baculovirus) (0.238 U). The Core-1-GalT1 enzyme solution and a solution of UDP-Gal in 50 mM Tris-HCl, 20 mM NaCl, 0.02% NaN$_3$, pH 7.4 (24 micromoles, 0.1 mL) were added to the hGH-GalNAc reaction mixture with gentle mixing and the resulting solution was incubated for 15 hrs at room temperature. At this time additional Core-1-GalT1 enzyme (0.238 U) and MnCl$_2$ solution (0.1 M MnCl$_2$ in 50 mM Tris-HCl, 20 mM NaCl, 0.02% NaN$_3$, pH 7.4, 19 microliters) were added to the hGH reaction mixture. The reaction mixture was incubated at room temperature for an additional 17.5 hrs and the addition of Gal was determined to be complete by MALDI analysis. The CMP-SA-Cys-PEG-40 kDa (4.85 micromoles) was added to the hGH-GalNAc-Gal reaction mixture as a solution in 50 mM Tris-HCl, 20 mM NaCl, 0.02% NaN$_3$, pH 7.4 (1 mL) and ST3 Gal1 enzyme (produced in baculovirus) (4.26 U) was added with gentle mixing. The reaction mixture was incubated at room temperature for 50 hrs and was monitored for extent of PEGylation by SDS PAGE and RP-HPLC. The product, hGH-GalNAc-Gal-SA-cys-PEG-40 kDa, was purified using SP Sepharose, SEC (Superdex 200), and Phenyl Sepharose chromatography. The purified hGH-GalNAc-Gal-SA-cys-PEG-40 kDa was concentrated and then formulated. The product was analyzed by a BCA protein assay, SDS-PAGE gels (silver stain), RP-HPLC, and for cell proliferation. This process yielded 6.11 mg of active hGH-GalNAc-Gal-SA-cys-PEG-40 kDa in >96% purity.

Example 2

Figure 7A:
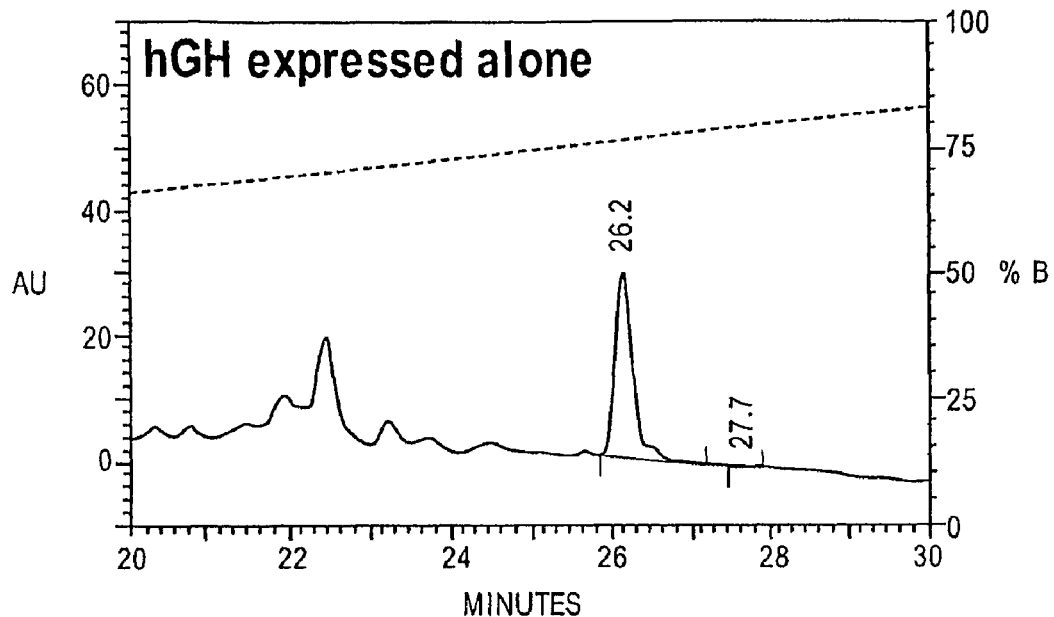
FIG. 7A is a control RP-HPLC of crude lysate from trxB, gor, supp E. coli expressing hGH alone.
Figure 7B:
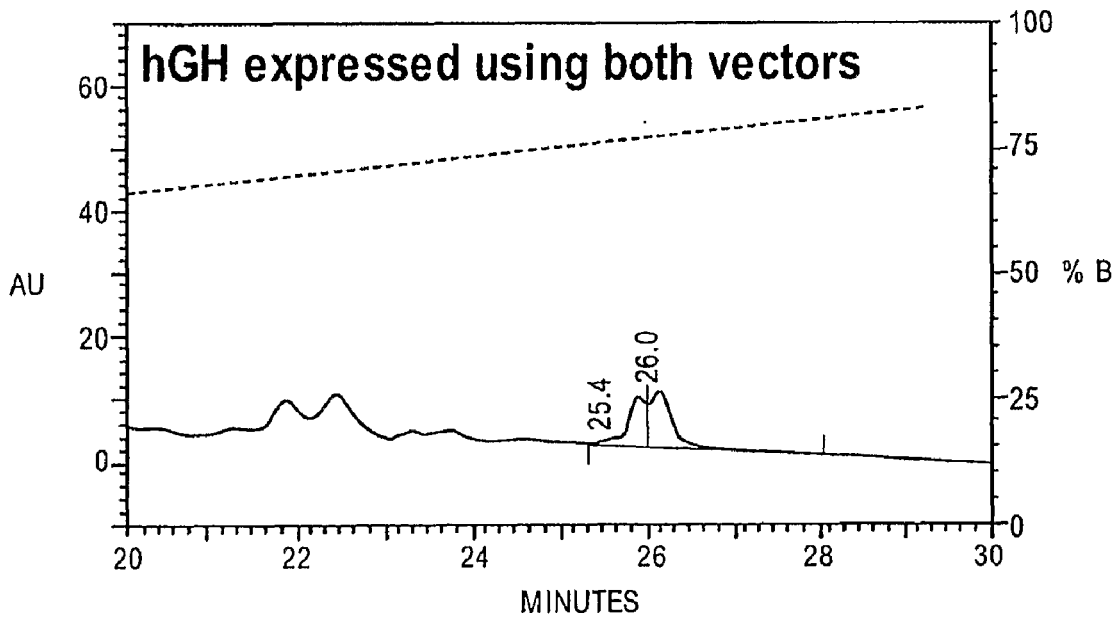
FIG. 7B shows RP-HPLC of crude lysate from trxB, gor, supp E. coli coexpressing hGH with GalNAc-T2 Δ51 Δ445 and GalE. The peak shift in the lower graph, as compared to the control, indicates that the hGH was glycosylated in vivo.
Figure 9A:
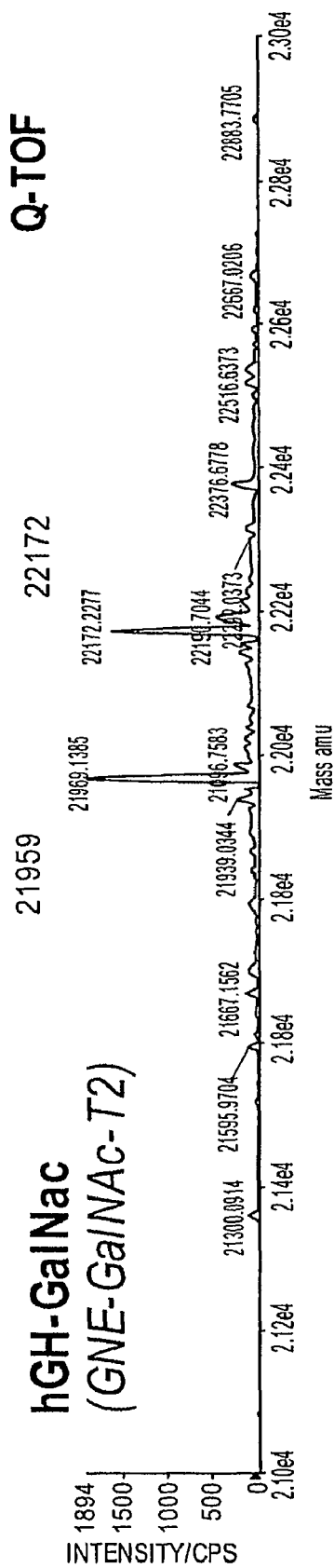
FIG. 9 shows LC/MS of the in vivo glycosylation of hGH that verifies the glycosylation reaction occurred. Crude cell lysates from a trxB, gor, supp E. coli strain expressing hGH, GalNAc-T2 Δ51 Δ445, and either GNE (FIG. 9A) or GalE (FIG. 9B) were analyzed. The expected mass due to addition of GalNAc (expected +203.2, observed +203 for both) to hGH was observed.
Figure 9B:
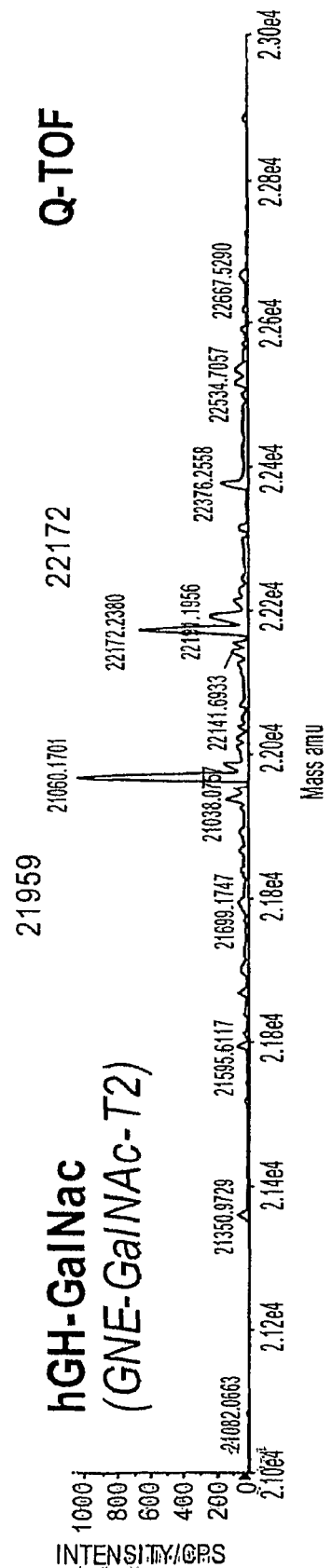

Expression of Soluble, Glycosylated Human Growth Hormone in Bacteria hGH was expressed from a pACYC184-derived vector carrying the expression cassette from pCWin2 with a modified 5' UTR, in a trxB, gor, supp *E. coli* strain. The *E. coli* cells also included a vector that expressed GalNAc-T2 (Δ51 Δ445) with GalE (SEQ ID NO:79) or another epimerase, GNE (SEQ ID NO:80), from pCWin-2 derived expression cassettes with modified 5' UTRs. Thus, the trxb, gor, supp *E. coli* strain expressed hGH P254 at relatively low expression levels, and GalNAc-T2 (Δ51 Δ445) and a dual specificity Glc/GlcNAc epimerase at relatively high expression levels. Cells were grown in medium in shake flasks. RP-HPLC was used to monitor the reaction. Results are shown in FIG. 7. A chromatogram of cell lysate from a control *E. coli* culture that expressed only hGH (peak 26.2) is shown in FIG. 7A. A chromatogram of the cell lysate from hGH (split peak circa 26.0) and enzyme-expressing *E. coli* strain is shown in FIG. 7B. The hGH elution profile is different for the two cultures, indicating that hGH is glycosylated when grown in the presence of the GalNAc-T2 (Δ51 Δ445) protein. The table in FIG. 8 summarized the expressed yield and percent conversion of hGH to hGH-GalNac in *E. coli* cells that expressed either GalE or GNE with the GalNAc-T2 (Δ51 Δ445) protein. The percent conversions ranged from 31.2% to 41.2%, with a slightly higher conversion observed with expression of the GalE protein. The presence of hGH-GalNac in lysates from *E. coli* cells that expressed hGH, GalNAc-T2 (Δ51 Δ445), and an epimerase was verified by LC/MS. Results are shown in FIG. 9.

Additional glycosyltransferases of the O-linked glycosylation pathway can be co-expressed with GalNAc-T2 (Δ445) and hGH or a therapeutic protein of interest in a trxB, gor, supp *E. coli* strain. An exemplary reaction scheme is presented in FIG. 10.

Figure 12:
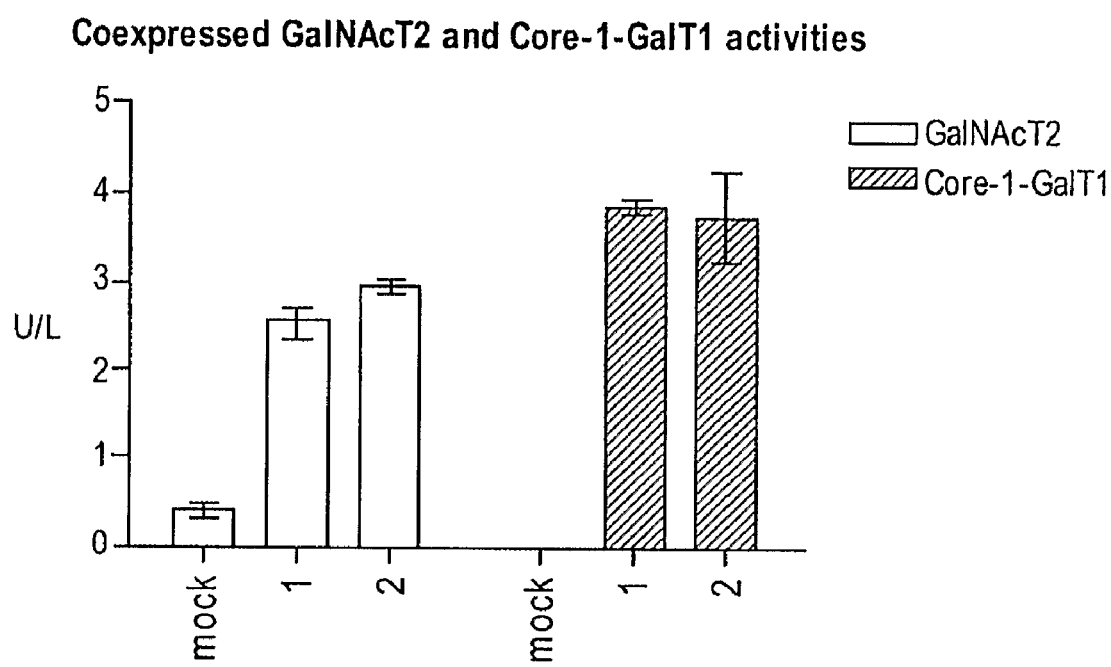
FIG. 12 demonstrates the soluble crude lysate activity levels of GalNAcT2 and Core-1-GalT1 expressed from polycistronic expression cassettes in trxB, gor, supp E. coli. The mock control is from cells handled in parallel bearing an empty expression vector.
Figure 13:
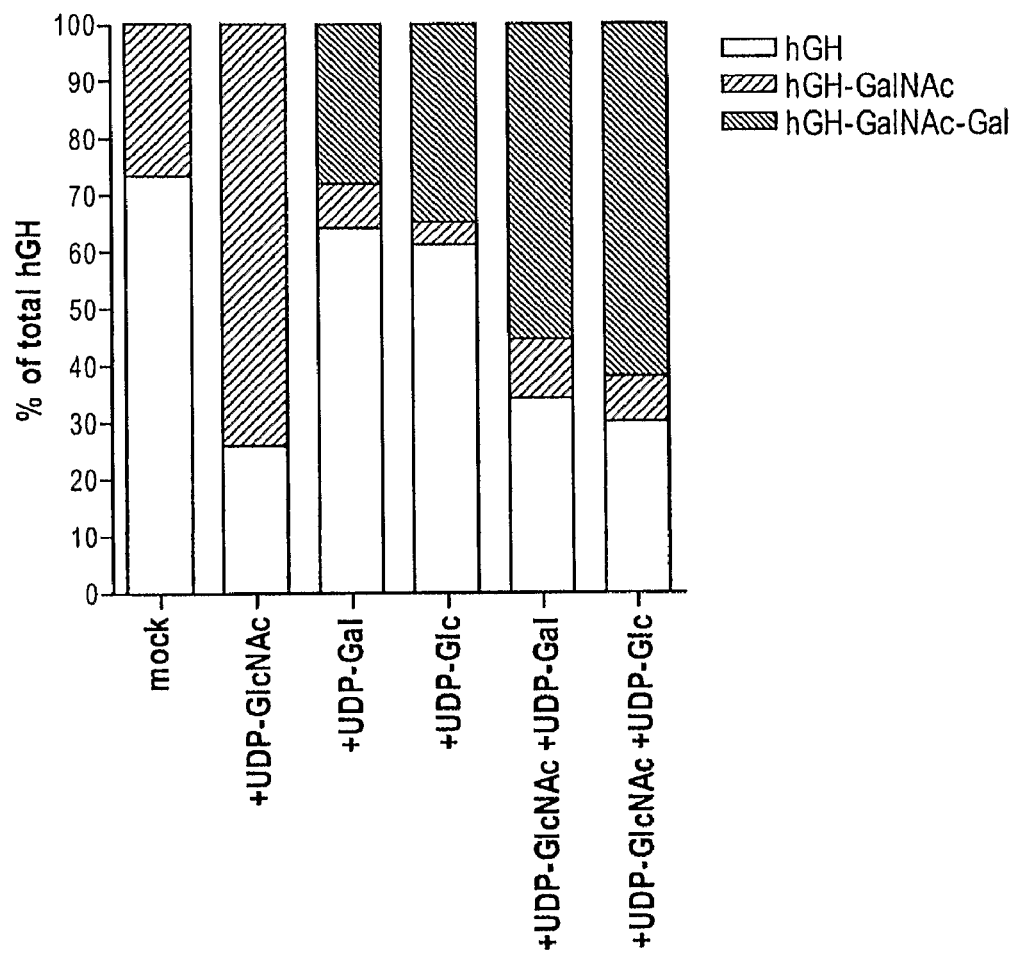
FIG. 13 provides the distribution of total hGH as nonglycosylated hGH (clear), hGH-GalNAc (light gray), and hGH-GalNAc-Gal (dark gray) when crude coexpression lysate was reacted in vitro with additional sugar nucleotides. hGH was coexpressed with glycosyltransferases and accessory enzymes in trxB, gor, supp E. coli using a polycistronic expression cassette. The mock treated sample was handled in parallel but did not receive exogenous sugar nucleotide.
Figure 14B:
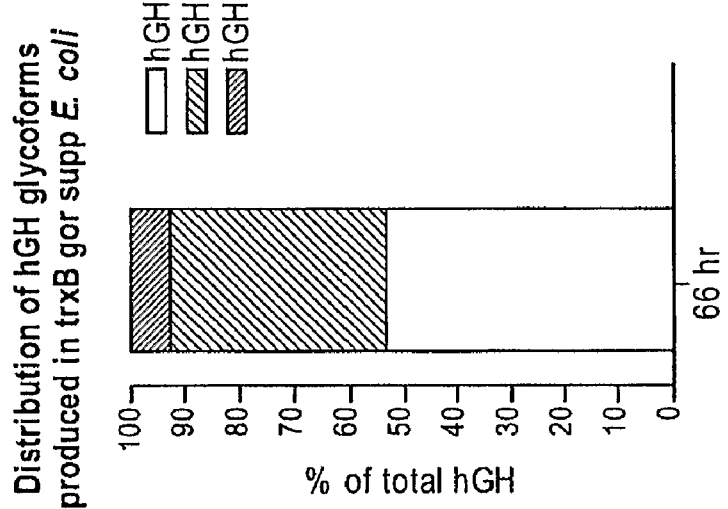
FIG. 14B shows distribution of in vivo glycosylated hGH product after 66 hours of induction.
Figure 14A:
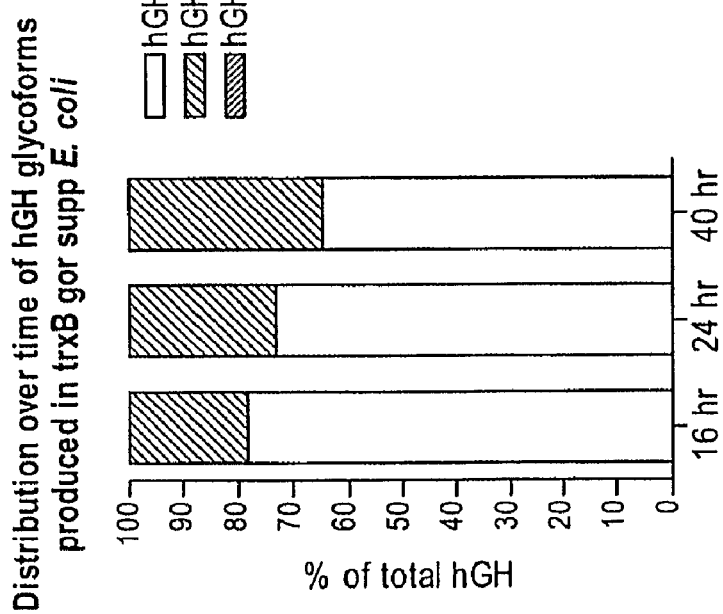
FIG. 14A shows the distribution of in vivo glycosylated hGH product over an induction time course from 16 to 40 hours.

For example, glycosylated hGH was produced by the coexpression of hGH with GalNAcT2 (Δ53 Δ445), Core-1-GalT1 and GNE in trxB, gor, supp *E. coli* from a polycistronic expression cassette on a single plasmid. Expression was induced in shake flasks at 20° C. for approximately 16 hours. Two cassettes were tested; in the first, an extended 5' UTR precedes each cistron. In the second cassette, an extended 5' UTR only precedes the first two cistrons, while simple Shine-Dalgarno sequences precede the last two cistrons. Crude cell lysates from induced cells bearing either of these two polycistronic constructs was assayed for hGH levels and glycosylation by RP-HPLC and LC/MS. As summarized in FIG. 11, total hGH expression was approximately 50-60 mg/L, with 30% conversion yielding approximately 15-18 mg/L hGH-GalNAc. In a separate experiment, GalNAcT2 and Core-1-GalT1 activity was measured in lysates similarly prepared from these strains (FIG. 12). Both enzymes were active. In addition, hGH in lysate from trxB, gor, supp *E. coli* expressed from polycistronic expression cassette 2 was further glycosylated in vitro in a reaction of clarified lysate with 50 mM Tris pH 7, 20 mM NaCl, 0.2% NaN$_3$, 0.01% Tween-80, 20 mM MnCl$_2$, and 10 mM of the indicated sugar nucleotides (FIG. 13). The reaction was carried out for five hours at 32° C., and conversion of hGH monitored by LC/MS. As plotted in FIG. 13, yield of hGH-GalNAc was increased by the addition of UDP-GlcNAc. In turn, hGH-GalNAc was readily converted to hGH-GalNAc-Gal with the addition of UDP-Gal or UDP-Glc. The addition of both UDP-GlcNAc and UDP-Glc resulted in the conversion of over 60% of total hGH into hGH-GalNAc-Gal. Finally, trxB, gor, supp *E. coli* cells bearing polycistronic expression cassette 2 were induced up to 40 hours in shake flasks at 20° C. The distribution of hGH glycosylation in crude extract from these cells was determined by LC/MS, and is plotted in FIG. 14A. In a separate experiment, cells bearing polycistronic expression cassette 2 were induced in shake flasks at 20° C. for 66 hours. The distribution of hGH glycosylation in crude extract from these cells was determined by LC/MS as shown in FIG. 14B. After the 66 hour induction, the hGH-GalNAc-Gal product was detected.

Example 3

Co-Expression of Glycosyltransferases with a Protein Disulfide Isomerase

MBP-tagged human GalNAcT2 Δ51 (SEQ ID NO:28) and MBP-tagged rat ST3Gal3 (Δ72, SEQ ID NO:78) were co-expressed in trxB gor supp mutant *E. coli* cells with a protein disulfide isomerase. *E. coli* DsbC (D22H Δ20) was cloned by PCR into a ampicillin-selectable vector derived from pACYC177 bearing the expression cassette from pCWin2 with a modified 5' UTR. Numbering of the N-terminal deletion and the D22H mutation is based on full length DsbC, SEQ ID NO:18. The deletion of DsbC residues 1-20 removes its signal sequence and is predicted to result in the cytoplasmic expression of DsbC. Methods, including protein induction, lysate preparation, and activity analyses, were essentially as described in Examples 4 and 6.

Either GalNAcT2 alone or DsbC and GalNAcT2 expression plasmids together were transformed into trxB gor supp mutant cells, and induced for expression overnight at 20° C. in shake flask cultures. As shown in Table 2, MBP-GalNAc-T2 was solubly expressed at higher levels when coexpressed with DsbC. Similarly, coexpression of MBP-ST3Gal3 with DsbC in trxB gor supp mutant cells improved expressed activity levels relative to the MBP-ST3Gal3-only cells.

TABLE 2

Yields based on observed enzyme activity of glycosyltransferases coexpressed with a protein disulfide isomerase

| Expressed Glycosyltransferase | Expressed, in trxB gor supp mutant cells Enzyme Activity (U/L) | Coexpressed in trxB gor supp mutant cells with a protein disulfide isomerase, DsbC Enzyme Activity (U/L) |
|---|---|---|
| MBP-GalNAcT2 | 6.4 | 25 |
| MBP-ST3Gal3 | 4 | 20 |

A summary of the highest observed activities in lysate samples for the indicated glycosyltransferases expressed in trxB gor supp mutant *E. coli* with or without coexpression of a protein disulfide isomerase.

Example 4

Expression of Eukaryotic Glycosyltransferase Mutants as Soluble Proteins in Bacteria

Eukaryotic Glycosyltransferases from the O-Linked Glycosylation Pathway

Figure 15:
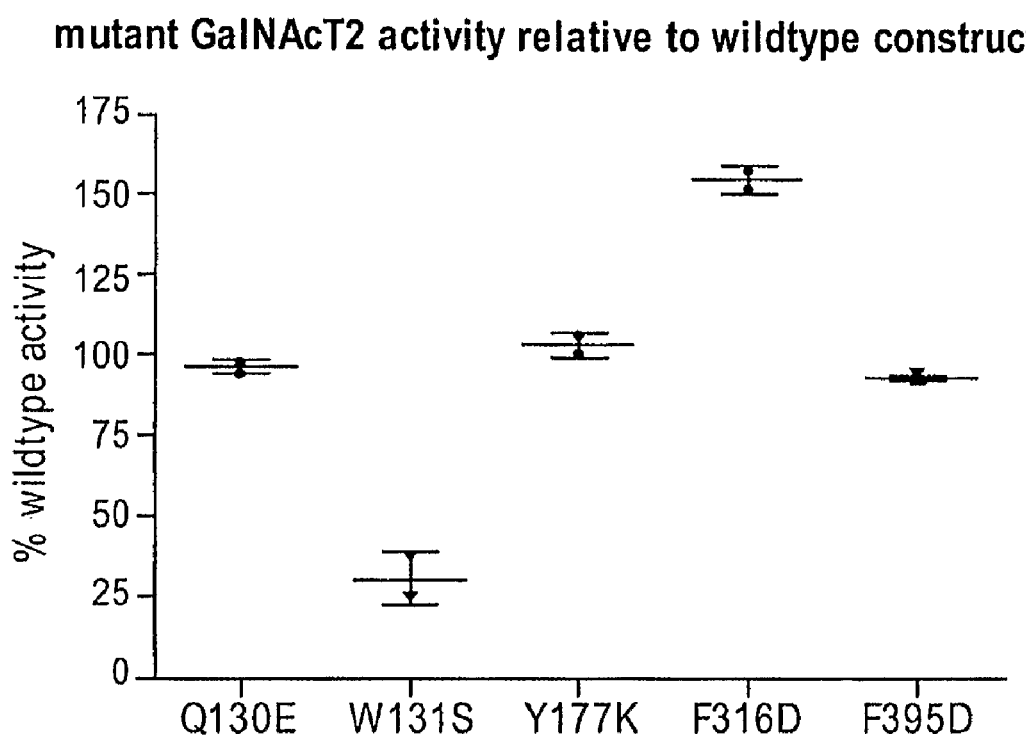
FIG. 15 provides the comparison of soluble lysate activity levels of catalytic domain GalNAc-T2 substitution mutants relative to non-mutated GalNAc-T2 when expressed in trxB gor supp mutant *E. coli*.

GalNAcT2 Δ51 Δ445 wildtype and mutant constructs designed to alter putative solvent exposed residues (Q130E, W131S, Y177K, F316D, and F395D, mutation positions indicated based on full length wildtype human GalNAcT2) were expressed in a trxB, gor, supp *E. coli* strain. Cells were grown in shake flasks, and induced for at least 16 hours at 20° C. with IPTG. Crude lysates were prepared and tested for expressed GalNAc transferase activity in a reaction with 20 mM Tris pH 7, 10 mM MnCl$_2$, 1.5 mM UDP-GalNAc, 1 mM synthetic peptide acceptor. Following a 30 minute incubation at 37° C., the reaction was quenched with 0.01N HCl, and the peptide acceptor was separated from the reaction mix by centrifugation through a 10,000 MWCO concentrator. Peptide and GalNAc-peptide were detected and quantified by RP-HPLC. One of the GalNAcT2 substitution mutants, F316D, improved enzyme activity expressed in trxB, gor, supp E. coli by 50% (FIG. 15). Only the W131S mutation exhibited reduced enzymatic activity as compared to the unmutated GalNAcT2 protein. Activities of the other three mutants were about equal to those of the unmutated GalNAcT2 protein.

Core-1-GalT1 Δ50 and Δ31 were expressed in trxB, gor, supp E. coli shake flask cultures induced with IPTG at 20° C. for at least 16 hours. Clarified cell lysates were tested for relative galactosyltransferase activities in a reaction with a synthetic acceptor glycopeptide containing a GalNAc-Thr residue. GalNAc-peptide and Gal-GalNAc-peptide were detected and quantified by RP-HPLC. The shorter Δ50 form of untagged Core-1-GalT1 solubly expressed at 5.1 U/L, whereas the longer Δ31 form solubly expressed at 1.7 U/L.

Eukaryotic Glycosyltransferases from the N-Linked Glycosylation Pathway

MBP-tagged ST3Gal3 Δ72 and untagged ST3Gal3 Δ72 constructs were expressed in a trxB, gor, supp E. coli strain. Both were grown in shake flasks, and untagged ST3Gal3 was also grown in a 10 L batch fermentation. Clarified lysates were prepared and tested for expressed sialyltransferase activity in a reaction with 20 mM MOPS pH 6.5, 0.1 mg/ml BSA, 10 mM MnCl$_2$, 2 mM CMP-NAN, and 30 mM lacto-n-neotetraose. Following a two hour incubation at 30° C., the reaction was stopped by heat inactivation, and the reaction substrate and product detected and quantified by HPLC. In shake flasks, MBP-ST3Gal3 and untagged ST3Gal3 solubly expressed at 4.6 and 1 U/L, respectively. In the fermentor, soluble expression of untagged ST3Gal3 reached 2 U/L by 48 hours post-induction.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

INFORMAL SEQUENCE LISTING

Human FGF-20
SEQ ID NO: 1
MAPLAEVGGFLGGLEGLGQQVGSHFLLPPAGERPPLLGERRSAAERSARG
GPGAAQLAHLHGILRRRQLYCRTGFHLQILPDGSVQGTRQDHSLFGILEF
ISVAVGLVSIRGVDSGLYLGMNDKGELYGSEKLTSECIFREQFEENWYNT
YSSNIYKHGDTGRRYFVALNKDGTPRDGARSKRHQKFTHFLPRPVDPERV
PELYKDLLMYT.

Human mature FGF-21
SEQ ID NO: 2
MDSDETGFEHSGLWVSVLAGLLLGACQAHPIPDSSPLLQFGGQVRQRYLY
TDDAQQTEAHLEIREDGTVGGAADQSPESLLQLKALKPGVIQILGVKTSR -continued FLCQRPDGALYGSLHFDPEACSFRELLLEDGYNVYQSEAHGLPLHLPGNK
SPHRDPAPRGPARFLPLPGLPPALPEPPGILAPQPPDVGSSDPLSMVGPS
QGRSPSYAS.

Human Glucocerebrosidase aa 38-536
SEQ ID NO: 3
MGARPCIPKSFGYSSVVCVCNATYCDSFDPPTFPALGTFSRYESTRSGRR
MELSMGPIQANHTGTGLLLTLQPEQKFQKVKGFGGAMTDAAALNILALSP
PAQNLLLKSYFSEEGIGYNIIRVPMASCDFSIRTYTYADTPDDFQLHNFS
LPEEDTKLKIPLIHRALQLAQRPVSLLASPWTSPTWLKTNGAVNGKGSLK
GQPGDIYHQTWARYFVKFLDAYAEHKLQFWAVTAENEPSAGLLSGYPFQC
LGFTPEHQRDFIARDLGPTLANSTHHNVRLLMLDDQRLLLPHWAKVVLTD
PEAAKYVHGIAVHWYLDFLAPAKATLGETHRLFPNTMLFASEACVGSKFW
EQSVRLGSWDRGMQYSHSIITNLLYHVVGWTDWNLALNPEGGPNWVRNFV
DSPIIVDITKDTFYKQPMFYHLGHFSKFIPEGSQRVGLVASQKNDLDAVA
LMHPDGSAVVVVLNRSSKDVPLTIKDPAVGFLETISPGYSIHTYLWRRQ.

Human NT3
SEQ ID NO: 4
MYAEHKSHRGEYSVCDSESLWVTDKSSAIDIRGHQVTVLGEIKTGNSPVK
QYFYETRCKEARPVKNGCRGIDDKHWNSQCKTSQTYVRALTSENNKLVGW
RWIRIDTSCVCALSRKIGRT.

MBP-tagged human pro-NT-3
SEQ ID NO: 5
MKTEEGKLVIWINGDKGYNGLAEVGKKFEKDTGIKVTVEHPDKLEEKFPQ
VAATGDGPDIIFWAHDRFGGYAQSGLLAEITPDKAFQDKLYPFTWDAVRY
NGKLIAYPIAVEALSLIYNKDLLPNPPKTWEEIPALDKELKARGKSALMF
NLQEPYFTWPLIAADGGYAFKYENGKYDIKDVGVDMAGAKAGLTFLVDLI
KNKHMNADTDYSIAEAAFNKGETAMTINGPWAWSNIDTSKVNYGVTVLPT
FKGQPSKPFVGVLSAGINAASPNKELAKEFLENYLLTDEGLEAVNKDKPL
GAVALKSYEEELAKDPRIAATMENAQKGEIMPNIPQMSAFWYAVRTAVIN
AASGRQTVDEALKDAQTNSSSNNNNNNNNNNLGPGAAHYVEFGSHMQGNN
MDQRSLPEDSLNSLIIKLIQADILKNKLSKQMVDVKENYQSTLPKAEAPR
EPERGGPAKSAFQPVIAMDTELLRQQRRYNSPRVLLSDSTPLEPPFLYLM
EDYVGSPVVANRTSRRKRYAEHKSHRGEYSVCDSESLWVTDKSSAIDIRG
HQVTVLGEIKTGNSPVKQYFYETRCKEARPVKNGCRGIDDKHWNSQCKTS
QTYVRALTSENNKLVGWRWIRIDTSCVCALSRKIGRT.

Mutant human GH #1
SEQ ID NO: 6
MFPTIPLSRLFDNAMLRAHRLHQLAFDTYQEFEEAYIPKEQKYSFLQNPQ
TSLCFSESIPTPSNREETQQKSNLELLRISLLLIQSWLEPVQFLRSVFAN
SLVYGASDSNVYDLLKDLEEGIQTLMGRLEDGSPTINTIFKQTYSKFDTN
SHNDDALLKNYGLLYCFRKDMDKVETFLRIVQCRSVEGSCGF.

Mutant human GH #2
SEQ ID NO: 7
MFPTIFLSRLFDNAMLRAHRLHQLAFDTYQEFEEAYIPKEQKASFLQNPQ
TSLCFSESIPTPSNREETQQKSNLELLRISLLLIQSWLEPVQFLRSVFAN -continued
SLVYGASDSNVYDLLKDLEEGIQTLMGRLEDGSPTINTIANQTASKFDTN

SHNDDALLKNYGLLYCFRKDMDKVETFLRIVQCRSVEGSCGF.

dnaK *E. coli* EG10242 HSP-70-type molecular
chaperone, heat-inducible
SEQ ID NO: 8
MGKIIGIDLGTTNSCVAIMDGTTPRVLENAEGDRTTPSIIAYTQDGETLV

GQPAKRQAVTNPQNTLFAIKRLIGRRFQDEEVQRDVSIMPFKIIAADNGD

AWVEVKGQKMAPPQISAEVLKKMKKTAEDYLGEPVTEAVITVFAYFNDAQ

RQATKDAGRIAGLEVKRIINEPTAAALAYGLDKGTGNRTIAVYDLGGGTF

DISIIEIDEVDGEKTFEVLATNGDTHLGGEDFDSRLINYLVEEFKKDQGI

DLRNDPLAMQRLKEAAEKAKIELSSAQQTDVNLPYITADATGPKHMNIKV

TRAKLESLVEDLVNRSIEPLKVALQDAGLSVSDIDDVILVGGQTRMPMVQ

KKVAEFFGKEPRKDVNPDEAVAIGAAVQGGVLTGDVKDVLLLDVTPLSLG

IETMGGVMTTLIAKNTTIPTKHSQVFSTAEDNQSAVTIHVLQGERKRAAD

NKSLGQFNLDGINPAPRGMPQIEVTFDIDADGILHVSAKDKNSGKEQKIT

IKASSGLNEDEIQKMVRDAEANAEADRKFEELVQTRNQGDHLLHSTRKQV

EEAGDKLPADDKTAIESALTALETALKGEDKAAIEAKMQELAQVSQKLME

IAQQQHAQQQTAGADASANNAKDDDVVDAEFEEVKDKK.

clpB, *E. coli* EG10157 ClpB protease, ATP dependent
SEQ ID NO: 9
MRLDRLTNKFQLALADAQSLALGHDNQFIEPLHLMSALLNQEGGSVSPLL

TSAGINAGQLRTDINQALNRLPQVEGTGGDVQPSQSLVRVLNLCDKLAQK

RGDNFISSELFVLAALESRGTLADILKAAGATTANITQAIEQMRGGESVN

DQGAEDQRQALKKYTIDLTERAEQGKLDFVIGRDEEIRRTIQVLQRRTKN

NPVLIGEPGVGKTAIVEGLAQRIINGEVPEGLKGRRVLALDMGALVAGAK

YRGEFEERLKGVLNDLAKQEGNVILFIDELHTMVGAGKADGAMDAGNMLK

PALARGELHCVGATTLDEYRQYIEKDAALERRFQKVFVAEPSVEDTIAIL

RGLKERYELHHMVQITDPAIVAAATLSHRYIADRQLPDKAIDLIDEAASS

IRMQIDSKPEELDRLDRRIIQLKLEQQALMKESDEASKKRLDMLNEELSD

KERQYSELEEEWKAEKASLSGTQTEKAELEQAKIAIEQARRVGDLARMSE

LQYGKIPELEKQLEAATQLEGKTMRLLRNKVTDAEIAEVLARWTGIPVSR

NMESEREKLLRMEQELHHRVIGQNEAVDAVSNAIRRSRAGLADPNRPIGS

FLFLGPTGVGKTELCKALANFMFDSDEAMVRIDMSEFMEKHSVSRLVGAP

PGYVGYEEGGYLTEAVRRRPYSVILLDEVEKAHPDVFNILLQVLDDGRLT

DGQGRTVDFRNTVVIMTSNLGSDLIQERFGELDYAHMKELVLGVVSHNFR

PEFINRIDEVVVFHPLGEQHIASIAQIQLKRLYKRLEERGYEIHISDEAL

KLLSENGYDPVYGARPLKRAIQQQIENPLAQQILSGELVPGKVIRLEVNE

DRIVAVQ.

GroEL, *E. coli*
SEQ ID NO: 10
AAKDVKFGNDARVKMLRGVNVLADAVKVTLGPKGRNVVLDKSFGAPTITK

DGVSVAREIELEDKFENMGAQMVKEVASKANDAAGDGTTTATVLAQAIIT

EGLKAVAAGMNPMDLKRGIDKAVTAAVEELKALSVPCSDSKAIAQVGTIS

ANSDETVGKLIAEAMDKVGKEGVITVEDGTGLQDELDVVEGMQFDRGYLS

-continued
PYFINKPETGAVELESPFILLADKKISNIREMLPVLEAVAKAGKPLLIIA

EDVEGEALATLVVNTMRGIVKVAAVKAPGFGDRRKAMLQDIATLTGGTVI

SEEIGMELEKATLEDLGQAKRVVINKDTTTIIDGVGEEAAIQGRVAQIRQ

QIEEATSDYDREKLQERVAKLAGGVAVIKVGAATEVEMKEKKARVEDALH

ATRAAVEEGVVAGGGVALIRVASKLADLRGQNEDQNVGIKVALRAMEAPL

RQIVLNCGEEPSVVANTVKGGDGNYGYNAATEEYGNMIDMGILDPTKVTR

SALQYAASVAGLMITTECMVTDLPKNDAADLGAAGGMGGM.

Cpn10, *Oleispira* antarctica
SEQ ID NO: 11
MKIRPLHDRIVVRRKEEETATAGGIILPGAAAEKPNQGVVISVGTGRILD

NGSVQALAVNEGDVVVFGKYSGQNTIDIDGEELLILNESDIYGVLEA.

Cpn 60, *Oleispira* Antarctica
SEQ ID NO: 12
MAAKDVLFGDSARAKMLVGVNILADAVRVTLGPKGRNVVIEKSFGAPIIT

KDGVSVAREIELKDKFENMGAQMVKEVASQANDQAGDGTTTATVLAQAII

SEGLKSVAAGMNFMDLKRGIDKATAAVVAAIKEQAQPCLDTKAIAQVGTI

SANADETVGRLIAEAMEKVGKEGVITVEEGKGLEDELDVVEGMQFDRGYL

SPYFINNQEKMTVEMENPLILLVDKKIDNLQELLPILENVAKSGRPLLIV

AEDVEGQALATLVVNNLRGTFKVAAVKAPGFGDRRKAMLQDLAILTGGQV

ISEELGMSLETADPSSLGTASKVVIDKENTVIVDGAGTEASVNTRVDQIR

AEIESSTSDYDIEKLQERVAKLAGGVAVIKVGAGSEMEMKEKKDRVDDAL

HATRAAVEEGVVAGGGVALIRALSSVTVVGDNEDQNVGIALALRAMEAPI

RQIAGNAGAEGSVVVDKVKSGTGSFGFNASTGEYGDMIAMGILDPAKVTR

SSLQAAASIAGLMITTEAMVADAPVEEGAGGMPDMGGMGGMGGMPGMM.

Rat PDI protein, PDIA1_RAT
SEQ ID NO: 13
MLSRALLCLALAWAARVGADALEEEDNVLVLKKSNFAEALAAHNYLLVEF

YAPWCGHCKALAPEYAKAAAKLKAEGSEIRLAKVDATEESDLAQQYGVRG

YPTIKFFKNGDTASFKEYTAGREADDIVNWLKKRTGPAATTLSDTAAAES

LVDSSEVTVIGFFKDAGSDSAKQFLLAAEAVDDIPFGITSNSDVFSKYQL

DKDGVVLFKKFDEGRNNFEGEITKEKLLDFIKHNQLPLVIEFTEQTAPKI

FGGEIKTHILLFLPKSVSDYDGKLSNFKKAAEGFKGKILFIFIDSDHTDN

QRILEFFGLKKEECPAVRLITLEEEMTKYKPESDELTAEKITQFCHHFLE

GKIKPHLMSQELPEDWDKQPVKVLVGKNFEEVAFDEKKNVFVEFYAPWCG

HCKQLAPIWDKLGETYKDHENIVIAKMDSTANEVEAVKVHSFPTLKFFPA

SADRTVIDYNGERTLDGFKKFLESGGQDGAGDNDDLDLEEALEPDMEEDD

DQKAVKDEL.

*Erolp Sacchromyces*
SEQ ID NO: 14
MRLRTAIATLCLTAFTSATSNNSYIATDQTQNAFNDTHFCKVDRNDHVSP

SCNVTFNELNAINENIRDDLSALLKSDFFKYFRLDLYKQCSFWDANDGLC

LNRACSVDVVEDWDTLPEYWQPEILGSFNNDTMKEADDSDDECKFLDQLC

QTSKKPVDIEDTINYCDVNDFNGKNAVLIDLTANPERFTGYGGKQAGQIW

STIYQDNCFTIGETGESLAKDAFYRLVSGFHASIGTHLSKEYLNTKTGKW

EPNLDLFMARIGNFPDRVTNMYFNYAVVAKALWKIQPYLPEFSFCDLVNK

-continued

EIKNKMDNVISQLDTKIFNEDLVFANDLSLTLKDEFRSRFKNVTKIMDCV
QCDRCRLWGKIQTTGYATALKILFEINDADEFTKQHIVGKLTKYELTALL
QTFGRLSESIESVNMFEKMYGKRLNGSENRLSSFFQNNFFNILKEAGKSI
RYTIENINSTKEGKKKTNNSQSHVFDDLKMPKAEIVPRPSNGTVNKWKKA
WNTEVNNVLEAFRFIYRSYLDLPRNIWELSLMKVYKFWNKFIGVADYVSE
ETREPISYKLDIQ.

Pdilp Sacchromyces
SEQ ID NO: 15
MKMNLKRLVVTFFSCITFLLKFTIAAAEPPEGFPEPLNPTNFKEELSKGL
HIIDFYSPYCPHCKHLAPVWMETWEEFKEESKTLNITFSQVNCIESADLC
GDENIEYFPEIRLYNPSGYIKSFTETPRTKESLIAFARRESMDPNNLDTD
LDSAKSESQYLEGFDFLELIAGKATRPHLVSFWPTKDMNKSDDSLEFKNC
DKCHEFQRTWKIISRQLAVDDINTGHVNCESNPTICEELGFGDLVKITNH
RADREPKVALVLPNKTSNNLFDYPNGYSAKSDGYVDFARRTFTNSKFPNI
TEGELEKKANRDIDFLQERGRVTNNDIHLVFSYDPETVVIEDFDILEYLI
EPLSKIPNIYLHQIDKNLINLSRNLFGRMYEKINYDASQTQKVFNKEYFT
MNTVTQLFTFFMFKDGDPISYVFPGYSTTEMRNIDAIMDWVKKYSNPLVT
EVDSSNLKKLISFQTKSYSDLAIQLISSTDHKHIKGSNKLIKNLLLASWE
YEHIRMENNFEEINERRARKADGIKKIKEKKKPANKIVDKMREEIPHMDQ
KKLLLGYLDISKEKNFFRKYGITGEYKIGDVIIIDKSUNYYYNKDNFGNS
LTSNNPQLLREAFVSLNIPSKALYSSKLKGRLINSPFHNVLSFLDIIHGN
GMPGYLIVIVLFIAILKGPSIYRRYKVRKHYRAKRNAVGILGNMEKKKNQ
D.

DsbB protein, E. coli
SEQ ID NO: 16
NLRFLNQCSQGRGAWLLMAFTALALELTALWFQHVNLLKPCVLCIYERCA
LFGVLGAALIGAIAPKTPLRYVAMVIWLYSAFRGVQLTYEHTNLQLYPSP
FATCDFMVRFPEWLPLDKWVPQVFVASGDCAERQWDFLGLEMPQWLLGIF
IAYLIVAVLVVISQPFKAKKRDLFGR.

DsbA protein, E. coli
SEQ ID NO: 17
MKKIWLALAGLVLAFSASAAQYEDGKQYTTLEKPVAGAPQVLEFFSFFCP
HCYQFEEVLHISDNVKKKLPEGVKMTKYHVNFMGGDLGKDLTQAWAVAMA
LGVEDKVTVPLFEGVQKTQTIRSASDIRDVFINAGIKGEEYDAAWNSFVV
KSLVAQQEKAAADVQLRGVPAMFVNGKYQLNPQGMDTSNMDVFVQQYADT
VKYLSEKK.

DsbC protein, E. coli
SEQ ID NO: 18
MKKGFMLFTLLAAFSGFAQADDAAIQQTLAKMGIKSSDIQPAPVAGMKTV
LTNSGVLYITDDGKHIIQGPMYDVSGTAPVNVTNKMLLKQLNALEKEMIV
YKAPQEKHVITVFTDITCGYCHKLHEQMADYWALGITVRYLAFPRQGLDS
DAEEKEMKAIWCAKDKNKAFDDVMAGKSVAPASCDVDIADHYALGVQLGVS
GTPAVVLSNGTLVPGYQPPKEMKEFLDEHQKMTSGK.

DsbD protein, E. coli
SEQ ID NO: 19
MAQRIFTLILLLCSTSVFAGLFDAPGRSQFVPADQAFAFDFQQNQHDLNL
TWQIKDGYYLYRKQIRITPEHAKIADVQLPQGVWHEDEFYGKSEIYRDRL
TLPVTINQASAGATLTVTYQGCADAGFCYPPETKTVPLSEVVANNAAPQQ
VSVPQQEQPTAQLPFSALWALLIGIGIAFTPCVLPMYPLISGIVLGGKQR
LSTARALLLTFIYVQGMALTYTALGLVVAAAGLQFQAALQHPYVLIGLAI
VFTLLAMSMFGLFTLQLPSSLQTRLTLMSNRQQGGSPGGVFVMGAIAGLI
CSPCTTAPLSAILLYIAQSGNMWLGGGTLYLYALGMGLPLMLITVFGNRL
LPKSGPWMEQVKTAFGFVILALPVFLLERVIGDVWGLRLWSALGVAFFGW
AFITSLQAKRGWMRIVQIILLAAALVSVRPLQDWAFGATHTAQTQTHLNF
TQIKTVDELNQALVEAKGKPVMLDLYADWCVACKEFEKYTFSDPQVQKAL
ADTVLLQANVTANDAQDVALLKHLNVLGLPTILFFDGQGQEHPQARVTGF
MDAETFSAHLRDRQP.

DsbG protein, E. coli
SEQ ID NO: 20
MTVIGYAFYSTFALTEKDKLMLKKILLLALLPAIAFAEELPAPVKAIEKQ
GITIIKTFDAPGGMKGYLGKYQDMGVTIYLTPDGKHAISGYMYNEKGENL
SNTLIEKEIYAPAGREMWQRMEQSHWLLDGKKDAPVIVYVFADPFCPYCK
QFWQQARPWVDSGKVQLRTLLVGVIKPESPATAAAILASKDPAKTWQQYE
ASGGKLKLNVPANVSTEQMKVLSDNEKLMDDLGANVTPAIYYMSKENTLQ
QAVGLPDQKTLNIIMGNK.

human UDP-N-acetylgalactosaminyltransferase 2 (GalNAcT2)
SEQ ID NO: 21
MRRRSRMLLCFAFLWVLGIAYYMYSGGGSALAGGAGGGAGRKEDWNEIDP
IKKKDLHHSNGEEKAQSMETLPFGKVRWPDFNQEAYVOGTMVRSGQDPYA
RNKFNQVESDKLRMDRAIPDTRHDQCQRKQWRVDLPATSVVITFHNEARS
ALLRTVSVLKKSPPHLIKEIILVDDYSNDPEDGALLGKIEKVRVLRNDR
REGLMRSRVRGADAAQAKVLTFLDSHCECNEHWLEPLLERVAEDRTRVVS
PIIDVINMDNFQYVGASADLKGGFDWNLVFKWDYMTPEQRRSRQGNPVAP
IKTPMIAGGLFVMDKFYEELGKYDMMMDVWGGENLEISFRVWQCGGSLE
IIPCSRVGHVFRKQHPYTFPGGSGTVFARNTRRAAEVWMDEYKNFYYAAV
PSARNVPYGNIQSRLELRKKLSCKPFKWYLENVYPELRVPDHQDIAFGAL
QQQGTNCLDTLGHFADGVVGVYECHNAGGNQEWALTKEKSVKHMDLCLTVV
DRAPGSLIKLQGCRENDSRQKWEQIEGNSKLRHVGSNLCLDSRTAKSGGL
SVEVCGPALSQQWKFTLNLQQ.

Drosophila UDP-N-acetylgalactosaminyltransferase 2 (GalNAcT2)
SEQ ID NO: 22
MRRNIKLIVFVSIIWMFVMVYYFQSSTEKVENRALRLREVATAMQQYQDD
SSSAAAASTARQWAPAGGGAGPGAAAGAAGSGADDPGGNVILIGSVKDFE
RNAVHGLKLNGIVALEETSQGLSGGTGGPGGRLPVAPSGRGTEVEYFNEA
GYIRAGALRNGEDPYIRNRFNQEASDALPSNRDIPDTRNPMCRTKKYRED
LPETSVIITFHNEARSTLLRTIVSVLNRSPEHLIREIVLVDDYSDHPEDG
LELAKIDKVRVIRNDKREGLVRSRVKGADAAVSSVLTFLDSHVECNEMWL

EPLLERVREDPTRVVCPVIDVISMDNFQYIGASADLRGGFDWNLIFKWEY

LSPSERAMRHNDPTTAIRTPMIAGGLEVIDKAYFNKLGKYDMKMDVWGGE

NLEISFRVWQCGGSLEIIPCSRVGHVFRKRHPYTFPGGSGNVFARNTRRA

AEVWMDDYKQHYYNAVPLAKNIPFGNIDDRLALKEKLHCKPFKWYLENVY

PDLQAPDPQEVGQFRQDSTECLDTMGHLIDGTVGIFFCHNTGGNQEWAFT

KRGEIKHDDLCLTLVTFARGSQVVLKACDDSENQRWIMREGGLVRHYKIN

VCLDSRDQSQQGVSAQHCNSALGTQRWSFGKYA.

mouse UDP-N-acetylgalactosaminyltransferase 2
(GalNAcT2)
SEQ ID NO: 23
MRRRSRMLLCFALLWVLGIAYYMYSGGGSALAAGGGGAGRKGDWNDIDSI

KKKDLHHSRGDEKAQGVETLPPGKVRWPDFNQEAYVGGTMVRSGQDPYAR

NKFNQVESDKLHMDRGIPDTRHDQCQRKQWRVDLPATSVVITFHNEARSA

LLRTVVSVLKRSPPHLIKEIILVDDYSNDPEDGALLGKIEKVRVLRNDRR

EGLMRSRVRGADAAQAKVLTFLDSHCECNERWLEPLLERVAEDRTRVVSP

IIDVINMDNFQYVGASADLKGGFDWNLVFKWDYMTPEQRRSRQGNPVAPI

KTPMIAGGLFVMDECLYFEELGKYDMMMDVWGGENLEISFRWQCGGSLEI

IPCSRVGHVFRKQHPYTFPGGSGTVFARNTRRAAEVWMDEYKHFYYAAVP

SARNVPYGNIQSRLELRKKLGCKPFKWYLDNVYPELRVPDHQDIAFGALQ

QGTNCLDTLGHFADGVVGIYECHNAGGNQEWALTKEKSVKHMDLCLTVVD

RSPGSLIRLQGCRENDSRQKWEQIEGNSKLRHVGSNLCLDSRTAKSGGLS

VEVCGPALSQQWKFSLNLQQ.

Truncated human
UDP-N-acetylgalactosaminyltransferase 2
(GalNAc-T2 Δ51)
SEQ ID NO: 24
KKKDLHHSNGEEKAQSMETLPPGKVRWPDFNQEAYVGGTMVRSGQDPYAR

NKFNQVESDKLRMDRAIPDTRHDQCQRKQWRVDLPATSVVITFHNEARSA

LLRTVVSVLKKSPFHLIKEIILVDDYSNDPEDGALLGKIEKVRVLRNDRR

EGLNRSRVRGADAAQAKVLTFLDSHCECNEHWLEPLLERVAEDRTRVVSP

IIDVINMDNFQYVGASADLKGGFDWNLVFKWDYMTPEQRRSRQGNPVAPI

KTFMIAGGLFVMDKFYFEELGKYDMMMDVWGGENLEISFRVWQCGGSLEI

IPCSRVGHVFRKQHPYTFPGGSGTVFARNTRRAAEVWMDEYKNFYYAAVP

SARNVPYGNIQSRLELRKKLSCKPFKWYLENVYPELRVPDHQDIAFGALQ

QGTNCLDTLGHFADGVVGVYECHNAGGNQEWALTKEKSVKHMDLCLTVVD

RAPGSLIKLQGCRENDSRQKWEQIEGNSKLRHVGSNLCLDSRTAKSGGLS

VEVCGPALSQQWKFTLNLQQ.

Truncated human
UDP-N-acetylgalactosaminyltransferase 2
(GalNAcT2 Δ1-51 Δ445-571)
SEQ ID NO: 25
KKKDLHHSNGEEKAQSMETLPPGKVRWPDFNQEAYVGGTMVRSGQDPYAR

NKFNQVESDKLRMDRAIPDTRHDQCQRKQWRVDLPATSVVITFHNEARSA

LLRTVVSVLKKSPPHLIKEIILVDDYSNDPEDGALLGKIEKVRVLRNDRR

EGLMRSRVRGADAAQAKVLTFLDSHCECNEHWLEPLLERVAEDRTRVVSP

IIDVINMDNFQYVGASADLKGGFDWNLVFKWDYMTPEQRRSRQGNPVAPI

KTPMIAGGLFVMDKFYFEELGKYDMMMDVWGGENLEISFRVWQCGGSLEI

IPCSRVGHVFRKQHFYTFPGGSGTVFARNTRRAAEVWMDEYKNFYYAAVP

SARNVPYGNIQSRLELRKKLSCKPFKWYLENVYPELRVPDHQD.

Truncated human
UDP-N-acetylgalactosaminyltransferase 2
(GalNAcT2 Δ51) alternate form
SEQ ID NO: 26
MSKKKDLHHSNGEEKAQSMETLPPGKVRWPDFNQEAYVGGTMVRSGQDPY

ARNKFNQVESDKLRNDRAIPDTRHDQCQRKQWRVDLPATSVVITFHNEAR

SALLRTVVSVLRKSPPHLIKEIILVDDYSNDPEDGALLGKIEKVRVLRND

RREGLMRSRVRGADAAQAKVLTFLDSHCECNEHWLEPLLERVAEDRTRVV

SPIIDVINMDNFQYVGASADLKGGFDWNLVFKWDYMTPEQRRSRQGNPVA

PIKTPMIAGGLFVMDKFYFEELGKYDMMMDVWGGENLEISFRVWQCGGSL

EIIPCSRVGHVFRKQHPYTFPGGSGTVFARNTRRAAEVWNDEYKNFYYAA

VPSARNVPYGNIQSRLELRKKLSCKPFKWYLENVYPELRVPDHQDIAFGA

LQQGTNCLDTLGHFADGVVGVYECHNAGGNQEWALTKEKSVKHMDLCLTV

VDRAPGSLIKLQGCRENDSRQKWEQIEGNSKLRHVGSNLCLDSRTAKSGG

LSVEVCGPALSQQWKFTLNLQQ.

Truncated human
UDP-N-acetylgalactosaminyltransferase 2
(GalNAcT2 Δ1-51 Δ44-5571) alternate form
SEQ ID NO: 27
MSKKKDLHHSNGEEKAQSMETLPPGKVRWPDFNQEAYVGGTMVRSGQDPY

ARNKFNQVESDKLRMDRAIPDTRHDQCQRKQWRVDLPATSVVITFHNEAR

SALLRTVVSVLKKSPPHLIKEIILVDDYSNDPEDGALLGKIEKVRVLRND

RREGLMRSRVRGADAAQAKVLTFLDSHCECNEHWLEPLLERVAEDRTRVV

SPIIDVINMDNFQYVGASADLKGGFDWNLVFKWDYMTPEQRRSRQGNPVA

PIKTPMIAGGLFVMDKFYFEELGKYDMMMDVWGGENLEISFRVWQCGGSL

EIIPCSRVGHVFRKQHPYTFPGGSGTVFARNTRRAAEVWMDEYKNFYYAA

VPSARNVPYGNIQSRLELRKKLSCKPFKWYLENVYPELRVPDHQD.

Maltose binding protein-tagged truncated human UDP-
N-acetylgalactosaminyltransferase 2 (MBPGalNAc-T2
Δ51)
SEQ ID NO: 28
MKIEEGKLVIWINGDKGYNGLAEVGKKFEKDTGIKVTVEHPDKLEEKFPQ

VAATGDGPDIIFWAHDRFGGYAQSGLLAEITPDKAFQDKLYPFTWDAVRY

NGKLIAYPIAVEALSLIYNKDLLPNPPKTWEEIPALDKELKAKGKSALMF

NLQEPYFTWPLIAADGGYAFKYENGKYDIKDVGVDNAGAKAGLTFLVDLI

KNKHMNADTDYSIAEEAAFNKGETAMTINGPWAWSNIDTSKVNYGVTVLPT

FKGQPSKPFVGVLSAGINAASPNKELAKEFLENYLLTDEGLEAVNKDKPL

GAVALKSYEEELAKDPRIAATMENAQKGEIMPNIPQMSAFWYAVRTAVIN

AASGRQTVDEALKDAQTNSSSNNNNNNNNNLGIEGRISEFGSKKKDLHH

SNGEEKAQSMETLPPGKVRWPDFNQEAYVGGTMVRSGQDPYARNKFNQVE

SDKLRMDRAIPDTRHDQCQRKQWRVDLPATSVVITFHNEARSALLRTVVS

VLKKSPPHLIKEIILVDDYSNDPEDGALLGKIEKVRVLRNDRREGLMRSR

VRGADAAQAKVLTFLDSHCECNEHWLEPLLERVAEDRTRVVSPIIDVINM

-continued
DNFQYVGASADLKGGFDWNLVFKWDYMTPEQRRSRQGNPVAPIKTPMIAG
GLFVMDKFYFEELGKYDMMMDVWGGENLEISFRVWQCGGSLEIIPCSRVG
HVFRKQHPYTFPGGSGTVFARNTRRAAEVWMDEYKNFYYAAVPSARNVPY
GNIQSRLELRKKLSCKPFKWYLENVYPELRVPDHQDIAFGALQQGTNCLD
TLGHFADGVVGVYECHNAGGNQEWALTKEKSVKHMDLCLTVVDRAPGSLI
KLQGCRENDSRQKWEQIEGNSKLRHVGSNLCLDSRTAKSGGLSVEVCGPA
LSQQWKFTLNLQQ.

Truncated human
UDP-N-acetylgalactosaminyltransferase 2
(GalNAc-T2 Δ53)
SEQ ID NO: 29
KDLHHSNGEEKAQSMETLPPGKVRWPDFNQEAYVGGTMVRSGQDPYARNK
FNQVESDKLRMDRAIPDTRHDQCQRKQWRVDLPATSVVITFHNEARSALL
RTVVSVLKKSPPHLIKEIILVDDYSNDPEDGALLGKIEKVRVLRNDRREG
LMRSRVRGADAAQAKVLTFLDSHCECNEHWLEPLLERVAEDRTRVVSPII
DVINMDNFQYVGASADLKGGFDWNLVFKWDYMTPEQRRSRQGNPVAPIKT
PMIAGGLFVMDKFYFEELGKYDMMMDVWGGENLEISFRVWQCGGSLEIIP
CSRVGHVFRKQHPYTFPGGSGTVFARNTRRAAEVWMDEYKNFYYAAVPSA
RNVPYGNIQSRLELRKKLSCKPFKWYLENVYPELRVPDHQDIAFGALQQG
TNCLDTLGHFADGVVGVYECHNAGGNQEWALTKEKSVKHMDLCLTVVDRA
PGSLIKLQGCRENDSRQKWEQIEGNSKLRHVGSNLCLDSRTAKSGGLSVE
VCGPALSQQWKFTLNLQQ.

Truncated human
UDP-N-acetylgalactosaminyltransferase 2
(GalNAcT2 Δ1-53 Δ445-571)
SEQ ID NO: 30
KDLHHSNGEEKAQSMETLPPGKVRWPDFNQEAYVGGTMVRSGQDPYARNK
FNQVESDKLRMDRAIPDTRHDQCQRKQWRVDLPATSVVITFHNEARSALL
RTVVSVLKKSPPHLIKEIILVDDYSNDPEDGALLGKIEKVRVLRNDRREG
LMRSRVRGADAAQAKVLTFLDSHCECNEHWLEPLLERVAEDRTRVVSPII
DVINMDNFQYVGASADLKGGFDWNLVFKWDYMTPEQRRSRQGNPVAPIKT
PMIAGGLFVMDKFYFEELGKYDMMMDVWGGENLEISFRVWQCGGSLEIIP
CSRVGHVFRKQHPYTFPGGSGTVFARNTRRAAEVWMDEYKNFYYAAVPSA
RNVPYGNIQSRLELRKKLSCKPFKWYLENVYPELRVPDHQD.

Truncated human
UDP-N-acetylgalactosaminyltransferase 2
(GalNAcT2 Δ53) alternate form
SEQ ID NO: 31
MSKDLHHSNGEEKAQSMETLPPGKVRWPDFNQEAYVGGTMVRSGQDPYAR
NKFNQVESDKLRMDRAIPDTRHDQCQRKQWRVDLPATSVVITFHNEARSA
LLRTVVSVLKKSPPHLIKEIILVDDYSNDPEDGALLGKIEKVRVLRNDRR
EGLMRSRVRGADAAQAKVLTFLDSHCECNEHWLEPLLERVAEDRTRVVSP
IIDVINNDNFQYVGASADLKGGFDWNLVFKWDYMTPEQRRSRQGNPVAPI
KTPMIAGGLFVMDKFYFEELGKYDMMMDVWGGENLEISFRVWQCGGSLEI
IPCSRVGHVFRKQHPYTFPGGSGTVFARNTRRAAEVWMDEYKNFYYAAVP
SARNVPYGNIQSRLELRKKLSCKPFKWYLENVYPELRVPDHQDIAFGALQ
QGTNCLDTLGHFADGVVGVYECHNAGGNQEWALTKEKSVKHMDLCLTVVD

RAPGSLIKLQGCRENDSRQKWEQIEGNSKLRHVGSNLCLDSRTAKSGGL
SVEVCGPALSQQWKFTLNLQQ.

Truncated human
UDP-N-acetylgalactosaminyltransferase 2
(GalNAc-T2 Δ1-53 Δ445-571) alternate form
SEQ ID NO: 32
MSKDLHHSNGEEKAQSMETLPPGKVRWPDFNQEAYVGGTMVRSGQDPYAR
NKFNQVESDKLRMDRAIPDTRHDQCQRKQWRVDLPATSVVITFHNEARSA
LLRTVVSVLKKSPPHLIKEIILVDDYSNDPEDGALLGKIEKVRVLRNDRR
EGLMRSRVRGADAAQAKVLTFLDSHCECNEHWLEPLLERVAEDRTRVVSP
IIDVINMDNFQYVGASADLKGGFDWNLVFKWDYMTPEQRRSRQGNPVAPI
KTPMIAGGLFVMDKFYFEELGKYDMMMDVWGGENLEISFRVWQCGGSLEI
IPCSRVGHVFRKQHPYTFPGGSGTVFARNTRRAAEVWMDEYKNFYYAAVP
SARNVPYGNIQSRLELRKKLSCKPFKWYLENVYPELRVPDHQDIAFGALQ
QGTNCLDTLGHFADGVVGVYECHNAGGNQEWALTKEKSVKHMDLCLTVVD
RAPGSLIKLQGCRENDSRQKWEQIEGNSKLRHVGSNLCLDSRTAKSGGLS
VEVCGPALSQQWKFTLNLQQ.

Maltose binding protein tagged truncated human UDP-
N-acetylgalactosaluinyltransferase 2
(MBP-GalNAcT2 Δ1-53 Δ445-571)
SEQ ID NO: 33
MKIEEGKLVIWINGDKGYNGLAEVGKKFEKDTGIKVTVEHPDKLEEKFPQ
VAATGDGPDIIFWAHDRFGGYAQSGLLAEITPDKAFQDKLYPFTWDAVRY
NGKLIAYPIAVEALSLIYNKDLLPNPPKTWEEIPALDKELKAKGRSALMF
NLQEPYFTWPLIAADGGYAFKYENGKYDIKDVGVDNAGAKAGLTFLVDLI
KNKHMNADTDYSIAEAAFNKGETAMTINGPWAWSNIDTSKVNYGVYVLPT
FKGQPSKPFVGVLSAGINAASPNKELAKEFLENYLLTDEGLEAVNKDKPL
GAVALRSYEEELAKDPRIAATMENAQKGEIMPNIPQMSAFWYAVRTAVIN
AASGRQTVDEALKDAQTNSSSNNNNNNNNNNLGIEGRISEFGSHMSKDLH
HSNGEEKAQSMETLPPGKVRWPDFNQEAYVGGTMVRSGQDPYARNKFNQV
ESDKLRMDRAIPDTRHDQCQRKQWRVDLPATSVVITFHNEARSALLRTVV
SVLKKSPPHLIKEIILVDDYSNDPEDGALLGKIEKVRVLRNDRREGLMRS
RVRGADAAQAKVLTFLDSHCECNEHWLEPLLERVAEDRTRVVSPIIDVIN
MDNFQYVGASADLKGGFDWNLVFKWDYMTPEQRRSRQGNPVAPIKTPMIA
GGLFVMDKFYFEELGKYDMMMDVWGGENLEISFRVWQCGGSLEIIPCSRV
GHVFRKQRPYTFPGGSGTVFARNTRRAAEVWMDEYKNFYYAAVPSARNVP
YGNIQSRLELRKKLSCKPFKWYLENVYPELRVPDHQDIAFGALQQGTNCL
DTLGHFADGVVGVYECHNAGGNQEWALTKEKSVKHMDLCLTVVDRAPGSL
IKLQGCRENDSRQKWEQIEGNSKLRHVGSNLCLDSRTARSGGLSVEVCGP
ALSQQWKFTLNLQQ.

Maltose binding protein-tagged truncated human UDP-
N-acetylgalactosarminyltransferase 2
(MBP-GalNAcT2 Δ53)
SEQ ID NO: 34
MKIEEGKLVIWINGDKGYNGLAEVGKKFEKDTGIKVTVEHPDKLEEKFPQ
VAATGDGPDIIFWAHDRFGGYAQSGLLAEITPDKAFQDKLYPFTWDAVRY

NGKLIAYPIAVEALSLIYNKDLLPNPPKTWEEIPALDKELKAKGKSALMF

NLQEPYFTWPLIAADGGYAFKYENGKYDIKDVGVDNAGAKAGLTFLVDLI

KNRHMNADTDYSIAEAAFNKGETAMTINGPWAWSNIDTSKVNYGVTVLPT

FKGQPSKPFVGVLSAGINAASPNKELAKEFLENYLLTDEGLEAVNKDKPL

GAVALKSYEEELAKDPRIAATMENAQKGEIMPNIPQMSAFWYAVRTAVIN

AASGRQTVDEALKDAQTNSSSNNNNNNNNNLGIEGRISEFGSHMSKDLH

HSNGEEKAQSMETLPPGKVRWPDFNQEAYVGGTMVRSGQDPYARNKFNQV

ESDKLRMDRAIPDTRHDQCQRKQWRVDLFATSVVITFHNEARSALLRTVV

SVLKKSPPHLIKEIILVDDYSNDPEDGALLGKIEKVRVLRNDRREGLMRS

RVRGADAAQAKVLTFLDSHCECNEHWLEPLLERVAEDRTRVVSPIIDVIN

MDNFQYVGASADLKGGFDWNLVFKWDYMTFEQRRSRQGNPVAPIKTPMIA

GGLFVMDKFYFEELGKYDMMMDVWGGENLEISFRVWQCGGSLEIIPCSRV

GHVFRKQHPYTFPGGSGTVFARNTRRAAEVWMDEYKNFYYAAVPSARNVP

YGNIQSRLELRKKLSCKPFKWYLENVYPELRVPDHQDIAFGALQQGTNCL

DTLGHFADGVVGVYECHNAGGNQEWALTKEKSVKHMDLCLTVVDRAPGSL

IKLQGCRENDSRQKWEQIEGNSKLRHVGSNLCLDSRTAKSGGLSVEVCGP

ALSQQWKFTLNLQQ.

Maltose binding protein-tagged truncated human
UDP-N-acetylgalactosaminyltransferase 2
(GalNAc-T2 Δ1-51 Δ445-571)
SEQ ID NO: 35 mkieegklviwingdkgynglaevgkkfekdtgikvtvehpdkleekfpq vaatgdgpdiifwahdrfggyaqsgllaeitpdkafqdklypftwdavry ngkliaypiavealsliynkdllpnppktweeipaldkelkakgksalmf nlqepyftwpliaadggyafkyengkydikavgvdnagakagltflvdli knkhmnadtdysiaeaafnkgetamtingpwawsnidtskvnygvtvlpt fkgqpskpfvgvlsaginaaspnkelakeflenylltdegleavnkdkpl gavalksyeeelakdpriaatmenaqkgeimpnipqmsafwyavrtavin aasgrqtvdealkdaqtnsssnnnnnnnnnlgiegrisefgSKKKDLHH

SNGEEKAQSMETLPPGKVRWPDFNQEAYVGGTMVRSGQDPYARNKFNQVE

SDKLRMDRAIPDTRHDQCQRKQWRVDLPATSVVITFHNEARSALLRTVVS

VLKKSPPHLIKEIILVDDYSNDPEDGALLGKIEKVRVLRNDRREGLMRSR

VRGADAAQAKVLTFLDSHCECNEHWLEPLLERVAEDRTRVVSPIIDVINM

DNFQYVGASADLKGGFDWNLVFKWDYMTPEQRRSRQGNPVAPIKTPMIAG

GLFVMDKFYFEELGKYDMMMDVWGGENLEISFRVWQCGGSLEIIPCSRVG

HVFRKQHPYTFPGGSGTVFARNTRRAAEVWMDEYKNFYYAAVPSARNVPY

GNIQSRLELRKKLSCKPFKWYLENVYPELRVPDHQD.

Human UDP-galactose:N-acetylgalactosamine-alpha-R
beta-1,3-galactosyltransferase (Core-1-Gal-T1)
SEQ ID NO: 36

MASKSWLNFLTFLCGSAIGFLLCSQLFSILLGEKVDTQPNVLHNDPHARH

SDDNGQNHLEGQMNFNADSSQHKDENTDIAENLYQKVRILCWVMTGPQNL

EKKAKHVKATWAQRCNKVLFMSSEENKDFPAVGLKTKEGRDQLYWKTIKA

FQYVHEHYLEDADWFLKADDDTYVILDNLRWLLSKYDPEEPIYFGRREKF

YVKQGYMSGGAGYVLSKEALKRFVDAFKTDKCTHSSSIEDLALGRCMEIM

NVEAGDSRDTIGKETFHPFVPEHHLIKGYLPRTFWYWNYNYYPPVEGPGC

CSDLAVSFHYVDSTTMYELEYLVYHLRPYGYLRYQPTLPERILKEISQA

NKNEDTKVKLGNP.

Drosophila UDP-galactose:N-acetylgalactosamine-
alpha-R beta-1,3-galactosyltransferase
(Core-1-Gal-T1)
SEQ ID NO: 37

MTANSLLGRSILNEGRSNKRSFVSLIVGLIVGFCLAELFVYSTPERSEFM

PYDGHRHGDVNDAHHSHDMMEMSGPEQDVGGHEHVHENSTIAERLYSEVR

VLCWIMTNPSNHQKKARHVKRTWGKRCNKLIFMSSAKDDELDAVALPVGE

GRNNLWGKTKEAYKYTYEHHINDADWFLKADDDTYTIVENMRYMLYPYSP

ETPVYFGCKFKPYVKQGYMSGGAGYVLSREAVRRFVVEALPNPKLCKSDN

SGAEDVEIGKCLQNVNVLAGDSRDSNGRGRFFPFVPEHHLIPSHTDKKFW

YWQYIFYKTDEGLDCCSDNAISFHYVSPNQMYVLDYLIYHLRPYGIINTP

DALPNKLAVGELMPEIKEQATESTSDGVSKRSAETKTQ.

mouse UDP-galactose:N-acetylgalactosamine-alpha-R
BETA-1,3-galactosyltransferase (Core-1-Gal-T1)
SEQ ID NO: 38

MASKSWLNFLVFLCGSAIGFFLCSQLLSILLREEAAIQPNMLHNDPHARH

SDDNGHSHLKGQMNFNADSSQHKDENIDVAENLYQKVKILCWVMTSPQNL

EKKAKHVKATWAQRCNKVLFMSSEENQDFPTVGLKTKEGREQLYWKTIKA

FQYVNDHYLEDADWFMKADDDTYVIVDNLRWLLSKYDPEQPIYFGRRFKP

YVKQGYMSGGAGYVLSKEALRRFVDAFKTEKCTHSSSIEDLALGRCMEII

NVEAGDSRDTIGKETFHPFVPEHHLIKGYLPKTFWYWNYNYYPPIEGPGC

CSDIAVSFHYVDGTTMYELEYLVYRLRPYGCLRYQPALPENILKEINQV

NRKEDTKIKLGNP.

rat UDP-galactose:N-acetylgalactosamine-alpha-R
beta-1,3-galactosyltransferase (Core-1-Gal-T1)
SEQ ID NO: 39

MASKSWLNFLTFLCGSAIGFFLCSQLLNILLQEQADVQPNMLHNDPHARH

SDDSGHNHLKGQMDFNADSSQHKDENTDVAENLYQKVKVLCWVMTSPQNL

EKKAKHVKATWAQRCNKVLFNSSEENKDFPTVGLETKEGREQLYWKTIKA

FQYVHDHYLEDADWFMKADDDTYVILDNLRWLLSKYNPEQPIYFGRRFKP

YVKQGYMSGGAGYVLSKEALRRFVDAFKTEKCTHSSSIEDLALGRCMEII

KVEAGDSRDPTGKETFHPFVPEHHLIKGYLPKTFWYWNYNYYPPVEGPGC

CSDIAVSFHYVDSTTMYELEYLVYHLRPYGYLRYQPALPENILKEINQV

NKKEDTKIKLGNP.

Drosophila UDP-galactose:N-acetylgalactosamine-
alpha-R beta-1,3-galactosyltransferase
(Core-1-Gal-T1) A383T mutant
SEQ ID NO: 40

MTANSLLGRSILNEGRSNKRSFVSLIVGLIVGFCLAELFVYSTPERSEFM

PYDGHRHGDVNDAHHSHDMMEMSGPEQDVGGHEHVHENSTIAERLYSEVR

VLCWIMTNPSNHQKKARHVKRTWGKRCNKLIFMSSAKDDELDAVALPVGE

GRNNLWGKTKEAYKYIYEHHINDADWFLKADDDTYTIVENMRYMLYPYSP

ETPVYFGCKFKPYVKQGYMSGGAGYVLSREAVRRFVVEALPNPKLCKSDN

SGAEDVEIGKCLQNVNVLAGDSRDSNGRGRFFPFVPEHHLIPSHTDKKFW

-continued

YWQYIFYKTDEGLDCCSDNAISFHYVSPNQMYVLDYLIYHLRPYGIINTP

DALPNKLAVGELMPEIKEQATESTSDGVSKRSTETKTQ.

Truncated *Drosophila* UDP-galactose:
N-acetylgalactosamine-alpha-R beta-1,3-
galactosyltransferase (Core-1-Gal-T1 Δ31) A383T
mutant
SEQ ID NO: 41
GFCLAELFVYSTPERSEFMPYDGHRHGDVNDAHHSHDMMEMSGPEQDVGG

HEHVHENSTIAERLYSEVRVLCWIMTNPSNHQKKARHVKRTWGKRCNKLI

FMSSAKDDELDAVALPVGEGRNNLWGKTKEAYKYIYEHHINDADWFLKAD

DDTYTIVENMRYMLYPYSPETPVYFGCKFKPYVKQGYMSGGAGYVLSREA

VRRFVVEALPNPKLCKSDNSGAEDVEIGKCLQNVNVLAGDSRDSNGRGRF

FPPFVPEHHLIPSHTDKKFWYWQYIFYKTDEGLDCCSDNAISFHYVSPNQM

YVLDYLIYHLRPYGIINTPDALPNKLAVGELMPEIKEQATESTSDGVSKR

STETKTQ.

Truncated *Drosophila* UDP-galactose:
N-acetylgalactosamine-alpha-R beta-1,3-
galactosyltransferase (Core-1-Gal-T1 Δ31) A383T
mutant alternate form
SEQ ID NO: 42
MGFCLAELFVYSTPERSEFMPYDGHRHGDVNDAHHSHDMMEMSGPEQDVG

GHEHVHENSTIAERLYSEVRVLCWIMTNPSNHQKKARHVKRTWGKRCNKL

IFMSSAKDDELDAVALPVGEGRNNLWGKTKEAYKYIYEHHINDADWFLKA

DDDTYTIVENMRYMLYPYSPETPVYFGCKFKPYVKQGYMSGGAGYVLSRE

AVRRFVVEALPNPKLCKSDNDGAEDVEIGKCLQNVNVLAGDSRDSNGRGR

FFPFVPEHHLIPSHTDKKFWYWQUIFYKTDEGLDCCSDNAISFHYVSPNQ

MYVLDLIYHLRPYGIINTPDALPNKLAVGELMPEIKEQATESTSDGVSKR

STETKTQ.

Truncated *Drosophila* UDP-galactose:
N-acetylgalactosamine-alpha-R beta-1,3-
galactosyltransferase (Core-1-Gal-T1 Δ50)
SEQ ID NO: 43
PYDGHRHGDVNDAHHSHDMMEMSGPEQDVGGHEHVHENSTIAERLYSEVR

VLCWIMTNPSNHQKKARHVKRTWGKRCNKLIFMSSAKDDELDAVALPVGE

GRNNLWGKTKEAYKYIYEHHINDADWFLKADDDTYTIVENMRYMLYPYSP

ETPVYFGCKFKPYVKQGYMSGGAGYVLSREAVRRFVVEALPNPKLCKSDN

SGAEDVEIGKCLQNVNVLAGDSRDSNGRGRFFPFVPEHHLIPSHTDKRFW

YWQYIFYKTDEGLDCCSDNAISFHYVSPNQMYVLDYLIYHLRPYGIINTP

DALPNKLAVGELMPEIKEQATESTSDGVSKRSAETKTQ.

Truncated *Drosophila* UDP-galactose:
N-acetylgalactosamine-alpha-R beta-1,3-
galactosyltransferase (Core-1-Gal-T1 Δ50) A383T
mutant
SEQ ID NO: 44
PYDGHRHGDVNDAHHSHDMMEMSGPEQDVGGHEHVHENSTIAERLYSEVR

VLCWIMTNPSNHQKKARHVKRTWGKRCNKLIFMSSAKDDELDAVALPVGE

GRNNLWGKTKEAYKYIYEHHINDADWFLKADDDTYTIVENMRYMLYPYSP

ETPVYFGCKFKPYVKQGYMSGGAGYVLSREAVRRFVVEALPNPKLCKSDN

SGAEDVEIGKCLQNVNVLAGDSRDSNGRGRFFPFVPEHHLIPSHTDKKFW

YWQYIFYKTDEGLDCCSDNAISFHYVSPNQMYVLDYLIYHLRPYGIINTP

DALPNKLAVGELMPEIKEQATESTSDGVSKRSTETKTQ.

Truncated *Drosophila* UDP-galactose:
N-acetylgalactosamine-alpha-R beta-1,3-
galactosyltransferase (Core-1-Gal-T1 Δ50) A383T
mutant alternate form
SEQ ID NO: 45
MSPYDGHRHGDVNDAHHSHDMMEMSGPEQDVGGHEHVHENSTIAERLYSE

VRVLCWIMTNPSNHQKKARHVKRTWGKRCNKLIFMSSAKDDELDAVALPV

GEGRNNLWGKTKEAYKYIYEHHINDADWFLKADDDTYTIVENMRYMLYPY

SPETPVYFGCKFKPYVKQGYMSGGAGYVLSREAVRRFVVEALPNPKLCKS

DNSGAEDVEIGKCLQNVNVLAGDSRDSNGRGRFFPFVPEHHLIPSHTDKK

FWYWQYIFYKTDEGLDCCSDNAISFHYVSPNQMYVLDYLIYHLRPYGIIN

TPDALPNKLAVGELMPEIKEQATESTSDGVSKRSTETKTQ.

Maltose binding protein-tagged truncated
Drosophila UDP-galactose:N-acetylgalactosamine-
alpha-R beta-1,3-galactosyltransferase
(MBP-Core-1-Gal-T1 Δ50) A383T mutant
SEQ ID NO: 46
MKIEEGKLVIWINGDKGYNGLAEVGKKFEKDTGIKVTVEHPDKLEEKFPQ

VAATGDGPDIIFWAHDRFGGYAQSGLLAEITPDKAFQDKLYPFTWDAVRY

NGKLIAYPIAVEALSLIYNKDLLPNPPKTWEEIPALDKELKAKGKSALMF

NLQEPYFTWPLIAADGGYAFKYENGKYDIKDVGVDNAGAKAGLTFLVDLI

KNKHMNADTDYSIAEAAFNKGETAMTINGPWAWSNIDTSKVNYGVTVLPT

FKGQPSKPFVGVLSAGINAASPNKELAKEFLENYLLTDEGLEAVNKDKPL

GAVALKSYEEELAKDPRIAATMENAQKGEIMPNIPQMSAFWYAVRTAVIN

AASGRQTVDEALKDAQTNSSSNNNNNNNNNLGIEGRISEFGSPYDGHRH

GDVNDAHHSHDMMEMSGPEQDVGGHEHVHENSTIAERLYSEVRVLCWIMT

NPSNHQKKARHVKRTWGKRCNKLIFMSSAKDDELDAVALPVGEGRNNLWG

KTKEAYKYIYEHHINDADWFLKADDDTYTIVENMRYMLYPYSPETPVYFG

CKFKPYVKQGYMSGGAGYVLSREAVRRFVVEALPNPKLCKSDNSGAEDVE

IGKCLQNVNVLAGDSRDSNGRGRFFPFVPEHHLIPSHTDKKFWYWQYIFY

KTDEGLDCCSDNAISFHYVSPNQMYVLDYLIYHLRPYGIINTPDALPNKL

AVGELMPEIKEQATESTSDGVSKRSTETKTQ.

Human Core-1-Gal-T1 chaperone 1/COSMC
SEQ ID NO: 47
MLSESSSFLKGVMLGSIFCALITMLGHIRIGHGNRMHHHEHHHLQAPNKE

DILKISEDERMELSKSFRVYCIILVKPKDVSLWAAVKETWTKHCDKAEFF

SSENVKVFESINMDTNDMWLMMRKAYKYAFDKYRDQYNWFFLARPTTFAI

IENLKYFLLKKDPSQPFYLGHTIKSGDLEYVGMEGGIVLSVESMKRLNSL

LNIPEKCPEQGGNIWKISEDKQLAVCLKYAGVFAENAEDADGKDVFNTKS

VGLSIKEAMTYHPNQVVEGCCSDMAVTFNGLTPNQMHVMMYGVYRLPAFG

HIFNDALVFLPPNGSND.

*Drosophila* UDP-galactose:N-acetylgalactosamine-
alpha-R beta-1,3-galactosyltransferase
(Core-1-Gal-T1 Δ31)
SEQ ID NO: 48
GFCLAELFVYSTPERSEFMPYDGHRHGDVNDAHHSHDMMEMSGPEQDVGG

HEHVHENSTIAERLYSEVRVLCWIMTNPSNHQKKARHVKRTWGKRCNKLI

-continued

FMSSAKDDELDAVALPVGEGRNNLWGKTKEAYKYIYEHHINDADWFLKAD

DDTYTIVENMRYMLYPYSPETPVYFGCKFKPYVKQGYMSGGAGYVLSREA

VRRFVVEALPNPKLCKSDNSGAEDVEIGKCLQNVNVLAGDSRDSNGRGRF

FPPFVPEHHLIPSNTDKKFWYWQYIFYKTDEGLDCCSDNAISFHYVSPNQM

YVLDYLIYHLRPYGIINTPDALPNKLAVGELMPEIKEQATESTSDGVSKR

SAETKTQ.

Maltose binding protein-tagged truncated
Drosophila UDP-galactose:N-acetylgalactosamine-
alpha-R beta-1,3-galactosyltransferase
(MBP-Core-1-Gal-T1 Δ31) A383T mutant
SEQ ID NO: 49
MKIEEGKLVIWINGDKGYNGLAEVGKKFEKDTGIKVTVEHPDKLEEKFPQ

VAATGDGPDIIFWAHDRFGGYAQSGLLAEITPDKAFQDKLYPFTWDAVRY

NGKLIAYPIAVEALSLIYNKDLLPNPPKTWEEIPALDKELKAKGKSALMF

NLQEPYFTWPLIAADGGYAFKYENGKYDIKDVGVDNAGAKAGLTFLVDLI

KNKHMNADTDYSIAEAAFNKGETAMTINGPWAWSNIDTSKVNYGVTVLPT

FKGQPSKPFVGVLSAGINAASPNKELAKEFLENYLLTDEGLEAVNKDKPL

GAVALKSYEEELAKDPRIAATMENAQKGEIMPNIPQMSAFWYAVRTAVIN

AASGRQTVDEALKDAQTNSSSNNNNNNNNNLGIEGRISEFGSHMGFCLA

ELFVYSTPERSEFMPYDGHRHGDVNDAHHSHDMMEMSGPEQDVGGHEHVH

ENSTIAERLYSEVRVLCWIMTNPSNHQKKARHVKRTWGKRCNKLIFMSSA

KDDELDAVALPVGEGRNNLWGKTKEAYKYIYEHHINDADWFLKADDDTYT

IVENMRYMLYPYSPETPVYFGCKFKPYVKQGYMSGGAGYVLSREAVRRFV

VEALPNPKLCKSDNSGAEDVEIGKCLQNVNVLAGDSRDSNGRGRFFPPFVP

EHHLIPSHTDKKFWYWQYIFYKTDEGLDCCSDNAISFHYVSPNQMYVLDY

LIYHLRPYGIINTPDALPNKLAVGELMPEIKEQATESTSDGVSKRSTETK

TQ.

human Gal beta-1,3-GalNAc alpha-2,
3-sialyltransferase 1 (ST3Gal-1)
SEQ ID NO: 50
MVTLRKRTLKVLTFLVLFIFLTSFFLNYSHTMVATTWFPKQMVLELSENL

KRLIKHRPCTCTHCIGQRKLSAWFDERFNQTMQPLLTAQNALLEDDTYRW

WLRLQREKKPNNLNDTIKELFRVVPGNVDPMLEKRSVGCRRCAVVGNSGN

LRESSYGPEIDSHDFVLRMNKAPTAGFEADVGTKTTHHLVYPESFRELGD

NVSMILVPFKTIDLEWVVSAITTGISHTYIPVPAKIRVKQDKILIYHPA

FIKYVFDNWLQGHGRYPSTGILSVIFSMHVCDEVDLYGFGADSKGNWHHY

WENNPSAGAFRKTGVHDADFESNVTATLASINKIRIFKGR.

porcine Gal beta-1,3-GalNAc alpha-2,
3-sialyltransferase 1 (ST3Gal1)
SEQ ID NO: 51
MAPMRKKSTLKLLTLLVLFIFLTSFFLNYSHTVVTTAWFPKQMVIELSEN

FKKLMKYPYRPCTCTRCIEEQRVSAWFDERFNRSMQPLLTAKNAHLEEDT

YKWWLRLQREKQPNNLNDTIRELFQVVPGNVDPLLEKRLVSCRRCAVVGN

SGNLKESYYGPQIDSHDFVLRMNKAPTEGFEADVGSKTTHHFVYPESFRE

LAQEVSMILVPFKTTDLEWVISATTTGTISHTYVPVPAKIKVKKEKILIY

HPAFIKYVFDRWLQGHGRYPSTGILSVIFSLHICDEVDLYGFGADSKGNW

HHYWENNPSAGAFRKTGVHDGDFESNVTTILASINKIRIFKGR.

mouse Gal beta-1,3-GalNAc alpha-2,
3-sialyltransferase 1 (ST3Gal-1)
SEQ ID NO: 52
MRRKTLKYLTFFLLLFIFLTSFVLNYSNTGVPSAWFPKQMLLELSENFRRF

IKSQPCTCRHCISQDKVSYWFDQRFNKTMQPLLTVHNALMEEDTYRWWLR

LQRERKPNNLSDTVKELFRLVPGNVDPMLNKRLVGCRRCAVVGNSGNLKD

SSYGPEIDSHDFVLRMNKAPTVGFEADVGSRTTHHLVYPESFRELGENVN

MVLVPFKTTDLQWVISATTTGTITHTYVPVPPKIKVKQEKILIYHPAFIK

YVFDNWLQGHGRYPSTGILSIIFSIHICDEVDLYGFGADSKGNWHHYWEN

NPSAGAFRKTGVHDGDFEYNITTTLAAINKIRIFKGR.

rat Gal beta-1,3-GalNAc alpha-2,
3-sialyltransferase 1 (ST3Gal-1)
SEQ ID NO: 53
MVNMRKRTLKYLTFFLLFIFLTSFVLNYSNSGVPSAWFPKQMVLEFSENF

RKFIKSQPCTCRHCISQGKVSYWFDQRFNKTMQPLLTVHNALMEEDTYRW

WLRLQRERKPNNLSDTVKELFRLVPGNVDPMLNKRLVGCRRCAVVGNSGN

LKDSSYGPEIDSHDFVLRNNRAPTVGFEADVGSRTTNHLVYPESFRELGE

NVNMVLVPFKITDLQWVISATTTGTITHTYVPVPPKIKVKQEKILIYHPA

FIKYVFDNWLQGHGRYPSTGILSVIFSIHICDEVDLYGFGADSKGNWHHY

WENNPSAGAFRKTGVHDGDFEYNVTTTLAAINKIRIFKGR.

chimp Gal beta-1,3-GalNAc alpha-2,
3-sialyltransferase 1 (ST3GaL11)
SEQ ID NO: 54
MVTLRKRTLKVLTFLVLFIFLTSFFLNYSHTMVATTWFPKQMVLELSENL

KRLIKHRPCTCTHCIGQRKLSAWFDERFNQTVQPLLTAQNALLEDDTYRW

WLRLQREKKPNNLNDTIKELFRVVPGNVDPMLEKRSVGCRRCAVVGNSGN

LRESSYGPEIDSHDFVLRMNKAPTAGFEADVGTKTTHHLVYPESFTELGD

NVSMILVPFKTIDLEWVVSAITTGTISHTYTPVLVKIRVKQDKILIYHPA

FIKYVFDNWLQGHGRYPSTGILSVIFSMHVCDEVDLYGFGADSKGNWHHY

WENNPSAGAFRKTGVHDADFESNVTATLAAINKIRIFKGR.

Truncated pig Gal beta-1,3-GalNAc alpha-2,
3-sialyltransferase 1 (ST3Gal-1 Δ45)
SEQ ID NO: 55
ELSENFKKLMKYPYRPCTCTRCIEEQRVSAWFDERFNRSMQPLLTAKNAH

LEEDTYKWWLRLQREKQPNNLNDTIRELFQVVPGNVDPLLEKRLVSCRRC

AVVGNSGNLKESYYGPQIDSHDFVLRMNKAPTEGFEADVGSKTTHHFVYP

ESFRELAQEVSMILVPFKTTDLENVISATTTGTISHTYVPVPAKIKVKKE

KILIYHPAFIKYVFDRWLQGHGRYPSTGILSVIFSLHICDEVDLYGFGAD

SKGNWHHYWENNPSAGAFRKTGVHDGDFESNVTTILASINKIRIFKGR.

Truncated pig Gal beta-1,3-GalNAc alpha-2,
3-sialyltransferase 1 (ST3Gal-1 Δ56)
SEQ ID NO: 56
YPYRPCTCTRCIEEQRVSAWFDERFNRSMQPLLTAKNAHLEEDTYKWWIR

LQREKQPNNLNDTIRELFQVVPGNVDPLLEKRLVSCRRCAVVGNSGNLKE

SYYGPQIDSHDFVLRMNKAPTEGFEADVGSKTTHHFVYPESFRELAQEVS

MILVPFKTTDLEWVISATTTGTISHTYVPVPAKIKVKKEKILIYNPAFIK

YVEDRWLQGHGRYPSTGILSVIFSLHICDEVDLYGFGADSKGNWHHYWEN

NPSAGAFRKTGVHDGDFESNVTTILASINKIRIFKGR.

maltose binding protein-tagged truncated pig Gal
beta-1,3-GalNAc alpha-2,3-sialyltransferase 1
(MBP-ST3Gal-1 Δ45)
SEQ ID NO: 57
MKIEEGKLVIWINGDKGYNGLAEVGKKFEKDTGIKVTVEHPDKLEEKFPQ

VAATGDGPDIIFWAHDRFGGYAQSGLLAEITPDKAFQDKLYPFTWDAVRY

NGKLIAYPIAVEALSLIYNKDLLPNPPKTWEEIPALDKELKAKGKSALMF

NLQEPYFTWPLIAADGGYAFKYENGKYDIKDVGVDNAGAKAGLTFLVDLI

KNKHMNADTDYSIAEAAFNKGETANTINGPWAWSNIDTSKVNYGVTVLPT

FKGQPSKPFVGVLSAGINAASPNKELAKEFLENYLLTDEGLEAVNKDKPL

GAVALKSYEEELAKDPRIAATMENAQKGEIMPNIPQMSAFWYAVRTAVIN

AASGRQTVDEALKDAQTNSSSNNNNNNNNNLGIEGRISEFGSELSENFK

KLMKYPYRPCTCTRCIEEQRVSAWFDERFNRSNQPLLTAKNAHLEEDTYK

WWLRLQREKQPNNLNDTIRELFQVVPGNVDPLLEKRLVSCRRCAVVGNSG

NLKESYYGPQIDSHDFVLRMNKAPTEGFEADVGSKTTHHFVYPESFRELA

QEVSMILVPFKTTDLEWVISATTTGRISHTYVPVPAKIKVKKEKILIYHP

AFIKYVFDRWLQGHGRYPSTGILSVIFSLHICDEVDLYGFGADSKGNWHH

YWENNPSAGAFRKTGVHDGDFESNVTTILASINKIRIFKGR.

maltose binding protein-starch binding domain-
tagged truncated pig Gal beta-1,3-GalNAc alpha-2,
3-sialyltransferase 1 (MBP-SBD-ST3Gal-1 Δ45)
SEQ ID NO: 58
MKIEEGKLVIWINGDKGYNGLAEVGKKFEKDTGIKVTVEHPDKLEEKFPQ

VAATGDGPDIIFWAHDRFGGYAQSGLLAEITPDKAFQDKLYPFTWDAVRY

NGKLIAYPIAVEALSLIYNKDLLPNPPKTWEEIPALDKELKAKGKSALMF

NLQEPYFTWPLIAADGGYAFKYENGKYDIKDVGVDNAGAKAGLTFLVDLI

KNKHMNADTDYSIAEAAFNKGETANTINGPWAWSNIDTSKVNYGVTVLPT

FKGQPSKPFVGVLSAGINAASPNKELAKEFLENYLLTDEGLEAVNKDKPL

GAVALKSYEEELAKDPRIAATMENAQKGEIMPNIPQMSAFWYAVRTAVIN

AASGRQTVDEALKDAQTNSSSNNNNNNNNNLGIEGRISEFGSIVATGGT

TTTATPTGSGSVTSTSKTTATASKTSTSTSSTSCTTPTAVAVTFDLTATT

TYGENIYLVGSISQLGDWETSDGIALSADKYTSSDFLWYVTVTLPAGESF

EYKFIRIESDDSVEWESDPNREYTVPQACGTSTATVTDTWRGSELSENFK

KLMKYPYRPCTCTRCIEEQRVSAWFDERFNRSMQPLLTAKNAHLEEDTYK

WWLRLQREKQPNNLNDTIRELFQVVPGNVDPLLEKRLVSCRRCAVVGNSG

NLKESYYGFQIDSHDFVLRMNKAPTEGFEADVGSKTTHHFVYPESFRELA

QEVSMILVPFKTTDLEWVISATTTGRISHTYVPVPAKIKVKKEKILIYHP

AFIKYVFDRWLQGHGRYPSTGILSVIFSLHICDEVDLYGFGADSKGNWHH

YWENNPSAGAFRKTGVHDGDFESNVTTILASINKIRIFKGR.

human alpha-N-acetylgalactosaminide alpha-2,
6-sialyltransferase I (ST6GalNAc-1)
SEQ ID NO: 59
MRSCLWRCRHLSQGVQWSLLLAVLVFFLFALPSFIKEPQTKPSRHQRTEN

IKERSLQSLAKPKSQAPTRARRTTIYAEPVPENNALNTQTQPKAHTTGDR

GKEANQAPPEEQDKVPHTAQRAAWKSPEKEKTMVNTLSPRGQDAGMASGR

TEAQSWKSQDTKTTQGNGGQTRKLTASRTVSEKHQGKAATTAKTLIPKSQ

HRMLAPTGAVSTRTRQKGVTTAVIPPKEKKPQATPPPAPFQSPTTQRNQR

LKAANFKSEPRWDFEEKYSFEIGGLQTTCPDSVKIKASKSLWLQKLFLPN

LTLELDSRHFNQSEWDRLEHFAPPFGFMELNYSLVQKVVTRFPPVPQQQL

LLASLPAGSLRCITCAVVGNGGILNNSHNGQEIDSHDYVFRLSGALIKGY

EQDVGTRTSFYGFTAFSLTQSLLILGNRGFKNVPLGKDVRYLHFLEGTRD

YEWLEALLMNQTVMSKNLFWFRHRPQEAFREALHMDRYLLLHPDFLRYMK

NRFLRsKTLDGAHWRIYRPTTGALLLLTALQLGDQVSAYGFITEGHERFS

DHYYDTSWKRLIFYINHDFKLEREVWKRLHDEGIIRLYQRPGPGTAKAK

N.

human N-acetylgalactosamine-alpha2,6-
sialyltransferase I (ST6GalNAcI), from
pcDNA3.1 (+) ST6GalNAcI-N1C1#1
SEQ ID NO: 60
MRSCLWRCRHLSQGVQWSLLLAVLVFFFLFALPSFIKEFQTKPSRHQRTEN

IKERSLQSLAKPKSQAPTRARRTTIYAEPVPENNALNTQTQPKAHTTGDR

GKEANQAPPEEQDKVPHTAQRAAWKSPEKEKTMVNTLSPRGQDAGMASGR

TEAQSWKSQDTKTTKGNGGQTRKLTASRTVSEKHQGKAATTAKTLIPKSQ

HRMLAPTGAVSTRTRQKGVTTAVIPPKEKKPQATPPPAPFQSPTTQRNQR

LKAANFKSEPRWDFEEKYSFEIGGLQTTCPDSVKIKASKSLWLQKLFLPN

LTLFLDSRHFNQSEWDRLEHFAPPFGFMELNYSLVQKVVTRFPPVPQQQL

LLASLPAGSLRCITCAVVGNGGILNNSHIGQEIDSHDYVFRLSGALIKGY

EQDVGTRTSFYGFTAFSLTQSLLILGNRGFKNVPLGKDVRYLHFLEGTRD

YEWLEALLMNQTVMSKNLFWFRHRPQEAFREALRMDRYLLLHPDFLRYMK

NRFLRSKTLDGAHWRIYRPTTGALLLLTALQLCDQVSAYGFITEGHERFS

DRYYDTSWKRLIFYINHDFKLEREVWKRLHDEGIIRLYQRPGPGTAKAK

N.

mouse alpha-N-acetylgalactosaminide alpha-2,
6-sialyltransferase I (ST6GalNAc-1)
SEQ ID NO: 61
MTRYCRGLSQRQAFLLLLTVLALLFILLFVVKDPRAKDSRRQFILNNDSSA

QEILQKAEPQGPIMTLSPRVHNKEATSVSSKDLKKQEREAVQGEQAEGKE

KRKLETIRPAPENPQSKAEPAAFKPVSEHLDKVPRTPGALSTRKTPMATG

AVPAKKKVVQATKSPASSPHPTTRRRQRLKASEFKSEPRWDFEEEYSLDM

SSLQTNCSASVKIKASKSPWLQNIFLPNITLFLDSGRFTQSEWNRLEHFA

PPFGFMELNQSLVQKVVTRFPPVRQQQLLLASLPTGYSKCITCAVVGNGG

ILNDSRVGREIDSHDYVFRLSGAVIKGYEQDVGTRTSFYGFTAFSLTQSI

LILGRRGFQHVPLGKDVRYLHFLEGTRNYEWLEAMFLNQTLAKTRLSWFR

HRPQEAFRNALDLDRYLLRPDFLRYMKNRFLRSKTLDTAXWRIYRPTTG

ALLLLTALHLCDKVSAYGFITEGHERFSDHYYDTSWKRLIFYINHDFRLE

RMVWKRLHDEGIIWLYQRPQSDKAKN.

chicken alpha-N-acetylgalactosaminide alpha-2,
6-sialyltransferase I (ST6GalNAc-1)

SEQ ID NO: 62

MGFLIRRLPKDSRIFRWLLILTVFSFIITSFSALFGMEKSIFRQLKIYQS
IAHMLQVDTQDQQGSNYSANGRISKVGLERDIAWLELNTAVSTPSGEGKE
EQKKTVKPVAKVEEAKEKVTVKPFFPEVMGITNTTASTASVVERTKEKTTA
RPVPGVGEADGKRTTIALPSMKEDKEKATVKPSFGMKVAHANSTSKDKPK
AEEPPASVKAIRPVTQAATVTEKKKLRAADFKTEPQWDFDDEYILDSSSP
VSTCSESVRAKAAKSDWLRDLFLPNITLFIDKSYFNVSEWDRLEHFAPPY
GFMELNYSLVEEVMSRLPPNPHQQLLLANSSSNVSTCISCAVVGNGGILN
NSGMGQEIDSHDYVFRVSGAVIKGYEKDVGTKTSFYGFTAYSLVSSLQNL
GHKGFKKIPQGKHIRYIHFLEAVRDYEWLKALLLDKDIRKGFLNYYGRRP
RERFDEDFTMNKYLVAHPDFLRYLKNRFLKSKNLQKPYWRLYRPTTGALL
LLTALHLCDRVSAYGYITEGHQKYSDHYYDKEWKRLVFYVNHDFNLEKQV
WKRLHDENIMKLYQRS.

rat alpha-N-acetylgalactosaminide alpha-2,
6-sialyltransferase I (ST6GalNAc-1)

SEQ ID NO: 63

MENRCRGLSQGQTFLLLTGLMLLFILPSVVKEPSTRVSRQFIEDNESSLQ
GVPQKPAPQGPIVTLTPTVHNKKTTSVRTKWVELQKQDRATARGERGEGV
EKKLQAIRLAPENPKGKAEPEVKTPASKHLDKLPRATGALSTRKTQMATG
AAPAKKKVVQPTPTPASFPHLTTQRRQRLKASDFKSEPRWDFEEEYSLDG
GSLQTLPWFLKITVSHSPWVQNIFLPNITLFLDSGRFNQSEWYRLEHFTP
PFGFMELNQSLVQKVVSRFPPVPQQQLLLASLPTRNLTCITCAVVGNGGI
LNNSRNGQEIDSHDYVFRLSGTVIKGYEQDVGTRTSFYGFTAFSLGQSIL
NLGSSRFSACAFLGKDVRYLHFLEGTRDYEWLEANFLNRTMANTKLYWFR
HRPQEAFREALDLDRYFLVHPDFLRYMKNRFLRSKTLDTAHWRLYRPTTG
ALLLLTALHLCDKVSAYGFITQGHERFSDHYYDTSWKRLIFYINHDFALE
RTVWKRLHDEGIIQLYQRP.

chimp alpha-N-acetylgalactosaminide alpha-2,
6-sialyltransferase I (ST6GalNAc-1)

SEQ ID NO: 64

MRSCLWRCRHLSQGVQWSLLLAVLVFFLFALPSFIKEFQTKPSREFAPEN
NALNTQTQPKAHTAGDRGKEANQAPPEEQDKVPHTAQRAAWKSPEKEKTM
VNTLSPRGQDAGMASGRTQAQSWKSQDTKTTQGNGGQTRKLMASRTVSEK
HQGKAATTAKTLIPKSQHRMLAPTGAVSTRTRQKGVTTAVIPPKEKKPQA
TPPPAPFQSPTTQRNQRLKAANFKSEPRWDFEEKYSFEIGGLQTTCPDSV
KIKASKSLWLQKLFLPNLTLFLDSRHFNQSEWDRLEHFAPPFGFMELNYS
LVQKVVTRFPPVPQQQLLLASLPAGSLRCITCAVVGNGGILNNSHMGQEI
DSHDYVFRLSGVLIKGYEQDAVDRTSFYGFTAFSLTQSLLILGNRGFKNV
PLGKDVRYLHFLEGTRDYEWLEALLMNQTVMSKNLFWFRHRPQEAFREAL
HMDRYLLLHPDFLRYMKNRFLRSKTLDGAHWRIYRPTTGALLLLTALQLC
DQVSAYGFITEGHERFSDHYYDTSWKRLIFYTNHDFKLEREVWKRLHDEG
IIRLYQRPGPGTAKAKN.

cow alpha-N-acetylgalactosaminide alpha-2,
6-sialyltransferase I (ST6GalNAc-1)

SEQ ID NO: 65

MATCPACGRLRSLLRPGSRKNEHQQNIKERSPELLQNATSQAPTPRRRAT
THVESVQGTRTRDTHPKATTLTADQRRRVQTSKARAEEPGRVPTPIGKAA
PQTQASKDTRADTLPPMAGGGGVASSRTEAPSLNSQNPRMTKGSGDRKAR
PTGPRAVPTKLRDSPSPATQRSQKLKATNFKSEPQWDFEEEYSLEVGGLQ
TGTRTRDTHPKATTLTADQRRRVQTSKARAEEPGRVPTPIGKAAPQTQAS
KDTRADTLPPMAGGGGVASSRTEAFSLNSQNPRMTKGSGDRKDRAQPTRS
SAPLQSPATQRSQKLKATNFKSEPQWDFEDEYSLEVGGLQTTCPDSVKIK
ASKSPWLRTLFLPNLTLFLDSGHFNQSEWDRLEHFAPPFGFMELNFSLVQ
KVVARFPPVPQQQLLLASLPAGSSRCISCAVVGNGGILNNSHVGPEIDSH
DYVFRLSGAIIKGYEHDVGTRTSFYGFTAFSLTQSLLILGSRGFPPHAPLG
QDVRYLHFLEGTRDYEWLEALLLNRTLTSRNLSWFRRRPQEAFQEALQLD
RYLLLHPDLLRYNKNRFLRSKTLNTAHWRIYRPTTGALLLLTALQLCDQV
SAYGFITEGHERFSDHYYDKSWKRTIFYTNHDFKLERALWKRLHDEGIIR
LYQRPITSKPTI.

dog alpha-N-acetylgalactosaminide alpha-2,
6-sialyltransferase I (ST6GalNAc-1)

SEQ ID NO: 66

MKIRLCRLSHLDQTTQWFLLSAVLTFFVFILPSFVKEPNTKPFRHQHIRN
EERSPESLHEVTGQAFTAGDRTMAPAVASAQEKSVWAPQALATAYAAQED
TRAEALEATSAQPTSMRGQERKDTMPDTLPPRAQDKGVASDRTGLPSVMS
QDTRTIKGRRDQKEEPTATRKVTPGPQSKARTTRRTPVPESQAKALTTPG
AGPMGRTRKGATTAAAPHRDTARATPPSTSSQGRTTRRSPSLRAANFKSE
PRWDFEEQYSFDTEALQPTCPDSVKVKASKSPWLQNLFLANLTLFLDSSR
FSQREWDRLEHFAPPFGFMELNQSLVQKGVTRFPPVPQQQLLPASLPAGS
SQCITCAVVGNGGILNDSRVGQEIDGHDHVFRLSGAVTKGYEQDVGTRTS
FYGFTAFSITQSLLALGGRGFPHVPLGKDVRYLHFLEGTRDYEWLEALLL
NQTLVKSSLSWFRRRPQEAFRDTLQLDRYLLLHPDFMRYMKNRFLRSKTL
NNIHWRIYRPTTGALLLLTALHLCDQVSAYGFITEGHERFSDHYYDKSWK
RTIFYTNHDFPLERTLWKRLHDEGIIRLYQRPIISKPKMVQTRPQAPPDS
PGDTGTKEENPHCRRPLDLAIQRHPHFRALFDLSTPVLLSGSLFTQELWD
SLSQHKAPYGWQGLSHQAINSTLSLLNGSESSQLFATSRKPLSSCIRCAV
VGNGGILNGSRQGLNIDAHDYVFRQTLKTERGGRVPARRGPPGRMSPEVR
RCGDGLDGDSGGRGQHSYPFPDGNVSVQGHPAAKIIKVQPPLTTPALGLP
PPSLSCLFDDLRYIFIPSDIRDYVMLRSAILGVPVPEGPDKGDRSPSHSP
ATSASYIGPVRGIPSYIAPYVPRFLKEPPFFQPPTVLVGGKPHVVPTVLA
ATFYTPFFRYYAQPWPYRPHRKRPSLSGARSSRGLVWVEPNLIWDNPYKG
PGSRLDLELGLYPVSAYFGITSNYWKFSDHYFERVKKPLIFYVNHDLSLE
ASLWRDLHKAGILQLYQR.

zebrafish alpha-N-acetylgalactosaminide alpha-2,
6-sialyltransferase I (ST6GalNAc-1)
SEQ ID NO: 67

MDYFLWPSVLFTLLAGIVAAFVLVKNKPAHHQSSVVVEEEKKADAGVSSQ

EQHCEHWDESCQLKTVEKRLQTEDKTLEKAKDLNRDDLEEDALVQPTARE

EEPGIRSALREYAFSPDAESKPLKYMAGMLRTCQLEKMMTKEELEEEQSK

TIIISSLILSPLGNTNLFKTQKHLNVERKVNITPIPVLYKKNFTKLPVWD

FEDVYLRDSNARKPTCPKSLHNTEDPEFKESVLPDIQLWLYKGQLNMSEW

NRLAHFNNPFGFMEYNYNEIKRAVDLIPKPRSSILLPVPKGSRDGCIRCA

VVGAGGILNNSKMGREIDSHDYVFRVNGAVTKGYEEDVGNRTSVYVHTAF

SLYATILTLKKYGFHNIPQDEGIKYVMIPEGLRDFEWLQGLLQGKAANGS

FKGVRPLNFFNGHFNESRFNVLHPDFLRYIRNRFMFSKQMQGNYWAMYRP

TNGAFALFLAIHTCDMVNAYGFITEDHHKYSNYYYEKFKKTSVIFYINHD

YGLEIKTWKKLHDSGIIRLFQRH.

zebrafish 2 alpha-N-acetylgalactosaminide alpha-2,
6-sialyltransferase I (ST6GalNAc-1)
SEQ ID NO: 68

MFLLRIFLVTTFIASLPLEIFVTFYNGTSTLQIKWRQYYYWLNQGQVACS

LLTIVEPEPTNSSALTDILANTTTMRLDPFETLSTPLPIMDKHKFTSLPH

WKFDDLYRLDPHFKPSECATSLQNSSNPTFKKKFIPNIQLFLQSDHLNMS

EWNRLYHFNNPFGYMGLNYTAIKAAVETIHKPASSQLLQVHPGVKDGCIR

CAVVGASGILNGSKLGKEIDSSDYVFRMNAAIIAGHEEDVGKRTSVYVHT

AHSIIQSLMIHKKRGFKQIPTDKDIKYVLIPEGPRDYNFLESLMKNRKIP

SGAYRGRTPRKYYSGHFNESSYYILHPDFLRYVRNRFLRAKQLKTKRWWV

VRPTNGAFTLLLAMHTCDIVRVYGFCTADYRKYPSYYYDTKHTKLVFYGN

HDYRLEMKTWKKFHDDKLIWMYLGKSN.

xenopus alpha-N-acetylgalactosaminide alpha-2,
6-sialyltransferase I (ST6GalNAc-1)
SEQ ID NO: 69

MRPRWLRAVGITIGALTVCSLFYGHYYSSLVSVARSPQGGVGYDLPSKGL

EWIPAVPHGRERNRELAETLRVQRPSKVPGTCPTSLQLRVKNDSYFKTIF

NFEVPLLLWNSHLTENNWDTLSKRPVPYGWKDLPREDVASALKLLNDSAN

KAMFERQGPQKCIRCAVVGNGGILNGSKKGKEIDGHDYVFRLNGAVIKGF

EKDVGTKTSFYGFTVNTMKNSLISYQEHGFTETPKGKDLHYIFIPSDLRD

YVMLRSGILGVKVPSGYDEGDKPSEYFGPKPSPKKFKMLHPDFLLYTRDR

FLKSDILNTEYASLYMPSTGGLMLLTALHSCDQVSAYGFITPDYNRYSDH

YYERQKVFLEVDANHDMLMEMQLWGRLHDRGIIKLYKR.

Takifugu alpha-N-acetylgalactosaminide alpha-2,
6-sialyltransferase I (ST6GalNAc-1)
SEQ ID NO: 70

SSGSLESMKLSDQQIKVDSRTTATPAYVKSSGPRQHTEHRAREQEIQNVS

RSTPRSRGANQTRIEVFVKKPQQPTQETRTTDPPFIGDTYMSEEIPPQTT

CPDGIRTRRTNTEFSGMFLNNVFVLQWARHATHEEYGRLSQHRGAHGWGG

VDYNTLVDALSVLNSSANWQMLDDWKDRSNNSECIRCAVVGNGGILKDSK

RGAEIDSHHYVFRTNGAVIKGFEKDVGSRTTHYTFSATTLMNSIRAYAGV

GFKAPPVSKETRYIFLPENDRDYLLVKAAATHTLVERGPQRNQKPASFFG

KDVSAEKVKMYHPDFVRYLRNRFLRSATLKTKYKDIYRPSTGAVMLLVAL

HTCDKVSAYGFMTPDYMKYSDHYYDKKQKSVVFFKNHDLRMEMALWQRLH

QAGLIQLYMRQ.

sea urchin alpha-N-acetylgalactosaminide alpha-2,
6-sialyltransferase I (ST6GalNAc-1)
SEQ ID NO: 71

MRLWRKLTSCKTRSRFVLLAFWYTMIALSVSLLYSLRGTHHSQDDSGTTS

RRSRFYNSLFPFSRNDVADYATLTQHDVADDIVAPPHVGATGEIGPEKNV

AIDDNKQIQHLIRRNSGGIAGQSGNLIGDMLNDEEQRTFEVVEEEVAEQE

EIEVVNEFRDLNGKRPSGDDPRAPVTSTIDVTSIHFVNATVKPTPPPEVQ

GYYNVQTKDKLRMRCSQCALVSSSGHLVNTSAGAEIDSY2CVLRMNSAPV

RGYEVDVGRRTTIRIMGHVNLKVLNASNELQDEILINSTTRAEKIIVPWL

YNVKVNQATDMYYKSARNLSSLYPHVEFYLLTPDKMKIAESLFQTETGLT

RQETRTWLSTGWMNMLYAVDVCDKVDIFGLVPENYCLKNPNSSVLYHYYE

SDGLKECDYYTISEERLTSGHKFITEKAVFARWATKFNMVIPPTSLEPHG

RCPY.

Truncated human alpha-N-acetylgalactosaminide
alpha-2,6-sialyltransferase I (ST6GalNAc-1 Δ35)
SEQ ID NO: 72

KEPQTKPSRHQRTENIKERSLQSLAKPKSQAPTRARRTTIYAEPVFENNA

LNTQTQPKAHTTGDRGKEANQAPPEEQDKVPHTAQRAAWKSPEKEKTMVN

TLSPRGQDAGMASGRTEAQSWKSQDTKTTQGNGGQTRKLTASRTVSEKHQ

GKAATTAKTLIPKSQHRMLAPTGAVSTRTRQKGVTTAVIPPKEKKPQATP

PPAPFQSPTTQRNQRLKAANFKSEPRWDFEEKYSFEIGGLQTTCPDSVKI

KASKSLWLQKLFLPNLTLFLDSRHFNQSEWDRLEHFAPPEGFMELNYSLV

QKVVTRFPPVPQQQLLLASLPAGSLRCITCAVVGNGGILNNSHMGQEIDS

HDYVFRLSGALIKGYEQDVGTRTSFYGFTAFSLTQSLLILGNRGFKNVPL

GKDVRYLHFLEGTRDYEWLEALLMNQTVMSKNLFWFRHRPQEAFREALHM

DRYLLLHPDFLRYMKNRFLRSKTLDGAHWRIYRPTTGALLLLTALQLCDQ

VSAYGFITEGHERFSDHYYDTSWKRLIFYINHDFKLEREVWERLHDEGII

RLYQRPGPGTAKAKN.

maltose binding protein-tagged truncated human
alpha-N-acetylgalactosaminide alpha-2,
6-sialyltransferase I (MBP-ST6GalNAc-1 Δ35)
SEQ ID NO: 73

MKIEEGKLVIWINGDKGYNGLAEVGKKFEKDTGIKVTVEHPDKLEEKFPQ

VAATGDGPDIIFWAHDRFGGYAQSGLLAEITPDKAFQDKLYPFTWDAVRY

NGKLIAYPIAVEALSLIYNKDLLPNPPKTWEEIPALDKELKAKGKSALMF

NLQEPYFTWPLIAADGGYAFKYENGKYDIKDVGVDNAGAKAGLTFLVDLI

KNKHMNADTDYSIAEAAFNKGETAMTINGPWAWSNIDTSKVNYGVTVLPT

FKGQPSEPFVGVLSAGINAASPNKELAKEFLENYLLTDEGLEAVNKDKPL

GAVALKSYEEELAKDPRIAATMENAQKGEIMPNIPQMSAFWYAVRTAVIN

AASGRQTVDEALKDAQTNSSSNNNNNNNNNNLGIEGRISEFGSKEPQTKP

SRHQRTENIKERSLQSLAKPKSQAPTRARRTTIYAEPVPENNALNTQTQP

KAHTTGDRGKEANQAPPEEQDKVPHTAQRAAWKSPEKEKTMVNTLSPRGQ

DAGMASGRTEAQSWKSQDTKTTQGNGGQTRKLTASRTVSEKHQGKAATTA

KTLIPKSQHRMLAPTGAVSTRTRQKGVTTAVIPPKEKKPQATPPPAPFQS

PTTQRNQRLKAANFKSEPRWDFEEKYSFEIGGLQTTCPDSVKIKASKSLW

LQKLFLPNLTLFLDSRHFNQSEWDRLEHFAPPFGFMELNYSLVQKVVTRF

PPVPQQQLLLASLPAGSLRCITCAVVGNGGILNNSHMGQEIDSHDYVFRL

SGALIKGYEQOVGTRTSFYGFTAFSLTQSLLILGNRGFKNVPLGKDVRYL

HFLEGTRDYEWLEALLMNQTVMSKNLFWFRHRPQEAFREALHMDRYLLLH

PDFLRYMKNRFLRSKTLDGAHWRIYRPTTGALLLLTALQLCDQVSAYGFI

TEGHERFSDHYYDTSWKRLIFYINHDFKLEREVWKRLHDEGIIRLYQRPG

PGTAKAKN.

Truncated chicken N-acetylgalactosamine-alpha-2,
6-sialyltransferase I (ST6GalNAc-1 Δ231)
SEQ ID NO: 74
KTEPQWDFDDEYILDSSSPVSTCSESVRAKAAKSDWLRDLFLPNITLFID

KSYFNVSEWDRLEHFAPPYGFMELNYSLVEEVMSRLPPNPHQQLLLANSS

SNVSTCISCAVVGNGGILNNSGMGQEIDSHDYVFRVSGAVIKGYEKDVGT

KTSFYGFTAYSLVSSSLQNLGHKGFKKIPQGKHIRYIHFLEAVRDYEWLKA

LLLDKDIRKGFLNYYGRRPRERFDEDFTMNKYLVAHPDFLRYLKNRFLKS

KNLQKPYWRLYRPTTGALLLLTALHLCDRVSAYGYITEGHQKYSDHYYDK

EWKRLVFYVNHDFNLEKQVWKRLHDENIMKLYQRS.

human Gal beta-1,3-GalNAc alpha-2,3-
sialyltransferase III (ST3Gal3)
SEQ ID NO: 75
MGLLVFVRNLLLALCLFLVLGFLYYSAWKLHLLQWEEDSNSVVLSFDSAG

QTLGSEYDRLGFLLNLDSKLPAELATKYANFSEGACKPGYASALMTAIFP

RFSKPAPMFLDDSFRKWARIREFVPPFGIKGQDNLIKAILSVTKEYRLTP

ALDSLRCRRCIIVGNGGVLANKSLGSRIDDYDIVVRLNSAPVKGFEKDVG

SKTTLRITYPEGANQRPEQYERDSLFVLAGFKWQDFKWLKYIVYKERVSA

SDGFWKSVATRVPKEPPEIRILNPYFIQEAAFTLIGLPFNNGLMGRGNIP

TLGSVAVTMALHGCDEVAVAGFGYDMSTPNAPLHYYETVRMAAIKESWTH

NIQREKEFLRKLVKARVITDLSSGI.

rat Gal beta-1,3-GalNAc alpha-2,3-
sialyltransferase III (ST3Gal3)
SEQ ID NO: 76
MGLLVFVRNLLLALCLFLVLGFLYYSAWKLHLLQWEDSNSLILSLDSAGQ

TLGTEYDRLGFLLKLDSKLPAELATKYANFSEGACKPGYASAMMTAIFPR

FSKPAPMFLDDSFRKWARIREFVPPFGIKGQDNLIKAILSVTKEYRLTPA

LDSLHCRRCIIVGNGGVLANKSLGSRIDDYDIVIRLNSAPVKGFEKDVGS

KTTLRITYPEGAMQRPEQYERDSLFVLAGFKWQDEKWLKYIVYKERVSAS

DGPWKSVATRVPKEPPEIRILNPYFIQEAAFTLIGLPFNNGLMGRGNIPT

LGSVAVTMALDGCDEVAVAGFGYDMNTPNAPLHYYETVRMAAIKESWTHN

IQREKEFLRKLVKARVITDLSSGI.

Truncated rat Gal beta-1,3-GalNAc alpha-2,3-
sialyltransferase III (ST3Gal3 Δ72) V162I D311H
mutant
SEQ ID NO: 77
LATKYANFSEGACKPGYASAMMTAIFPRFSKPAPMFLDDSFRKWARIREF

VPPFGIKGQDNLIKAILSVTKEYRLTPALDSLHCRRCIIIGRGGVLANKS

LGSRIDDYDIVIRLNSAPVKGFEKDVGSKTTLRITYPEGAMQRPEQYERD

SLFVLAGFKWQDFKWLKYIVYKERVSASDGFWKSVATRVPKEPPEIRILN

PYFIQEAAFTLIGLPFNNGLMGRGNIPTLGSVAVTMALNGCDEVAVAGFG

YDMNTPNAPLHYYETVRMAAIKESWTHNIQREKEFLRKLVKARVITDLSS

GI.

MBP-tagged truncated rat Gal beta-1,3-GalNAc
alpha-2,3-sialyltransferase II (ST3Gal3 Δ72) V162I
D311H mutant
SEQ ID NO: 78
MKIEEGKLVIWINGDKGYNGLAEVGKKFEKDTGIKVTVEHPDKLEEKFPQ

VAATGDGPDIIFWAHDRFGGYAQSGLLAEITPDKAFQDKLYPFTWDAVRY

NGKLIAYPIAVEALSLIYNKDLLPNPPKTWEEIPALDKELKAKGKSALMF

NLQEPYFTWPLIAADGGYAFKYENGKYDIKDVGVDNAGAKAGLTFLVDLI

KNKHMNADTDYSIAEAAFNKGETAMTINGPWAWSNIDTSKVNYGVTVLPT

FKGQPSKPFVGVLSAGINAASPNKELAKEFLENYLLTDEGLEAVNKDKPL

GAVALKSYEEELAKDPRIAATMENAQKGEIMPNIPQMSAFWYAVRTAVIN

AASGRQTVDEALKDAQTNSSSNNNNNNNNNLGIEGRISEFGSLATKYAN

FSEGACKPGYASAMMTAIFPRFSKPAPMFLDDSFRKWARIREFVPPFGIK

GQDNLIKAILSVTKEYRLTPALDSLHCRRCIIIGNGGVLANKSLGSRIDD

YDIVIRLNSAPVKGFEKDVGSKTTLRITYPEGAMQRPEQYERDSLFVLAF

GKWQDFKWLKYIVYKERVSASDGFWKSVATRVPKEPPEIRILNPYFIQEA

AFTLIGLPFNNGLMGRGNIPTLGSVAVTMALHGCDEVAVAGFGYDMNTPN

APLHYYETVRMAAIKESWTHNIQREKEFLRKLVKARVITDLSSGI.

Rat GalE
SEQ ID NO: 79
MEEKVLVTGGAGYIGSHTVLELLEAGYSPVVIDNFHNSIRGEDSMPESLR

RVQELTGRSVEFEEMDILDQAALQHLFKKHNFKAVIHFAGLKAVGESVQK

PLDYYRVNLTGTIQLLEIMRAHGVKSLVFSSSATVYGNPQYLPLDEAHPT

GGCTNPYGKSKFFIEEMIQDLCRADTAWNAVLLRYFNPIGAHASGRIGED

PQGIPNNLMPYVSQVAIGRREALNVFGDDYATEDGTGVRDYIHVVDLAKG

HIAALKKLKEQCGCRIYNLGTGTGYSVLQMVQAMEKASGKKIPYKVVARR

EGDVAACYANPSLAHEELGWTAALGLDRMCEDLWRWQKQNPSGFGAHG.

Campylobacter jejuni GNE
SEQ ID NO: 80
MKILISGGAGYIGSNTLRQFLKTDHEICVLDNLSKGSKIAIEDLQKTRAF

KFFEQDLSDFQGVKALFEREKFDAIVHFAASIEVFESMQNPLKYYMNNTV

NTTNLIETCLQTGVNKFIFSSTAATYGEPQTPVVSETSPLAPINPYGRSK

LMSEEVLRDASMANPEFKHCILRYFNVAGACMDYTLGQRYPKATLLIKVA

AECAAGKRDKLFIFGDDYDTKDGTCIRDFIHVDDISSAHLAALDYLKENE

SNVFNVGYGHGFSVKEVIEAMKKVSGVDFKVELAPRRAGDPSVLISDASK

IRNLTSWQPKYDDLELICKSAFDWEKQC.

Human G-CSF 174 aa form
SEQ ID NO: 81
MTPLGPASSLPQSFLLKCLEQVRKIQGDGAALQEKLCATYKLCHPEELVL
LGHSLGIPWAPLSSCPSQALQLAGCLSQHSGLFLYQGLLQALEGISPEL
GPTLDTLQLDVADFATTIWQQMEELGMAPALQPTQGAMPAFASAFQRRAG
GVLVASHLQSFLEVSYRVLRHLAQP.

What is claimed is:

1. An in vivo method of producing an O-glycosylated soluble therapeutic protein inside of a prokaryotic microorganism comprising:
   a) expressing a soluble therapeutic protein in the cytoplasm of a prokaryotic microorganism,
   b) expressing a heterologous soluble active nucleotide sugar:polypeptide glycosyltransferase in the cytoplasm of the prokaryotic microorganism, and
   c) growing the prokaryotic microorganism under conditions that allow intracellular transfer of a first sugar moiety from a first donor substrate to an amino acid acceptor substrate on the therapeutic protein by the heterologous soluble active nucleotide sugar:polypeptide glycosyltransferase, thereby producing the O-glycosylated soluble therapeutic protein inside of the prokaryotic microorganism.

2. The method of claim 1, wherein the prokaryotic microorganism has an oxidizing cytoplasm.

3. The method of claim 2, wherein the prokaryotic microorganism is genetically modified to have the oxidizing cytoplasm.

4. The method of claim 1, wherein the prokaryotic microorganism is an E. coli or a Pseudomonas bacterium.

5. The method of claim 3, wherein the microorganism is E. coli.

6. The method of claim 5, wherein the prokaryotic microorganism has a mutation in an endogenous reductase nucleic acid.

7. The method of claim 1, wherein the heterologous soluble active nucleotide sugar:polypeptide glycosyltransferase is a soluble active eukaryotic N-acetylgalactosaminyl transferase (GalNAcT).

8. The method of claim 1, further comprising
   d) expressing a first heterologous soluble active glycosyltransferase in the prokaryotic microorganism and allowing intracellular transfer of a second sugar moiety from a second donor substrate to a first acceptor substrate on the therapeutic protein by the first heterologous soluble active glycosyltransferase, thereby producing the O-glycosylated soluble therapeutic protein.

9. The method of claim 8, wherein the first heterologous soluble active glycosyltransferase is a eukaryotic core I galactosyltransferase (Core 1 GalT1) or an α-N-acetylgalactosaminide α-2,6-sialyltransferase I (ST6 GalNAc 1).

10. The method of claim 9, further comprising
    e) expressing a second heterologous soluble active glycosyltransferase in the prokaryotic microorganism, and allowing intracellular transfer of a third sugar moiety from a third donor substrate to a second acceptor substrate on the therapeutic protein by the second soluble active glycosyltransferase, thereby producing the O-glycosylated soluble therapeutic protein.

11. The method of claim 10, wherein the second heterologous soluble active glycosyltransferase is a sialyltransferase selected from the group consisting of a eukaryotic α(2,3) sialyltransferase (ST3Gal1) and a bacterial α(2,3)sialyltransferase.

12. The method of claim 1, wherein the microorganism is grown in a medium that comprises a precursor of the donor substrate.

13. The method of claim 1, wherein the prokaryotic microorganism is grown at a temperature lower than an optimal growth temperature.

14. The method of claim 1, further comprising isolating the O-glycosylated soluble therapeutic protein from the prokaryotic microorganism.

15. The method of claim 1, wherein the O-glycosylated soluble therapeutic protein is produced on a commercial scale.

16. The method of claim 1, wherein the prokaryotic microorganism expresses an accessory enzyme, and wherein the accessory enzyme is selected from the group consisting of a UDP-glucose 4' epimerase protein, a UDP-GlcNAc 4' epimerase protein, and a dual function UDP-glucose 4' epimerase protein/UDP-GlcNAc 4' epimerase protein.

17. The method of claim 1, further comprising modifying the O-glycosylated therapeutic protein by addition of a poly (ethylene glycol) (PEG) moiety.

18. The method of claim 17, wherein the PEG moiety is added by enzymatic transfer of a modified sugar comprising a PEG moiety to an amino acid or glycosyl residue of the O-glycosylated soluble therapeutic protein mediated by a glycosyltransferase.

19. The method of claim 1, wherein the soluble therapeutic protein is selected from the group consisting of granulocyte colony stimulating factor (G-CSF), granulocyte-macrophage colony stimulating factor (GM-CSF), thrombopoietin (TPO), erythropoietin (EPO), follicle stimulating hormone (FSH), human growth hormone (HGH), insulin, tumor necrosis factor alpha (TNF-α), leptin, human chorionic gonadotropin, bone morphogenetic protein 2 (BMP-2), bone morphogenetic protein 7 (BMP-7), fibroblast growth factor-7 (FGF-7), FGF-20, FGF-21, neurotrophin-3, tissue type plasminogen activator (TPA), urokinase, Factor VII, Factor VIII, Factor IX, Factor X, Factor XIII, hrDNase, glucocerebrosidase, hirudin, α1 antitrypsin, antithrombin III, acid α-glucosidase, α galactosidase A, α-L-iduronidase, interleukin-1 (IL-1), IL-1B, IL-2, IL-3, IL-4, IL-21, IL-22, interferon-alpha (IFN-α), IFN-α-2b, IFN-β, IFN-γ, IFN-omega, CD4, tumor necrosis factor receptor (TNF-R), TNF-R-IgG Fc fusion, α-CD20, PSGL-1, GlyCAM, N-CAM, anti-RSV monoclonal antibody (MAb), anti-IL-2 receptor MAb, anti-CEA MAb, anti-glycoprotein IIb/IIIa MAb, anti-EGF MAb, anti-Her-2 MAb, anti-CD20 MAb, anti-α-CD3 MAb, TNF-R-IgG Fc fusion, anti-TNFα, anti-CD4 MAb, anti-PSGL-1 MAb, anti-F protein of Respiratory Syncytial Virus MAb, anti-thrombin-III MAb, hepatitis B surface antigen (HbsAg), chimeric diphtheria toxin-IL-2, and transferrin.

* * * * *

SEQUENCE LISTING

<160> NUMBER OF SEQ ID NOS: 85

<210> SEQ ID NO 1
<211> LENGTH: 211
<212> TYPE: PRT
<213> ORGANISM: Homo sapiens
<220> FEATURE:
<223> OTHER INFORMATION: FGF-20

<400> SEQUENCE: 1

Met Ala Pro Leu Ala Glu Val Gly Gly Phe Leu Gly Gly Leu Glu Gly
 1               5                  10                  15

Leu Gly Gln Gln Val Gly Ser His Phe Leu Leu Pro Pro Ala Gly Glu
            20                  25                  30

Arg Pro Pro Leu Leu Gly Glu Arg Arg Ser Ala Ala Glu Arg Ser Ala
        35                  40                  45

Arg Gly Gly Pro Gly Ala Ala Gln Leu Ala His Leu His Gly Ile Leu
    50                  55                  60

Arg Arg Arg Gln Leu Tyr Cys Arg Thr Gly Phe His Leu Gln Ile Leu
65                  70                  75                  80

Pro Asp Gly Ser Val Gln Gly Thr Arg Gln Asp His Ser Leu Phe Gly
                85                  90                  95

Ile Leu Glu Phe Ile Ser Val Ala Val Gly Leu Val Ser Ile Arg Gly
            100                 105                 110

Val Asp Ser Gly Leu Tyr Leu Gly Met Asn Asp Lys Gly Glu Leu Tyr
        115                 120                 125

Gly Ser Glu Lys Leu Thr Ser Glu Cys Ile Phe Arg Glu Gln Phe Glu
    130                 135                 140

Glu Asn Trp Tyr Asn Thr Tyr Ser Ser Asn Ile Tyr Lys His Gly Asp
145                 150                 155                 160

Thr Gly Arg Arg Tyr Phe Val Ala Leu Asn Lys Asp Gly Thr Pro Arg
                165                 170                 175

Asp Gly Ala Arg Ser Lys Arg His Gln Lys Phe Thr His Phe Leu Pro
            180                 185                 190

Arg Pro Val Asp Pro Glu Arg Val Pro Glu Leu Tyr Lys Asp Leu Leu
        195                 200                 205

Met Tyr Thr
    210

<210> SEQ ID NO 2
<211> LENGTH: 209
<212> TYPE: PRT
<213> ORGANISM: Homo sapiens
<220> FEATURE:
<223> OTHER INFORMATION: mature FGF-21

<400> SEQUENCE: 2

Met Asp Ser Asp Glu Thr Gly Phe Glu His Ser Gly Leu Trp Val Ser

```
                1               5              10              15
        Val Leu Ala Gly Leu Leu Leu Gly Ala Cys Gln Ala His Pro Ile Pro
                        20                  25                  30

Asp Ser Ser Pro Leu Leu Gln Phe Gly Gly Gln Val Arg Gln Arg Tyr
                        35                  40                  45

Leu Tyr Thr Asp Asp Ala Gln Gln Thr Glu Ala His Leu Glu Ile Arg
                    50                  55                  60

Glu Asp Gly Thr Val Gly Gly Ala Ala Asp Gln Ser Pro Glu Ser Leu
        65                  70                  75                  80

Leu Gln Leu Lys Ala Leu Lys Pro Gly Val Ile Gln Ile Leu Gly Val
                        85                  90                  95

Lys Thr Ser Arg Phe Leu Cys Gln Arg Pro Asp Gly Ala Leu Tyr Gly
                        100                 105                 110

Ser Leu His Phe Asp Pro Glu Ala Cys Ser Phe Arg Glu Leu Leu Leu
                        115                 120                 125

Glu Asp Gly Tyr Asn Val Tyr Gln Ser Glu Ala His Gly Leu Pro Leu
                    130                 135                 140

His Leu Pro Gly Asn Lys Ser Pro His Arg Asp Pro Ala Pro Arg Gly
        145                 150                 155                 160

Pro Ala Arg Phe Leu Pro Leu Pro Gly Leu Pro Pro Ala Leu Pro Glu
                        165                 170                 175

Pro Pro Gly Ile Leu Ala Pro Gln Pro Pro Asp Val Gly Ser Ser Asp
                        180                 185                 190

Pro Leu Ser Met Val Gly Pro Ser Gln Gly Arg Ser Pro Ser Tyr Ala
                        195                 200                 205

Ser

<210> SEQ ID NO 3
<211> LENGTH: 499
<212> TYPE: PRT
<213> ORGANISM: Homo sapiens
<220> FEATURE:
<223> OTHER INFORMATION: Glucocerebrosidase aa 38-536

<400> SEQUENCE: 3

Met Gly Ala Arg Pro Cys Ile Pro Lys Ser Phe Gly Tyr Ser Ser Val
        1               5                   10                  15

Val Cys Val Cys Asn Ala Thr Tyr Cys Asp Ser Phe Asp Pro Pro Thr
                        20                  25                  30

Phe Pro Ala Leu Gly Thr Phe Ser Arg Tyr Glu Ser Thr Arg Ser Gly
                    35                  40                  45

Arg Arg Met Glu Leu Ser Met Gly Pro Ile Gln Ala Asn His Thr Gly
                50                  55                  60

Thr Gly Leu Leu Leu Thr Leu Gln Pro Glu Gln Lys Phe Gln Lys Val
        65                  70                  75                  80

Lys Gly Phe Gly Gly Ala Met Thr Asp Ala Ala Ala Leu Asn Ile Leu
                        85                  90                  95

Ala Leu Ser Pro Pro Ala Gln Asn Leu Leu Leu Lys Ser Tyr Phe Ser
                        100                 105                 110

Glu Glu Gly Ile Gly Tyr Asn Ile Ile Arg Val Pro Met Ala Ser Cys
                        115                 120                 125

Asp Phe Ser Ile Arg Thr Tyr Thr Tyr Ala Asp Thr Pro Asp Asp Phe
                    130                 135                 140

Gln Leu His Asn Phe Ser Leu Pro Glu Glu Asp Thr Lys Leu Lys Ile
        145                 150                 155                 160
```

```
Pro Leu Ile His Arg Ala Leu Gln Leu Ala Gln Arg Pro Val Ser Leu
            165                 170                 175
Leu Ala Ser Pro Trp Thr Ser Pro Thr Trp Leu Lys Thr Asn Gly Ala
        180                 185                 190
Val Asn Gly Lys Gly Ser Leu Lys Gly Gln Pro Gly Asp Ile Tyr His
    195                 200                 205
Gln Thr Trp Ala Arg Tyr Phe Val Lys Phe Leu Asp Ala Tyr Ala Glu
210                 215                 220
His Lys Leu Gln Phe Trp Ala Val Thr Ala Glu Asn Glu Pro Ser Ala
225                 230                 235                 240
Gly Leu Leu Ser Gly Tyr Pro Phe Gln Cys Leu Gly Phe Thr Pro Glu
                245                 250                 255
His Gln Arg Asp Phe Ile Ala Arg Asp Leu Gly Pro Thr Leu Ala Asn
            260                 265                 270
Ser Thr His His Asn Val Arg Leu Leu Met Leu Asp Asp Gln Arg Leu
        275                 280                 285
Leu Leu Pro His Trp Ala Lys Val Val Leu Thr Asp Pro Glu Ala Ala
    290                 295                 300
Lys Tyr Val His Gly Ile Ala Val His Trp Tyr Leu Asp Phe Leu Ala
305                 310                 315                 320
Pro Ala Lys Ala Thr Leu Gly Glu Thr His Arg Leu Phe Pro Asn Thr
                325                 330                 335
Met Leu Phe Ala Ser Glu Ala Cys Val Gly Ser Lys Phe Trp Glu Gln
            340                 345                 350
Ser Val Arg Leu Gly Ser Trp Asp Arg Gly Met Gln Tyr Ser His Ser
        355                 360                 365
Ile Ile Thr Asn Leu Leu Tyr His Val Val Gly Trp Thr Asp Trp Asn
    370                 375                 380
Leu Ala Leu Asn Pro Glu Gly Gly Pro Asn Trp Val Arg Asn Phe Val
385                 390                 395                 400
Asp Ser Pro Ile Ile Val Asp Ile Thr Lys Asp Thr Phe Tyr Lys Gln
                405                 410                 415
Pro Met Phe Tyr His Leu Gly His Phe Ser Lys Phe Ile Pro Glu Gly
            420                 425                 430
Ser Gln Arg Val Gly Leu Val Ala Ser Gln Lys Asn Asp Leu Asp Ala
        435                 440                 445
Val Ala Leu Met His Pro Asp Gly Ser Ala Val Val Val Val Leu Asn
    450                 455                 460
Arg Ser Ser Lys Asp Val Pro Leu Thr Ile Lys Asp Pro Ala Val Gly
465                 470                 475                 480
Phe Leu Glu Thr Ile Ser Pro Gly Tyr Ser Ile His Thr Tyr Leu Trp
                485                 490                 495
Arg Arg Gln

<210> SEQ ID NO 4
<211> LENGTH: 120
<212> TYPE: PRT
<213> ORGANISM: Homo sapiens
<220> FEATURE:
<223> OTHER INFORMATION: NT-3

<400> SEQUENCE: 4

Met Tyr Ala Glu His Lys Ser His Arg Gly Glu Tyr Ser Val Cys Asp
1               5                   10                  15
Ser Glu Ser Leu Trp Val Thr Asp Lys Ser Ser Ala Ile Asp Ile Arg
            20                  25                  30
```

```
Gly His Gln Val Thr Val Leu Gly Glu Ile Lys Thr Gly Asn Ser Pro
         35                  40                  45

Val Lys Gln Tyr Phe Tyr Glu Thr Arg Cys Lys Glu Ala Arg Pro Val
 50                  55                  60

Lys Asn Gly Cys Arg Gly Ile Asp Asp Lys His Trp Asn Ser Gln Cys
 65                  70                  75                  80

Lys Thr Ser Gln Thr Tyr Val Arg Ala Leu Thr Ser Glu Asn Asn Lys
                 85                  90                  95

Leu Val Gly Trp Arg Trp Ile Arg Ile Asp Thr Ser Cys Val Cys Ala
                100                 105                 110

Leu Ser Arg Lys Ile Gly Arg Thr
            115                 120
```

<210> SEQ ID NO 5
<211> LENGTH: 637
<212> TYPE: PRT
<213> ORGANISM: Artificial Sequence
<220> FEATURE:
<223> OTHER INFORMATION: MBP-tagged pro-NT-3

<400> SEQUENCE: 5

```
Met Lys Thr Glu Glu Gly Lys Leu Val Ile Trp Ile Asn Gly Asp Lys
  1               5                  10                  15

Gly Tyr Asn Gly Leu Ala Glu Val Gly Lys Lys Phe Glu Lys Asp Thr
                 20                  25                  30

Gly Ile Lys Val Thr Val Glu His Pro Asp Lys Leu Glu Glu Lys Phe
             35                  40                  45

Pro Gln Val Ala Ala Thr Gly Asp Gly Pro Asp Ile Ile Phe Trp Ala
 50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270
```

Asn Lys Glu Leu Ala Lys Glu Phe Leu Glu Asn Tyr Leu Leu Thr Asp
    275                 280                 285

Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
                355                 360                 365

Ser Ser Ser Asn Asn Asn Asn Asn Asn Asn Asn Asn Leu Gly Pro
370                 375                 380

Gly Ala Ala His Tyr Val Glu Phe Gly Ser His Met Gln Gly Asn Asn
385                 390                 395                 400

Met Asp Gln Arg Ser Leu Pro Glu Asp Ser Leu Asn Ser Leu Ile Ile
                405                 410                 415

Lys Leu Ile Gln Ala Asp Ile Leu Lys Asn Lys Leu Ser Lys Gln Met
                420                 425                 430

Val Asp Val Lys Glu Asn Tyr Gln Ser Thr Leu Pro Lys Ala Glu Ala
                435                 440                 445

Pro Arg Glu Pro Glu Arg Gly Gly Pro Ala Lys Ser Ala Phe Gln Pro
450                 455                 460

Val Ile Ala Met Asp Thr Glu Leu Leu Arg Gln Arg Arg Tyr Asn
465                 470                 475                 480

Ser Pro Arg Val Leu Leu Ser Asp Ser Thr Pro Leu Glu Pro Pro
                485                 490                 495

Leu Tyr Leu Met Glu Asp Tyr Val Gly Ser Pro Val Val Ala Asn Arg
                500                 505                 510

Thr Ser Arg Arg Lys Arg Tyr Ala Glu His Lys Ser His Arg Gly Glu
                515                 520                 525

Tyr Ser Val Cys Asp Ser Glu Ser Leu Trp Val Thr Asp Lys Ser Ser
530                 535                 540

Ala Ile Asp Ile Arg Gly His Gln Val Thr Val Leu Gly Glu Ile Lys
545                 550                 555                 560

Thr Gly Asn Ser Pro Val Lys Gln Tyr Phe Tyr Glu Thr Arg Cys Lys
                565                 570                 575

Glu Ala Arg Pro Val Lys Asn Gly Cys Arg Gly Ile Asp Asp Lys His
                580                 585                 590

Trp Asn Ser Gln Cys Lys Thr Ser Gln Thr Tyr Val Arg Ala Leu Thr
                595                 600                 605

Ser Glu Asn Asn Lys Leu Val Gly Trp Arg Trp Ile Arg Ile Asp Thr
610                 615                 620

Ser Cys Val Cys Ala Leu Ser Arg Lys Ile Gly Arg Thr
625                 630                 635

<210> SEQ ID NO 6
<211> LENGTH: 192
<212> TYPE: PRT
<213> ORGANISM: Homo sapiens
<220> FEATURE:
<223> OTHER INFORMATION: Mutant GH #1

<400> SEQUENCE: 6

Met Phe Pro Thr Ile Pro Leu Ser Arg Leu Phe Asp Asn Ala Met Leu

-continued

```
                1               5                  10                 15
Arg Ala His Arg Leu His Gln Leu Ala Phe Asp Thr Tyr Gln Glu Phe
                    20                  25                  30

Glu Glu Ala Tyr Ile Pro Lys Glu Gln Lys Tyr Ser Phe Leu Gln Asn
                    35                  40                  45

Pro Gln Thr Ser Leu Cys Phe Ser Glu Ser Ile Pro Thr Pro Ser Asn
                50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                    85                  90                  95

Val Phe Ala Asn Ser Leu Val Tyr Gly Ala Ser Asp Ser Asn Val Tyr
                    100                 105                 110

Asp Leu Leu Lys Asp Leu Glu Glu Gly Ile Gln Thr Leu Met Gly Arg
                    115                 120                 125

Leu Glu Asp Gly Ser Pro Thr Ile Asn Thr Ile Phe Lys Gln Thr Tyr
                    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                    165                 170                 175

Phe Leu Arg Ile Val Gln Cys Arg Ser Val Glu Gly Ser Cys Gly Phe
                    180                 185                 190
```

<210> SEQ ID NO 7
<211> LENGTH: 192
<212> TYPE: PRT
<213> ORGANISM: Homo sapiens
<220> FEATURE:
<223> OTHER INFORMATION: Mutant GH #2

<400> SEQUENCE: 7

```
Met Phe Pro Thr Ile Pro Leu Ser Arg Leu Phe Asp Asn Ala Met Leu
1               5                   10                  15

Arg Ala His Arg Leu His Gln Leu Ala Phe Asp Thr Tyr Gln Glu Phe
                    20                  25                  30

Glu Glu Ala Tyr Ile Pro Lys Glu Gln Lys Ala Ser Phe Leu Gln Asn
                    35                  40                  45

Pro Gln Thr Ser Leu Cys Phe Ser Glu Ser Ile Pro Thr Pro Ser Asn
                50                  55                  60

Arg Glu Glu Thr Gln Gln Lys Ser Asn Leu Glu Leu Leu Arg Ile Ser
65                  70                  75                  80

Leu Leu Leu Ile Gln Ser Trp Leu Glu Pro Val Gln Phe Leu Arg Ser
                    85                  90                  95

Val Phe Ala Asn Ser Leu Val Tyr Gly Ala Ser Asp Ser Asn Val Tyr
                    100                 105                 110

Asp Leu Leu Lys Asp Leu Glu Glu Gly Ile Gln Thr Leu Met Gly Arg
                    115                 120                 125

Leu Glu Asp Gly Ser Pro Thr Ile Asn Thr Ile Ala Asn Gln Thr Ala
                    130                 135                 140

Ser Lys Phe Asp Thr Asn Ser His Asn Asp Asp Ala Leu Leu Lys Asn
145                 150                 155                 160

Tyr Gly Leu Leu Tyr Cys Phe Arg Lys Asp Met Asp Lys Val Glu Thr
                    165                 170                 175

Phe Leu Arg Ile Val Gln Cys Arg Ser Val Glu Gly Ser Cys Gly Phe
                    180                 185                 190
```

```
<210> SEQ ID NO 8
<211> LENGTH: 638
<212> TYPE: PRT
<213> ORGANISM: Escherichia coli
<220> FEATURE:
<223> OTHER INFORMATION: dnaK HSP-70-type molecular chaperone,
      heat-inducible

<400> SEQUENCE: 8

Met Gly Lys Ile Ile Gly Ile Asp Leu Gly Thr Thr Asn Ser Cys Val
 1               5                  10                  15

Ala Ile Met Asp Gly Thr Thr Pro Arg Val Leu Glu Asn Ala Glu Gly
             20                  25                  30

Asp Arg Thr Thr Pro Ser Ile Ile Ala Tyr Thr Gln Asp Gly Glu Thr
         35                  40                  45

Leu Val Gly Gln Pro Ala Lys Arg Gln Ala Val Thr Asn Pro Gln Asn
     50                  55                  60

Thr Leu Phe Ala Ile Lys Arg Leu Ile Gly Arg Arg Phe Gln Asp Glu
 65                  70                  75                  80

Glu Val Gln Arg Asp Val Ser Ile Met Pro Phe Lys Ile Ile Ala Ala
                 85                  90                  95

Asp Asn Gly Asp Ala Trp Val Glu Val Lys Gly Gln Lys Met Ala Pro
            100                 105                 110

Pro Gln Ile Ser Ala Glu Val Leu Lys Lys Met Lys Lys Thr Ala Glu
        115                 120                 125

Asp Tyr Leu Gly Glu Pro Val Thr Glu Ala Val Ile Thr Val Pro Ala
    130                 135                 140

Tyr Phe Asn Asp Ala Gln Arg Gln Ala Thr Lys Asp Ala Gly Arg Ile
145                 150                 155                 160

Ala Gly Leu Glu Val Lys Arg Ile Ile Asn Glu Pro Thr Ala Ala Ala
                165                 170                 175

Leu Ala Tyr Gly Leu Asp Lys Gly Thr Gly Asn Arg Thr Ile Ala Val
            180                 185                 190

Tyr Asp Leu Gly Gly Gly Thr Phe Asp Ile Ser Ile Ile Glu Ile Asp
        195                 200                 205

Glu Val Asp Gly Glu Lys Thr Phe Glu Val Leu Ala Thr Asn Gly Asp
    210                 215                 220

Thr His Leu Gly Gly Glu Asp Phe Asp Ser Arg Leu Ile Asn Tyr Leu
225                 230                 235                 240

Val Glu Glu Phe Lys Lys Asp Gln Gly Ile Asp Leu Arg Asn Asp Pro
                245                 250                 255

Leu Ala Met Gln Arg Leu Lys Glu Ala Ala Glu Lys Ala Lys Ile Glu
            260                 265                 270

Leu Ser Ser Ala Gln Gln Thr Asp Val Asn Leu Pro Tyr Ile Thr Ala
        275                 280                 285

Asp Ala Thr Gly Pro Lys His Met Asn Ile Lys Val Thr Arg Ala Lys
    290                 295                 300

Leu Glu Ser Leu Val Glu Asp Leu Val Asn Arg Ser Ile Glu Pro Leu
305                 310                 315                 320

Lys Val Ala Leu Gln Asp Ala Gly Leu Ser Val Ser Asp Ile Asp Asp
                325                 330                 335

Val Ile Leu Val Gly Gly Gln Thr Arg Met Pro Met Val Gln Lys Lys
            340                 345                 350

Val Ala Glu Phe Phe Gly Lys Glu Pro Arg Lys Asp Val Asn Pro Asp
        355                 360                 365
```

```
Glu Ala Val Ala Ile Gly Ala Ala Val Gln Gly Gly Val Leu Thr Gly
    370                 375                 380

Asp Val Lys Asp Val Leu Leu Leu Asp Val Thr Pro Leu Ser Leu Gly
385                 390                 395                 400

Ile Glu Thr Met Gly Gly Val Met Thr Thr Leu Ile Ala Lys Asn Thr
                405                 410                 415

Thr Ile Pro Thr Lys His Ser Gln Val Phe Ser Thr Ala Glu Asp Asn
            420                 425                 430

Gln Ser Ala Val Thr Ile His Val Leu Gln Gly Glu Arg Lys Arg Ala
                435                 440                 445

Ala Asp Asn Lys Ser Leu Gly Gln Phe Asn Leu Asp Gly Ile Asn Pro
            450                 455                 460

Ala Pro Arg Gly Met Pro Gln Ile Glu Val Thr Phe Asp Ile Asp Ala
465                 470                 475                 480

Asp Gly Ile Leu His Val Ser Ala Lys Asp Lys Asn Ser Gly Lys Glu
                485                 490                 495

Gln Lys Ile Thr Ile Lys Ala Ser Ser Gly Leu Asn Glu Asp Glu Ile
                500                 505                 510

Gln Lys Met Val Arg Asp Ala Glu Ala Asn Ala Glu Ala Asp Arg Lys
            515                 520                 525

Phe Glu Glu Leu Val Gln Thr Arg Asn Gln Gly Asp His Leu Leu His
            530                 535                 540

Ser Thr Arg Lys Gln Val Glu Glu Ala Gly Asp Lys Leu Pro Ala Asp
545                 550                 555                 560

Asp Lys Thr Ala Ile Glu Ser Ala Leu Thr Ala Leu Glu Thr Ala Leu
                565                 570                 575

Lys Gly Glu Asp Lys Ala Ala Ile Glu Ala Lys Met Gln Glu Leu Ala
                580                 585                 590

Gln Val Ser Gln Lys Leu Met Glu Ile Ala Gln Gln Gln His Ala Gln
            595                 600                 605

Gln Gln Thr Ala Gly Ala Asp Ala Ser Ala Asn Asn Ala Lys Asp Asp
            610                 615                 620

Asp Val Val Asp Ala Glu Phe Glu Glu Val Lys Asp Lys Lys
625                 630                 635

<210> SEQ ID NO 9
<211> LENGTH: 857
<212> TYPE: PRT
<213> ORGANISM: Escherichia coli
<220> FEATURE:
<223> OTHER INFORMATION: clpB, ClpB protease, ATP dependent

<400> SEQUENCE: 9

Met Arg Leu Asp Arg Leu Thr Asn Lys Phe Gln Leu Ala Leu Ala Asp
1               5                   10                  15

Ala Gln Ser Leu Ala Leu Gly His Asp Asn Gln Phe Ile Glu Pro Leu
            20                  25                  30

His Leu Met Ser Ala Leu Leu Asn Gln Glu Gly Gly Ser Val Ser Pro
        35                  40                  45

Leu Leu Thr Ser Ala Gly Ile Asn Ala Gly Gln Leu Arg Thr Asp Ile
    50                  55                  60

Asn Gln Ala Leu Asn Arg Leu Pro Gln Val Glu Gly Thr Gly Gly Asp
65                  70                  75                  80

Val Gln Pro Ser Gln Asp Leu Val Arg Val Leu Asn Leu Cys Asp Lys
                85                  90                  95
```

```
Leu Ala Gln Lys Arg Gly Asp Asn Phe Ile Ser Ser Glu Leu Phe Val
                100                 105                 110

Leu Ala Ala Leu Glu Ser Arg Gly Thr Leu Ala Asp Ile Leu Lys Ala
            115                 120                 125

Ala Gly Ala Thr Thr Ala Asn Ile Thr Gln Ala Ile Glu Gln Met Arg
130                 135                 140

Gly Gly Glu Ser Val Asn Asp Gln Gly Ala Glu Asp Gln Arg Gln Ala
145                 150                 155                 160

Leu Lys Lys Tyr Thr Ile Asp Leu Thr Glu Arg Ala Glu Gln Gly Lys
                165                 170                 175

Leu Asp Pro Val Ile Gly Arg Asp Glu Glu Ile Arg Arg Thr Ile Gln
            180                 185                 190

Val Leu Gln Arg Arg Thr Lys Asn Asn Pro Val Leu Ile Gly Glu Pro
        195                 200                 205

Gly Val Gly Lys Thr Ala Ile Val Glu Gly Leu Ala Gln Arg Ile Ile
        210                 215                 220

Asn Gly Glu Val Pro Glu Gly Leu Lys Gly Arg Arg Val Leu Ala Leu
225                 230                 235                 240

Asp Met Gly Ala Leu Val Ala Gly Ala Lys Tyr Arg Gly Glu Phe Glu
                245                 250                 255

Glu Arg Leu Lys Gly Val Leu Asn Asp Leu Ala Lys Gln Glu Gly Asn
            260                 265                 270

Val Ile Leu Phe Ile Asp Glu Leu His Thr Met Val Gly Ala Gly Lys
        275                 280                 285

Ala Asp Gly Ala Met Asp Ala Gly Asn Met Leu Lys Pro Ala Leu Ala
        290                 295                 300

Arg Gly Glu Leu His Cys Val Gly Ala Thr Thr Leu Asp Glu Tyr Arg
305                 310                 315                 320

Gln Tyr Ile Glu Lys Asp Ala Ala Leu Glu Arg Arg Phe Gln Lys Val
                325                 330                 335

Phe Val Ala Glu Pro Ser Val Glu Asp Thr Ile Ala Ile Leu Arg Gly
            340                 345                 350

Leu Lys Glu Arg Tyr Glu Leu His His His Val Gln Ile Thr Asp Pro
        355                 360                 365

Ala Ile Val Ala Ala Thr Leu Ser His Arg Tyr Ile Ala Asp Arg
        370                 375                 380

Gln Leu Pro Asp Lys Ala Ile Asp Leu Ile Asp Glu Ala Ala Ser Ser
385                 390                 395                 400

Ile Arg Met Gln Ile Asp Ser Lys Pro Glu Glu Leu Asp Arg Leu Asp
                405                 410                 415

Arg Arg Ile Ile Gln Leu Lys Leu Glu Gln Gln Ala Leu Met Lys Glu
            420                 425                 430

Ser Asp Glu Ala Ser Lys Lys Arg Leu Asp Met Leu Asn Glu Glu Leu
        435                 440                 445

Ser Asp Lys Glu Arg Gln Tyr Ser Glu Leu Glu Glu Trp Lys Ala
        450                 455                 460

Glu Lys Ala Ser Leu Ser Gly Thr Gln Thr Ile Lys Ala Glu Leu Glu
465                 470                 475                 480

Gln Ala Lys Ile Ala Ile Glu Gln Ala Arg Arg Val Gly Asp Leu Ala
                485                 490                 495

Arg Met Ser Glu Leu Gln Tyr Gly Lys Ile Pro Glu Leu Glu Lys Gln
            500                 505                 510

Leu Glu Ala Ala Thr Gln Leu Glu Gly Lys Thr Met Arg Leu Leu Arg
        515                 520                 525
```

Asn Lys Val Thr Asp Ala Glu Ile Ala Glu Val Leu Ala Arg Trp Thr
530                 535                 540

Gly Ile Pro Val Ser Arg Met Met Glu Ser Glu Arg Glu Lys Leu Leu
545                 550                 555                 560

Arg Met Glu Gln Glu Leu His His Arg Val Ile Gly Gln Asn Glu Ala
                565                 570                 575

Val Asp Ala Val Ser Asn Ala Ile Arg Arg Ser Arg Ala Gly Leu Ala
                580                 585                 590

Asp Pro Asn Arg Pro Ile Gly Ser Phe Leu Phe Leu Gly Pro Thr Gly
                595                 600                 605

Val Gly Lys Thr Glu Leu Cys Lys Ala Leu Ala Asn Phe Met Phe Asp
610                 615                 620

Ser Asp Glu Ala Met Val Arg Ile Asp Met Ser Glu Phe Met Glu Lys
625                 630                 635                 640

His Ser Val Ser Arg Leu Val Gly Ala Pro Pro Gly Tyr Val Gly Tyr
                645                 650                 655

Glu Glu Gly Gly Tyr Leu Thr Glu Ala Val Arg Arg Arg Pro Tyr Ser
                660                 665                 670

Val Ile Leu Leu Asp Glu Val Glu Lys Ala His Pro Asp Val Phe Asn
                675                 680                 685

Ile Leu Leu Gln Val Leu Asp Asp Gly Arg Leu Thr Asp Gly Gln Gly
690                 695                 700

Arg Thr Val Asp Phe Arg Asn Thr Val Val Ile Met Thr Ser Asn Leu
705                 710                 715                 720

Gly Ser Asp Leu Ile Gln Glu Arg Phe Gly Glu Leu Asp Tyr Ala His
                725                 730                 735

Met Lys Glu Leu Val Leu Gly Val Val Ser His Asn Phe Arg Pro Glu
                740                 745                 750

Phe Ile Asn Arg Ile Asp Glu Val Val Phe His Pro Leu Gly Glu
                755                 760                 765

Gln His Ile Ala Ser Ile Ala Gln Ile Gln Leu Lys Arg Leu Tyr Lys
                770                 775                 780

Arg Leu Glu Glu Arg Gly Tyr Glu Ile His Ile Ser Asp Glu Ala Leu
785                 790                 795                 800

Lys Leu Leu Ser Glu Asn Gly Tyr Asp Pro Val Tyr Gly Ala Arg Pro
                805                 810                 815

Leu Lys Arg Ala Ile Gln Gln Ile Glu Asn Pro Leu Ala Gln Gln
                820                 825                 830

Ile Leu Ser Gly Glu Leu Val Pro Gly Lys Val Ile Arg Leu Glu Val
        835                 840                 845

Asn Glu Asp Arg Ile Val Ala Val Gln
    850                 855

<210> SEQ ID NO 10
<211> LENGTH: 540
<212> TYPE: PRT
<213> ORGANISM: Escherichia coli
<220> FEATURE:
<223> OTHER INFORMATION: GroEL

<400> SEQUENCE: 10

Ala Ala Lys Asp Val Lys Phe Gly Asn Asp Ala Arg Val Lys Met Leu
1               5                   10                  15

Arg Gly Val Asn Val Leu Ala Asp Ala Val Lys Val Thr Leu Gly Pro
            20                  25                  30

-continued

Lys Gly Arg Asn Val Val Leu Asp Lys Ser Phe Gly Ala Pro Thr Ile
         35                  40                  45

Thr Lys Asp Gly Val Ser Val Ala Arg Glu Ile Glu Leu Glu Asp Lys
 50                  55                  60

Phe Glu Asn Met Gly Ala Gln Met Val Lys Glu Val Ala Ser Lys Ala
 65                  70                  75                  80

Asn Asp Ala Ala Gly Asp Gly Thr Thr Thr Ala Thr Val Leu Ala Gln
                 85                  90                  95

Ala Ile Ile Thr Glu Gly Leu Lys Ala Val Ala Ala Gly Met Asn Pro
             100                 105                 110

Met Asp Leu Lys Arg Gly Ile Asp Lys Ala Val Thr Ala Ala Val Glu
         115                 120                 125

Glu Leu Lys Ala Leu Ser Val Pro Cys Ser Asp Ser Lys Ala Ile Ala
 130                 135                 140

Gln Val Gly Thr Ile Ser Ala Asn Ser Asp Glu Thr Val Gly Lys Leu
 145                 150                 155                 160

Ile Ala Glu Ala Met Asp Lys Val Gly Lys Glu Gly Val Ile Thr Val
                 165                 170                 175

Glu Asp Gly Thr Gly Leu Gln Asp Glu Leu Asp Val Val Glu Gly Met
             180                 185                 190

Gln Phe Asp Arg Gly Tyr Leu Ser Pro Tyr Phe Ile Asn Lys Pro Glu
         195                 200                 205

Thr Gly Ala Val Glu Leu Glu Ser Pro Phe Ile Leu Leu Ala Asp Lys
 210                 215                 220

Lys Ile Ser Asn Ile Arg Glu Met Leu Pro Val Leu Glu Ala Val Ala
 225                 230                 235                 240

Lys Ala Gly Lys Pro Leu Leu Ile Ile Ala Glu Asp Val Glu Gly Glu
                 245                 250                 255

Ala Leu Ala Thr Leu Val Val Asn Thr Met Arg Gly Ile Val Lys Val
             260                 265                 270

Ala Ala Val Lys Ala Pro Gly Phe Gly Asp Arg Arg Lys Ala Met Leu
         275                 280                 285

Gln Asp Ile Ala Thr Leu Thr Gly Gly Thr Val Ile Ser Glu Glu Ile
 290                 295                 300

Gly Met Glu Leu Glu Lys Ala Thr Leu Glu Asp Leu Gly Gln Ala Lys
305                 310                 315                 320

Arg Val Val Ile Asn Lys Asp Thr Thr Thr Ile Ile Asp Gly Val Gly
                 325                 330                 335

Glu Glu Ala Ala Ile Gln Gly Arg Val Ala Gln Ile Arg Gln Gln Ile
             340                 345                 350

Glu Glu Ala Thr Ser Asp Tyr Asp Arg Glu Lys Leu Gln Glu Arg Val
         355                 360                 365

Ala Lys Leu Ala Gly Gly Val Ala Val Ile Lys Val Gly Ala Ala Thr
 370                 375                 380

Glu Val Glu Met Lys Glu Lys Lys Ala Arg Val Glu Asp Ala Leu His
385                 390                 395                 400

Ala Thr Arg Ala Ala Val Glu Glu Gly Val Val Ala Gly Gly Gly Val
                 405                 410                 415

Ala Leu Ile Arg Val Ala Ser Lys Leu Ala Asp Leu Arg Gly Gln Asn
             420                 425                 430

Glu Asp Gln Asn Val Gly Ile Lys Val Ala Leu Arg Ala Met Glu Ala
         435                 440                 445

Pro Leu Arg Gln Ile Val Leu Asn Cys Gly Glu Glu Pro Ser Val Val
 450                 455                 460

```
Ala Asn Thr Val Lys Gly Gly Asp Gly Asn Tyr Gly Tyr Asn Ala Ala
465                 470                 475                 480

Thr Glu Glu Tyr Gly Asn Met Ile Asp Met Gly Ile Leu Asp Pro Thr
                485                 490                 495

Lys Val Thr Arg Ser Ala Leu Gln Tyr Ala Ala Ser Val Ala Gly Leu
            500                 505                 510

Met Ile Thr Thr Glu Cys Met Val Thr Asp Leu Pro Lys Asn Asp Ala
        515                 520                 525

Ala Asp Leu Gly Ala Ala Gly Gly Met Gly Gly Met
    530                 535                 540
```

<210> SEQ ID NO 11
<211> LENGTH: 97
<212> TYPE: PRT
<213> ORGANISM: Oleispira antarctica
<220> FEATURE:
<223> OTHER INFORMATION: Cpn10

<400> SEQUENCE: 11

```
Met Lys Ile Arg Pro Leu His Asp Arg Ile Val Val Arg Arg Lys Glu
1               5                   10                  15

Glu Glu Thr Ala Thr Ala Gly Gly Ile Ile Leu Pro Gly Ala Ala Ala
            20                  25                  30

Glu Lys Pro Asn Gln Gly Val Val Ile Ser Val Gly Thr Gly Arg Ile
        35                  40                  45

Leu Asp Asn Gly Ser Val Gln Ala Leu Ala Val Asn Glu Gly Asp Val
    50                  55                  60

Val Val Phe Gly Lys Tyr Ser Gly Gln Asn Thr Ile Asp Ile Asp Gly
65                  70                  75                  80

Glu Glu Leu Leu Ile Leu Asn Glu Ser Asp Ile Tyr Gly Val Leu Glu
                85                  90                  95

Ala
```

<210> SEQ ID NO 12
<211> LENGTH: 548
<212> TYPE: PRT
<213> ORGANISM: Oleispira Antarctica
<220> FEATURE:
<223> OTHER INFORMATION: Cpn 60

<400> SEQUENCE: 12

```
Met Ala Ala Lys Asp Val Leu Phe Gly Asp Ser Ala Arg Ala Lys Met
1               5                   10                  15

Leu Val Gly Val Asn Ile Leu Ala Asp Ala Val Arg Val Thr Leu Gly
            20                  25                  30

Pro Lys Gly Arg Asn Val Val Ile Glu Lys Ser Phe Gly Ala Pro Ile
        35                  40                  45

Ile Thr Lys Asp Gly Val Ser Val Ala Arg Glu Ile Glu Leu Lys Asp
    50                  55                  60

Lys Phe Glu Asn Met Gly Ala Gln Met Val Lys Glu Val Ala Ser Gln
65                  70                  75                  80

Ala Asn Asp Gln Ala Gly Asp Gly Thr Thr Thr Ala Thr Val Leu Ala
                85                  90                  95

Gln Ala Ile Ile Ser Glu Gly Leu Lys Ser Val Ala Ala Gly Met Asn
            100                 105                 110

Pro Met Asp Leu Lys Arg Gly Ile Asp Lys Ala Thr Ala Ala Val Val
        115                 120                 125
```

```
Ala Ala Ile Lys Glu Gln Ala Gln Pro Cys Leu Asp Thr Lys Ala Ile
            130                 135                 140

Ala Gln Val Gly Thr Ile Ser Ala Asn Ala Asp Glu Thr Val Gly Arg
145                 150                 155                 160

Leu Ile Ala Glu Ala Met Glu Lys Val Gly Lys Glu Gly Val Ile Thr
                165                 170                 175

Val Glu Glu Gly Lys Gly Leu Glu Asp Glu Leu Asp Val Val Glu Gly
                180                 185                 190

Met Gln Phe Asp Arg Gly Tyr Leu Ser Pro Tyr Phe Ile Asn Asn Gln
            195                 200                 205

Glu Lys Met Thr Val Glu Met Glu Asn Pro Leu Ile Leu Leu Val Asp
210                 215                 220

Lys Lys Ile Asp Asn Leu Gln Glu Leu Leu Pro Ile Leu Glu Asn Val
225                 230                 235                 240

Ala Lys Ser Gly Arg Pro Leu Leu Ile Val Ala Glu Asp Val Glu Gly
                245                 250                 255

Gln Ala Leu Ala Thr Leu Val Val Asn Asn Leu Arg Gly Thr Phe Lys
            260                 265                 270

Val Ala Ala Val Lys Ala Pro Gly Phe Gly Asp Arg Arg Lys Ala Met
            275                 280                 285

Leu Gln Asp Leu Ala Ile Leu Thr Gly Gly Gln Val Ile Ser Glu Glu
290                 295                 300

Leu Gly Met Ser Leu Glu Thr Ala Asp Pro Ser Ser Leu Gly Thr Ala
305                 310                 315                 320

Ser Lys Val Val Ile Asp Lys Glu Asn Thr Val Ile Val Asp Gly Ala
                325                 330                 335

Gly Thr Glu Ala Ser Val Asn Thr Arg Val Asp Gln Ile Arg Ala Glu
            340                 345                 350

Ile Glu Ser Ser Thr Ser Asp Tyr Asp Ile Glu Lys Leu Gln Glu Arg
            355                 360                 365

Val Ala Lys Leu Ala Gly Gly Val Ala Val Ile Lys Val Gly Ala Gly
            370                 375                 380

Ser Glu Met Glu Met Lys Glu Lys Lys Asp Arg Val Asp Asp Ala Leu
385                 390                 395                 400

His Ala Thr Arg Ala Ala Val Glu Glu Gly Val Val Ala Gly Gly Gly
                405                 410                 415

Val Ala Leu Ile Arg Ala Leu Ser Ser Val Thr Val Val Gly Asp Asn
                420                 425                 430

Glu Asp Gln Asn Val Gly Ile Ala Leu Ala Leu Arg Ala Met Glu Ala
            435                 440                 445

Pro Ile Arg Gln Ile Ala Gly Asn Ala Gly Ala Glu Gly Ser Val Val
450                 455                 460

Val Asp Lys Val Lys Ser Gly Thr Gly Ser Phe Gly Phe Asn Ala Ser
465                 470                 475                 480

Thr Gly Glu Tyr Gly Asp Met Ile Ala Met Gly Ile Leu Asp Pro Ala
                485                 490                 495

Lys Val Thr Arg Ser Ser Leu Gln Ala Ala Ala Ser Ile Ala Gly Leu
                500                 505                 510

Met Ile Thr Thr Glu Ala Met Val Ala Asp Ala Pro Val Glu Glu Gly
            515                 520                 525

Ala Gly Gly Met Pro Asp Met Gly Gly Met Gly Gly Met Gly Gly Met
            530                 535                 540

Pro Gly Met Met
545
```

-continued

<210> SEQ ID NO 13
<211> LENGTH: 509
<212> TYPE: PRT
<213> ORGANISM: Rattus norvegicus
<220> FEATURE:
<223> OTHER INFORMATION: PDI protein, PDIA1_RAT

<400> SEQUENCE: 13

| Met | Leu | Ser | Arg | Ala | Leu | Leu | Cys | Leu | Ala | Leu | Ala | Trp | Ala | Ala | Arg |
|---|---|---|---|---|---|---|---|---|---|---|---|---|---|---|---|
| 1 | | | | 5 | | | | | 10 | | | | | 15 | |

| Val | Gly | Ala | Asp | Ala | Leu | Glu | Glu | Asp | Asn | Val | Leu | Val | Leu | Lys |
|---|---|---|---|---|---|---|---|---|---|---|---|---|---|---|
| | | | 20 | | | | | 25 | | | | | 30 | |

| Lys | Ser | Asn | Phe | Ala | Glu | Ala | Leu | Ala | Ala | His | Asn | Tyr | Leu | Leu | Val |
|---|---|---|---|---|---|---|---|---|---|---|---|---|---|---|---|
| | 35 | | | | | 40 | | | | | 45 | | | | |

| Glu | Phe | Tyr | Ala | Pro | Trp | Cys | Gly | His | Cys | Lys | Ala | Leu | Ala | Pro | Glu |
|---|---|---|---|---|---|---|---|---|---|---|---|---|---|---|---|
| | 50 | | | | | 55 | | | | | 60 | | | | |

| Tyr | Ala | Lys | Ala | Ala | Ala | Lys | Leu | Lys | Ala | Glu | Gly | Ser | Glu | Ile | Arg |
|---|---|---|---|---|---|---|---|---|---|---|---|---|---|---|---|
| 65 | | | | | 70 | | | | | 75 | | | | | 80 |

| Leu | Ala | Lys | Val | Asp | Ala | Thr | Glu | Glu | Ser | Asp | Leu | Ala | Gln | Gln | Tyr |
|---|---|---|---|---|---|---|---|---|---|---|---|---|---|---|---|
| | | | | 85 | | | | | 90 | | | | | 95 | |

| Gly | Val | Arg | Gly | Tyr | Pro | Thr | Ile | Lys | Phe | Phe | Lys | Asn | Gly | Asp | Thr |
|---|---|---|---|---|---|---|---|---|---|---|---|---|---|---|---|
| | | | 100 | | | | | 105 | | | | | 110 | | |

| Ala | Ser | Pro | Lys | Glu | Tyr | Thr | Ala | Gly | Arg | Glu | Ala | Asp | Asp | Ile | Val |
|---|---|---|---|---|---|---|---|---|---|---|---|---|---|---|---|
| | | | 115 | | | | | 120 | | | | | 125 | | |

| Asn | Trp | Leu | Lys | Lys | Arg | Thr | Gly | Pro | Ala | Ala | Thr | Thr | Leu | Ser | Asp |
|---|---|---|---|---|---|---|---|---|---|---|---|---|---|---|---|
| | 130 | | | | | 135 | | | | | 140 | | | | |

| Thr | Ala | Ala | Ala | Glu | Ser | Leu | Val | Asp | Ser | Ser | Glu | Val | Thr | Val | Ile |
|---|---|---|---|---|---|---|---|---|---|---|---|---|---|---|---|
| 145 | | | | | 150 | | | | | 155 | | | | | 160 |

| Gly | Phe | Phe | Lys | Asp | Ala | Gly | Ser | Asp | Ser | Ala | Lys | Gln | Phe | Leu | Leu |
|---|---|---|---|---|---|---|---|---|---|---|---|---|---|---|---|
| | | | | 165 | | | | | 170 | | | | | 175 | |

| Ala | Ala | Glu | Ala | Val | Asp | Asp | Ile | Pro | Phe | Gly | Ile | Thr | Ser | Asn | Ser |
|---|---|---|---|---|---|---|---|---|---|---|---|---|---|---|---|
| | | | 180 | | | | | 185 | | | | | 190 | | |

| Asp | Val | Phe | Ser | Lys | Tyr | Gln | Leu | Asp | Lys | Asp | Gly | Val | Val | Leu | Phe |
|---|---|---|---|---|---|---|---|---|---|---|---|---|---|---|---|
| | | | 195 | | | | | 200 | | | | | 205 | | |

| Lys | Lys | Phe | Asp | Glu | Gly | Arg | Asn | Asn | Phe | Glu | Gly | Glu | Ile | Thr | Lys |
|---|---|---|---|---|---|---|---|---|---|---|---|---|---|---|---|
| | 210 | | | | | 215 | | | | | 220 | | | | |

| Glu | Lys | Leu | Leu | Asp | Phe | Ile | Lys | His | Asn | Gln | Leu | Pro | Leu | Val | Ile |
|---|---|---|---|---|---|---|---|---|---|---|---|---|---|---|---|
| 225 | | | | | 230 | | | | | 235 | | | | | 240 |

| Glu | Phe | Thr | Glu | Gln | Thr | Ala | Pro | Lys | Ile | Phe | Gly | Gly | Glu | Ile | Lys |
|---|---|---|---|---|---|---|---|---|---|---|---|---|---|---|---|
| | | | | 245 | | | | | 250 | | | | | 255 | |

| Thr | His | Ile | Leu | Leu | Phe | Leu | Pro | Lys | Ser | Val | Ser | Asp | Tyr | Asp | Gly |
|---|---|---|---|---|---|---|---|---|---|---|---|---|---|---|---|
| | | | 260 | | | | | 265 | | | | | 270 | | |

| Lys | Leu | Ser | Asn | Phe | Lys | Lys | Ala | Ala | Glu | Gly | Phe | Lys | Gly | Lys | Ile |
|---|---|---|---|---|---|---|---|---|---|---|---|---|---|---|---|
| | | | 275 | | | | | 280 | | | | | 285 | | |

| Leu | Phe | Ile | Phe | Ile | Asp | Ser | Asp | His | Thr | Asp | Asn | Gln | Arg | Ile | Leu |
|---|---|---|---|---|---|---|---|---|---|---|---|---|---|---|---|
| | 290 | | | | | 295 | | | | | 300 | | | | |

| Glu | Phe | Phe | Gly | Leu | Lys | Lys | Glu | Glu | Cys | Pro | Ala | Val | Arg | Leu | Ile |
|---|---|---|---|---|---|---|---|---|---|---|---|---|---|---|---|
| 305 | | | | | 310 | | | | | 315 | | | | | 320 |

| Thr | Leu | Glu | Glu | Glu | Met | Thr | Lys | Tyr | Lys | Pro | Glu | Ser | Asp | Glu | Leu |
|---|---|---|---|---|---|---|---|---|---|---|---|---|---|---|---|
| | | | | 325 | | | | | 330 | | | | | 335 | |

| Thr | Ala | Glu | Lys | Ile | Thr | Gln | Phe | Cys | His | His | Phe | Leu | Glu | Gly | Lys |
|---|---|---|---|---|---|---|---|---|---|---|---|---|---|---|---|
| | | | 340 | | | | | 345 | | | | | 350 | | |

| Ile | Lys | Pro | His | Leu | Met | Ser | Gln | Glu | Leu | Pro | Glu | Asp | Trp | Asp | Lys |
|---|---|---|---|---|---|---|---|---|---|---|---|---|---|---|---|
| | | | 355 | | | | | 360 | | | | | 365 | | |

```
Gln Pro Val Lys Val Leu Val Gly Lys Asn Phe Glu Glu Val Ala Phe
        370                 375                 380

Asp Glu Lys Lys Asn Val Phe Val Glu Phe Tyr Ala Pro Trp Cys Gly
385                 390                 395                 400

His Cys Lys Gln Leu Ala Pro Ile Trp Asp Lys Leu Gly Glu Thr Tyr
                405                 410                 415

Lys Asp His Glu Asn Ile Val Ile Ala Lys Met Asp Ser Thr Ala Asn
            420                 425                 430

Glu Val Glu Ala Val Lys Val His Ser Phe Pro Thr Leu Lys Phe Phe
        435                 440                 445

Pro Ala Ser Ala Asp Arg Thr Val Ile Asp Tyr Asn Gly Glu Arg Thr
450                 455                 460

Leu Asp Gly Phe Lys Lys Phe Leu Glu Ser Gly Gly Gln Asp Gly Ala
465                 470                 475                 480

Gly Asp Asn Asp Asp Leu Asp Leu Glu Glu Ala Leu Glu Pro Asp Met
                485                 490                 495

Glu Glu Asp Asp Asp Gln Lys Ala Val Lys Asp Glu Leu
                500                 505
```

```
<210> SEQ ID NO 14
<211> LENGTH: 563
<212> TYPE: PRT
<213> ORGANISM: Saccharomyces cerevisiae
<220> FEATURE:
<223> OTHER INFORMATION: Ero1p

<400> SEQUENCE: 14

Met Arg Leu Arg Thr Ala Ile Ala Thr Leu Cys Leu Thr Ala Phe Thr
  1               5                  10                  15

Ser Ala Thr Ser Asn Asn Ser Tyr Ile Ala Thr Asp Gln Thr Gln Asn
             20                  25                  30

Ala Phe Asn Asp Thr His Phe Cys Lys Val Asp Arg Asn Asp His Val
         35                  40                  45

Ser Pro Ser Cys Asn Val Thr Phe Asn Glu Leu Asn Ala Ile Asn Glu
     50                  55                  60

Asn Ile Arg Asp Asp Leu Ser Ala Leu Leu Lys Ser Asp Phe Phe Lys
 65                  70                  75                  80

Tyr Phe Arg Leu Asp Leu Tyr Lys Gln Cys Ser Phe Trp Asp Ala Asn
                 85                  90                  95

Asp Gly Leu Cys Leu Asn Arg Ala Cys Ser Val Asp Val Val Glu Asp
            100                 105                 110

Trp Asp Thr Leu Pro Glu Tyr Trp Gln Pro Glu Ile Leu Gly Ser Phe
        115                 120                 125

Asn Asn Asp Thr Met Lys Glu Ala Asp Ser Asp Asp Glu Cys Lys
    130                 135                 140

Phe Leu Asp Gln Leu Cys Gln Thr Ser Lys Lys Pro Val Asp Ile Glu
145                 150                 155                 160

Asp Thr Ile Asn Tyr Cys Asp Val Asn Asp Phe Asn Gly Lys Asn Ala
                165                 170                 175

Val Leu Ile Asp Leu Thr Ala Asn Pro Glu Arg Phe Thr Gly Tyr Gly
            180                 185                 190

Gly Lys Gln Ala Gly Gln Ile Trp Ser Thr Ile Tyr Gln Asp Asn Cys
        195                 200                 205

Phe Thr Ile Gly Glu Thr Gly Glu Ser Leu Ala Lys Asp Ala Phe Tyr
    210                 215                 220

Arg Leu Val Ser Gly Phe His Ala Ser Ile Gly Thr His Leu Ser Lys
```

```
                225                 230                 235                 240
Glu Tyr Leu Asn Thr Lys Thr Gly Lys Trp Glu Pro Asn Leu Asp Leu
                245                 250                 255

Phe Met Ala Arg Ile Gly Asn Phe Pro Asp Arg Val Thr Asn Met Tyr
            260                 265                 270

Phe Asn Tyr Ala Val Val Ala Lys Ala Leu Trp Lys Ile Gln Pro Tyr
        275                 280                 285

Leu Pro Glu Phe Ser Phe Cys Asp Leu Val Asn Lys Glu Ile Lys Asn
    290                 295                 300

Lys Met Asp Asn Val Ile Ser Gln Leu Asp Thr Lys Ile Phe Asn Glu
305                 310                 315                 320

Asp Leu Val Phe Ala Asn Asp Leu Ser Leu Thr Leu Lys Asp Glu Phe
                325                 330                 335

Arg Ser Arg Phe Lys Asn Val Thr Lys Ile Met Asp Cys Val Gln Cys
            340                 345                 350

Asp Arg Cys Arg Leu Trp Gly Lys Ile Gln Thr Thr Gly Tyr Ala Thr
        355                 360                 365

Ala Leu Lys Ile Leu Phe Glu Ile Asn Asp Ala Asp Glu Phe Thr Lys
    370                 375                 380

Gln His Ile Val Gly Lys Leu Thr Lys Tyr Glu Leu Ile Ala Leu Leu
385                 390                 395                 400

Gln Thr Phe Gly Arg Leu Ser Glu Ser Ile Glu Ser Val Asn Met Phe
                405                 410                 415

Glu Lys Met Tyr Gly Lys Arg Leu Asn Gly Ser Glu Asn Arg Leu Ser
            420                 425                 430

Ser Phe Phe Gln Asn Asn Phe Phe Asn Ile Leu Lys Glu Ala Gly Lys
        435                 440                 445

Ser Ile Arg Tyr Thr Ile Glu Asn Ile Asn Ser Thr Lys Glu Gly Lys
    450                 455                 460

Lys Lys Thr Asn Asn Ser Gln Ser His Val Phe Asp Asp Leu Lys Met
465                 470                 475                 480

Pro Lys Ala Glu Ile Val Pro Arg Pro Ser Asn Gly Thr Val Asn Lys
                485                 490                 495

Trp Lys Lys Ala Trp Asn Thr Glu Val Asn Asn Val Leu Glu Ala Phe
            500                 505                 510

Arg Phe Ile Tyr Arg Ser Tyr Leu Asp Leu Pro Arg Asn Ile Trp Glu
        515                 520                 525

Leu Ser Leu Met Lys Val Tyr Lys Phe Trp Asn Lys Phe Ile Gly Val
    530                 535                 540

Ala Asp Tyr Val Ser Glu Glu Thr Arg Glu Pro Ile Ser Tyr Lys Leu
545                 550                 555                 560

Asp Ile Gln

<210> SEQ ID NO 15
<211> LENGTH: 701
<212> TYPE: PRT
<213> ORGANISM: Saccharomyces cerevisiae
<220> FEATURE:
<223> OTHER INFORMATION: Pdi1p

<400> SEQUENCE: 15

Met Lys Met Asn Leu Lys Arg Leu Val Val Thr Phe Phe Ser Cys Ile
1               5                   10                  15

Thr Phe Leu Leu Lys Phe Thr Ile Ala Ala Glu Pro Pro Glu Gly
            20                  25                  30
```

-continued

```
Phe Pro Glu Pro Leu Asn Pro Thr Asn Phe Lys Glu Leu Ser Lys
         35                  40                  45

Gly Leu His Ile Ile Asp Phe Tyr Ser Pro Tyr Cys Pro His Cys Lys
 50                      55                  60

His Leu Ala Pro Val Trp Met Glu Thr Trp Glu Phe Lys Glu Glu
 65                  70                  75                  80

Ser Lys Thr Leu Asn Ile Thr Phe Ser Gln Val Asn Cys Ile Glu Ser
                     85                  90                  95

Ala Asp Leu Cys Gly Asp Glu Asn Ile Glu Tyr Phe Pro Glu Ile Arg
                100                 105                 110

Leu Tyr Asn Pro Ser Gly Tyr Ile Lys Ser Phe Thr Glu Thr Pro Arg
            115                 120                 125

Thr Lys Glu Ser Leu Ile Ala Phe Ala Arg Arg Glu Ser Met Asp Pro
        130                 135                 140

Asn Asn Leu Asp Thr Asp Leu Asp Ser Ala Lys Ser Glu Ser Gln Tyr
145                 150                 155                 160

Leu Glu Gly Phe Asp Phe Leu Glu Leu Ile Ala Gly Lys Ala Thr Arg
                165                 170                 175

Pro His Leu Val Ser Phe Trp Pro Thr Lys Asp Met Lys Asn Ser Asp
            180                 185                 190

Asp Ser Leu Glu Phe Lys Asn Cys Asp Lys Cys His Glu Phe Gln Arg
        195                 200                 205

Thr Trp Lys Ile Ile Ser Arg Gln Leu Ala Val Asp Asp Ile Asn Thr
210                 215                 220

Gly His Val Asn Cys Glu Ser Asn Pro Thr Ile Cys Glu Glu Leu Gly
225                 230                 235                 240

Phe Gly Asp Leu Val Lys Ile Thr Asn His Arg Ala Asp Arg Glu Pro
                245                 250                 255

Lys Val Ala Leu Val Leu Pro Asn Lys Thr Ser Asn Asn Leu Phe Asp
            260                 265                 270

Tyr Pro Asn Gly Tyr Ser Ala Lys Ser Asp Gly Tyr Val Asp Phe Ala
        275                 280                 285

Arg Arg Thr Phe Thr Asn Ser Lys Phe Pro Asn Ile Thr Glu Gly Glu
290                 295                 300

Leu Glu Lys Lys Ala Asn Arg Asp Ile Asp Phe Leu Gln Glu Arg Gly
305                 310                 315                 320

Arg Val Thr Asn Asn Asp Ile His Leu Val Phe Ser Tyr Asp Pro Glu
                325                 330                 335

Thr Val Val Ile Glu Asp Phe Asp Ile Leu Glu Tyr Leu Ile Glu Pro
            340                 345                 350

Leu Ser Lys Ile Pro Asn Ile Tyr Leu His Gln Ile Asp Lys Asn Leu
        355                 360                 365

Ile Asn Leu Ser Arg Asn Leu Phe Gly Arg Met Tyr Glu Lys Ile Asn
370                 375                 380

Tyr Asp Ala Ser Gln Thr Gln Lys Val Phe Asn Lys Glu Tyr Phe Thr
385                 390                 395                 400

Met Asn Thr Val Thr Gln Leu Pro Thr Phe Phe Met Phe Lys Asp Gly
                405                 410                 415

Asp Pro Ile Ser Tyr Val Phe Pro Gly Tyr Ser Thr Thr Glu Met Arg
            420                 425                 430

Asn Ile Asp Ala Ile Met Asp Trp Val Lys Lys Tyr Ser Asn Pro Leu
        435                 440                 445

Val Thr Glu Val Asp Ser Ser Asn Leu Lys Lys Leu Ile Ser Phe Gln
450                 455                 460
```

```
Thr Lys Ser Tyr Ser Asp Leu Ala Ile Gln Leu Ile Ser Ser Thr Asp
465                 470                 475                 480

His Lys His Ile Lys Gly Ser Asn Lys Leu Ile Lys Asn Leu Leu Leu
                485                 490                 495

Ala Ser Trp Glu Tyr Glu His Ile Arg Met Glu Asn Asn Phe Glu Glu
            500                 505                 510

Ile Asn Glu Arg Arg Ala Arg Lys Ala Asp Gly Ile Lys Lys Ile Lys
        515                 520                 525

Glu Lys Lys Ala Pro Ala Asn Lys Ile Val Asp Lys Met Arg Glu Glu
    530                 535                 540

Ile Pro His Met Asp Gln Lys Lys Leu Leu Leu Gly Tyr Leu Asp Ile
545                 550                 555                 560

Ser Lys Glu Lys Asn Phe Phe Arg Lys Tyr Gly Ile Thr Gly Glu Tyr
                565                 570                 575

Lys Ile Gly Asp Val Ile Ile Ile Asp Lys Ser Asn Asn Tyr Tyr Tyr
            580                 585                 590

Asn Lys Asp Asn Phe Gly Asn Ser Leu Thr Ser Asn Asn Pro Gln Leu
        595                 600                 605

Leu Arg Glu Ala Phe Val Ser Leu Asn Ile Pro Ser Lys Ala Leu Tyr
    610                 615                 620

Ser Ser Lys Leu Lys Gly Arg Leu Ile Asn Ser Pro Phe His Asn Val
625                 630                 635                 640

Leu Ser Phe Leu Asp Ile Ile His Gly Asn Gly Met Pro Gly Tyr Leu
                645                 650                 655

Ile Val Ile Val Leu Phe Ile Ala Ile Leu Lys Gly Pro Ser Ile Tyr
            660                 665                 670

Arg Arg Tyr Lys Val Arg Lys His Tyr Arg Ala Lys Arg Asn Ala Val
        675                 680                 685

Gly Ile Leu Gly Asn Met Glu Lys Lys Lys Asn Gln Asp
    690                 695                 700

<210> SEQ ID NO 16
<211> LENGTH: 176
<212> TYPE: PRT
<213> ORGANISM: Escherichia coli
<220> FEATURE:
<223> OTHER INFORMATION: DsbB protein

<400> SEQUENCE: 16

Met Leu Arg Phe Leu Asn Gln Cys Ser Gln Gly Arg Gly Ala Trp Leu
1               5                   10                  15

Leu Met Ala Phe Thr Ala Leu Ala Leu Glu Leu Thr Ala Leu Trp Phe
            20                  25                  30

Gln His Val Met Leu Leu Lys Pro Cys Val Leu Cys Ile Tyr Glu Arg
        35                  40                  45

Cys Ala Leu Phe Gly Val Leu Gly Ala Ala Leu Ile Gly Ala Ile Ala
    50                  55                  60

Pro Lys Thr Pro Leu Arg Tyr Val Ala Met Val Ile Trp Leu Tyr Ser
65                  70                  75                  80

Ala Phe Arg Gly Val Gln Leu Thr Tyr Glu His Thr Met Leu Gln Leu
                85                  90                  95

Tyr Pro Ser Pro Phe Ala Thr Cys Asp Phe Met Val Arg Phe Pro Glu
            100                 105                 110

Trp Leu Pro Leu Asp Lys Trp Val Pro Gln Val Phe Val Ala Ser Gly
        115                 120                 125
```

```
Asp Cys Ala Glu Arg Gln Trp Asp Phe Leu Gly Leu Glu Met Pro Gln
            130                 135                 140

Trp Leu Leu Gly Ile Phe Ile Ala Tyr Leu Ile Val Ala Val Leu Val
145                 150                 155                 160

Val Ile Ser Gln Pro Phe Lys Ala Lys Lys Arg Asp Leu Phe Gly Arg
                165                 170                 175
```

<210> SEQ ID NO 17
<211> LENGTH: 208
<212> TYPE: PRT
<213> ORGANISM: Escherichia coli
<220> FEATURE:
<223> OTHER INFORMATION: DsbA protein

<400> SEQUENCE: 17

```
Met Lys Lys Ile Trp Leu Ala Leu Ala Gly Leu Val Leu Ala Phe Ser
1               5                   10                  15

Ala Ser Ala Ala Gln Tyr Glu Asp Gly Lys Gln Tyr Thr Thr Leu Glu
            20                  25                  30

Lys Pro Val Ala Gly Ala Pro Gln Val Leu Glu Phe Phe Ser Phe Phe
            35                  40                  45

Cys Pro His Cys Tyr Gln Phe Glu Glu Val Leu His Ile Ser Asp Asn
        50                  55                  60

Val Lys Lys Lys Leu Pro Glu Gly Val Lys Met Thr Lys Tyr His Val
65                  70                  75                  80

Asn Phe Met Gly Gly Asp Leu Gly Lys Asp Leu Thr Gln Ala Trp Ala
                85                  90                  95

Val Ala Met Ala Leu Gly Val Glu Asp Lys Val Thr Val Pro Leu Phe
            100                 105                 110

Glu Gly Val Gln Lys Thr Gln Thr Ile Arg Ser Ala Ser Asp Ile Arg
            115                 120                 125

Asp Val Phe Ile Asn Ala Gly Ile Lys Gly Glu Glu Tyr Asp Ala Ala
        130                 135                 140

Trp Asn Ser Phe Val Val Lys Ser Leu Val Ala Gln Gln Glu Lys Ala
145                 150                 155                 160

Ala Ala Asp Val Gln Leu Arg Gly Val Pro Ala Met Phe Val Asn Gly
                165                 170                 175

Lys Tyr Gln Leu Asn Pro Gln Gly Met Asp Thr Ser Asn Met Asp Val
            180                 185                 190

Phe Val Gln Gln Tyr Ala Asp Thr Val Lys Tyr Leu Ser Glu Lys Lys
            195                 200                 205
```

<210> SEQ ID NO 18
<211> LENGTH: 236
<212> TYPE: PRT
<213> ORGANISM: Escherichia coli
<220> FEATURE:
<223> OTHER INFORMATION: DsbC protein

<400> SEQUENCE: 18

```
Met Lys Lys Gly Phe Met Leu Phe Thr Leu Leu Ala Ala Phe Ser Gly
1               5                   10                  15

Phe Ala Gln Ala Asp Asp Ala Ala Ile Gln Gln Thr Leu Ala Lys Met
            20                  25                  30

Gly Ile Lys Ser Ser Asp Ile Gln Pro Ala Pro Val Ala Gly Met Lys
            35                  40                  45

Thr Val Leu Thr Asn Ser Gly Val Leu Tyr Ile Thr Asp Asp Gly Lys
        50                  55                  60
```

His Ile Ile Gln Gly Pro Met Tyr Asp Val Ser Gly Thr Ala Pro Val
65                  70                  75                  80

Asn Val Thr Asn Lys Met Leu Leu Lys Gln Leu Asn Ala Leu Glu Lys
                85                  90                  95

Glu Met Ile Val Tyr Lys Ala Pro Gln Glu Lys His Val Ile Thr Val
            100                 105                 110

Phe Thr Asp Ile Thr Cys Gly Tyr Cys His Lys Leu His Glu Gln Met
        115                 120                 125

Ala Asp Tyr Asn Ala Leu Gly Ile Thr Val Arg Tyr Leu Ala Phe Pro
    130                 135                 140

Arg Gln Gly Leu Asp Ser Asp Ala Glu Lys Glu Met Lys Ala Ile Trp
145                 150                 155                 160

Cys Ala Lys Asp Lys Asn Lys Ala Phe Asp Asp Val Met Ala Gly Lys
                165                 170                 175

Ser Val Ala Pro Ala Ser Cys Asp Val Asp Ile Ala Asp His Tyr Ala
            180                 185                 190

Leu Gly Val Gln Leu Gly Val Ser Gly Thr Pro Ala Val Val Leu Ser
        195                 200                 205

Asn Gly Thr Leu Val Pro Gly Tyr Gln Pro Pro Lys Glu Met Lys Glu
    210                 215                 220

Phe Leu Asp Glu His Gln Lys Met Thr Ser Gly Lys
225                 230                 235

<210> SEQ ID NO 19
<211> LENGTH: 565
<212> TYPE: PRT
<213> ORGANISM: Escherichia coli
<220> FEATURE:
<223> OTHER INFORMATION: DsbD protein

<400> SEQUENCE: 19

Met Ala Gln Arg Ile Phe Thr Leu Ile Leu Leu Cys Ser Thr Ser
1               5                   10                  15

Val Phe Ala Gly Leu Phe Asp Ala Pro Gly Arg Ser Gln Phe Val Pro
            20                  25                  30

Ala Asp Gln Ala Phe Ala Phe Asp Phe Gln Gln Asn Gln His Asp Leu
        35                  40                  45

Asn Leu Thr Trp Gln Ile Lys Asp Gly Tyr Tyr Leu Tyr Arg Lys Gln
    50                  55                  60

Ile Arg Ile Thr Pro Glu His Ala Lys Ile Ala Asp Val Gln Leu Pro
65                  70                  75                  80

Gln Gly Val Trp His Glu Asp Glu Phe Tyr Gly Lys Ser Glu Ile Tyr
                85                  90                  95

Arg Asp Arg Leu Thr Leu Pro Val Thr Ile Asn Gln Ala Ser Ala Gly
            100                 105                 110

Ala Thr Leu Thr Val Thr Tyr Gln Gly Cys Ala Asp Ala Gly Phe Cys
        115                 120                 125

Tyr Pro Pro Glu Thr Lys Thr Val Pro Leu Ser Glu Val Val Ala Asn
    130                 135                 140

Asn Ala Ala Pro Gln Pro Val Ser Val Pro Gln Gln Glu Gln Pro Thr
145                 150                 155                 160

Ala Gln Leu Pro Phe Ser Ala Leu Trp Ala Leu Leu Ile Gly Ile Gly
                165                 170                 175

Ile Ala Phe Thr Pro Cys Val Leu Pro Met Tyr Pro Leu Ile Ser Gly
            180                 185                 190

Ile Val Leu Gly Gly Lys Gln Arg Leu Ser Thr Ala Arg Ala Leu Leu

```
              195                 200                 205
Leu Thr Phe Ile Tyr Val Gln Gly Met Ala Leu Thr Tyr Thr Ala Leu
210                 215                 220

Gly Leu Val Val Ala Ala Gly Leu Gln Phe Gln Ala Ala Leu Gln
225                 230                 235                 240

His Pro Tyr Val Leu Ile Gly Leu Ala Ile Val Phe Thr Leu Leu Ala
                    245                 250                 255

Met Ser Met Phe Gly Leu Phe Thr Leu Gln Leu Pro Ser Ser Leu Gln
                260                 265                 270

Thr Arg Leu Thr Leu Met Ser Asn Arg Gln Gln Gly Gly Ser Pro Gly
                275                 280                 285

Gly Val Phe Val Met Gly Ala Ile Ala Gly Leu Ile Cys Ser Pro Cys
            290                 295                 300

Thr Thr Ala Pro Leu Ser Ala Ile Leu Leu Tyr Ile Ala Gln Ser Gly
305                 310                 315                 320

Asn Met Trp Leu Gly Gly Thr Leu Tyr Leu Tyr Ala Leu Gly Met
                    325                 330                 335

Gly Leu Pro Leu Met Leu Ile Thr Val Phe Gly Asn Arg Leu Leu Pro
                340                 345                 350

Lys Ser Gly Pro Trp Met Glu Gln Val Lys Thr Ala Phe Gly Phe Val
                355                 360                 365

Ile Leu Ala Leu Pro Val Phe Leu Leu Glu Arg Val Ile Gly Asp Val
370                 375                 380

Trp Gly Leu Arg Leu Trp Ser Ala Leu Gly Val Ala Phe Phe Gly Trp
385                 390                 395                 400

Ala Phe Ile Thr Ser Leu Gln Ala Lys Arg Gly Trp Met Arg Ile Val
                    405                 410                 415

Gln Ile Ile Leu Leu Ala Ala Ala Leu Val Ser Val Arg Pro Leu Gln
                420                 425                 430

Asp Trp Ala Phe Gly Ala Thr His Thr Ala Gln Thr Gln Thr His Leu
                435                 440                 445

Asn Phe Thr Gln Ile Lys Thr Val Asp Glu Leu Asn Gln Ala Leu Val
450                 455                 460

Glu Ala Lys Gly Lys Pro Val Met Leu Asp Leu Tyr Ala Asp Trp Cys
465                 470                 475                 480

Val Ala Cys Lys Glu Phe Glu Lys Tyr Thr Phe Ser Asp Pro Gln Val
                    485                 490                 495

Gln Lys Ala Leu Ala Asp Thr Val Leu Leu Gln Ala Asn Val Thr Ala
                500                 505                 510

Asn Asp Ala Gln Asp Val Ala Leu Leu Lys His Leu Asn Val Leu Gly
                515                 520                 525

Leu Pro Thr Ile Leu Phe Phe Asp Gly Gln Gly Gln Glu His Pro Gln
530                 535                 540

Ala Arg Val Thr Gly Phe Met Asp Ala Glu Thr Phe Ser Ala His Leu
545                 550                 555                 560

Arg Asp Arg Gln Pro
                565

<210> SEQ ID NO 20
<211> LENGTH: 268
<212> TYPE: PRT
<213> ORGANISM: Escherichia coli
<220> FEATURE:
<223> OTHER INFORMATION: DsbG protein

<400> SEQUENCE: 20
```

```
Met Thr Val Ile Gly Tyr Ala Phe Tyr Ser Thr Phe Ala Leu Thr Glu
1               5                   10                  15

Lys Asp Lys Leu Met Leu Lys Lys Ile Leu Leu Ala Leu Leu Leu Pro
            20                  25                  30

Ala Ile Ala Phe Ala Glu Glu Leu Pro Ala Pro Val Lys Ala Ile Glu
        35                  40                  45

Lys Gln Gly Ile Thr Ile Ile Lys Thr Phe Asp Ala Pro Gly Gly Met
    50                  55                  60

Lys Gly Tyr Leu Gly Lys Tyr Gln Asp Met Gly Val Thr Ile Tyr Leu
65              70                  75                  80

Thr Pro Asp Gly Lys His Ala Ile Ser Gly Tyr Met Tyr Asn Glu Lys
                85                  90                  95

Gly Glu Asn Leu Ser Asn Thr Leu Ile Glu Lys Glu Ile Tyr Ala Pro
                100                 105                 110

Ala Gly Arg Glu Met Trp Gln Arg Met Glu Gln Ser His Trp Leu Leu
        115                 120                 125

Asp Gly Lys Lys Asp Ala Pro Val Ile Val Tyr Val Phe Ala Asp Pro
    130                 135                 140

Phe Cys Pro Tyr Cys Lys Gln Phe Trp Gln Gln Ala Arg Pro Trp Val
145                 150                 155                 160

Asp Ser Gly Lys Val Gln Leu Arg Thr Leu Leu Val Gly Val Ile Lys
                165                 170                 175

Pro Glu Ser Pro Ala Thr Ala Ala Ile Leu Ala Ser Lys Asp Pro
                180                 185                 190

Ala Lys Thr Trp Gln Gln Tyr Glu Ala Ser Gly Gly Lys Leu Lys Leu
    195                 200                 205

Asn Val Pro Ala Asn Val Ser Thr Glu Gln Met Lys Val Leu Ser Asp
210                 215                 220

Asn Glu Lys Leu Met Asp Asp Leu Gly Ala Asn Val Thr Pro Ala Ile
225                 230                 235                 240

Tyr Tyr Met Ser Lys Glu Asn Thr Leu Gln Gln Ala Val Gly Leu Pro
                245                 250                 255

Asp Gln Lys Thr Leu Asn Ile Ile Met Gly Asn Lys
                260                 265

<210> SEQ ID NO 21
<211> LENGTH: 571
<212> TYPE: PRT
<213> ORGANISM: Homo sapiens
<220> FEATURE:
<223> OTHER INFORMATION: UDP-N-acetylgalactosaminyltransferase 2
      (GalNAc-T2)

<400> SEQUENCE: 21

Met Arg Arg Arg Ser Arg Met Leu Leu Cys Phe Ala Phe Leu Trp Val
1               5                   10                  15

Leu Gly Ile Ala Tyr Tyr Met Tyr Ser Gly Gly Ser Ala Leu Ala
            20                  25                  30

Gly Gly Ala Gly Gly Ala Gly Arg Lys Glu Asp Trp Asn Glu Ile
        35                  40                  45

Asp Pro Ile Lys Lys Lys Asp Leu His His Ser Asn Gly Glu Glu Lys
    50                  55                  60

Ala Gln Ser Met Glu Thr Leu Pro Pro Gly Lys Val Arg Trp Pro Asp
65              70                  75                  80

Phe Asn Gln Glu Ala Tyr Val Gly Gly Thr Met Val Arg Ser Gly Gln
                85                  90                  95
```

-continued

```
Asp Pro Tyr Ala Arg Asn Lys Phe Asn Gln Val Glu Ser Asp Lys Leu
            100                 105                 110

Arg Met Asp Arg Ala Ile Pro Asp Thr Arg His Asp Gln Cys Gln Arg
            115                 120                 125

Lys Gln Trp Arg Val Asp Leu Pro Ala Thr Ser Val Val Ile Thr Phe
        130                 135                 140

His Asn Glu Ala Arg Ser Ala Leu Leu Arg Thr Val Val Ser Val Leu
145                 150                 155                 160

Lys Lys Ser Pro Pro His Leu Ile Lys Glu Ile Ile Leu Val Asp Asp
                165                 170                 175

Tyr Ser Asn Asp Pro Glu Asp Gly Ala Leu Leu Gly Lys Ile Glu Lys
            180                 185                 190

Val Arg Val Leu Arg Asn Asp Arg Arg Glu Gly Leu Met Arg Ser Arg
        195                 200                 205

Val Arg Gly Ala Asp Ala Ala Gln Ala Lys Val Leu Thr Phe Leu Asp
    210                 215                 220

Ser His Cys Glu Cys Asn Glu His Trp Leu Glu Pro Leu Leu Glu Arg
225                 230                 235                 240

Val Ala Glu Asp Arg Thr Arg Val Val Ser Pro Ile Ile Asp Val Ile
                245                 250                 255

Asn Met Asp Asn Phe Gln Tyr Val Gly Ala Ser Ala Asp Leu Lys Gly
            260                 265                 270

Gly Phe Asp Trp Asn Leu Val Phe Lys Trp Asp Tyr Met Thr Pro Glu
        275                 280                 285

Gln Arg Arg Ser Arg Gln Gly Asn Pro Val Ala Pro Ile Lys Thr Pro
    290                 295                 300

Met Ile Ala Gly Gly Leu Phe Val Met Asp Lys Phe Tyr Phe Glu Glu
305                 310                 315                 320

Leu Gly Lys Tyr Asp Met Met Met Asp Val Trp Gly Gly Glu Asn Leu
                325                 330                 335

Glu Ile Ser Phe Arg Val Trp Gln Cys Gly Gly Ser Leu Glu Ile Ile
            340                 345                 350

Pro Cys Ser Arg Val Gly His Val Phe Arg Lys Gln His Pro Tyr Thr
        355                 360                 365

Phe Pro Gly Gly Ser Gly Thr Val Phe Ala Arg Asn Thr Arg Arg Ala
    370                 375                 380

Ala Glu Val Trp Met Asp Glu Tyr Lys Asn Phe Tyr Tyr Ala Ala Val
385                 390                 395                 400

Pro Ser Ala Arg Asn Val Pro Tyr Gly Asn Ile Gln Ser Arg Leu Glu
                405                 410                 415

Leu Arg Lys Lys Leu Ser Cys Lys Pro Phe Lys Trp Tyr Leu Glu Asn
            420                 425                 430

Val Tyr Pro Glu Leu Arg Val Pro Asp His Gln Asp Ile Ala Phe Gly
        435                 440                 445

Ala Leu Gln Gln Gly Thr Asn Cys Leu Asp Thr Leu Gly His Phe Ala
    450                 455                 460

Asp Gly Val Val Gly Val Tyr Glu Cys His Asn Ala Gly Gly Asn Gln
465                 470                 475                 480

Glu Trp Ala Leu Thr Lys Glu Lys Ser Val Lys His Met Asp Leu Cys
                485                 490                 495

Leu Thr Val Val Asp Arg Ala Pro Gly Ser Leu Ile Lys Leu Gln Gly
            500                 505                 510

Cys Arg Glu Asn Asp Ser Arg Gln Lys Trp Glu Gln Ile Glu Gly Asn
```

```
                515                 520                 525
Ser Lys Leu Arg His Val Gly Ser Asn Leu Cys Leu Asp Ser Arg Thr
    530                 535                 540

Ala Lys Ser Gly Gly Leu Ser Val Glu Val Cys Gly Pro Ala Leu Ser
545                 550                 555                 560

Gln Gln Trp Lys Phe Thr Leu Asn Leu Gln Gln
                565                 570

<210> SEQ ID NO 22
<211> LENGTH: 633
<212> TYPE: PRT
<213> ORGANISM: Drosophila melanogaster
<220> FEATURE:
<223> OTHER INFORMATION: UDP-N-acetylgalactosaminyltransferase 2
      (GalNAc-T2)

<400> SEQUENCE: 22

Met Arg Arg Asn Ile Lys Leu Ile Val Phe Val Ser Ile Ile Trp Met
  1               5                  10                  15

Phe Val Met Val Tyr Tyr Phe Gln Ser Ser Thr Glu Lys Val Glu Asn
                 20                  25                  30

Arg Ala Leu Arg Leu Arg Glu Val Ala Thr Ala Met Gln Gln Tyr Gln
             35                  40                  45

Asp Asp Ser Ser Ala Ala Ala Ser Thr Ala Arg Gln Trp Ala
 50                  55                  60

Pro Ala Gly Gly Gly Ala Gly Pro Gly Ala Ala Gly Ala Ala Gly
 65                  70                  75                  80

Ser Gly Ala Asp Asp Pro Gly Gly Asn Val Ile Leu Ile Gly Ser Val
                 85                  90                  95

Lys Asp Phe Glu Arg Asn Ala Val His Gly Leu Lys Leu Asn Gly Ile
                100                 105                 110

Val Ala Leu Glu Glu Thr Ser Gln Gly Leu Ser Gly Gly Thr Gly Gly
            115                 120                 125

Pro Gly Gly Arg Leu Pro Val Ala Pro Ser Gly Arg Gly Thr Glu Val
        130                 135                 140

Glu Tyr Phe Asn Glu Ala Gly Tyr Ile Arg Ala Gly Ala Leu Arg Asn
145                 150                 155                 160

Gly Glu Asp Pro Tyr Ile Arg Asn Arg Phe Asn Gln Glu Ala Ser Asp
                165                 170                 175

Ala Leu Pro Ser Asn Arg Asp Ile Pro Asp Thr Arg Asn Pro Met Cys
            180                 185                 190

Arg Thr Lys Lys Tyr Arg Glu Asp Leu Pro Glu Thr Ser Val Ile Ile
        195                 200                 205

Thr Phe His Asn Glu Ala Arg Ser Thr Leu Leu Arg Thr Ile Val Ser
    210                 215                 220

Val Leu Asn Arg Ser Pro Glu His Leu Ile Arg Glu Ile Val Leu Val
225                 230                 235                 240

Asp Asp Tyr Ser Asp His Pro Glu Asp Gly Leu Glu Leu Ala Lys Ile
                245                 250                 255

Asp Lys Val Arg Val Ile Arg Asn Asp Lys Arg Glu Gly Leu Val Arg
            260                 265                 270

Ser Arg Val Lys Gly Ala Asp Ala Ala Val Ser Ser Val Leu Thr Phe
        275                 280                 285

Leu Asp Ser His Val Glu Cys Asn Glu Met Trp Leu Glu Pro Leu Leu
    290                 295                 300

Glu Arg Val Arg Glu Asp Pro Thr Arg Val Val Cys Pro Val Ile Asp
```

```
            305                 310                 315                 320

Val Ile Ser Met Asp Asn Phe Gln Tyr Ile Gly Ala Ser Ala Asp Leu
                        325                 330                 335

Arg Gly Gly Phe Asp Trp Asn Leu Ile Phe Lys Trp Glu Tyr Leu Ser
                    340                 345                 350

Pro Ser Glu Arg Ala Met Arg His Asn Asp Pro Thr Thr Ala Ile Arg
                355                 360                 365

Thr Pro Met Ile Ala Gly Gly Leu Phe Val Ile Asp Lys Ala Tyr Phe
            370                 375                 380

Asn Lys Leu Gly Lys Tyr Asp Met Lys Met Asp Val Trp Gly Gly Glu
        385                 390                 395                 400

Asn Leu Glu Ile Ser Phe Arg Val Trp Gln Cys Gly Gly Ser Leu Glu
                        405                 410                 415

Ile Ile Pro Cys Ser Arg Val Gly His Val Phe Arg Lys His Pro
                    420                 425                 430

Tyr Thr Phe Pro Gly Gly Ser Gly Asn Val Phe Ala Arg Asn Thr Arg
                435                 440                 445

Arg Ala Ala Glu Val Trp Met Asp Asp Tyr Lys Gln His Tyr Tyr Asn
        450                 455                 460

Ala Val Pro Leu Ala Lys Asn Ile Pro Phe Gly Asn Ile Asp Asp Arg
        465                 470                 475                 480

Leu Ala Leu Lys Glu Lys Leu His Cys Lys Pro Phe Lys Trp Tyr Leu
                        485                 490                 495

Glu Asn Val Tyr Pro Asp Leu Gln Ala Pro Asp Pro Gln Glu Val Gly
                    500                 505                 510

Gln Phe Arg Gln Asp Ser Thr Glu Cys Leu Asp Thr Met Gly His Leu
                515                 520                 525

Ile Asp Gly Thr Val Gly Ile Phe Pro Cys His Asn Thr Gly Gly Asn
            530                 535                 540

Gln Glu Trp Ala Phe Thr Lys Arg Gly Glu Ile Lys His Asp Asp Leu
        545                 550                 555                 560

Cys Leu Thr Leu Val Thr Phe Ala Arg Gly Ser Gln Val Val Leu Lys
                        565                 570                 575

Ala Cys Asp Asp Ser Glu Asn Gln Arg Trp Ile Met Arg Glu Gly Gly
                    580                 585                 590

Leu Val Arg His Tyr Lys Ile Asn Val Cys Leu Asp Ser Arg Asp Gln
                595                 600                 605

Ser Gln Gln Gly Val Ser Ala Gln His Cys Asn Ser Ala Leu Gly Thr
            610                 615                 620

Gln Arg Trp Ser Phe Gly Lys Tyr Ala
        625                 630

<210> SEQ ID NO 23
<211> LENGTH: 570
<212> TYPE: PRT
<213> ORGANISM: Mus musculus
<220> FEATURE:
<223> OTHER INFORMATION: UDP-N-acetylgalactosaminyltransferase 2
      (GalNAc-T2)

<400> SEQUENCE: 23

Met Arg Arg Arg Ser Arg Met Leu Leu Cys Phe Ala Leu Leu Trp Val
        1               5                   10                  15

Leu Gly Ile Ala Tyr Tyr Met Tyr Ser Gly Gly Gly Ser Ala Leu Ala
                    20                  25                  30

Ala Gly Gly Gly Gly Ala Gly Arg Lys Gly Asp Trp Asn Asp Ile Asp
```

```
                35                  40                  45
Ser Ile Lys Lys Lys Asp Leu His His Ser Arg Gly Asp Glu Lys Ala
 50                  55                  60
Gln Gly Val Glu Thr Leu Pro Pro Gly Lys Val Arg Trp Pro Asp Phe
 65                  70                  75                  80
Asn Gln Glu Ala Tyr Val Gly Thr Met Val Arg Ser Gly Gln Asp
                 85                  90                  95
Pro Tyr Ala Arg Asn Lys Phe Asn Gln Val Glu Ser Asp Lys Leu His
                100                 105                 110
Met Asp Arg Gly Ile Pro Asp Thr Arg His Asp Gln Cys Gln Arg Lys
                115                 120                 125
Gln Trp Arg Val Asp Leu Pro Ala Thr Ser Val Val Ile Thr Phe His
                130                 135                 140
Asn Glu Ala Arg Ser Ala Leu Leu Arg Thr Val Val Ser Val Leu Lys
145                 150                 155                 160
Arg Ser Pro Pro His Leu Ile Lys Glu Ile Ile Leu Val Asp Asp Tyr
                165                 170                 175
Ser Asn Asp Pro Glu Asp Gly Ala Leu Leu Gly Lys Ile Glu Lys Val
                180                 185                 190
Arg Val Leu Arg Asn Asp Arg Arg Glu Gly Leu Met Arg Ser Arg Val
                195                 200                 205
Arg Gly Ala Asp Ala Ala Gln Ala Lys Val Leu Thr Phe Leu Asp Ser
                210                 215                 220
His Cys Glu Cys Asn Glu Arg Trp Leu Glu Pro Leu Leu Glu Arg Val
225                 230                 235                 240
Ala Glu Asp Arg Thr Arg Val Val Ser Pro Ile Ile Asp Val Ile Asn
                245                 250                 255
Met Asp Asn Phe Gln Tyr Val Gly Ala Ser Ala Asp Leu Lys Gly Gly
                260                 265                 270
Phe Asp Trp Asn Leu Val Phe Lys Trp Asp Tyr Met Thr Pro Glu Gln
                275                 280                 285
Arg Arg Ser Arg Gln Gly Asn Pro Val Ala Pro Ile Lys Thr Pro Met
                290                 295                 300
Ile Ala Gly Gly Leu Phe Val Met Asp Lys Leu Tyr Phe Glu Glu Leu
305                 310                 315                 320
Gly Lys Tyr Asp Met Met Met Asp Val Trp Gly Gly Glu Asn Leu Glu
                325                 330                 335
Ile Ser Phe Arg Val Trp Gln Cys Gly Gly Ser Leu Glu Ile Ile Pro
                340                 345                 350
Cys Ser Arg Val Gly His Val Phe Arg Lys Gln His Pro Tyr Thr Phe
                355                 360                 365
Pro Gly Gly Ser Gly Thr Val Phe Ala Arg Asn Thr Arg Arg Ala Ala
                370                 375                 380
Glu Val Trp Met Asp Glu Tyr Lys His Phe Tyr Tyr Ala Ala Val Pro
385                 390                 395                 400
Ser Ala Arg Asn Val Pro Tyr Gly Asn Ile Gln Ser Arg Leu Glu Leu
                405                 410                 415
Arg Lys Lys Leu Gly Cys Lys Pro Phe Lys Trp Tyr Leu Asp Asn Val
                420                 425                 430
Tyr Pro Glu Leu Arg Val Pro Asp His Gln Asp Ile Ala Phe Gly Ala
                435                 440                 445
Leu Gln Gln Gly Thr Asn Cys Leu Asp Thr Leu Gly His Phe Ala Asp
                450                 455                 460
```

```
Gly Val Val Gly Ile Tyr Glu Cys His Asn Ala Gly Gly Asn Gln Glu
465                 470                 475                 480

Trp Ala Leu Thr Lys Glu Lys Ser Val Lys His Met Asp Leu Cys Leu
                485                 490                 495

Thr Val Val Asp Arg Ser Pro Gly Ser Leu Ile Arg Leu Gln Gly Cys
                500                 505                 510

Arg Glu Asn Asp Ser Arg Gln Lys Trp Glu Gln Ile Glu Gly Asn Ser
                515                 520                 525

Lys Leu Arg His Val Gly Ser Asn Leu Cys Leu Asp Ser Arg Thr Ala
                530                 535                 540

Lys Ser Gly Gly Leu Ser Val Glu Val Cys Gly Pro Ala Leu Ser Gln
545                 550                 555                 560

Gln Trp Lys Phe Ser Leu Asn Leu Gln Gln
                565                 570

<210> SEQ ID NO 24
<211> LENGTH: 520
<212> TYPE: PRT
<213> ORGANISM: Artificial Sequence
<220> FEATURE:
<223> OTHER INFORMATION: Truncated human
      UDP-N-acetylgalactosaminyltransferase 2 (GalNAc-T2
      delta 51)

<400> SEQUENCE: 24

Lys Lys Lys Asp Leu His His Ser Asn Gly Glu Glu Lys Ala Gln Ser
1               5                   10                  15

Met Glu Thr Leu Pro Pro Gly Lys Val Arg Trp Pro Asp Phe Asn Gln
                20                  25                  30

Glu Ala Tyr Val Gly Gly Thr Met Val Arg Ser Gly Gln Asp Pro Tyr
            35                  40                  45

Ala Arg Asn Lys Phe Asn Gln Val Glu Ser Asp Lys Leu Arg Met Asp
    50                  55                  60

Arg Ala Ile Pro Asp Thr Arg His Asp Gln Cys Gln Arg Lys Gln Trp
65                  70                  75                  80

Arg Val Asp Leu Pro Ala Thr Ser Val Val Ile Thr Phe His Asn Glu
                85                  90                  95

Ala Arg Ser Ala Leu Leu Arg Thr Val Val Ser Val Leu Lys Lys Ser
            100                 105                 110

Pro Pro His Leu Ile Lys Glu Ile Ile Leu Val Asp Asp Tyr Ser Asn
    115                 120                 125

Asp Pro Glu Asp Gly Ala Leu Leu Gly Lys Ile Glu Lys Val Arg Val
130                 135                 140

Leu Arg Asn Asp Arg Arg Glu Gly Leu Met Arg Ser Arg Val Arg Gly
145                 150                 155                 160

Ala Asp Ala Ala Gln Ala Lys Val Leu Thr Phe Leu Asp Ser His Cys
                165                 170                 175

Glu Cys Asn Glu His Trp Leu Glu Pro Leu Leu Glu Arg Val Ala Glu
            180                 185                 190

Asp Arg Thr Arg Val Val Ser Pro Ile Ile Asp Val Ile Asn Met Asp
    195                 200                 205

Asn Phe Gln Tyr Val Gly Ala Ser Ala Asp Leu Lys Gly Gly Phe Asp
210                 215                 220

Trp Asn Leu Val Phe Lys Trp Asp Tyr Met Thr Pro Glu Gln Arg Arg
225                 230                 235                 240

Ser Arg Gln Gly Asn Pro Val Ala Pro Ile Lys Thr Pro Met Ile Ala
                245                 250                 255
```

```
Gly Gly Leu Phe Val Met Asp Lys Phe Tyr Phe Glu Glu Leu Gly Lys
            260                 265                 270
Tyr Asp Met Met Met Asp Val Trp Gly Gly Glu Asn Leu Glu Ile Ser
            275                 280                 285
Phe Arg Val Trp Gln Cys Gly Gly Ser Leu Glu Ile Ile Pro Cys Ser
290                 295                 300
Arg Val Gly His Val Phe Arg Lys Gln His Pro Tyr Thr Phe Pro Gly
305                 310                 315                 320
Gly Ser Gly Thr Val Phe Ala Arg Asn Thr Arg Ala Ala Glu Val
                325                 330                 335
Trp Met Asp Glu Tyr Lys Asn Phe Tyr Tyr Ala Ala Val Pro Ser Ala
            340                 345                 350
Arg Asn Val Pro Tyr Gly Asn Ile Gln Ser Arg Leu Glu Leu Arg Lys
                355                 360                 365
Lys Leu Ser Cys Lys Pro Phe Lys Trp Tyr Leu Glu Asn Val Tyr Pro
370                 375                 380
Glu Leu Arg Val Pro Asp His Gln Asp Ile Ala Phe Gly Ala Leu Gln
385                 390                 395                 400
Gln Gly Thr Asn Cys Leu Asp Thr Leu Gly His Phe Ala Asp Gly Val
                405                 410                 415
Val Gly Val Tyr Glu Cys His Asn Ala Gly Gly Asn Gln Glu Trp Ala
                420                 425                 430
Leu Thr Lys Glu Lys Ser Val Lys His Met Asp Leu Cys Leu Thr Val
            435                 440                 445
Val Asp Arg Ala Pro Gly Ser Leu Ile Lys Leu Gln Gly Cys Arg Glu
            450                 455                 460
Asn Asp Ser Arg Gln Lys Trp Glu Gln Ile Glu Gly Asn Ser Lys Leu
465                 470                 475                 480
Arg His Val Gly Ser Asn Leu Cys Leu Asp Ser Arg Thr Ala Lys Ser
                485                 490                 495
Gly Gly Leu Ser Val Glu Val Cys Gly Pro Ala Leu Ser Gln Gln Trp
            500                 505                 510
Lys Phe Thr Leu Asn Leu Gln Gln
            515                 520

<210> SEQ ID NO 25
<211> LENGTH: 393
<212> TYPE: PRT
<213> ORGANISM: Artificial Sequence
<220> FEATURE:
<223> OTHER INFORMATION: Truncated human
      UDP-N-acetylgalactosaminyltransferase 2 (GalNAc-T2
      delta 1-51 delta 445-571)

<400> SEQUENCE: 25

Lys Lys Lys Asp Leu His His Ser Asn Gly Glu Glu Lys Ala Gln Ser
1               5                   10                  15
Met Glu Thr Leu Pro Pro Gly Lys Val Arg Trp Pro Asp Phe Asn Gln
            20                  25                  30
Glu Ala Tyr Val Gly Gly Thr Met Val Arg Ser Gly Gln Asp Pro Tyr
            35                  40                  45
Ala Arg Asn Lys Phe Asn Gln Val Glu Ser Asp Lys Leu Arg Met Asp
        50                  55                  60
Arg Ala Ile Pro Asp Thr Arg His Asp Gln Cys Gln Arg Lys Gln Trp
65                  70                  75                  80
Arg Val Asp Leu Pro Ala Thr Ser Val Val Ile Thr Phe His Asn Glu
```

```
                85                  90                  95
Ala Arg Ser Ala Leu Leu Arg Thr Val Val Ser Val Leu Lys Lys Ser
               100                 105                 110
Pro Pro His Leu Ile Lys Glu Ile Ile Leu Val Asp Asp Tyr Ser Asn
               115                 120                 125
Asp Pro Glu Asp Gly Ala Leu Leu Gly Lys Ile Glu Lys Val Arg Val
               130                 135                 140
Leu Arg Asn Asp Arg Arg Glu Gly Leu Met Arg Ser Arg Val Arg Gly
145                 150                 155                 160
Ala Asp Ala Ala Gln Ala Lys Val Leu Thr Phe Leu Asp Ser His Cys
                165                 170                 175
Glu Cys Asn Glu His Trp Leu Glu Pro Leu Leu Glu Arg Val Ala Glu
                180                 185                 190
Asp Arg Thr Arg Val Val Ser Pro Ile Ile Asp Val Ile Asn Met Asp
                195                 200                 205
Asn Phe Gln Tyr Val Gly Ala Ser Ala Asp Leu Lys Gly Gly Phe Asp
                210                 215                 220
Trp Asn Leu Val Phe Lys Trp Asp Tyr Met Thr Pro Glu Gln Arg Arg
225                 230                 235                 240
Ser Arg Gln Gly Asn Pro Val Ala Pro Ile Lys Thr Pro Met Ile Ala
                245                 250                 255
Gly Gly Leu Phe Val Met Asp Lys Phe Tyr Phe Glu Glu Leu Gly Lys
                260                 265                 270
Tyr Asp Met Met Met Asp Val Trp Gly Gly Glu Asn Leu Glu Ile Ser
                275                 280                 285
Phe Arg Val Trp Gln Cys Gly Gly Ser Leu Glu Ile Ile Pro Cys Ser
                290                 295                 300
Arg Val Gly His Val Phe Arg Lys Gln His Pro Tyr Thr Phe Pro Gly
305                 310                 315                 320
Gly Ser Gly Thr Val Phe Ala Arg Asn Thr Arg Arg Ala Ala Glu Val
                325                 330                 335
Trp Met Asp Glu Tyr Lys Asn Phe Tyr Tyr Ala Ala Val Pro Ser Ala
                340                 345                 350
Arg Asn Val Pro Tyr Gly Asn Ile Gln Ser Arg Leu Glu Leu Arg Lys
                355                 360                 365
Lys Leu Ser Cys Lys Pro Phe Lys Trp Tyr Leu Glu Asn Val Tyr Pro
                370                 375                 380
Glu Leu Arg Val Pro Asp His Gln Asp
385                 390

<210> SEQ ID NO 26
<211> LENGTH: 522
<212> TYPE: PRT
<213> ORGANISM: Artificial Sequence
<220> FEATURE:
<223> OTHER INFORMATION: Truncated human
      UDP-N-acetylgalactosaminyltransferase 2 (GalNAc-T2
      delta 51) alternate form

<400> SEQUENCE: 26

Met Ser Lys Lys Lys Asp Leu His His Ser Asn Gly Glu Glu Lys Ala
1               5                  10                  15
Gln Ser Met Glu Thr Leu Pro Pro Gly Lys Val Arg Trp Pro Asp Phe
                20                  25                  30
Asn Gln Glu Ala Tyr Val Gly Gly Thr Met Val Arg Ser Gly Gln Asp
                35                  40                  45
```

```
Pro Tyr Ala Arg Asn Lys Phe Asn Gln Val Glu Ser Asp Lys Leu Arg
 50                  55                  60

Met Asp Arg Ala Ile Pro Asp Thr Arg His Asp Gln Cys Gln Arg Lys
 65                  70                  75                  80

Gln Trp Arg Val Asp Leu Pro Ala Thr Ser Val Ile Thr Phe His
                 85                  90                  95

Asn Glu Ala Arg Ser Ala Leu Leu Arg Thr Val Val Ser Val Leu Lys
            100                 105                 110

Lys Ser Pro Pro His Leu Ile Lys Glu Ile Ile Leu Val Asp Asp Tyr
        115                 120                 125

Ser Asn Asp Pro Glu Asp Gly Ala Leu Leu Gly Lys Ile Glu Lys Val
130                 135                 140

Arg Val Leu Arg Asn Asp Arg Arg Glu Gly Leu Met Arg Ser Arg Val
145                 150                 155                 160

Arg Gly Ala Asp Ala Ala Gln Ala Lys Val Leu Thr Phe Leu Asp Ser
                165                 170                 175

His Cys Glu Cys Asn Glu His Trp Leu Glu Pro Leu Leu Glu Arg Val
            180                 185                 190

Ala Glu Asp Arg Thr Arg Val Val Ser Pro Ile Ile Asp Val Ile Asn
        195                 200                 205

Met Asp Asn Phe Gln Tyr Val Gly Ala Ser Ala Asp Leu Lys Gly Gly
210                 215                 220

Phe Asp Trp Asn Leu Val Phe Lys Trp Asp Tyr Met Thr Pro Glu Gln
225                 230                 235                 240

Arg Arg Ser Arg Gln Gly Asn Pro Val Ala Pro Ile Lys Thr Pro Met
                245                 250                 255

Ile Ala Gly Gly Leu Phe Val Met Asp Lys Phe Tyr Phe Glu Glu Leu
            260                 265                 270

Gly Lys Tyr Asp Met Met Met Asp Val Trp Gly Gly Glu Asn Leu Glu
        275                 280                 285

Ile Ser Phe Arg Val Trp Gln Cys Gly Gly Ser Leu Glu Ile Ile Pro
290                 295                 300

Cys Ser Arg Val Gly His Val Phe Arg Lys Gln His Pro Tyr Thr Phe
305                 310                 315                 320

Pro Gly Gly Ser Gly Thr Val Phe Ala Arg Asn Thr Arg Arg Ala Ala
                325                 330                 335

Glu Val Trp Met Asp Glu Tyr Lys Asn Phe Tyr Tyr Ala Ala Val Pro
            340                 345                 350

Ser Ala Arg Asn Val Pro Tyr Gly Asn Ile Gln Ser Arg Leu Glu Leu
        355                 360                 365

Arg Lys Lys Leu Ser Cys Lys Pro Phe Lys Trp Tyr Leu Glu Asn Val
370                 375                 380

Tyr Pro Glu Leu Arg Val Pro Asp His Gln Asp Ile Ala Phe Gly Ala
385                 390                 395                 400

Leu Gln Gln Gly Thr Asn Cys Leu Asp Thr Leu Gly His Phe Ala Asp
                405                 410                 415

Gly Val Val Gly Val Tyr Glu Cys His Asn Ala Gly Gly Asn Gln Glu
            420                 425                 430

Trp Ala Leu Thr Lys Glu Lys Ser Val Lys His Met Asp Leu Cys Leu
        435                 440                 445

Thr Val Val Asp Arg Ala Pro Gly Ser Leu Ile Lys Leu Gln Gly Cys
450                 455                 460

Arg Glu Asn Asp Ser Arg Gln Lys Trp Glu Gln Ile Glu Gly Asn Ser
465                 470                 475                 480
```

```
Lys Leu Arg His Val Gly Ser Asn Leu Cys Leu Asp Ser Arg Thr Ala
                485                 490                 495
Lys Ser Gly Gly Leu Ser Val Glu Val Cys Gly Pro Ala Leu Ser Gln
            500                 505                 510
Gln Trp Lys Phe Thr Leu Asn Leu Gln Gln
            515                 520
```

<210> SEQ ID NO 27
<211> LENGTH: 395
<212> TYPE: PRT
<213> ORGANISM: Artificial Sequence
<220> FEATURE:
<223> OTHER INFORMATION: Truncated human
      UDP-N-acetylgalactosaminyltransferase 2 (GalNAc-T2
      delta 1-51 delta 445-571) alternate form

<400> SEQUENCE: 27

```
Met Ser Lys Lys Asp Leu His His Ser Asn Gly Glu Glu Lys Ala
 1               5                  10                  15
Gln Ser Met Glu Thr Leu Pro Pro Gly Lys Val Arg Trp Pro Asp Phe
                20                  25                  30
Asn Gln Glu Ala Tyr Val Gly Thr Met Val Arg Ser Gly Gln Asp
                35                  40                  45
Pro Tyr Ala Arg Asn Lys Phe Asn Gln Val Glu Ser Asp Lys Leu Arg
 50                  55                  60
Met Asp Arg Ala Ile Pro Asp Thr Arg His Asp Gln Cys Gln Arg Lys
65                  70                  75                  80
Gln Trp Arg Val Asp Leu Pro Ala Thr Ser Val Val Ile Thr Phe His
                85                  90                  95
Asn Glu Ala Arg Ser Ala Leu Leu Arg Thr Val Val Ser Val Leu Lys
                100                 105                 110
Lys Ser Pro Pro His Leu Ile Lys Glu Ile Ile Leu Val Asp Asp Tyr
            115                 120                 125
Ser Asn Asp Pro Glu Asp Gly Ala Leu Leu Gly Lys Ile Glu Lys Val
        130                 135                 140
Arg Val Leu Arg Asn Asp Arg Arg Glu Gly Leu Met Arg Ser Arg Val
145                 150                 155                 160
Arg Gly Ala Asp Ala Ala Gln Ala Lys Val Leu Thr Phe Leu Asp Ser
                165                 170                 175
His Cys Glu Cys Asn Glu His Trp Leu Glu Pro Leu Leu Glu Arg Val
                180                 185                 190
Ala Glu Asp Arg Thr Arg Val Val Ser Pro Ile Ile Asp Val Ile Asn
            195                 200                 205
Met Asp Asn Phe Gln Tyr Val Gly Ala Ser Ala Asp Leu Lys Gly Gly
        210                 215                 220
Phe Asp Trp Asn Leu Val Phe Lys Trp Asp Tyr Met Thr Pro Glu Gln
225                 230                 235                 240
Arg Arg Ser Arg Gln Gly Asn Pro Val Ala Pro Ile Lys Thr Pro Met
                245                 250                 255
Ile Ala Gly Gly Leu Phe Val Met Asp Lys Phe Tyr Phe Glu Glu Leu
            260                 265                 270
Gly Lys Tyr Asp Met Met Met Asp Val Trp Gly Gly Glu Asn Leu Glu
        275                 280                 285
Ile Ser Phe Arg Val Trp Gln Cys Gly Gly Ser Leu Glu Ile Ile Pro
    290                 295                 300
Cys Ser Arg Val Gly His Val Phe Arg Lys Gln His Pro Tyr Thr Phe
```

```
                305                 310                 315                 320
Pro Gly Gly Ser Gly Thr Val Phe Ala Arg Asn Thr Arg Arg Ala Ala
                325                 330                 335

Glu Val Trp Met Asp Glu Tyr Lys Asn Phe Tyr Tyr Ala Ala Val Pro
                340                 345                 350

Ser Ala Arg Asn Val Pro Tyr Gly Asn Ile Gln Ser Arg Leu Glu Leu
                355                 360                 365

Arg Lys Lys Leu Ser Cys Lys Pro Phe Lys Trp Tyr Leu Glu Asn Val
                370                 375                 380

Tyr Pro Glu Leu Arg Val Pro Asp His Gln Asp
385                 390                 395

<210> SEQ ID NO 28
<211> LENGTH: 913
<212> TYPE: PRT
<213> ORGANISM: Artificial Sequence
<220> FEATURE:
<223> OTHER INFORMATION: Maltose binding protein-tagged truncated human
      UDP-N-acetylgalactosaminyltransferase 2
      (MBP-GalNAc-T2 delta 51)

<400> SEQUENCE: 28

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
        130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
        210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270
```

```
Asn Lys Glu Leu Ala Lys Glu Phe Leu Glu Asn Tyr Leu Leu Thr Asp
    275                 280                 285

Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
                355                 360                 365

Ser Ser Ser Asn Asn Asn Asn Asn Asn Asn Asn Leu Gly Ile
370                 375                 380

Glu Gly Arg Ile Ser Glu Phe Gly Ser Lys Lys Lys Asp Leu His His
385                 390                 395                 400

Ser Asn Gly Glu Glu Lys Ala Gln Ser Met Glu Thr Leu Pro Pro Gly
                405                 410                 415

Lys Val Arg Trp Pro Asp Phe Asn Gln Glu Ala Tyr Val Gly Gly Thr
                420                 425                 430

Met Val Arg Ser Gly Gln Asp Pro Tyr Ala Arg Asn Lys Phe Asn Gln
            435                 440                 445

Val Glu Ser Asp Lys Leu Arg Met Asp Arg Ala Ile Pro Asp Thr Arg
450                 455                 460

His Asp Gln Cys Gln Arg Lys Gln Trp Arg Val Asp Leu Pro Ala Thr
465                 470                 475                 480

Ser Val Val Ile Thr Phe His Asn Glu Ala Arg Ser Ala Leu Leu Arg
                485                 490                 495

Thr Val Val Ser Val Leu Lys Lys Ser Pro Pro His Leu Ile Lys Glu
                500                 505                 510

Ile Ile Leu Val Asp Asp Tyr Ser Asn Asp Pro Glu Asp Gly Ala Leu
            515                 520                 525

Leu Gly Lys Ile Glu Lys Val Arg Val Leu Arg Asn Asp Arg Arg Glu
530                 535                 540

Gly Leu Met Arg Ser Arg Val Arg Gly Ala Asp Ala Ala Gln Ala Lys
545                 550                 555                 560

Val Leu Thr Phe Leu Asp Ser His Cys Glu Cys Asn Glu His Trp Leu
                565                 570                 575

Glu Pro Leu Leu Glu Arg Val Ala Glu Asp Arg Thr Arg Val Val Ser
                580                 585                 590

Pro Ile Ile Asp Val Ile Asn Met Asp Asn Phe Gln Tyr Val Gly Ala
            595                 600                 605

Ser Ala Asp Leu Lys Gly Gly Phe Asp Trp Asn Leu Val Phe Lys Trp
610                 615                 620

Asp Tyr Met Thr Pro Glu Gln Arg Arg Ser Arg Gln Gly Asn Pro Val
625                 630                 635                 640

Ala Pro Ile Lys Thr Pro Met Ile Ala Gly Gly Leu Phe Val Met Asp
                645                 650                 655

Lys Phe Tyr Phe Glu Glu Leu Gly Lys Tyr Asp Met Met Met Asp Val
                660                 665                 670

Trp Gly Gly Glu Asn Leu Glu Ile Ser Phe Arg Val Trp Gln Cys Gly
            675                 680                 685

Gly Ser Leu Glu Ile Ile Pro Cys Ser Arg Val Gly His Val Phe Arg
690                 695                 700
```

```
Lys Gln His Pro Tyr Thr Phe Pro Gly Gly Ser Gly Thr Val Phe Ala
705                 710                 715                 720

Arg Asn Thr Arg Arg Ala Ala Glu Val Trp Met Asp Glu Tyr Lys Asn
            725                 730                 735

Phe Tyr Tyr Ala Ala Val Pro Ser Ala Arg Asn Val Pro Tyr Gly Asn
        740                 745                 750

Ile Gln Ser Arg Leu Glu Leu Arg Lys Lys Leu Ser Cys Lys Pro Phe
    755                 760                 765

Lys Trp Tyr Leu Glu Asn Val Tyr Pro Glu Leu Arg Val Pro Asp His
770                 775                 780

Gln Asp Ile Ala Phe Gly Ala Leu Gln Gln Gly Thr Asn Cys Leu Asp
785                 790                 795                 800

Thr Leu Gly His Phe Ala Asp Gly Val Val Gly Val Tyr Glu Cys His
                805                 810                 815

Asn Ala Gly Gly Asn Gln Glu Trp Ala Leu Thr Lys Glu Lys Ser Val
            820                 825                 830

Lys His Met Asp Leu Cys Leu Thr Val Val Asp Arg Ala Pro Gly Ser
        835                 840                 845

Leu Ile Lys Leu Gln Gly Cys Arg Glu Asn Asp Ser Arg Gln Lys Trp
    850                 855                 860

Glu Gln Ile Glu Gly Asn Ser Lys Leu Arg His Val Gly Ser Asn Leu
865                 870                 875                 880

Cys Leu Asp Ser Arg Thr Ala Lys Ser Gly Gly Leu Ser Val Glu Val
                885                 890                 895

Cys Gly Pro Ala Leu Ser Gln Gln Trp Lys Phe Thr Leu Asn Leu Gln
            900                 905                 910

Gln

<210> SEQ ID NO 29
<211> LENGTH: 518
<212> TYPE: PRT
<213> ORGANISM: Artificial Sequence
<220> FEATURE:
<223> OTHER INFORMATION: Truncated human
      UDP-N-acetylgalactosaminyltransferase 2 (GalNAc-T2
      delta 53)

<400> SEQUENCE: 29

Lys Asp Leu His His Ser Asn Gly Glu Glu Lys Ala Gln Ser Met Glu
1               5                   10                  15

Thr Leu Pro Pro Gly Lys Val Arg Trp Pro Asp Phe Asn Gln Glu Ala
            20                  25                  30

Tyr Val Gly Gly Thr Met Val Arg Ser Gly Gln Asp Pro Tyr Ala Arg
        35                  40                  45

Asn Lys Phe Asn Gln Val Glu Ser Asp Lys Leu Arg Met Asp Arg Ala
    50                  55                  60

Ile Pro Asp Thr Arg His Asp Gln Cys Gln Arg Lys Gln Trp Arg Val
65                  70                  75                  80

Asp Leu Pro Ala Thr Ser Val Val Ile Thr Phe His Asn Glu Ala Arg
                85                  90                  95

Ser Ala Leu Leu Arg Thr Val Val Ser Val Leu Lys Lys Ser Pro Pro
            100                 105                 110

His Leu Ile Lys Glu Ile Ile Leu Val Asp Asp Tyr Ser Asn Asp Pro
        115                 120                 125

Glu Asp Gly Ala Leu Leu Gly Lys Ile Glu Lys Val Arg Val Leu Arg
    130                 135                 140
```

Asn Asp Arg Arg Glu Gly Leu Met Arg Ser Arg Val Arg Gly Ala Asp
145                 150                 155                 160

Ala Ala Gln Ala Lys Val Leu Thr Phe Leu Asp Ser His Cys Glu Cys
            165                 170                 175

Asn Glu His Trp Leu Glu Pro Leu Leu Glu Arg Val Ala Glu Asp Arg
        180                 185                 190

Thr Arg Val Val Ser Pro Ile Ile Asp Val Ile Asn Met Asp Asn Phe
    195                 200                 205

Gln Tyr Val Gly Ala Ser Ala Asp Leu Lys Gly Gly Phe Asp Trp Asn
210                 215                 220

Leu Val Phe Lys Trp Asp Tyr Met Thr Pro Glu Gln Arg Arg Ser Arg
225                 230                 235                 240

Gln Gly Asn Pro Val Ala Pro Ile Lys Thr Pro Met Ile Ala Gly Gly
            245                 250                 255

Leu Phe Val Met Asp Lys Phe Tyr Phe Glu Glu Leu Gly Lys Tyr Asp
        260                 265                 270

Met Met Met Asp Val Trp Gly Gly Glu Asn Leu Glu Ile Ser Phe Arg
    275                 280                 285

Val Trp Gln Cys Gly Gly Ser Leu Glu Ile Ile Pro Cys Ser Arg Val
290                 295                 300

Gly His Val Phe Arg Lys Gln His Pro Tyr Thr Phe Pro Gly Gly Ser
305                 310                 315                 320

Gly Thr Val Phe Ala Arg Asn Thr Arg Arg Ala Ala Glu Val Trp Met
            325                 330                 335

Asp Glu Tyr Lys Asn Phe Tyr Tyr Ala Ala Val Pro Ser Ala Arg Asn
        340                 345                 350

Val Pro Tyr Gly Asn Ile Gln Ser Arg Leu Glu Leu Arg Lys Lys Leu
    355                 360                 365

Ser Cys Lys Pro Phe Lys Trp Tyr Leu Glu Asn Val Tyr Pro Glu Leu
370                 375                 380

Arg Val Pro Asp His Gln Asp Ile Ala Phe Gly Ala Leu Gln Gln Gly
385                 390                 395                 400

Thr Asn Cys Leu Asp Thr Leu Gly His Phe Ala Asp Gly Val Val Gly
            405                 410                 415

Val Tyr Glu Cys His Asn Ala Gly Gly Asn Gln Glu Trp Ala Leu Thr
        420                 425                 430

Lys Glu Lys Ser Val Lys His Met Asp Leu Cys Leu Thr Val Val Asp
    435                 440                 445

Arg Ala Pro Gly Ser Leu Ile Lys Leu Gln Gly Cys Arg Glu Asn Asp
450                 455                 460

Ser Arg Gln Lys Trp Glu Gln Ile Glu Gly Asn Ser Lys Leu Arg His
465                 470                 475                 480

Val Gly Ser Asn Leu Cys Leu Asp Ser Arg Thr Ala Lys Ser Gly Gly
            485                 490                 495

Leu Ser Val Glu Val Cys Gly Pro Ala Leu Ser Gln Gln Trp Lys Phe
        500                 505                 510

Thr Leu Asn Leu Gln Gln
        515

```
<210> SEQ ID NO 30
<211> LENGTH: 391
<212> TYPE: PRT
<213> ORGANISM: Artificial Sequence
<220> FEATURE:
<223> OTHER INFORMATION: Truncated human
```

```
UDP-N-acetylgalactosaminyltransferase 2 (GalNAc-T2
delta 1-53 delta 445-571)

<400> SEQUENCE: 30

Lys Asp Leu His His Ser Asn Gly Glu Glu Lys Ala Gln Ser Met Glu
  1               5                  10                  15

Thr Leu Pro Pro Gly Lys Val Arg Trp Pro Asp Phe Asn Gln Glu Ala
             20                  25                  30

Tyr Val Gly Gly Thr Met Val Arg Ser Gly Gln Asp Pro Tyr Ala Arg
         35                  40                  45

Asn Lys Phe Asn Gln Val Glu Ser Asp Lys Leu Arg Met Asp Arg Ala
     50                  55                  60

Ile Pro Asp Thr Arg His Asp Gln Cys Gln Arg Lys Gln Trp Arg Val
 65                  70                  75                  80

Asp Leu Pro Ala Thr Ser Val Val Ile Thr Phe His Asn Glu Ala Arg
                 85                  90                  95

Ser Ala Leu Leu Arg Thr Val Val Ser Val Leu Lys Lys Ser Pro Pro
            100                 105                 110

His Leu Ile Lys Glu Ile Ile Leu Val Asp Asp Tyr Ser Asn Asp Pro
        115                 120                 125

Glu Asp Gly Ala Leu Leu Gly Lys Ile Glu Lys Val Arg Val Leu Arg
    130                 135                 140

Asn Asp Arg Arg Glu Gly Leu Met Arg Ser Arg Val Arg Gly Ala Asp
145                 150                 155                 160

Ala Ala Gln Ala Lys Val Leu Thr Phe Leu Asp Ser His Cys Glu Cys
                165                 170                 175

Asn Glu His Trp Leu Glu Pro Leu Leu Glu Arg Val Ala Glu Asp Arg
            180                 185                 190

Thr Arg Val Val Ser Pro Ile Ile Asp Val Ile Asn Met Asp Asn Phe
        195                 200                 205

Gln Tyr Val Gly Ala Ser Ala Asp Leu Lys Gly Phe Asp Trp Asn
    210                 215                 220

Leu Val Phe Lys Trp Asp Tyr Met Thr Pro Glu Gln Arg Arg Ser Arg
225                 230                 235                 240

Gln Gly Asn Pro Val Ala Pro Ile Lys Thr Pro Met Ile Ala Gly Gly
                245                 250                 255

Leu Phe Val Met Asp Lys Phe Tyr Phe Glu Glu Leu Gly Lys Tyr Asp
            260                 265                 270

Met Met Met Asp Val Trp Gly Gly Glu Asn Leu Glu Ile Ser Phe Arg
        275                 280                 285

Val Trp Gln Cys Gly Gly Ser Leu Glu Ile Ile Pro Cys Ser Arg Val
    290                 295                 300

Gly His Val Phe Arg Lys Gln His Pro Tyr Thr Phe Pro Gly Gly Ser
305                 310                 315                 320

Gly Thr Val Phe Ala Arg Asn Thr Arg Arg Ala Ala Glu Val Trp Met
                325                 330                 335

Asp Glu Tyr Lys Asn Phe Tyr Tyr Ala Ala Val Pro Ser Ala Arg Asn
            340                 345                 350

Val Pro Tyr Gly Asn Ile Gln Ser Arg Leu Glu Leu Arg Lys Lys Leu
        355                 360                 365

Ser Cys Lys Pro Phe Lys Trp Tyr Leu Glu Asn Val Tyr Pro Glu Leu
    370                 375                 380

Arg Val Pro Asp His Gln Asp
385                 390
```

```
<210> SEQ ID NO 31
<211> LENGTH: 520
<212> TYPE: PRT
<213> ORGANISM: Artificial Sequence
<220> FEATURE:
<223> OTHER INFORMATION: Truncated human
      UDP-N-acetylgalactosaminyltransferase 2 (GalNAc-T2
      delta 53) alternate form

<400> SEQUENCE: 31
```

| Met | Ser | Lys | Asp | Leu | His | His | Ser | Asn | Gly | Glu | Glu | Lys | Ala | Gln | Ser |
|---|---|---|---|---|---|---|---|---|---|---|---|---|---|---|---|
| 1 | | | | 5 | | | | | 10 | | | | | 15 | |

| Met | Glu | Thr | Leu | Pro | Pro | Gly | Lys | Val | Arg | Trp | Pro | Asp | Phe | Asn | Gln |
| | | | 20 | | | | | 25 | | | | | 30 | | |

| Glu | Ala | Tyr | Val | Gly | Gly | Thr | Met | Val | Arg | Ser | Gly | Gln | Asp | Pro | Tyr |
| | | 35 | | | | | 40 | | | | | 45 | | | |

| Ala | Arg | Asn | Lys | Phe | Asn | Gln | Val | Glu | Ser | Asp | Lys | Leu | Arg | Met | Asp |
| | 50 | | | | | 55 | | | | | 60 | | | | |

| Arg | Ala | Ile | Pro | Asp | Thr | Arg | His | Asp | Gln | Cys | Gln | Arg | Lys | Gln | Trp |
| 65 | | | | | 70 | | | | | 75 | | | | | 80 |

| Arg | Val | Asp | Leu | Pro | Ala | Thr | Ser | Val | Val | Ile | Thr | Phe | His | Asn | Glu |
| | | | | 85 | | | | | 90 | | | | | 95 | |

| Ala | Arg | Ser | Ala | Leu | Leu | Arg | Thr | Val | Val | Ser | Val | Leu | Lys | Lys | Ser |
| | | | 100 | | | | | 105 | | | | | 110 | | |

| Pro | Pro | His | Leu | Ile | Lys | Glu | Ile | Ile | Leu | Val | Asp | Asp | Tyr | Ser | Asn |
| | | 115 | | | | | 120 | | | | | 125 | | | |

| Asp | Pro | Glu | Asp | Gly | Ala | Leu | Leu | Gly | Lys | Ile | Glu | Lys | Val | Arg | Val |
| | 130 | | | | | 135 | | | | | 140 | | | | |

| Leu | Arg | Asn | Asp | Arg | Arg | Glu | Gly | Leu | Met | Arg | Ser | Arg | Val | Arg | Gly |
| 145 | | | | | 150 | | | | | 155 | | | | | 160 |

| Ala | Asp | Ala | Ala | Gln | Ala | Lys | Val | Leu | Thr | Phe | Leu | Asp | Ser | His | Cys |
| | | | | 165 | | | | | 170 | | | | | 175 | |

| Glu | Cys | Asn | Glu | His | Trp | Leu | Glu | Pro | Leu | Leu | Glu | Arg | Val | Ala | Glu |
| | | | 180 | | | | | 185 | | | | | 190 | | |

| Asp | Arg | Thr | Arg | Val | Val | Ser | Pro | Ile | Ile | Asp | Val | Ile | Asn | Met | Asp |
| | | 195 | | | | | 200 | | | | | 205 | | | |

| Asn | Phe | Gln | Tyr | Val | Gly | Ala | Ser | Ala | Asp | Leu | Lys | Gly | Gly | Phe | Asp |
| | 210 | | | | | 215 | | | | | 220 | | | | |

| Trp | Asn | Leu | Val | Phe | Lys | Trp | Asp | Tyr | Met | Thr | Pro | Glu | Gln | Arg | Arg |
| 225 | | | | | 230 | | | | | 235 | | | | | 240 |

| Ser | Arg | Gln | Gly | Asn | Pro | Val | Ala | Pro | Ile | Lys | Thr | Pro | Met | Ile | Ala |
| | | | | 245 | | | | | 250 | | | | | 255 | |

| Gly | Gly | Leu | Phe | Val | Met | Asp | Lys | Phe | Tyr | Phe | Glu | Glu | Leu | Gly | Lys |
| | | | 260 | | | | | 265 | | | | | 270 | | |

| Tyr | Asp | Met | Met | Met | Asp | Val | Trp | Gly | Gly | Glu | Asn | Leu | Glu | Ile | Ser |
| | | 275 | | | | | 280 | | | | | 285 | | | |

| Phe | Arg | Val | Trp | Gln | Cys | Gly | Gly | Ser | Leu | Glu | Ile | Ile | Pro | Cys | Ser |
| | 290 | | | | | 295 | | | | | 300 | | | | |

| Arg | Val | Gly | His | Val | Phe | Arg | Lys | Gln | His | Pro | Tyr | Thr | Phe | Pro | Gly |
| 305 | | | | | 310 | | | | | 315 | | | | | 320 |

| Gly | Ser | Gly | Thr | Val | Phe | Ala | Arg | Asn | Thr | Arg | Arg | Ala | Ala | Glu | Val |
| | | | | 325 | | | | | 330 | | | | | 335 | |

| Trp | Met | Asp | Glu | Tyr | Lys | Asn | Phe | Tyr | Tyr | Ala | Ala | Val | Pro | Ser | Ala |
| | | | 340 | | | | | 345 | | | | | 350 | | |

| Arg | Asn | Val | Pro | Tyr | Gly | Asn | Ile | Gln | Ser | Arg | Leu | Glu | Leu | Arg | Lys |
| | | 355 | | | | | 360 | | | | | 365 | | | |

```
Lys Leu Ser Cys Lys Pro Phe Lys Trp Tyr Leu Glu Asn Val Tyr Pro
        370                 375                 380

Glu Leu Arg Val Pro Asp His Gln Asp Ile Ala Phe Gly Ala Leu Gln
385                 390                 395                 400

Gln Gly Thr Asn Cys Leu Asp Thr Leu Gly His Phe Ala Asp Gly Val
                405                 410                 415

Val Gly Val Tyr Glu Cys His Asn Ala Gly Asn Gln Glu Trp Ala
            420                 425                 430

Leu Thr Lys Glu Lys Ser Val Lys His Met Asp Leu Cys Leu Thr Val
        435                 440                 445

Val Asp Arg Ala Pro Gly Ser Leu Ile Lys Leu Gln Gly Cys Arg Glu
    450                 455                 460

Asn Asp Ser Arg Gln Lys Trp Glu Gln Ile Glu Gly Asn Ser Lys Leu
465                 470                 475                 480

Arg His Val Gly Ser Asn Leu Cys Leu Asp Ser Arg Thr Ala Lys Ser
                485                 490                 495

Gly Gly Leu Ser Val Glu Val Cys Gly Pro Ala Leu Ser Gln Gln Trp
            500                 505                 510

Lys Phe Thr Leu Asn Leu Gln Gln
        515                 520

<210> SEQ ID NO 32
<211> LENGTH: 393
<212> TYPE: PRT
<213> ORGANISM: Artificial Sequence
<220> FEATURE:
<223> OTHER INFORMATION: Truncated human
      UDP-N-acetylgalactosaminyltransferase 2 (GalNAc-T2
      delta 1-53 delta 445-571) alternate form

<400> SEQUENCE: 32

Met Ser Lys Asp Leu His His Ser Asn Gly Glu Glu Lys Ala Gln Ser
1               5                   10                  15

Met Glu Thr Leu Pro Pro Gly Lys Val Arg Trp Pro Asp Phe Asn Gln
            20                  25                  30

Glu Ala Tyr Val Gly Gly Thr Met Val Arg Ser Gly Gln Asp Pro Tyr
        35                  40                  45

Ala Arg Asn Lys Phe Asn Gln Val Glu Ser Asp Lys Leu Arg Met Asp
    50                  55                  60

Arg Ala Ile Pro Asp Thr Arg His Asp Gln Cys Gln Arg Lys Gln Trp
65                  70                  75                  80

Arg Val Asp Leu Pro Ala Thr Ser Val Ile Thr Phe His Asn Glu
            85                  90                  95

Ala Arg Ser Ala Leu Leu Arg Thr Val Val Ser Val Leu Lys Lys Ser
        100                 105                 110

Pro Pro His Leu Ile Lys Glu Ile Ile Leu Val Asp Asp Tyr Ser Asn
    115                 120                 125

Asp Pro Glu Asp Gly Ala Leu Leu Gly Lys Ile Glu Lys Val Arg Val
130                 135                 140

Leu Arg Asn Asp Arg Arg Glu Gly Leu Met Arg Ser Arg Val Arg Gly
145                 150                 155                 160

Ala Asp Ala Ala Gln Ala Lys Val Leu Thr Phe Leu Asp Ser His Cys
                165                 170                 175

Glu Cys Asn Glu His Trp Leu Glu Pro Leu Leu Glu Arg Val Ala Glu
            180                 185                 190

Asp Arg Thr Arg Val Val Ser Pro Ile Ile Asp Val Ile Asn Met Asp
```

```
              195                 200                 205
Asn Phe Gln Tyr Val Gly Ala Ser Ala Asp Leu Lys Gly Gly Phe Asp
210                 215                 220

Trp Asn Leu Val Phe Lys Trp Asp Tyr Met Thr Pro Glu Gln Arg Arg
225                 230                 235                 240

Ser Arg Gln Gly Asn Pro Val Ala Pro Ile Lys Thr Pro Met Ile Ala
                    245                 250                 255

Gly Gly Leu Phe Val Met Asp Lys Phe Tyr Phe Glu Glu Leu Gly Lys
                260                 265                 270

Tyr Asp Met Met Met Asp Val Trp Gly Gly Glu Asn Leu Glu Ile Ser
                275                 280                 285

Phe Arg Val Trp Gln Cys Gly Gly Ser Leu Glu Ile Ile Pro Cys Ser
290                 295                 300

Arg Val Gly His Val Phe Arg Lys Gln His Pro Tyr Thr Phe Pro Gly
305                 310                 315                 320

Gly Ser Gly Thr Val Phe Ala Arg Asn Thr Arg Arg Ala Ala Glu Val
                325                 330                 335

Trp Met Asp Glu Tyr Lys Asn Phe Tyr Tyr Ala Ala Val Pro Ser Ala
                340                 345                 350

Arg Asn Val Pro Tyr Gly Asn Ile Gln Ser Arg Leu Glu Leu Arg Lys
                355                 360                 365

Lys Leu Ser Cys Lys Pro Phe Lys Trp Tyr Leu Glu Asn Val Tyr Pro
370                 375                 380

Glu Leu Arg Val Pro Asp His Gln Asp
385                 390

<210> SEQ ID NO 33
<211> LENGTH: 914
<212> TYPE: PRT
<213> ORGANISM: Artificial Sequence
<220> FEATURE:
<223> OTHER INFORMATION: Maltose binding protein-tagged truncated human
      UDP-N-acetylgalactosaminyltransferase 2
      (MBP-GalNAc-T2 delta 1-53 delta 445-571)

<400> SEQUENCE: 33

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
130                 135                 140

Lys Ser Ala Leu Met Phe Asn Leu Gln Glu Pro Tyr Phe Thr Trp Pro
145                 150                 155                 160
```

```
Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg Ile Ser Glu Phe Gly Ser His Met Ser Lys Asp Leu His
385                 390                 395                 400

His Ser Asn Gly Glu Glu Lys Ala Gln Ser Met Glu Thr Leu Pro Pro
                405                 410                 415

Gly Lys Val Arg Trp Pro Asp Phe Asn Gln Glu Ala Tyr Val Gly Gly
            420                 425                 430

Thr Met Val Arg Ser Gly Gln Asp Pro Tyr Ala Arg Asn Lys Phe Asn
        435                 440                 445

Gln Val Glu Ser Asp Lys Leu Arg Met Asp Arg Ala Ile Pro Asp Thr
    450                 455                 460

Arg His Asp Gln Cys Gln Arg Lys Gln Trp Arg Val Asp Leu Pro Ala
465                 470                 475                 480

Thr Ser Val Val Ile Thr Phe His Asn Glu Ala Arg Ser Ala Leu Leu
                485                 490                 495

Arg Thr Val Val Ser Val Leu Lys Lys Ser Pro Pro His Leu Ile Lys
            500                 505                 510

Glu Ile Ile Leu Val Asp Asp Tyr Ser Asn Asp Pro Glu Asp Gly Ala
        515                 520                 525

Leu Leu Gly Lys Ile Glu Lys Val Arg Val Leu Arg Asn Asp Arg Arg
    530                 535                 540

Glu Gly Leu Met Arg Ser Arg Val Arg Gly Ala Asp Ala Ala Gln Ala
545                 550                 555                 560

Lys Val Leu Thr Phe Leu Asp Ser His Cys Glu Cys Asn Glu His Trp
                565                 570                 575

Leu Glu Pro Leu Leu Glu Arg Val Ala Glu Asp Arg Thr Arg Val Val
            580                 585                 590
```

```
Ser Pro Ile Ile Asp Val Ile Asn Met Asp Asn Phe Gln Tyr Val Gly
            595                 600                 605
Ala Ser Ala Asp Leu Lys Gly Gly Phe Asp Trp Asn Leu Val Phe Lys
            610                 615                 620
Trp Asp Tyr Met Thr Pro Glu Gln Arg Arg Ser Arg Gln Gly Asn Pro
625                 630                 635                 640
Val Ala Pro Ile Lys Thr Pro Met Ile Ala Gly Gly Leu Phe Val Met
            645                 650                 655
Asp Lys Phe Tyr Phe Glu Glu Leu Gly Lys Tyr Asp Met Met Met Asp
            660                 665                 670
Val Trp Gly Gly Glu Asn Leu Glu Ile Ser Phe Arg Val Trp Gln Cys
            675                 680                 685
Gly Gly Ser Leu Glu Ile Ile Pro Cys Ser Arg Val Gly His Val Phe
            690                 695                 700
Arg Lys Gln His Pro Tyr Thr Phe Pro Gly Gly Ser Gly Thr Val Phe
705                 710                 715                 720
Ala Arg Asn Thr Arg Arg Ala Ala Glu Val Trp Met Asp Glu Tyr Lys
            725                 730                 735
Asn Phe Tyr Tyr Ala Ala Val Pro Ser Ala Arg Asn Val Pro Tyr Gly
            740                 745                 750
Asn Ile Gln Ser Arg Leu Glu Leu Arg Lys Lys Leu Ser Cys Lys Pro
            755                 760                 765
Phe Lys Trp Tyr Leu Glu Asn Val Tyr Pro Glu Leu Arg Val Pro Asp
770                 775                 780
His Gln Asp Ile Ala Phe Gly Ala Leu Gln Gln Gly Thr Asn Cys Leu
785                 790                 795                 800
Asp Thr Leu Gly His Phe Ala Asp Gly Val Val Gly Val Tyr Glu Cys
            805                 810                 815
His Asn Ala Gly Gly Asn Gln Glu Trp Ala Leu Thr Lys Glu Lys Ser
            820                 825                 830
Val Lys His Met Asp Leu Cys Leu Thr Val Val Asp Arg Ala Pro Gly
            835                 840                 845
Ser Leu Ile Lys Leu Gln Gly Cys Arg Glu Asn Asp Ser Arg Gln Lys
            850                 855                 860
Trp Glu Gln Ile Glu Gly Asn Ser Lys Leu Arg His Val Gly Ser Asn
865                 870                 875                 880
Leu Cys Leu Asp Ser Arg Thr Ala Lys Ser Gly Gly Leu Ser Val Glu
            885                 890                 895
Val Cys Gly Pro Ala Leu Ser Gln Gln Trp Lys Phe Thr Leu Asn Leu
            900                 905                 910
Gln Gln

<210> SEQ ID NO 34
<211> LENGTH: 914
<212> TYPE: PRT
<213> ORGANISM: Artificial Sequence
<220> FEATURE:
<223> OTHER INFORMATION: Maltose binding protein-tagged truncated human
      UDP-N-acetylgalactosaminyltransferase 2
      (MBP-GalNAc-T2 delta 53)

<400> SEQUENCE: 34

Met Lys Ile Glu Glu Gly Lys Leu Val Ile Trp Ile Asn Gly Asp Lys
1               5                   10                  15
Gly Tyr Asn Gly Leu Ala Glu Val Gly Lys Lys Phe Glu Lys Asp Thr
            20                  25                  30
```

```
Gly Ile Lys Val Thr Val Glu His Pro Asp Lys Leu Glu Glu Lys Phe
         35                  40                  45

Pro Gln Val Ala Ala Thr Gly Asp Gly Pro Asp Ile Ile Phe Trp Ala
 50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
        130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
        210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
        290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
370                 375                 380

Glu Gly Arg Ile Ser Glu Phe Gly Ser His Met Ser Lys Asp Leu His
385                 390                 395                 400

His Ser Asn Gly Glu Glu Lys Ala Gln Ser Met Glu Thr Leu Pro Pro
                405                 410                 415

Gly Lys Val Arg Trp Pro Asp Phe Asn Gln Glu Ala Tyr Val Gly Gly
                420                 425                 430

Thr Met Val Arg Ser Gly Gln Asp Pro Tyr Ala Arg Asn Lys Phe Asn
            435                 440                 445

Gln Val Glu Ser Asp Lys Leu Arg Met Asp Arg Ala Ile Pro Asp Thr
```

```
              450                 455                 460
Arg His Asp Gln Cys Gln Arg Lys Gln Trp Arg Val Asp Leu Pro Ala
465                 470                 475                 480

Thr Ser Val Val Ile Thr Phe His Asn Glu Ala Arg Ser Ala Leu Leu
                485                 490                 495

Arg Thr Val Val Ser Val Leu Lys Lys Ser Pro Pro His Leu Ile Lys
            500                 505                 510

Glu Ile Ile Leu Val Asp Asp Tyr Ser Asn Asp Pro Glu Asp Gly Ala
        515                 520                 525

Leu Leu Gly Lys Ile Glu Lys Val Arg Val Leu Arg Asn Asp Arg Arg
    530                 535                 540

Glu Gly Leu Met Arg Ser Arg Val Arg Gly Ala Asp Ala Ala Gln Ala
545                 550                 555                 560

Lys Val Leu Thr Phe Leu Asp Ser His Cys Glu Cys Asn Glu His Trp
                565                 570                 575

Leu Glu Pro Leu Leu Glu Arg Val Ala Glu Asp Arg Thr Arg Val Val
            580                 585                 590

Ser Pro Ile Ile Asp Val Ile Asn Met Asp Asn Phe Gln Tyr Val Gly
        595                 600                 605

Ala Ser Ala Asp Leu Lys Gly Gly Phe Asp Trp Asn Leu Val Phe Lys
    610                 615                 620

Trp Asp Tyr Met Thr Pro Glu Gln Arg Arg Ser Arg Gln Gly Asn Pro
625                 630                 635                 640

Val Ala Pro Ile Lys Thr Pro Met Ile Ala Gly Gly Leu Phe Val Met
                645                 650                 655

Asp Lys Phe Tyr Phe Glu Glu Leu Gly Lys Tyr Asp Met Met Met Asp
            660                 665                 670

Val Trp Gly Gly Glu Asn Leu Glu Ile Ser Phe Arg Val Trp Gln Cys
        675                 680                 685

Gly Gly Ser Leu Glu Ile Ile Pro Cys Ser Arg Val Gly His Val Phe
    690                 695                 700

Arg Lys Gln His Pro Tyr Thr Phe Pro Gly Gly Ser Gly Thr Val Phe
705                 710                 715                 720

Ala Arg Asn Thr Arg Arg Ala Ala Glu Val Trp Met Asp Glu Tyr Lys
                725                 730                 735

Asn Phe Tyr Tyr Ala Ala Val Pro Ser Ala Arg Asn Val Pro Tyr Gly
            740                 745                 750

Asn Ile Gln Ser Arg Leu Glu Leu Arg Lys Lys Leu Ser Cys Lys Pro
        755                 760                 765

Phe Lys Trp Tyr Leu Glu Asn Val Tyr Pro Glu Leu Arg Val Pro Asp
    770                 775                 780

His Gln Asp Ile Ala Phe Gly Ala Leu Gln Gln Gly Thr Asn Cys Leu
785                 790                 795                 800

Asp Thr Leu Gly His Phe Ala Asp Gly Val Val Gly Val Tyr Glu Cys
                805                 810                 815

His Asn Ala Gly Gly Asn Gln Glu Trp Ala Leu Thr Lys Glu Lys Ser
            820                 825                 830

Val Lys His Met Asp Leu Cys Leu Thr Val Val Asp Arg Ala Pro Gly
        835                 840                 845

Ser Leu Ile Lys Leu Gln Gly Cys Arg Glu Asn Asp Ser Arg Gln Lys
    850                 855                 860

Trp Glu Gln Ile Glu Gly Asn Ser Lys Leu Arg His Val Gly Ser Asn
865                 870                 875                 880
```

```
Leu Cys Leu Asp Ser Arg Thr Ala Lys Ser Gly Gly Leu Ser Val Glu
            885                 890                 895

Val Cys Gly Pro Ala Leu Ser Gln Gln Trp Lys Phe Thr Leu Asn Leu
        900                 905                 910

Gln Gln

<210> SEQ ID NO 35
<211> LENGTH: 786
<212> TYPE: PRT
<213> ORGANISM: Artificial Sequence
<220> FEATURE:
<223> OTHER INFORMATION: Maltose binding protein-tagged truncated human
      UDP-N-acetylgalactosaminyltransferase 2 (GalNAc-T2
      delta 1-51 delta 445-571)

<400> SEQUENCE: 35

Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320
```

```
Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
370                 375                 380

Glu Gly Arg Ile Ser Glu Phe Gly Ser Lys Lys Lys Asp Leu His His
385                 390                 395                 400

Ser Asn Gly Glu Glu Lys Ala Gln Ser Met Glu Thr Leu Pro Pro Gly
                405                 410                 415

Lys Val Arg Trp Pro Asp Phe Asn Gln Glu Ala Tyr Val Gly Gly Thr
                420                 425                 430

Met Val Arg Ser Gly Gln Asp Pro Tyr Ala Arg Asn Lys Phe Asn Gln
            435                 440                 445

Val Glu Ser Asp Lys Leu Arg Met Asp Arg Ala Ile Pro Asp Thr Arg
        450                 455                 460

His Asp Gln Cys Gln Arg Lys Gln Trp Arg Val Asp Leu Pro Ala Thr
465                 470                 475                 480

Ser Val Val Ile Thr Phe His Asn Glu Ala Arg Ser Ala Leu Leu Arg
                485                 490                 495

Thr Val Val Ser Val Leu Lys Lys Ser Pro His Leu Ile Lys Glu
                500                 505                 510

Ile Ile Leu Val Asp Asp Tyr Ser Asn Asp Pro Glu Asp Gly Ala Leu
        515                 520                 525

Leu Gly Lys Ile Glu Lys Val Arg Val Leu Arg Asn Asp Arg Arg Glu
530                 535                 540

Gly Leu Met Arg Ser Arg Val Arg Gly Ala Asp Ala Ala Gln Ala Lys
545                 550                 555                 560

Val Leu Thr Phe Leu Asp Ser His Cys Glu Cys Asn Glu His Trp Leu
                565                 570                 575

Glu Pro Leu Leu Glu Arg Val Ala Glu Asp Arg Thr Arg Val Val Ser
                580                 585                 590

Pro Ile Ile Asp Val Ile Asn Met Asp Asn Phe Gln Tyr Val Gly Ala
            595                 600                 605

Ser Ala Asp Leu Lys Gly Gly Phe Asp Trp Asn Leu Val Phe Lys Trp
        610                 615                 620

Asp Tyr Met Thr Pro Glu Gln Arg Arg Ser Arg Gln Gly Asn Pro Val
625                 630                 635                 640

Ala Pro Ile Lys Thr Pro Met Ile Ala Gly Gly Leu Phe Val Met Asp
                645                 650                 655

Lys Phe Tyr Phe Glu Glu Leu Gly Lys Tyr Asp Met Met Met Asp Val
                660                 665                 670

Trp Gly Gly Glu Asn Leu Glu Ile Ser Phe Arg Val Trp Gln Cys Gly
            675                 680                 685

Gly Ser Leu Glu Ile Ile Pro Cys Ser Arg Val Gly His Val Phe Arg
        690                 695                 700

Lys Gln His Pro Tyr Thr Phe Pro Gly Gly Ser Gly Thr Val Phe Ala
705                 710                 715                 720

Arg Asn Thr Arg Arg Ala Ala Glu Val Trp Met Asp Glu Tyr Lys Asn
                725                 730                 735

Phe Tyr Tyr Ala Ala Val Pro Ser Ala Arg Asn Val Pro Tyr Gly Asn
                740                 745                 750
```

```
Ile Gln Ser Arg Leu Glu Leu Arg Lys Lys Leu Ser Cys Lys Pro Phe
            755                 760                 765
Lys Trp Tyr Leu Glu Asn Val Tyr Pro Glu Leu Arg Val Pro Asp His
            770                 775                 780
Gln Asp
785

<210> SEQ ID NO 36
<211> LENGTH: 363
<212> TYPE: PRT
<213> ORGANISM: Homo sapiens
<220> FEATURE:
<223> OTHER INFORMATION: UDP-galactose:N-acetylgalactosamine-alpha-R
      beta-1,3-galactosyltransferase (Core-1-Gal-T1)

<400> SEQUENCE: 36

Met Ala Ser Lys Ser Trp Leu Asn Phe Leu Thr Phe Leu Cys Gly Ser
  1               5                  10                  15
Ala Ile Gly Phe Leu Leu Cys Ser Gln Leu Phe Ser Ile Leu Leu Gly
             20                  25                  30
Glu Lys Val Asp Thr Gln Pro Asn Val Leu His Asn Asp Pro His Ala
         35                  40                  45
Arg His Ser Asp Asp Asn Gly Gln Asn His Leu Glu Gly Gln Met Asn
     50                  55                  60
Phe Asn Ala Asp Ser Ser Gln His Lys Asp Glu Asn Thr Asp Ile Ala
 65                  70                  75                  80
Glu Asn Leu Tyr Gln Lys Val Arg Ile Leu Cys Trp Val Met Thr Gly
                 85                  90                  95
Pro Gln Asn Leu Glu Lys Lys Ala Lys His Val Lys Ala Thr Trp Ala
            100                 105                 110
Gln Arg Cys Asn Lys Val Leu Phe Met Ser Ser Glu Glu Asn Lys Asp
        115                 120                 125
Phe Pro Ala Val Gly Leu Lys Thr Lys Glu Gly Arg Asp Gln Leu Tyr
    130                 135                 140
Trp Lys Thr Ile Lys Ala Phe Gln Tyr Val His Glu His Tyr Leu Glu
145                 150                 155                 160
Asp Ala Asp Trp Phe Leu Lys Ala Asp Asp Asp Thr Tyr Val Ile Leu
                165                 170                 175
Asp Asn Leu Arg Trp Leu Leu Ser Lys Tyr Asp Pro Glu Glu Pro Ile
            180                 185                 190
Tyr Phe Gly Arg Arg Phe Lys Pro Tyr Val Lys Gln Gly Tyr Met Ser
        195                 200                 205
Gly Gly Ala Gly Tyr Val Leu Ser Lys Glu Ala Leu Lys Arg Phe Val
    210                 215                 220
Asp Ala Phe Lys Thr Asp Lys Cys Thr His Ser Ser Ser Ile Glu Asp
225                 230                 235                 240
Leu Ala Leu Gly Arg Cys Met Glu Ile Met Asn Val Glu Ala Gly Asp
                245                 250                 255
Ser Arg Asp Thr Ile Gly Lys Glu Thr Phe His Pro Phe Val Pro Glu
            260                 265                 270
His His Leu Ile Lys Gly Tyr Leu Pro Arg Thr Phe Trp Tyr Trp Asn
        275                 280                 285
Tyr Asn Tyr Tyr Pro Pro Val Glu Gly Pro Gly Cys Cys Ser Asp Leu
    290                 295                 300
Ala Val Ser Phe His Tyr Val Asp Ser Thr Thr Met Tyr Glu Leu Glu
305                 310                 315                 320
```

```
Tyr Leu Val Tyr His Leu Arg Pro Tyr Gly Tyr Leu Tyr Arg Tyr Gln
                325                 330                 335

Pro Thr Leu Pro Glu Arg Ile Leu Lys Glu Ile Ser Gln Ala Asn Lys
            340                 345                 350

Asn Glu Asp Thr Lys Val Lys Leu Gly Asn Pro
355                 360
```

<210> SEQ ID NO 37
<211> LENGTH: 388
<212> TYPE: PRT
<213> ORGANISM: Drosophila melanogaster
<220> FEATURE:
<223> OTHER INFORMATION: UDP-galactose:N-acetylgalactosamine-alpha-R beta-1,3-galactosyltransferase (Core-1-Gal-T1)

<400> SEQUENCE: 37

```
Met Thr Ala Asn Ser Leu Leu Gly Arg Ser Ile Leu Asn Glu Gly Arg
 1               5                  10                  15

Ser Asn Lys Arg Ser Phe Val Ser Leu Ile Val Gly Leu Ile Val Gly
            20                  25                  30

Phe Cys Leu Ala Glu Leu Phe Val Tyr Ser Thr Pro Glu Arg Ser Glu
        35                  40                  45

Phe Met Pro Tyr Asp Gly His Arg His Gly Asp Val Asn Asp Ala His
    50                  55                  60

His Ser His Asp Met Met Glu Met Ser Gly Pro Gln Asp Val Gly
65                  70                  75                  80

Gly His Glu His Val His Glu Asn Ser Thr Ile Ala Glu Arg Leu Tyr
                85                  90                  95

Ser Glu Val Arg Val Leu Cys Trp Ile Met Thr Asn Pro Ser Asn His
            100                 105                 110

Gln Lys Lys Ala Arg His Val Lys Arg Thr Trp Gly Lys Arg Cys Asn
        115                 120                 125

Lys Leu Ile Phe Met Ser Ser Ala Lys Asp Asp Glu Leu Asp Ala Val
    130                 135                 140

Ala Leu Pro Val Gly Glu Gly Arg Asn Asn Leu Trp Gly Lys Thr Lys
145                 150                 155                 160

Glu Ala Tyr Lys Tyr Ile Tyr Glu His His Ile Asn Asp Ala Asp Trp
                165                 170                 175

Phe Leu Lys Ala Asp Asp Asp Thr Tyr Thr Ile Val Glu Asn Met Arg
            180                 185                 190

Tyr Met Leu Tyr Pro Tyr Ser Pro Glu Thr Pro Val Tyr Phe Gly Cys
        195                 200                 205

Lys Phe Lys Pro Tyr Val Lys Gln Gly Tyr Met Ser Gly Gly Ala Gly
    210                 215                 220

Tyr Val Leu Ser Arg Glu Ala Val Arg Arg Phe Val Val Glu Ala Leu
225                 230                 235                 240

Pro Asn Pro Lys Leu Cys Lys Ser Asp Asn Ser Gly Ala Glu Asp Val
                245                 250                 255

Glu Ile Gly Lys Cys Leu Gln Asn Val Asn Val Leu Ala Gly Asp Ser
            260                 265                 270

Arg Asp Ser Asn Gly Arg Gly Arg Phe Phe Pro Phe Val Pro Glu His
        275                 280                 285

His Leu Ile Pro Ser His Thr Asp Lys Lys Phe Trp Tyr Trp Gln Tyr
    290                 295                 300

Ile Phe Tyr Lys Thr Asp Glu Gly Leu Asp Cys Cys Ser Asp Asn Ala
305                 310                 315                 320
```

```
Ile Ser Phe His Tyr Val Ser Pro Asn Gln Met Tyr Val Leu Asp Tyr
                325                 330                 335

Leu Ile Tyr His Leu Arg Pro Tyr Gly Ile Ile Asn Thr Pro Asp Ala
                340                 345                 350

Leu Pro Asn Lys Leu Ala Val Gly Glu Leu Met Pro Glu Ile Lys Glu
                355                 360                 365

Gln Ala Thr Glu Ser Thr Ser Asp Gly Val Ser Lys Arg Ser Ala Glu
                370                 375                 380

Thr Lys Thr Gln
385

<210> SEQ ID NO 38
<211> LENGTH: 363
<212> TYPE: PRT
<213> ORGANISM: Mus musculus
<220> FEATURE:
<223> OTHER INFORMATION: UDP-galactose:N-acetylgalactosamine-alpha-R
      beta-1,3-galactosyltransferase (Core-1-Gal-T1)

<400> SEQUENCE: 38

Met Ala Ser Lys Ser Trp Leu Asn Phe Leu Val Phe Leu Cys Gly Ser
  1               5                  10                  15

Ala Ile Gly Phe Phe Leu Cys Ser Gln Leu Leu Ser Ile Leu Leu Arg
                 20                  25                  30

Glu Glu Ala Ala Ile Gln Pro Asn Met Leu His Asn Asp Pro His Ala
             35                  40                  45

Arg His Ser Asp Asp Asn Gly His Ser His Leu Lys Gly Gln Met Asn
         50                  55                  60

Phe Asn Ala Asp Ser Ser Gln His Lys Asp Glu Asn Ile Asp Val Ala
 65                  70                  75                  80

Glu Asn Leu Tyr Gln Lys Val Lys Ile Leu Cys Trp Val Met Thr Ser
                 85                  90                  95

Pro Gln Asn Leu Glu Lys Lys Ala Lys His Val Lys Ala Thr Trp Ala
                100                 105                 110

Gln Arg Cys Asn Lys Val Leu Phe Met Ser Ser Glu Glu Asn Gln Asp
            115                 120                 125

Phe Pro Thr Val Gly Leu Lys Thr Lys Glu Gly Arg Glu Gln Leu Tyr
        130                 135                 140

Trp Lys Thr Ile Lys Ala Phe Gln Tyr Val His Asp His Tyr Leu Glu
145                 150                 155                 160

Asp Ala Asp Trp Phe Met Lys Ala Asp Asp Thr Tyr Val Ile Val
                165                 170                 175

Asp Asn Leu Arg Trp Leu Leu Ser Lys Tyr Asp Pro Glu Gln Pro Ile
                180                 185                 190

Tyr Phe Gly Arg Arg Phe Lys Pro Tyr Val Lys Gln Gly Tyr Met Ser
            195                 200                 205

Gly Gly Ala Gly Tyr Val Leu Ser Lys Glu Ala Leu Arg Arg Phe Val
        210                 215                 220

Asn Ala Phe Lys Thr Glu Lys Cys Thr His Ser Ser Ser Ile Glu Asp
225                 230                 235                 240

Leu Ala Leu Gly Arg Cys Met Glu Ile Ile Asn Val Glu Ala Gly Asp
                245                 250                 255

Ser Arg Asp Thr Ile Gly Lys Glu Thr Phe His Pro Phe Val Pro Glu
            260                 265                 270

His His Leu Ile Lys Gly Tyr Leu Pro Lys Thr Phe Trp Tyr Trp Asn
        275                 280                 285
```

```
Tyr Asn Tyr Tyr Pro Pro Ile Glu Gly Pro Gly Cys Cys Ser Asp Ile
        290                 295                 300

Ala Val Ser Phe His Tyr Val Asp Gly Thr Thr Met Tyr Glu Leu Glu
305                 310                 315                 320

Tyr Leu Val Tyr Arg Leu Arg Pro Tyr Gly Cys Leu Tyr Arg Tyr Gln
                325                 330                 335

Pro Ala Leu Pro Glu Asn Ile Leu Lys Glu Ile Asn Gln Val Asn Arg
            340                 345                 350

Lys Glu Asp Thr Lys Ile Lys Leu Gly Asn Pro
        355                 360
```

<210> SEQ ID NO 39
<211> LENGTH: 363
<212> TYPE: PRT
<213> ORGANISM: Rattus norvegicus
<220> FEATURE:
<223> OTHER INFORMATION: UDP-galactose:N-acetylgalactosamine-alpha-R
      beta-1,3-galactosyltransferase (Core-1-Gal-T1)

<400> SEQUENCE: 39

```
Met Ala Ser Lys Ser Trp Leu Asn Phe Leu Thr Phe Leu Cys Gly Ser
  1               5                  10                  15

Ala Ile Gly Phe Phe Leu Cys Ser Gln Leu Leu Asn Ile Leu Leu Gln
             20                  25                  30

Glu Gln Ala Asp Val Gln Pro Asn Met Leu His Asn Asp Pro His Ala
         35                  40                  45

Arg His Ser Asp Asp Ser Gly His Asn His Leu Lys Gly Gln Met Asp
     50                  55                  60

Phe Asn Ala Asp Ser Ser Gln His Lys Asp Glu Asn Thr Asp Val Ala
 65                  70                  75                  80

Glu Asn Leu Tyr Gln Lys Val Lys Val Leu Cys Trp Val Met Thr Ser
                 85                  90                  95

Pro Gln Asn Leu Glu Lys Lys Ala Lys His Val Lys Ala Thr Trp Ala
            100                 105                 110

Gln Arg Cys Asn Lys Val Leu Phe Met Ser Ser Glu Glu Asn Lys Asp
        115                 120                 125

Phe Pro Thr Val Gly Leu Glu Thr Lys Glu Gly Arg Glu Gln Leu Tyr
    130                 135                 140

Trp Lys Thr Ile Lys Ala Phe Gln Tyr Val His Asp His Tyr Leu Glu
145                 150                 155                 160

Asp Ala Asp Trp Phe Met Lys Ala Asp Asp Thr Tyr Val Ile Leu
                165                 170                 175

Asp Asn Leu Arg Trp Leu Leu Ser Lys Tyr Asn Pro Glu Gln Pro Ile
            180                 185                 190

Tyr Phe Gly Arg Arg Phe Lys Pro Tyr Val Lys Gln Gly Tyr Met Ser
        195                 200                 205

Gly Gly Ala Gly Tyr Val Leu Ser Lys Glu Ala Leu Arg Arg Phe Val
    210                 215                 220

Asp Ala Phe Lys Thr Glu Lys Cys Thr His Ser Ser Ser Ile Glu Asp
225                 230                 235                 240

Leu Ala Leu Gly Arg Cys Met Glu Ile Ile Lys Val Glu Ala Gly Asp
                245                 250                 255

Ser Arg Asp Pro Thr Gly Lys Glu Thr Phe His Pro Phe Val Pro Glu
            260                 265                 270

His His Leu Ile Lys Gly Tyr Leu Pro Lys Thr Phe Trp Tyr Trp Asn
        275                 280                 285
```

```
Tyr Asn Tyr Tyr Pro Pro Val Glu Gly Pro Gly Cys Cys Ser Asp Ile
            290                 295                 300

Ala Val Ser Phe His Tyr Val Asp Ser Thr Thr Met Tyr Glu Leu Glu
305                 310                 315                 320

Tyr Leu Val Tyr His Leu Arg Pro Tyr Gly Tyr Leu Tyr Arg Tyr Gln
                    325                 330                 335

Pro Ala Leu Pro Glu Asn Ile Leu Lys Glu Ile Asn Gln Val Asn Lys
            340                 345                 350

Lys Glu Asp Thr Lys Ile Lys Leu Gly Asn Pro
            355                 360

<210> SEQ ID NO 40
<211> LENGTH: 388
<212> TYPE: PRT
<213> ORGANISM: Drosophila melanogaster
<220> FEATURE:
<223> OTHER INFORMATION: UDP-galactose:N-acetylgalactosamine-alpha-R
      beta-1,3-galactosyltransferase (Core-1-Gal-T1)
      A383T mutant

<400> SEQUENCE: 40

Met Thr Ala Asn Ser Leu Leu Gly Arg Ser Ile Leu Asn Glu Gly Arg
 1               5                  10                  15

Ser Asn Lys Arg Ser Phe Val Ser Leu Ile Val Gly Leu Ile Val Gly
            20                  25                  30

Phe Cys Leu Ala Glu Leu Phe Val Tyr Ser Thr Pro Glu Arg Ser Glu
        35                  40                  45

Phe Met Pro Tyr Asp Gly His Arg His Gly Asp Val Asn Asp Ala His
    50                  55                  60

His Ser His Asp Met Met Glu Met Ser Gly Pro Glu Gln Asp Val Gly
65                  70                  75                  80

Gly His Glu His Val His Glu Asn Ser Thr Ile Ala Glu Arg Leu Tyr
                85                  90                  95

Ser Glu Val Arg Val Leu Cys Trp Ile Met Thr Asn Pro Ser Asn His
            100                 105                 110

Gln Lys Lys Ala Arg His Val Lys Arg Thr Trp Gly Lys Arg Cys Asn
        115                 120                 125

Lys Leu Ile Phe Met Ser Ser Ala Lys Asp Asp Glu Leu Asp Ala Val
130                 135                 140

Ala Leu Pro Val Gly Glu Gly Arg Asn Asn Leu Trp Gly Lys Thr Lys
145                 150                 155                 160

Glu Ala Tyr Lys Tyr Ile Tyr Glu His His Ile Asn Asp Ala Asp Trp
                165                 170                 175

Phe Leu Lys Ala Asp Asp Asp Thr Tyr Thr Ile Val Glu Asn Met Arg
            180                 185                 190

Tyr Met Leu Tyr Pro Tyr Ser Pro Glu Thr Pro Val Tyr Phe Gly Cys
        195                 200                 205

Lys Phe Lys Pro Tyr Val Lys Gln Gly Tyr Met Ser Gly Gly Ala Gly
    210                 215                 220

Tyr Val Leu Ser Arg Glu Ala Val Arg Arg Phe Val Glu Ala Leu
225                 230                 235                 240

Pro Asn Pro Lys Leu Cys Lys Ser Asp Asn Ser Gly Ala Glu Asp Val
                245                 250                 255

Glu Ile Gly Lys Cys Leu Gln Asn Val Asn Val Leu Ala Gly Asp Ser
            260                 265                 270

Arg Asp Ser Asn Gly Arg Gly Arg Phe Phe Pro Phe Val Pro Glu His
```

```
                275                 280                 285
His Leu Ile Pro Ser His Thr Asp Lys Lys Phe Trp Tyr Trp Gln Tyr
        290                 295                 300

Ile Phe Tyr Lys Thr Asp Glu Gly Leu Asp Cys Cys Ser Asp Asn Ala
305                 310                 315                 320

Ile Ser Phe His Tyr Val Ser Pro Asn Gln Met Tyr Val Leu Asp Tyr
            325                 330                 335

Leu Ile Tyr His Leu Arg Pro Tyr Gly Ile Ile Asn Thr Pro Asp Ala
                340                 345                 350

Leu Pro Asn Lys Leu Ala Val Gly Glu Leu Met Pro Glu Ile Lys Glu
            355                 360                 365

Gln Ala Thr Glu Ser Thr Ser Asp Gly Val Ser Lys Arg Ser Thr Glu
        370                 375                 380

Thr Lys Thr Gln
385

<210> SEQ ID NO 41
<211> LENGTH: 357
<212> TYPE: PRT
<213> ORGANISM: Artificial Sequence
<220> FEATURE:
<223> OTHER INFORMATION: Truncated Drosophila
      UDP-galactose:N-acetylgalactosamine-alpha-R
      beta-1,3-galactosyltransferase (Core-1-Gal-T1
      delta 31) A383T mutant

<400> SEQUENCE: 41

Gly Phe Cys Leu Ala Glu Leu Phe Val Tyr Ser Thr Pro Glu Arg Ser
1               5                   10                  15

Glu Phe Met Pro Tyr Asp Gly His Arg His Gly Asp Val Asn Asp Ala
            20                  25                  30

His His Ser His Asp Met Met Glu Met Ser Gly Pro Glu Gln Asp Val
        35                  40                  45

Gly Gly His Glu His Val His Glu Asn Ser Thr Ile Ala Glu Arg Leu
    50                  55                  60

Tyr Ser Glu Val Arg Val Leu Cys Trp Ile Met Thr Asn Pro Ser Asn
65                  70                  75                  80

His Gln Lys Lys Ala Arg His Val Lys Arg Thr Trp Gly Lys Arg Cys
                85                  90                  95

Asn Lys Leu Ile Phe Met Ser Ser Ala Lys Asp Asp Glu Leu Asp Ala
            100                 105                 110

Val Ala Leu Pro Val Gly Glu Gly Arg Asn Asn Leu Trp Gly Lys Thr
        115                 120                 125

Lys Glu Ala Tyr Lys Tyr Ile Tyr Glu His His Ile Asn Asp Ala Asp
    130                 135                 140

Trp Phe Leu Lys Ala Asp Asp Asp Thr Tyr Thr Ile Val Glu Asn Met
145                 150                 155                 160

Arg Tyr Met Leu Tyr Pro Tyr Ser Pro Glu Thr Pro Val Tyr Phe Gly
                165                 170                 175

Cys Lys Phe Lys Pro Tyr Val Lys Gln Gly Tyr Met Ser Gly Gly Ala
            180                 185                 190

Gly Tyr Val Leu Ser Arg Glu Ala Val Arg Arg Phe Val Val Glu Ala
        195                 200                 205

Leu Pro Asn Pro Lys Leu Cys Lys Ser Asp Asn Ser Gly Ala Glu Asp
    210                 215                 220

Val Glu Ile Gly Lys Cys Leu Gln Asn Val Asn Val Leu Ala Gly Asp
225                 230                 235                 240
```

```
Ser Arg Asp Ser Asn Gly Arg Gly Arg Phe Phe Pro Phe Val Pro Glu
            245                 250                 255

His His Leu Ile Pro Ser His Thr Asp Lys Lys Phe Trp Tyr Trp Gln
            260                 265                 270

Tyr Ile Phe Tyr Lys Thr Asp Glu Gly Leu Asp Cys Cys Ser Asp Asn
            275                 280                 285

Ala Ile Ser Phe His Tyr Val Ser Pro Asn Gln Met Tyr Val Leu Asp
            290                 295                 300

Tyr Leu Ile Tyr His Leu Arg Pro Tyr Gly Ile Ile Asn Thr Pro Asp
305                 310                 315                 320

Ala Leu Pro Asn Lys Leu Ala Val Gly Glu Leu Met Pro Glu Ile Lys
                325                 330                 335

Glu Gln Ala Thr Glu Ser Thr Ser Asp Gly Val Ser Lys Arg Ser Thr
            340                 345                 350

Glu Thr Lys Thr Gln
            355

<210> SEQ ID NO 42
<211> LENGTH: 358
<212> TYPE: PRT
<213> ORGANISM: Artificial Sequence
<220> FEATURE:
<223> OTHER INFORMATION: Truncated Drosophila
      UDP-galactose:N-acetylgalactosamine-alpha-R
      beta-1,3-galactosyltransferase (Core-1-Gal-T1
      delta 31) A383T mutant alternate form

<400> SEQUENCE: 42

Met Gly Phe Cys Leu Ala Glu Leu Phe Val Tyr Ser Thr Pro Glu Arg
1               5                   10                  15

Ser Glu Phe Met Pro Tyr Asp Gly His Arg His Gly Asp Val Asn Asp
            20                  25                  30

Ala His His Ser His Asp Met Met Glu Met Ser Gly Pro Glu Gln Asp
            35                  40                  45

Val Gly Gly His Glu His Val His Glu Asn Ser Thr Ile Ala Glu Arg
        50                  55                  60

Leu Tyr Ser Glu Val Arg Val Leu Cys Trp Ile Met Thr Asn Pro Ser
65                  70                  75                  80

Asn His Gln Lys Lys Ala Arg His Val Lys Arg Thr Trp Gly Lys Arg
                85                  90                  95

Cys Asn Lys Leu Ile Phe Met Ser Ser Ala Lys Asp Asp Glu Leu Asp
            100                 105                 110

Ala Val Ala Leu Pro Val Gly Glu Gly Arg Asn Asn Leu Trp Gly Lys
            115                 120                 125

Thr Lys Glu Ala Tyr Lys Tyr Ile Tyr Glu His His Ile Asn Asp Ala
        130                 135                 140

Asp Trp Phe Leu Lys Ala Asp Asp Asp Thr Tyr Thr Ile Val Glu Asn
145                 150                 155                 160

Met Arg Tyr Met Leu Tyr Pro Tyr Ser Pro Glu Thr Pro Val Tyr Phe
                165                 170                 175

Gly Cys Lys Phe Lys Pro Tyr Val Lys Gln Gly Tyr Met Ser Gly Gly
            180                 185                 190

Ala Gly Tyr Val Leu Ser Arg Glu Ala Val Arg Arg Phe Val Val Glu
        195                 200                 205

Ala Leu Pro Asn Pro Lys Leu Cys Lys Ser Asp Asn Ser Gly Ala Glu
    210                 215                 220
```

```
Asp Val Glu Ile Gly Lys Cys Leu Gln Asn Val Asn Val Leu Ala Gly
225                 230                 235                 240

Asp Ser Arg Asp Ser Asn Gly Arg Gly Arg Phe Phe Pro Phe Val Pro
            245                 250                 255

Glu His His Leu Ile Pro Ser His Thr Asp Lys Lys Phe Trp Tyr Trp
            260                 265                 270

Gln Tyr Ile Phe Tyr Lys Thr Asp Glu Gly Leu Asp Cys Cys Ser Asp
            275                 280                 285

Asn Ala Ile Ser Phe His Tyr Val Ser Pro Asn Gln Met Tyr Val Leu
            290                 295                 300

Asp Tyr Leu Ile Tyr His Leu Arg Pro Tyr Gly Ile Ile Asn Thr Pro
305                 310                 315                 320

Asp Ala Leu Pro Asn Lys Leu Ala Val Gly Glu Leu Met Pro Glu Ile
            325                 330                 335

Lys Glu Gln Ala Thr Glu Ser Thr Ser Asp Gly Val Ser Lys Arg Ser
            340                 345                 350

Thr Glu Thr Lys Thr Gln
            355

<210> SEQ ID NO 43
<211> LENGTH: 338
<212> TYPE: PRT
<213> ORGANISM: Artificial Sequence
<220> FEATURE:
<223> OTHER INFORMATION: Truncated Drosophila
      UDP-galactose:N-acetylgalactosamine-alpha-R
      beta-1,3-galactosyltransferase (Core-1-Gal-T1
      delta 50)

<400> SEQUENCE: 43

Pro Tyr Asp Gly His Arg His Gly Asp Val Asn Asp Ala His His Ser
1               5                   10                  15

His Asp Met Met Glu Met Ser Gly Pro Glu Gln Asp Val Gly Gly His
            20                  25                  30

Glu His Val His Glu Asn Ser Thr Ile Ala Glu Arg Leu Tyr Ser Glu
            35                  40                  45

Val Arg Val Leu Cys Trp Ile Met Thr Asn Pro Ser Asn His Gln Lys
50                  55                  60

Lys Ala Arg His Val Lys Arg Thr Trp Gly Lys Arg Cys Asn Lys Leu
65                  70                  75                  80

Ile Phe Met Ser Ser Ala Lys Asp Asp Glu Leu Asp Ala Val Ala Leu
            85                  90                  95

Pro Val Gly Glu Gly Arg Asn Asn Leu Trp Gly Lys Thr Lys Glu Ala
            100                 105                 110

Tyr Lys Tyr Ile Tyr Glu His His Ile Asn Asp Ala Asp Trp Phe Leu
            115                 120                 125

Lys Ala Asp Asp Asp Thr Tyr Thr Ile Val Glu Asn Met Arg Tyr Met
130                 135                 140

Leu Tyr Pro Tyr Ser Pro Glu Thr Pro Val Tyr Phe Gly Cys Lys Phe
145                 150                 155                 160

Lys Pro Tyr Val Lys Gln Gly Tyr Met Ser Gly Gly Ala Gly Tyr Val
            165                 170                 175

Leu Ser Arg Glu Ala Val Arg Arg Phe Val Val Glu Ala Leu Pro Asn
            180                 185                 190

Pro Lys Leu Cys Lys Ser Asp Asn Ser Gly Ala Glu Asp Val Glu Ile
            195                 200                 205

Gly Lys Cys Leu Gln Asn Val Asn Val Leu Ala Gly Asp Ser Arg Asp
```

```
            210                 215                 220
Ser Asn Gly Arg Gly Arg Phe Phe Pro Phe Val Pro Glu His His Leu
225                 230                 235                 240

Ile Pro Ser His Thr Asp Lys Lys Phe Trp Tyr Trp Gln Tyr Ile Phe
                245                 250                 255

Tyr Lys Thr Asp Glu Gly Leu Asp Cys Cys Ser Asp Asn Ala Ile Ser
                260                 265                 270

Phe His Tyr Val Ser Pro Asn Gln Met Tyr Val Leu Asp Tyr Leu Ile
                275                 280                 285

Tyr His Leu Arg Pro Tyr Gly Ile Ile Asn Thr Pro Asp Ala Leu Pro
                290                 295                 300

Asn Lys Leu Ala Val Gly Glu Leu Met Pro Glu Ile Lys Glu Gln Ala
305                 310                 315                 320

Thr Glu Ser Thr Ser Asp Gly Val Ser Lys Arg Ser Ala Glu Thr Lys
                325                 330                 335

Thr Gln

<210> SEQ ID NO 44
<211> LENGTH: 338
<212> TYPE: PRT
<213> ORGANISM: Artificial Sequence
<220> FEATURE:
<223> OTHER INFORMATION: Truncated Drosophila
      UDP-galactose:N-acetylgalactosamine-alpha-R
      beta-1,3-galactosyltransferase (Core-1-Gal-T1
      delta 50) A383T mutant

<400> SEQUENCE: 44

Pro Tyr Asp Gly His Arg His Gly Asp Val Asn Asp Ala His His Ser
1               5                   10                  15

His Asp Met Met Glu Met Ser Gly Pro Glu Gln Asp Val Gly Gly His
                20                  25                  30

Glu His Val His Glu Asn Ser Thr Ile Ala Glu Arg Leu Tyr Ser Glu
                35                  40                  45

Val Arg Val Leu Cys Trp Ile Met Thr Asn Pro Ser Asn His Gln Lys
50                  55                  60

Lys Ala Arg His Val Lys Arg Thr Trp Gly Lys Arg Cys Asn Lys Leu
65                  70                  75                  80

Ile Phe Met Ser Ser Ala Lys Asp Asp Glu Leu Asp Ala Val Ala Leu
                85                  90                  95

Pro Val Gly Glu Gly Arg Asn Asn Leu Trp Gly Lys Thr Lys Glu Ala
                100                 105                 110

Tyr Lys Tyr Ile Tyr Glu His His Ile Asn Asp Ala Asp Trp Phe Leu
                115                 120                 125

Lys Ala Asp Asp Asp Thr Tyr Thr Ile Val Glu Asn Met Arg Tyr Met
130                 135                 140

Leu Tyr Pro Tyr Ser Pro Glu Thr Pro Val Tyr Phe Gly Cys Lys Phe
145                 150                 155                 160

Lys Pro Tyr Val Lys Gln Gly Tyr Met Ser Gly Gly Ala Gly Tyr Val
                165                 170                 175

Leu Ser Arg Glu Ala Val Arg Arg Phe Val Val Glu Ala Leu Pro Asn
                180                 185                 190

Pro Lys Leu Cys Lys Ser Asp Asn Ser Gly Ala Glu Asp Val Glu Ile
                195                 200                 205

Gly Lys Cys Leu Gln Asn Val Asn Val Leu Ala Gly Asp Ser Arg Asp
        210                 215                 220
```

```
Ser Asn Gly Arg Gly Arg Phe Phe Pro Phe Val Pro Glu His His Leu
225                 230                 235                 240

Ile Pro Ser His Thr Asp Lys Lys Phe Trp Tyr Trp Gln Tyr Ile Phe
                245                 250                 255

Tyr Lys Thr Asp Glu Gly Leu Asp Cys Cys Ser Asp Asn Ala Ile Ser
            260                 265                 270

Phe His Tyr Val Ser Pro Asn Gln Met Tyr Val Leu Asp Tyr Leu Ile
        275                 280                 285

Tyr His Leu Arg Pro Tyr Gly Ile Ile Asn Thr Pro Asp Ala Leu Pro
    290                 295                 300

Asn Lys Leu Ala Val Gly Glu Leu Met Pro Glu Ile Lys Glu Gln Ala
305                 310                 315                 320

Thr Glu Ser Thr Ser Asp Gly Val Ser Lys Arg Ser Thr Glu Thr Lys
                325                 330                 335

Thr Gln
```

<210> SEQ ID NO 45
<211> LENGTH: 340
<212> TYPE: PRT
<213> ORGANISM: Artificial Sequence
<220> FEATURE:
<223> OTHER INFORMATION: Truncated Drosophila Core-1-Gal-T1 delta 50 A383T mutant alternate form

<400> SEQUENCE: 45

```
Met Ser Pro Tyr Asp Gly His Arg His Gly Asp Val Asn Asp Ala His
1               5                   10                  15

His Ser His Asp Met Met Glu Met Ser Gly Pro Glu Gln Asp Val Gly
                20                  25                  30

Gly His Glu His Val His Glu Asn Ser Thr Ile Ala Glu Arg Leu Tyr
            35                  40                  45

Ser Glu Val Arg Val Leu Cys Trp Ile Met Thr Asn Pro Ser Asn His
    50                  55                  60

Gln Lys Lys Ala Arg His Val Lys Arg Thr Trp Gly Lys Arg Cys Asn
65                  70                  75                  80

Lys Leu Ile Phe Met Ser Ser Ala Lys Asp Asp Glu Leu Asp Ala Val
                85                  90                  95

Ala Leu Pro Val Gly Glu Gly Arg Asn Asn Leu Trp Gly Lys Thr Lys
            100                 105                 110

Glu Ala Tyr Lys Tyr Ile Tyr Glu His His Ile Asn Asp Ala Asp Trp
        115                 120                 125

Phe Leu Lys Ala Asp Asp Asp Thr Tyr Thr Ile Val Glu Asn Met Arg
    130                 135                 140

Tyr Met Leu Tyr Pro Tyr Ser Pro Glu Thr Pro Val Tyr Phe Gly Cys
145                 150                 155                 160

Lys Phe Lys Pro Tyr Val Lys Gln Gly Tyr Met Ser Gly Gly Ala Gly
                165                 170                 175

Tyr Val Leu Ser Arg Glu Ala Val Arg Arg Phe Val Glu Ala Leu
            180                 185                 190    Leu

Pro Asn Pro Lys Leu Cys Lys Ser Asp Asn Ser Gly Ala Glu Asp Val
        195                 200                 205

Glu Ile Gly Lys Cys Leu Gln Asn Val Asn Val Leu Ala Gly Asp Ser
    210                 215                 220

Arg Asp Ser Asn Gly Arg Gly Arg Phe Phe Pro Phe Val Pro Glu His
225                 230                 235                 240

His Leu Ile Pro Ser His Thr Asp Lys Lys Phe Trp Tyr Trp Gln Tyr
```

```
              245                 250                 255
Ile Phe Tyr Lys Thr Asp Glu Gly Leu Asp Cys Cys Ser Asp Asn Ala
            260                 265                 270
Ile Ser Phe His Tyr Val Ser Pro Asn Gln Met Tyr Val Leu Asp Tyr
            275                 280                 285
Leu Ile Tyr His Leu Arg Pro Tyr Gly Ile Ile Asn Thr Pro Asp Ala
            290                 295                 300
Leu Pro Asn Lys Leu Ala Val Gly Glu Leu Met Pro Glu Ile Lys Glu
305                 310                 315                 320
Gln Ala Thr Glu Ser Thr Ser Asp Gly Val Ser Lys Arg Ser Thr Glu
                325                 330                 335
Thr Lys Thr Gln
            340

<210> SEQ ID NO 46
<211> LENGTH: 731
<212> TYPE: PRT
<213> ORGANISM: Artificial Sequence
<220> FEATURE:
<223> OTHER INFORMATION: MBP-tagged truncated Drosophila
      Core-1-Gal-T1 delta 50 A383T mutant

<400> SEQUENCE: 46

Met Lys Ile Glu Glu Gly Lys Leu Val Ile Trp Ile Asn Gly Asp Lys
1               5                   10                  15
Gly Tyr Asn Gly Leu Ala Glu Val Gly Lys Lys Phe Glu Lys Asp Thr
            20                  25                  30
Gly Ile Lys Val Thr Val Glu His Pro Asp Lys Leu Glu Glu Lys Phe
        35                  40                  45
Pro Gln Val Ala Ala Thr Gly Asp Gly Pro Asp Ile Ile Phe Trp Ala
    50                  55                  60
His Asp Arg Phe Gly Gly Tyr Ala Gln Ser Gly Leu Leu Ala Glu Ile
65                  70                  75                  80
Thr Pro Asp Lys Ala Phe Gln Asp Lys Leu Tyr Pro Phe Thr Trp Asp
                85                  90                  95
Ala Val Arg Tyr Asn Gly Lys Leu Ile Ala Tyr Pro Ile Ala Val Glu
            100                 105                 110
Ala Leu Ser Leu Ile Tyr Asn Lys Asp Leu Leu Pro Asn Pro Pro Lys
        115                 120                 125
Thr Trp Glu Glu Ile Pro Ala Leu Asp Lys Glu Leu Lys Ala Lys Gly
    130                 135                 140
Lys Ser Ala Leu Met Phe Asn Leu Gln Glu Pro Tyr Phe Thr Trp Pro
145                 150                 155                 160
Leu Ile Ala Ala Asp Gly Gly Tyr Ala Phe Lys Tyr Glu Asn Gly Lys
                165                 170                 175
Tyr Asp Ile Lys Asp Val Gly Val Asp Asn Ala Gly Ala Lys Ala Gly
            180                 185                 190
Leu Thr Phe Leu Val Asp Leu Ile Lys Asn Lys His Met Asn Ala Asp
        195                 200                 205
Thr Asp Tyr Ser Ile Ala Glu Ala Ala Phe Asn Lys Gly Glu Thr Ala
    210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
Lys Pro Phe Val Gly Val Leu Ser Ala Gly Ile Asn Ala Ala Ser Pro
```

-continued

```
                260                 265                 270
Asn Lys Glu Leu Ala Lys Glu Phe Leu Glu Asn Tyr Leu Leu Thr Asp
            275                 280                 285
Glu Gly Leu Glu Ala Val Asn Lys Asp Lys Pro Leu Gly Ala Val Ala
            290                 295                 300
Leu Lys Ser Tyr Glu Glu Leu Ala Lys Asp Pro Arg Ile Ala Ala
305                 310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
                340                 345                 350
Ser Gly Arg Gln Thr Val Asp Glu Ala Leu Lys Asp Ala Gln Thr Asn
            355                 360                 365
Ser Ser Ser Asn Asn Asn Asn Asn Asn Asn Asn Asn Leu Gly Ile
            370                 375                 380
Glu Gly Arg Ile Ser Glu Phe Gly Ser Pro Tyr Asp Gly His Arg His
385                 390                 395                 400
Gly Asp Val Asn Asp Ala His His Ser His Asp Met Met Glu Met Ser
                405                 410                 415
Gly Pro Glu Gln Asp Val Gly Gly His Glu His Val His Glu Asn Ser
                420                 425                 430
Thr Ile Ala Glu Arg Leu Tyr Ser Glu Val Arg Val Leu Cys Trp Ile
            435                 440                 445
Met Thr Asn Pro Ser Asn His Gln Lys Lys Ala Arg His Val Lys Arg
450                 455                 460
Thr Trp Gly Lys Arg Cys Asn Lys Leu Ile Phe Met Ser Ser Ala Lys
465                 470                 475                 480
Asp Asp Glu Leu Asp Ala Val Ala Leu Pro Val Gly Glu Gly Arg Asn
            485                 490                 495
Asn Leu Trp Gly Lys Thr Lys Glu Ala Tyr Lys Tyr Ile Tyr Glu His
            500                 505                 510
His Ile Asn Asp Ala Asp Trp Phe Leu Lys Ala Asp Asp Thr Tyr
            515                 520                 525
Thr Ile Val Glu Asn Met Arg Tyr Met Leu Tyr Pro Tyr Ser Pro Glu
            530                 535                 540
Thr Pro Val Tyr Phe Gly Cys Lys Phe Lys Pro Tyr Val Lys Gln Gly
545                 550                 555                 560
Tyr Met Ser Gly Gly Ala Gly Tyr Val Leu Ser Arg Glu Ala Val Arg
                565                 570                 575
Arg Phe Val Val Glu Ala Leu Pro Asn Pro Lys Leu Cys Lys Ser Asp
            580                 585                 590
Asn Ser Gly Ala Glu Asp Val Glu Ile Gly Lys Cys Leu Gln Asn Val
            595                 600                 605
Asn Val Leu Ala Gly Asp Ser Arg Asp Ser Asn Gly Arg Gly Arg Phe
            610                 615                 620
Phe Pro Phe Val Pro Glu His His Leu Ile Pro Ser His Thr Asp Lys
625                 630                 635                 640
Lys Phe Trp Tyr Trp Gln Tyr Ile Phe Tyr Lys Thr Asp Glu Gly Leu
                645                 650                 655
Asp Cys Cys Ser Asp Asn Ala Ile Ser Phe His Tyr Val Ser Pro Asn
            660                 665                 670
Gln Met Tyr Val Leu Asp Tyr Leu Ile Tyr His Leu Arg Pro Tyr Gly
            675                 680                 685
```

```
Ile Ile Asn Thr Pro Asp Ala Leu Pro Asn Lys Leu Ala Val Gly Glu
        690             695             700

Leu Met Pro Glu Ile Lys Glu Gln Ala Thr Glu Ser Thr Ser Asp Gly
705             710             715             720

Val Ser Lys Arg Ser Thr Glu Thr Lys Thr Gln
            725             730
```

<210> SEQ ID NO 47
<211> LENGTH: 318
<212> TYPE: PRT
<213> ORGANISM: Homo sapiens
<220> FEATURE:
<223> OTHER INFORMATION: Core-1-Gal-T1 chaperone 1/COSMC

<400> SEQUENCE: 47

```
Met Leu Ser Glu Ser Ser Phe Leu Lys Gly Val Met Leu Gly Ser
1               5               10              15

Ile Phe Cys Ala Leu Ile Thr Met Leu Gly His Ile Arg Ile Gly His
            20              25              30

Gly Asn Arg Met His His His Glu His His His Leu Gln Ala Pro Asn
        35              40              45

Lys Glu Asp Ile Leu Lys Ile Ser Glu Asp Glu Arg Met Glu Leu Ser
50              55              60

Lys Ser Phe Arg Val Tyr Cys Ile Ile Leu Val Lys Pro Lys Asp Val
65              70              75              80

Ser Leu Trp Ala Ala Val Lys Glu Thr Trp Thr Lys His Cys Asp Lys
                85              90              95

Ala Glu Phe Phe Ser Ser Glu Asn Val Lys Val Phe Glu Ser Ile Asn
            100             105             110

Met Asp Thr Asn Asp Met Trp Leu Met Met Arg Lys Ala Tyr Lys Tyr
        115             120             125

Ala Phe Asp Lys Tyr Arg Asp Gln Tyr Asn Trp Phe Phe Leu Ala Arg
    130             135             140

Pro Thr Thr Phe Ala Ile Ile Glu Asn Leu Lys Tyr Phe Leu Leu Lys
145             150             155             160

Lys Asp Pro Ser Gln Pro Phe Tyr Leu Gly His Thr Ile Lys Ser Gly
                165             170             175

Asp Leu Glu Tyr Val Gly Met Gly Gly Gly Ile Val Leu Ser Val Glu
            180             185             190

Ser Met Lys Arg Leu Asn Ser Leu Leu Asn Ile Pro Glu Lys Cys Pro
        195             200             205

Glu Gln Gly Gly Met Ile Trp Lys Ile Ser Glu Asp Lys Gln Leu Ala
    210             215             220

Val Cys Leu Lys Tyr Ala Gly Val Phe Ala Glu Asn Ala Glu Asp Ala
225             230             235             240

Asp Gly Lys Asp Val Phe Asn Thr Lys Ser Val Gly Leu Ser Ile Lys
                245             250             255

Glu Ala Met Thr Tyr His Pro Asn Gln Val Val Glu Gly Cys Cys Ser
            260             265             270

Asp Met Ala Val Thr Phe Asn Gly Leu Thr Pro Asn Gln Met His Val
        275             280             285

Met Met Tyr Gly Val Tyr Arg Leu Arg Ala Phe Gly His Ile Phe Asn
    290             295             300

Asp Ala Leu Val Phe Leu Pro Pro Asn Gly Ser Asp Asn Asp
305             310             315
```

```
<210> SEQ ID NO 48
<211> LENGTH: 357
<212> TYPE: PRT
<213> ORGANISM: Drosophila melanogaster
<220> FEATURE:
<223> OTHER INFORMATION: UDP-galactose:N-acetylgalactosamine-alpha-R

<400> SEQUENCE: 48

Gly Phe Cys Leu Ala Glu Leu Phe Val Tyr Ser Thr Pro Glu Arg Ser
 1               5                   10                  15

Glu Phe Met Pro Tyr Asp Gly His Arg His Gly Asp Val Asn Asp Ala
             20                  25                  30

His His Ser His Asp Met Met Glu Met Ser Gly Pro Glu Gln Asp Val
         35                  40                  45

Gly Gly His Glu His Val His Glu Asn Ser Thr Ile Ala Glu Arg Leu
     50                  55                  60

Tyr Ser Glu Val Arg Val Leu Cys Trp Ile Met Thr Asn Pro Ser Asn
 65                  70                  75                  80

His Gln Lys Lys Ala Arg His Val Lys Arg Thr Trp Gly Lys Arg Cys
                 85                  90                  95

Asn Lys Leu Ile Phe Met Ser Ser Ala Lys Asp Asp Glu Leu Asp Ala
            100                 105                 110

Val Ala Leu Pro Val Gly Glu Gly Arg Asn Asn Leu Trp Gly Lys Thr
        115                 120                 125

Lys Glu Ala Tyr Lys Tyr Ile Tyr Glu His His Ile Asn Asp Ala Asp
    130                 135                 140

Trp Phe Leu Lys Ala Asp Asp Asp Thr Tyr Thr Ile Val Glu Asn Met
145                 150                 155                 160

Arg Tyr Met Leu Tyr Pro Tyr Ser Pro Glu Thr Pro Val Tyr Phe Gly
                165                 170                 175

Cys Lys Phe Lys Pro Tyr Val Lys Gln Gly Tyr Met Ser Gly Gly Ala
            180                 185                 190

Gly Tyr Val Leu Ser Arg Glu Ala Val Arg Arg Phe Val Val Glu Ala
        195                 200                 205

Leu Pro Asn Pro Lys Leu Cys Lys Ser Asp Asn Ser Gly Ala Glu Asp
    210                 215                 220

Val Glu Ile Gly Lys Cys Leu Gln Asn Val Asn Val Leu Ala Gly Asp
225                 230                 235                 240

Ser Arg Asp Ser Asn Gly Arg Gly Arg Phe Phe Pro Phe Val Pro Glu
                245                 250                 255

His His Leu Ile Pro Ser His Thr Asp Lys Lys Phe Trp Tyr Trp Gln
            260                 265                 270

Tyr Ile Phe Tyr Lys Thr Asp Glu Gly Leu Asp Cys Cys Ser Asp Asn
        275                 280                 285

Ala Ile Ser Phe His Tyr Val Ser Pro Asn Gln Met Tyr Val Leu Asp
    290                 295                 300

Tyr Leu Ile Tyr His Leu Arg Pro Tyr Gly Ile Ile Asn Thr Pro Asp
305                 310                 315                 320

Ala Leu Pro Asn Lys Leu Ala Val Gly Glu Leu Met Pro Glu Ile Lys
                325                 330                 335

Glu Gln Ala Thr Glu Ser Thr Ser Asp Gly Val Ser Lys Arg Ser Ala
            340                 345                 350

Glu Thr Lys Thr Gln
        355

<210> SEQ ID NO 49
```

```
<211> LENGTH: 752
<212> TYPE: PRT
<213> ORGANISM: Artificial Sequence
<220> FEATURE:
<223> OTHER INFORMATION: Maltose binding protein-tagged truncated
      Drosophila UDP-galactose:N-acetylgalactosamine-alpha-R
      beta-1,3-galactosyltransferase (MBP-Core-1-Gal-T1
      delta 31) A383T mutant

<400> SEQUENCE: 49
```

| | | | | | | | | | | | | | | | |
|---|---|---|---|---|---|---|---|---|---|---|---|---|---|---|---|
| Met | Lys | Ile | Glu | Glu | Gly | Lys | Leu | Val | Ile | Trp | Ile | Asn | Gly | Asp | Lys |
| 1 | | | | 5 | | | | | 10 | | | | | 15 | |
| Gly | Tyr | Asn | Gly | Leu | Ala | Glu | Val | Gly | Lys | Lys | Phe | Glu | Lys | Asp | Thr |
| | | | 20 | | | | | 25 | | | | | 30 | | |
| Gly | Ile | Lys | Val | Thr | Val | Glu | His | Pro | Asp | Lys | Leu | Glu | Glu | Lys | Phe |
| | | | 35 | | | | | 40 | | | | | 45 | | |
| Pro | Gln | Val | Ala | Ala | Thr | Gly | Asp | Gly | Pro | Asp | Ile | Ile | Phe | Trp | Ala |
| | 50 | | | | | 55 | | | | | 60 | | | | |
| His | Asp | Arg | Phe | Gly | Gly | Tyr | Ala | Gln | Ser | Gly | Leu | Leu | Ala | Glu | Ile |
| 65 | | | | | 70 | | | | | 75 | | | | | 80 |
| Thr | Pro | Asp | Lys | Ala | Phe | Gln | Asp | Lys | Leu | Tyr | Pro | Phe | Thr | Trp | Asp |
| | | | | 85 | | | | | 90 | | | | | 95 | |
| Ala | Val | Arg | Tyr | Asn | Gly | Lys | Leu | Ile | Ala | Tyr | Pro | Ile | Ala | Val | Glu |
| | | | 100 | | | | | 105 | | | | | 110 | | |
| Ala | Leu | Ser | Leu | Ile | Tyr | Asn | Lys | Asp | Leu | Leu | Pro | Asn | Pro | Pro | Lys |
| | | | 115 | | | | | 120 | | | | | 125 | | |
| Thr | Trp | Glu | Glu | Ile | Pro | Ala | Leu | Asp | Lys | Glu | Leu | Lys | Ala | Lys | Gly |
| | 130 | | | | | 135 | | | | | 140 | | | | |
| Lys | Ser | Ala | Leu | Met | Phe | Asn | Leu | Gln | Glu | Pro | Tyr | Phe | Thr | Trp | Pro |
| 145 | | | | | 150 | | | | | 155 | | | | | 160 |
| Leu | Ile | Ala | Ala | Asp | Gly | Gly | Tyr | Ala | Phe | Lys | Tyr | Glu | Asn | Gly | Lys |
| | | | | 165 | | | | | 170 | | | | | 175 | |
| Tyr | Asp | Ile | Lys | Asp | Val | Gly | Val | Asp | Asn | Ala | Gly | Ala | Lys | Ala | Gly |
| | | | 180 | | | | | 185 | | | | | 190 | | |
| Leu | Thr | Phe | Leu | Val | Asp | Leu | Ile | Lys | Asn | Lys | His | Met | Asn | Ala | Asp |
| | | | 195 | | | | | 200 | | | | | 205 | | |
| Thr | Asp | Tyr | Ser | Ile | Ala | Glu | Ala | Ala | Phe | Asn | Lys | Gly | Glu | Thr | Ala |
| | 210 | | | | | 215 | | | | | 220 | | | | |
| Met | Thr | Ile | Asn | Gly | Pro | Trp | Ala | Trp | Ser | Asn | Ile | Asp | Thr | Ser | Lys |
| 225 | | | | | 230 | | | | | 235 | | | | | 240 |
| Val | Asn | Tyr | Gly | Val | Thr | Val | Leu | Pro | Thr | Phe | Lys | Gly | Gln | Pro | Ser |
| | | | | 245 | | | | | 250 | | | | | 255 | |
| Lys | Pro | Phe | Val | Gly | Val | Leu | Ser | Ala | Gly | Ile | Asn | Ala | Ala | Ser | Pro |
| | | | 260 | | | | | 265 | | | | | 270 | | |
| Asn | Lys | Glu | Leu | Ala | Lys | Glu | Phe | Leu | Glu | Asn | Tyr | Leu | Leu | Thr | Asp |
| | | | 275 | | | | | 280 | | | | | 285 | | |
| Glu | Gly | Leu | Glu | Ala | Val | Asn | Lys | Asp | Lys | Pro | Leu | Gly | Ala | Val | Ala |
| | 290 | | | | | 295 | | | | | 300 | | | | |
| Leu | Lys | Ser | Tyr | Glu | Glu | Glu | Leu | Ala | Lys | Asp | Pro | Arg | Ile | Ala | Ala |
| 305 | | | | | 310 | | | | | 315 | | | | | 320 |
| Thr | Met | Glu | Asn | Ala | Gln | Lys | Gly | Glu | Ile | Met | Pro | Asn | Ile | Pro | Gln |
| | | | | 325 | | | | | 330 | | | | | 335 | |
| Met | Ser | Ala | Phe | Trp | Tyr | Ala | Val | Arg | Thr | Ala | Val | Ile | Asn | Ala | Ala |
| | | | 340 | | | | | 345 | | | | | 350 | | |
| Ser | Gly | Arg | Gln | Thr | Val | Asp | Glu | Ala | Leu | Lys | Asp | Ala | Gln | Thr | Asn |
| | | | 355 | | | | | 360 | | | | | 365 | | |

```
Ser Ser Ser Asn Asn Asn Asn Asn Asn Asn Asn Asn Leu Gly Ile
    370                 375                 380

Glu Gly Arg Ile Ser Glu Phe Gly Ser His Met Gly Phe Cys Leu Ala
385                 390                 395                 400

Glu Leu Phe Val Tyr Ser Thr Pro Glu Arg Ser Glu Phe Met Pro Tyr
                405                 410                 415

Asp Gly His Arg His Gly Asp Val Asn Asp Ala His His Ser His Asp
                420                 425                 430

Met Met Glu Met Ser Gly Pro Glu Gln Asp Val Gly His Glu His
            435                 440                 445

Val His Glu Asn Ser Thr Ile Ala Glu Arg Leu Tyr Ser Glu Val Arg
    450                 455                 460

Val Leu Cys Trp Ile Met Thr Asn Pro Ser Asn His Gln Lys Lys Ala
465                 470                 475                 480

Arg His Val Lys Arg Thr Trp Gly Lys Arg Cys Asn Lys Leu Ile Phe
                485                 490                 495

Met Ser Ser Ala Lys Asp Asp Glu Leu Asp Ala Val Ala Leu Pro Val
            500                 505                 510

Gly Glu Gly Arg Asn Asn Leu Trp Gly Lys Thr Lys Glu Ala Tyr Lys
            515                 520                 525

Tyr Ile Tyr Glu His His Ile Asn Asp Ala Asp Trp Phe Leu Lys Ala
    530                 535                 540

Asp Asp Asp Thr Tyr Thr Ile Val Glu Asn Met Arg Tyr Met Leu Tyr
545                 550                 555                 560

Pro Tyr Ser Pro Glu Thr Pro Val Tyr Phe Gly Cys Lys Phe Lys Pro
                565                 570                 575

Tyr Val Lys Gln Gly Tyr Met Ser Gly Ala Gly Tyr Val Leu Ser
            580                 585                 590

Arg Glu Ala Val Arg Arg Phe Val Val Glu Ala Leu Pro Asn Pro Lys
            595                 600                 605

Leu Cys Lys Ser Asp Asn Ser Gly Ala Glu Asp Val Glu Ile Gly Lys
    610                 615                 620

Cys Leu Gln Asn Val Asn Val Leu Ala Gly Asp Ser Arg Asp Ser Asn
625                 630                 635                 640

Gly Arg Gly Arg Phe Phe Pro Phe Val Pro Glu His His Leu Ile Pro
                645                 650                 655

Ser His Thr Asp Lys Lys Phe Trp Tyr Trp Gln Tyr Ile Phe Tyr Lys
            660                 665                 670

Thr Asp Glu Gly Leu Asp Cys Cys Ser Asp Asn Ala Ile Ser Phe His
            675                 680                 685

Tyr Val Ser Pro Asn Gln Met Tyr Val Leu Asp Tyr Leu Ile Tyr His
    690                 695                 700

Leu Arg Pro Tyr Gly Ile Ile Asn Thr Pro Asp Ala Leu Pro Asn Lys
705                 710                 715                 720

Leu Ala Val Gly Glu Leu Met Pro Glu Ile Lys Glu Gln Ala Thr Glu
                725                 730                 735

Ser Thr Ser Asp Gly Val Ser Lys Arg Ser Thr Glu Thr Lys Thr Gln
            740                 745                 750

<210> SEQ ID NO 50
<211> LENGTH: 340
<212> TYPE: PRT
<213> ORGANISM: Homo sapiens
<220> FEATURE:
<223> OTHER INFORMATION: Gal beta-1,3-GalNAc alpha-2,3-sialyltransferase
      1 (ST3Gal-1)
```

<400> SEQUENCE: 50

| Met | Val | Thr | Leu | Arg | Lys | Arg | Thr | Leu | Lys | Val | Leu | Thr | Phe | Leu | Val |
| 1 | | | | 5 | | | | | 10 | | | | | 15 | |

| Leu | Phe | Ile | Phe | Leu | Thr | Ser | Phe | Phe | Leu | Asn | Tyr | Ser | His | Thr | Met |
| | | | 20 | | | | | 25 | | | | | 30 | | |

| Val | Ala | Thr | Thr | Trp | Phe | Pro | Lys | Gln | Met | Val | Leu | Glu | Leu | Ser | Glu |
| | | 35 | | | | | 40 | | | | | 45 | | | |

| Asn | Leu | Lys | Arg | Leu | Ile | Lys | His | Arg | Pro | Cys | Thr | Cys | Thr | His | Cys |
| | 50 | | | | | 55 | | | | | 60 | | | | |

| Ile | Gly | Gln | Arg | Lys | Leu | Ser | Ala | Trp | Phe | Asp | Glu | Arg | Phe | Asn | Gln |
| 65 | | | | | 70 | | | | | 75 | | | | | 80 |

| Thr | Met | Gln | Pro | Leu | Leu | Thr | Ala | Gln | Asn | Ala | Leu | Leu | Glu | Asp | Asp |
| | | | | 85 | | | | | 90 | | | | | 95 | |

| Thr | Tyr | Arg | Trp | Trp | Leu | Arg | Leu | Gln | Arg | Glu | Lys | Lys | Pro | Asn | Asn |
| | | | | 100 | | | | | 105 | | | | | 110 | |

| Leu | Asn | Asp | Thr | Ile | Lys | Glu | Leu | Phe | Arg | Val | Val | Pro | Gly | Asn | Val |
| | | | | 115 | | | | | 120 | | | | | 125 | |

| Asp | Pro | Met | Leu | Glu | Lys | Arg | Ser | Val | Gly | Cys | Arg | Arg | Cys | Ala | Val |
| 130 | | | | | 135 | | | | | 140 | | | | | |

| Val | Gly | Asn | Ser | Gly | Asn | Leu | Arg | Glu | Ser | Ser | Tyr | Gly | Pro | Glu | Ile |
| 145 | | | | | 150 | | | | | 155 | | | | | 160 |

| Asp | Ser | His | Asp | Phe | Val | Leu | Arg | Met | Asn | Lys | Ala | Pro | Thr | Ala | Gly |
| | | | | 165 | | | | | 170 | | | | | 175 | |

| Phe | Glu | Ala | Asp | Val | Gly | Thr | Lys | Thr | Thr | His | His | Leu | Val | Tyr | Pro |
| | | | | 180 | | | | | 185 | | | | | 190 | |

| Glu | Ser | Phe | Arg | Glu | Leu | Gly | Asp | Asn | Val | Ser | Met | Ile | Leu | Val | Pro |
| | | | 195 | | | | | 200 | | | | | 205 | | |

| Phe | Lys | Thr | Ile | Asp | Leu | Glu | Trp | Val | Val | Ser | Ala | Ile | Thr | Thr | Gly |
| | | | 210 | | | | | 215 | | | | | 220 | | |

| Thr | Ile | Ser | His | Thr | Tyr | Ile | Pro | Val | Pro | Ala | Lys | Ile | Arg | Val | Lys |
| 225 | | | | | 230 | | | | | 235 | | | | | 240 |

| Gln | Asp | Lys | Ile | Leu | Ile | Tyr | His | Pro | Ala | Phe | Ile | Lys | Tyr | Val | Phe |
| | | | | 245 | | | | | 250 | | | | | 255 | |

| Asp | Asn | Trp | Leu | Gln | Gly | His | Gly | Arg | Tyr | Pro | Ser | Thr | Gly | Ile | Leu |
| | | | 260 | | | | | 265 | | | | | 270 | | |

| Ser | Val | Ile | Phe | Ser | Met | His | Val | Cys | Asp | Glu | Val | Asp | Leu | Tyr | Gly |
| | | | 275 | | | | | 280 | | | | | 285 | | |

| Phe | Gly | Ala | Asp | Ser | Lys | Gly | Asn | Trp | His | His | Tyr | Trp | Glu | Asn | Asn |
| | | | 290 | | | | | 295 | | | | | 300 | | |

| Pro | Ser | Ala | Gly | Ala | Phe | Arg | Lys | Thr | Gly | Val | His | Asp | Ala | Asp | Phe |
| 305 | | | | | 310 | | | | | 315 | | | | | 320 |

| Glu | Ser | Asn | Val | Thr | Ala | Thr | Leu | Ala | Ser | Ile | Asn | Lys | Ile | Arg | Ile |
| | | | | 325 | | | | | 330 | | | | | 335 | |

| Phe | Lys | Gly | Arg |
| | | | 340 |

<210> SEQ ID NO 51
<211> LENGTH: 343
<212> TYPE: PRT
<213> ORGANISM: Sus scrofa
<220> FEATURE:
<223> OTHER INFORMATION: Gal beta-1,3-GalNAc alpha-2,3-sialyltransferase 1 (ST3Gal1)

<400> SEQUENCE: 51

```
Met Ala Pro Met Arg Lys Lys Ser Thr Leu Lys Leu Leu Thr Leu Leu
 1               5                  10                  15

Val Leu Phe Ile Phe Leu Thr Ser Phe Leu Asn Tyr Ser His Thr
             20                  25                  30

Val Val Thr Thr Ala Trp Phe Pro Lys Gln Met Val Ile Glu Leu Ser
             35                  40                  45

Glu Asn Phe Lys Lys Leu Met Lys Tyr Pro Tyr Arg Pro Cys Thr Cys
 50                  55                  60

Thr Arg Cys Ile Glu Glu Gln Arg Val Ser Ala Trp Phe Asp Glu Arg
 65                  70                  75                  80

Phe Asn Arg Ser Met Gln Pro Leu Leu Thr Ala Lys Asn Ala His Leu
                 85                  90                  95

Glu Glu Asp Thr Tyr Lys Trp Trp Leu Arg Leu Gln Arg Glu Lys Gln
                100                 105                 110

Pro Asn Asn Leu Asn Asp Thr Ile Arg Glu Leu Phe Gln Val Val Pro
            115                 120                 125

Gly Asn Val Asp Pro Leu Leu Glu Lys Arg Leu Val Ser Cys Arg Arg
    130                 135                 140

Cys Ala Val Val Gly Asn Ser Gly Asn Leu Lys Glu Ser Tyr Tyr Gly
145                 150                 155                 160

Pro Gln Ile Asp Ser His Asp Phe Val Leu Arg Met Asn Lys Ala Pro
                165                 170                 175

Thr Glu Gly Phe Glu Ala Asp Val Gly Ser Lys Thr Thr His His Phe
            180                 185                 190

Val Tyr Pro Glu Ser Phe Arg Glu Leu Ala Gln Glu Val Ser Met Ile
        195                 200                 205

Leu Val Pro Phe Lys Thr Thr Asp Leu Glu Trp Val Ile Ser Ala Thr
    210                 215                 220

Thr Thr Gly Thr Ile Ser His Thr Tyr Val Pro Val Pro Ala Lys Ile
225                 230                 235                 240

Lys Val Lys Lys Glu Lys Ile Leu Ile Tyr His Pro Ala Phe Ile Lys
                245                 250                 255

Tyr Val Phe Asp Arg Trp Leu Gln Gly His Gly Arg Tyr Pro Ser Thr
            260                 265                 270

Gly Ile Leu Ser Val Ile Phe Ser Leu His Ile Cys Asp Glu Val Asp
    275                 280                 285

Leu Tyr Gly Phe Gly Ala Asp Ser Lys Gly Asn Trp His His Tyr Trp
    290                 295                 300

Glu Asn Asn Pro Ser Ala Gly Ala Phe Arg Lys Thr Gly Val His Asp
305                 310                 315                 320

Gly Asp Phe Glu Ser Asn Val Thr Thr Ile Leu Ala Ser Ile Asn Lys
                325                 330                 335

Ile Arg Ile Phe Lys Gly Arg
            340
```

<210> SEQ ID NO 52
<211> LENGTH: 337
<212> TYPE: PRT
<213> ORGANISM: Mus musculus
<220> FEATURE:
<223> OTHER INFORMATION: Gal beta-1,3-GalNAc alpha-2,3-sialyltransferase 1 (ST3Gal-1)

<400> SEQUENCE: 52

```
Met Arg Arg Lys Thr Leu Lys Tyr Leu Thr Phe Phe Leu Leu Phe Ile
 1               5                  10                  15
```

```
Phe Leu Thr Ser Phe Val Leu Asn Tyr Ser Asn Thr Gly Val Pro Ser
            20                  25                  30

Ala Trp Phe Pro Lys Gln Met Leu Glu Leu Ser Glu Asn Phe Arg
        35                  40                  45

Arg Phe Ile Lys Ser Gln Pro Cys Thr Cys Arg His Cys Ile Ser Gln
    50                  55                  60

Asp Lys Val Ser Tyr Trp Phe Asp Gln Arg Phe Asn Lys Thr Met Gln
65                  70                  75                  80

Pro Leu Leu Thr Val His Asn Ala Leu Met Glu Glu Asp Thr Tyr Arg
                85                  90                  95

Trp Trp Leu Arg Leu Gln Arg Glu Arg Lys Pro Asn Asn Leu Ser Asp
            100                 105                 110

Thr Val Lys Glu Leu Phe Arg Leu Val Pro Gly Asn Val Asp Pro Met
        115                 120                 125

Leu Asn Lys Arg Leu Val Gly Cys Arg Arg Cys Ala Val Val Gly Asn
130                 135                 140

Ser Gly Asn Leu Lys Asp Ser Ser Tyr Gly Pro Glu Ile Asp Ser His
145                 150                 155                 160

Asp Phe Val Leu Arg Met Asn Lys Ala Pro Thr Val Gly Phe Glu Ala
                165                 170                 175

Asp Val Gly Ser Arg Thr Thr His His Leu Val Tyr Pro Glu Ser Phe
            180                 185                 190

Arg Glu Leu Gly Glu Asn Val Asn Met Val Leu Val Pro Phe Lys Thr
        195                 200                 205

Thr Asp Leu Gln Trp Val Ile Ser Ala Thr Thr Thr Gly Thr Ile Thr
210                 215                 220

His Thr Tyr Val Pro Val Pro Pro Lys Ile Lys Val Lys Gln Glu Lys
225                 230                 235                 240

Ile Leu Ile Tyr His Pro Ala Phe Ile Lys Tyr Val Phe Asp Asn Trp
                245                 250                 255

Leu Gln Gly His Gly Arg Tyr Pro Ser Thr Gly Ile Leu Ser Ile Ile
            260                 265                 270

Phe Ser Ile His Ile Cys Asp Glu Val Asp Leu Tyr Gly Phe Gly Ala
        275                 280                 285

Asp Ser Lys Gly Asn Trp His His Tyr Trp Glu Asn Asn Pro Ser Ala
290                 295                 300

Gly Ala Phe Arg Lys Thr Gly Val His Asp Gly Asp Phe Glu Tyr Asn
305                 310                 315                 320

Ile Thr Thr Thr Leu Ala Ala Ile Asn Lys Ile Arg Ile Phe Lys Gly
                325                 330                 335

Arg

<210> SEQ ID NO 53
<211> LENGTH: 340
<212> TYPE: PRT
<213> ORGANISM: Rattus norvegicus
<220> FEATURE:
<223> OTHER INFORMATION: Gal beta-1,3-GalNAc alpha-2,3-sialyltransferase
      1 (ST3Gal-1)

<400> SEQUENCE: 53

Met Val Asn Met Arg Lys Arg Thr Leu Lys Tyr Leu Thr Phe Phe Leu
1               5                   10                  15

Leu Phe Ile Phe Leu Thr Ser Phe Val Leu Asn Tyr Ser Asn Ser Gly
            20                  25                  30

Val Pro Ser Ala Trp Phe Pro Lys Gln Met Val Leu Glu Phe Ser Glu
```

```
                35                  40                  45
Asn Phe Arg Lys Phe Ile Lys Ser Gln Pro Cys Thr Cys Arg His Cys
 50                  55                  60

Ile Ser Gln Gly Lys Val Ser Tyr Trp Phe Asp Gln Arg Phe Asn Lys
 65                  70                  75                  80

Thr Met Gln Pro Leu Leu Thr Val His Asn Ala Leu Met Glu Glu Asp
                 85                  90                  95

Thr Tyr Arg Trp Trp Leu Arg Leu Gln Arg Glu Arg Lys Pro Asn Asn
                100                 105                 110

Leu Ser Asp Thr Val Lys Glu Leu Phe Arg Leu Val Pro Gly Asn Val
                115                 120                 125

Asp Pro Met Leu Asn Lys Arg Leu Val Gly Cys Arg Arg Cys Ala Val
                130                 135                 140

Val Gly Asn Ser Gly Asn Leu Lys Asp Ser Ser Tyr Gly Pro Glu Ile
145                 150                 155                 160

Asp Ser His Asp Phe Val Leu Arg Met Asn Arg Ala Pro Thr Val Gly
                165                 170                 175

Phe Glu Ala Asp Val Gly Ser Arg Thr Thr His His Leu Val Tyr Pro
                180                 185                 190

Glu Ser Phe Arg Glu Leu Gly Glu Asn Val Asn Met Val Leu Val Pro
                195                 200                 205

Phe Lys Ile Thr Asp Leu Gln Trp Val Ile Ser Ala Thr Thr Thr Gly
                210                 215                 220

Thr Ile Thr His Thr Tyr Val Pro Val Pro Lys Ile Lys Val Lys
225                 230                 235                 240

Gln Glu Lys Ile Leu Ile Tyr His Pro Ala Phe Ile Lys Tyr Val Phe
                245                 250                 255

Asp Asn Trp Leu Gln Gly His Gly Arg Tyr Pro Ser Thr Gly Ile Leu
                260                 265                 270

Ser Val Ile Phe Ser Ile His Ile Cys Asp Glu Val Asp Leu Tyr Gly
                275                 280                 285

Phe Gly Ala Asp Ser Lys Gly Asn Trp His His Tyr Trp Glu Asn Asn
                290                 295                 300

Pro Ser Ala Gly Ala Phe Arg Lys Thr Gly Val His Asp Gly Asp Phe
305                 310                 315                 320

Glu Tyr Asn Val Thr Thr Thr Leu Ala Ala Ile Asn Lys Ile Arg Ile
                325                 330                 335

Phe Lys Gly Arg
            340

<210> SEQ ID NO 54
<211> LENGTH: 340
<212> TYPE: PRT
<213> ORGANISM: Pan troglodytes
<220> FEATURE:
<223> OTHER INFORMATION: Gal beta-1,3-GalNAc alpha-2,3-sialyltransferase
      1 (ST3Gal-1)

<400> SEQUENCE: 54

Met Val Thr Leu Arg Lys Arg Thr Leu Lys Val Leu Thr Phe Leu Val
  1               5                  10                  15

Leu Phe Ile Phe Leu Thr Ser Phe Phe Leu Asn Tyr Ser His Thr Met
                 20                  25                  30

Val Ala Thr Thr Trp Phe Pro Lys Gln Met Val Leu Glu Leu Ser Glu
                 35                  40                  45

Asn Leu Lys Arg Leu Ile Lys His Arg Pro Cys Thr Cys Thr His Cys
```

```
                50                  55                  60
Ile Gly Gln Arg Lys Leu Ser Ala Trp Phe Asp Glu Arg Phe Asn Gln
 65                  70                  75                  80

Thr Val Gln Pro Leu Leu Thr Ala Gln Asn Ala Leu Leu Glu Asp Asp
                 85                  90                  95

Thr Tyr Arg Trp Trp Leu Arg Leu Gln Arg Glu Lys Lys Pro Asn Asn
            100                 105                 110

Leu Asn Asp Thr Ile Lys Glu Leu Phe Arg Val Val Pro Gly Asn Val
        115                 120                 125

Asp Pro Met Leu Glu Lys Arg Ser Val Gly Cys Arg Arg Cys Ala Val
    130                 135                 140

Val Gly Asn Ser Gly Asn Leu Arg Glu Ser Ser Tyr Gly Pro Glu Ile
145                 150                 155                 160

Asp Ser His Asp Phe Val Leu Arg Met Asn Lys Ala Pro Thr Ala Gly
                165                 170                 175

Phe Glu Ala Asp Val Gly Thr Lys Thr Thr His His Leu Val Tyr Pro
            180                 185                 190

Glu Ser Phe Arg Glu Leu Gly Asp Asn Val Ser Met Ile Leu Val Pro
        195                 200                 205

Phe Lys Thr Ile Asp Leu Glu Trp Val Val Ser Ala Ile Thr Thr Gly
    210                 215                 220

Thr Ile Ser His Thr Tyr Thr Pro Val Leu Val Lys Ile Arg Val Lys
225                 230                 235                 240

Gln Asp Lys Ile Leu Ile Tyr His Pro Ala Phe Ile Lys Tyr Val Phe
                245                 250                 255

Asp Asn Trp Leu Gln Gly His Gly Arg Tyr Pro Ser Thr Gly Ile Leu
            260                 265                 270

Ser Val Ile Phe Ser Met His Val Cys Asp Glu Val Asp Leu Tyr Gly
        275                 280                 285

Phe Gly Ala Asp Ser Lys Gly Asn Trp His His Tyr Trp Glu Asn Asn
    290                 295                 300

Pro Ser Ala Gly Ala Phe Arg Lys Thr Gly Val His Asp Ala Asp Phe
305                 310                 315                 320

Glu Ser Asn Val Thr Ala Thr Leu Ala Ala Ile Asn Lys Ile Arg Ile
                325                 330                 335

Phe Lys Gly Arg
            340

<210> SEQ ID NO 55
<211> LENGTH: 298
<212> TYPE: PRT
<213> ORGANISM: Artificial Sequence
<220> FEATURE:
<223> OTHER INFORMATION: Truncated pig Gal beta-1,3-GalNAc
      alpha-2,3-sialyltransferase 1 (ST3Gal-1 delta 45)

<400> SEQUENCE: 55

Glu Leu Ser Glu Asn Phe Lys Lys Leu Met Lys Tyr Pro Tyr Arg Pro
 1               5                  10                  15

Cys Thr Cys Thr Arg Cys Ile Glu Glu Gln Arg Val Ser Ala Trp Phe
                20                  25                  30

Asp Glu Arg Phe Asn Arg Ser Met Gln Pro Leu Leu Thr Ala Lys Asn
            35                  40                  45

Ala His Leu Glu Glu Asp Thr Tyr Lys Trp Trp Leu Arg Leu Gln Arg
        50                  55                  60

Glu Lys Gln Pro Asn Asn Leu Asn Asp Thr Ile Arg Glu Leu Phe Gln
```

```
                    65                  70                  75                  80
Val Val Pro Gly Asn Val Asp Pro Leu Leu Glu Lys Arg Leu Val Ser
                        85                  90                  95
Cys Arg Arg Cys Ala Val Val Gly Asn Ser Gly Asn Leu Lys Glu Ser
                       100                 105                 110
Tyr Tyr Gly Pro Gln Ile Asp Ser His Asp Phe Val Leu Arg Met Asn
                       115                 120                 125
Lys Ala Pro Thr Glu Gly Phe Glu Ala Asp Val Gly Ser Lys Thr Thr
                       130                 135                 140
His His Phe Val Tyr Pro Glu Ser Phe Arg Glu Leu Ala Gln Glu Val
145                    150                 155                 160
Ser Met Ile Leu Val Pro Phe Lys Thr Thr Asp Leu Glu Trp Val Ile
                       165                 170                 175
Ser Ala Thr Thr Thr Gly Thr Ile Ser His Thr Tyr Val Pro Val Pro
                       180                 185                 190
Ala Lys Ile Lys Val Lys Lys Glu Lys Ile Leu Ile Tyr His Pro Ala
                       195                 200                 205
Phe Ile Lys Tyr Val Phe Asp Arg Trp Leu Gln Gly His Gly Arg Tyr
                       210                 215                 220
Pro Ser Thr Gly Ile Leu Ser Val Ile Phe Ser Leu His Ile Cys Asp
225                    230                 235                 240
Glu Val Asp Leu Tyr Gly Phe Gly Ala Asp Ser Lys Gly Asn Trp His
                       245                 250                 255
His Tyr Trp Glu Asn Asn Pro Ser Ala Gly Ala Phe Arg Lys Thr Gly
                       260                 265                 270
Val His Asp Gly Asp Phe Glu Ser Asn Val Thr Thr Ile Leu Ala Ser
                       275                 280                 285
Ile Asn Lys Ile Arg Ile Phe Lys Gly Arg
                       290                 295

<210> SEQ ID NO 56
<211> LENGTH: 287
<212> TYPE: PRT
<213> ORGANISM: Artificial Sequence
<220> FEATURE:
<223> OTHER INFORMATION: Truncated pig Gal beta-1,3-GalNAc
      alpha-2,3-sialyltransferase 1 (ST3Gal-1 delta 56)

<400> SEQUENCE: 56

Tyr Pro Tyr Arg Pro Cys Thr Cys Thr Arg Cys Ile Glu Glu Gln Arg
1                   5                  10                  15
Val Ser Ala Trp Phe Asp Glu Arg Phe Asn Arg Ser Met Gln Pro Leu
                    20                  25                  30
Leu Thr Ala Lys Asn Ala His Leu Glu Glu Asp Thr Tyr Lys Trp Trp
                    35                  40                  45
Leu Arg Leu Gln Arg Glu Lys Gln Pro Asn Asn Leu Asn Asp Thr Ile
                    50                  55                  60
Arg Glu Leu Phe Gln Val Val Pro Gly Asn Val Asp Pro Leu Leu Glu
65                  70                  75                  80
Lys Arg Leu Val Ser Cys Arg Arg Cys Ala Val Val Gly Asn Ser Gly
                    85                  90                  95
Asn Leu Lys Glu Ser Tyr Tyr Gly Pro Gln Ile Asp Ser His Asp Phe
                   100                 105                 110
Val Leu Arg Met Asn Lys Ala Pro Thr Glu Gly Phe Glu Ala Asp Val
                   115                 120                 125
Gly Ser Lys Thr Thr His His Phe Val Tyr Pro Glu Ser Phe Arg Glu
```

```
                130                 135                 140
Leu Ala Gln Glu Val Ser Met Ile Leu Val Pro Phe Lys Thr Thr Asp
145                 150                 155                 160

Leu Glu Trp Val Ile Ser Ala Thr Thr Thr Gly Thr Ile Ser His Thr
                165                 170                 175

Tyr Val Pro Val Pro Ala Lys Ile Lys Val Lys Lys Glu Lys Ile Leu
                180                 185                 190

Ile Tyr His Pro Ala Phe Ile Lys Tyr Val Phe Asp Arg Trp Leu Gln
                195                 200                 205

Gly His Gly Arg Tyr Pro Ser Thr Gly Ile Leu Ser Val Ile Phe Ser
                210                 215                 220

Leu His Ile Cys Asp Glu Val Asp Leu Tyr Gly Phe Gly Ala Asp Ser
225                 230                 235                 240

Lys Gly Asn Trp His His Tyr Trp Glu Asn Asn Pro Ser Ala Gly Ala
                245                 250                 255

Phe Arg Lys Thr Gly Val His Asp Gly Asp Phe Glu Ser Asn Val Thr
                260                 265                 270

Thr Ile Leu Ala Ser Ile Asn Lys Ile Arg Ile Phe Lys Gly Arg
                275                 280                 285

<210> SEQ ID NO 57
<211> LENGTH: 691
<212> TYPE: PRT
<213> ORGANISM: Artificial Sequence
<220> FEATURE:
<223> OTHER INFORMATION: maltose binding protein-tagged truncated pig
      Gal beta-1,3-GalNAc alpha-2,3-sialyltransferase 1
      (MBP-ST3Gal-1 delta 45)

<400> SEQUENCE: 57

Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
            130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
            195                 200                 205
```

-continued

```
Thr Asp Tyr Ser Ile Ala Glu Ala Ala Phe Asn Lys Gly Glu Thr Ala
    210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
Lys Pro Phe Val Gly Val Leu Ser Ala Gly Ile Asn Ala Ala Ser Pro
            260                 265                 270
Asn Lys Glu Leu Ala Lys Glu Phe Leu Glu Asn Tyr Leu Leu Thr Asp
        275                 280                 285
Glu Gly Leu Glu Ala Val Asn Lys Asp Lys Pro Leu Gly Ala Val Ala
    290                 295                 300
Leu Lys Ser Tyr Glu Glu Leu Ala Lys Asp Pro Arg Ile Ala Ala
305                 310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
            340                 345                 350
Ser Gly Arg Gln Thr Val Asp Glu Ala Leu Lys Asp Ala Gln Thr Asn
        355                 360                 365
Ser Ser Ser Asn Asn Asn Asn Asn Asn Asn Asn Asn Leu Gly Ile
    370                 375                 380
Glu Gly Arg Ile Ser Glu Phe Gly Ser Glu Leu Ser Glu Asn Phe Lys
385                 390                 395                 400
Lys Leu Met Lys Tyr Pro Tyr Arg Pro Cys Thr Cys Thr Arg Cys Ile
                405                 410                 415
Glu Glu Gln Arg Val Ser Ala Trp Phe Asp Glu Arg Phe Asn Arg Ser
            420                 425                 430
Met Gln Pro Leu Leu Thr Ala Lys Asn Ala His Leu Glu Glu Asp Thr
        435                 440                 445
Tyr Lys Trp Trp Leu Arg Leu Gln Arg Glu Lys Gln Pro Asn Asn Leu
    450                 455                 460
Asn Asp Thr Ile Arg Glu Leu Phe Gln Val Val Pro Gly Asn Val Asp
465                 470                 475                 480
Pro Leu Glu Lys Arg Leu Val Ser Cys Arg Arg Cys Ala Val Val
                485                 490                 495
Gly Asn Ser Gly Asn Leu Lys Glu Ser Tyr Tyr Gly Pro Gln Ile Asp
            500                 505                 510
Ser His Asp Phe Val Leu Arg Met Asn Lys Ala Pro Thr Glu Gly Phe
        515                 520                 525
Glu Ala Asp Val Gly Ser Lys Thr Thr His His Phe Val Tyr Pro Glu
    530                 535                 540
Ser Phe Arg Glu Leu Ala Gln Glu Val Ser Met Ile Leu Val Pro Phe
545                 550                 555                 560
Lys Thr Thr Asp Leu Glu Trp Val Ile Ser Ala Thr Thr Thr Gly Arg
                565                 570                 575
Ile Ser His Thr Tyr Val Pro Val Pro Ala Lys Ile Lys Val Lys Lys
            580                 585                 590
Glu Lys Ile Leu Ile Tyr His Pro Ala Phe Ile Lys Tyr Val Phe Asp
        595                 600                 605
Arg Trp Leu Gln Gly His Gly Arg Tyr Pro Ser Thr Gly Ile Leu Ser
    610                 615                 620
Val Ile Phe Ser Leu His Ile Cys Asp Glu Val Asp Leu Tyr Gly Phe
625                 630                 635                 640
```

```
Gly Ala Asp Ser Lys Gly Asn Trp His His Tyr Trp Glu Asn Asn Pro
                645                 650                 655

Ser Ala Gly Ala Phe Arg Lys Thr Gly Val His Asp Gly Asp Phe Glu
            660                 665                 670

Ser Asn Val Thr Thr Ile Leu Ala Ser Ile Asn Lys Ile Arg Ile Phe
        675                 680                 685

Lys Gly Arg
    690

<210> SEQ ID NO 58
<211> LENGTH: 841
<212> TYPE: PRT
<213> ORGANISM: Artificial Sequence
<220> FEATURE:
<223> OTHER INFORMATION: maltose binding protein-starch binding
      domain-tagged truncated pig Gal beta-1,3-GalNAc
      alpha-2,3-sialyltransferase 1 (MBP-SBD-ST3Gal-1
      delta 45)

<400> SEQUENCE: 58

Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285
```

```
Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                    325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
                355                 360                 365

Ser Ser Ser Asn Asn Asn Asn Asn Asn Asn Asn Leu Gly Ile
370                 375                 380

Glu Gly Arg Ile Ser Glu Phe Gly Ser Ile Val Ala Thr Gly Gly Thr
385                 390                 395                 400

Thr Thr Thr Ala Thr Pro Thr Gly Ser Gly Ser Val Thr Ser Thr Ser
                405                 410                 415

Lys Thr Thr Ala Thr Ala Ser Lys Thr Ser Thr Ser Thr Ser Ser Thr
                420                 425                 430

Ser Cys Thr Thr Pro Thr Ala Val Ala Val Thr Phe Asp Leu Thr Ala
                435                 440                 445

Thr Thr Thr Tyr Gly Glu Asn Ile Tyr Leu Val Gly Ser Ile Ser Gln
450                 455                 460

Leu Gly Asp Trp Glu Thr Ser Asp Gly Ile Ala Leu Ser Ala Asp Lys
465                 470                 475                 480

Tyr Thr Ser Ser Asp Pro Leu Trp Tyr Val Thr Val Thr Leu Pro Ala
                485                 490                 495

Gly Glu Ser Phe Glu Tyr Lys Phe Ile Arg Ile Glu Ser Asp Asp Ser
                500                 505                 510

Val Glu Trp Glu Ser Asp Pro Asn Arg Glu Tyr Thr Val Pro Gln Ala
                515                 520                 525

Cys Gly Thr Ser Thr Ala Thr Val Thr Asp Thr Trp Arg Gly Ser Glu
                530                 535                 540

Leu Ser Glu Asn Phe Lys Lys Leu Met Lys Tyr Pro Tyr Arg Pro Cys
545                 550                 555                 560

Thr Cys Thr Arg Cys Ile Glu Glu Gln Arg Val Ser Ala Trp Phe Asp
                565                 570                 575

Glu Arg Phe Asn Arg Ser Met Gln Pro Leu Leu Thr Ala Lys Asn Ala
                580                 585                 590

His Leu Glu Glu Asp Thr Tyr Lys Trp Trp Leu Arg Leu Gln Arg Glu
                595                 600                 605

Lys Gln Pro Asn Leu Asn Asp Thr Ile Arg Glu Leu Phe Gln Val
610                 615                 620

Val Pro Gly Asn Val Asp Pro Leu Leu Glu Lys Arg Leu Val Ser Cys
625                 630                 635                 640

Arg Arg Cys Ala Val Val Gly Asn Ser Gly Asn Leu Lys Glu Ser Tyr
                645                 650                 655

Tyr Gly Pro Gln Ile Asp Ser His Asp Phe Val Leu Arg Met Asn Lys
                660                 665                 670

Ala Pro Thr Glu Gly Phe Glu Ala Asp Val Gly Ser Lys Thr Thr His
                675                 680                 685

His Phe Val Tyr Pro Glu Ser Phe Arg Glu Leu Ala Gln Glu Val Ser
                690                 695                 700

Met Ile Leu Val Pro Phe Lys Thr Thr Asp Leu Glu Trp Val Ile Ser
705                 710                 715                 720
```

Ala Thr Thr Thr Gly Arg Ile Ser His Thr Tyr Val Pro Val Pro Ala
            725                 730                 735

Lys Ile Lys Val Lys Lys Glu Lys Ile Leu Ile Tyr His Pro Ala Phe
            740                 745                 750

Ile Lys Tyr Val Phe Asp Arg Trp Leu Gln Gly His Gly Arg Tyr Pro
            755                 760                 765

Ser Thr Gly Ile Leu Ser Val Ile Phe Ser Leu His Ile Cys Asp Glu
            770                 775                 780

Val Asp Leu Tyr Gly Phe Gly Ala Asp Ser Lys Gly Asn Trp His His
785                 790                 795                 800

Tyr Trp Glu Asn Asn Pro Ser Ala Gly Ala Phe Arg Lys Thr Gly Val
            805                 810                 815

His Asp Gly Asp Phe Glu Ser Asn Val Thr Thr Ile Leu Ala Ser Ile
            820                 825                 830

Asn Lys Ile Arg Ile Phe Lys Gly Arg
            835                 840

<210> SEQ ID NO 59
<211> LENGTH: 600
<212> TYPE: PRT
<213> ORGANISM: Homo sapiens
<220> FEATURE:
<223> OTHER INFORMATION: alpha-N-acetylgalactosaminide
      alpha-2,6-sialyltransferase I (ST6GalNAc-1)

<400> SEQUENCE: 59

Met Arg Ser Cys Leu Trp Arg Cys Arg His Leu Ser Gln Gly Val Gln
1               5                   10                  15

Trp Ser Leu Leu Leu Ala Val Leu Val Phe Phe Leu Phe Ala Leu Pro
            20                  25                  30

Ser Phe Ile Lys Glu Pro Gln Thr Lys Pro Ser Arg His Gln Arg Thr
            35                  40                  45

Glu Asn Ile Lys Glu Arg Ser Leu Gln Ser Leu Ala Lys Pro Lys Ser
        50                  55                  60

Gln Ala Pro Thr Arg Ala Arg Arg Thr Thr Ile Tyr Ala Glu Pro Val
65                  70                  75                  80

Pro Glu Asn Asn Ala Leu Asn Thr Gln Thr Gln Pro Lys Ala His Thr
            85                  90                  95

Thr Gly Asp Arg Gly Lys Glu Ala Asn Gln Ala Pro Glu Glu Gln
            100                 105                 110

Asp Lys Val Pro His Thr Ala Gln Arg Ala Ala Trp Lys Ser Pro Glu
            115                 120                 125

Lys Glu Lys Thr Met Val Asn Thr Leu Ser Pro Arg Gly Gln Asp Ala
        130                 135                 140

Gly Met Ala Ser Gly Arg Thr Glu Ala Gln Ser Trp Lys Ser Gln Asp
145                 150                 155                 160

Thr Lys Thr Thr Gln Gly Asn Gly Gly Gln Thr Arg Lys Leu Thr Ala
            165                 170                 175

Ser Arg Thr Val Ser Glu Lys His Gln Gly Lys Ala Ala Thr Thr Ala
            180                 185                 190

Lys Thr Leu Ile Pro Lys Ser Gln His Arg Met Leu Ala Pro Thr Gly
            195                 200                 205

Ala Val Ser Thr Arg Thr Arg Gln Lys Gly Val Thr Thr Ala Val Ile
            210                 215                 220

Pro Pro Lys Glu Lys Lys Pro Gln Ala Thr Pro Pro Ala Pro Phe
225                 230                 235                 240

Gln Ser Pro Thr Thr Gln Arg Asn Gln Arg Leu Lys Ala Ala Asn Phe
            245                 250                 255

Lys Ser Glu Pro Arg Trp Asp Phe Glu Lys Tyr Ser Phe Glu Ile
        260                 265                 270

Gly Gly Leu Gln Thr Thr Cys Pro Asp Ser Val Lys Ile Lys Ala Ser
            275                 280                 285

Lys Ser Leu Trp Leu Gln Lys Leu Phe Leu Pro Asn Leu Thr Leu Phe
290                 295                 300

Leu Asp Ser Arg His Phe Asn Gln Ser Glu Trp Asp Arg Leu Glu His
305                 310                 315                 320

Phe Ala Pro Pro Phe Gly Phe Met Glu Leu Asn Tyr Ser Leu Val Gln
                325                 330                 335

Lys Val Val Thr Arg Phe Pro Val Pro Gln Gln Gln Leu Leu Leu
            340                 345                 350

Ala Ser Leu Pro Ala Gly Ser Leu Arg Cys Ile Thr Cys Ala Val Val
            355                 360                 365

Gly Asn Gly Gly Ile Leu Asn Asn Ser His Met Gly Gln Glu Ile Asp
            370                 375                 380

Ser His Asp Tyr Val Phe Arg Leu Ser Gly Ala Leu Ile Lys Gly Tyr
385                 390                 395                 400

Glu Gln Asp Val Gly Thr Arg Thr Ser Phe Tyr Gly Phe Thr Ala Phe
                405                 410                 415

Ser Leu Thr Gln Ser Leu Leu Ile Leu Gly Asn Arg Gly Phe Lys Asn
                420                 425                 430

Val Pro Leu Gly Lys Asp Val Arg Tyr Leu His Phe Leu Glu Gly Thr
            435                 440                 445

Arg Asp Tyr Glu Trp Leu Glu Ala Leu Leu Met Asn Gln Thr Val Met
            450                 455                 460

Ser Lys Asn Leu Phe Trp Phe Arg His Arg Pro Gln Glu Ala Phe Arg
465                 470                 475                 480

Glu Ala Leu His Met Asp Arg Tyr Leu Leu Leu His Pro Asp Phe Leu
                485                 490                 495

Arg Tyr Met Lys Asn Arg Phe Leu Arg Ser Lys Thr Leu Asp Gly Ala
                500                 505                 510

His Trp Arg Ile Tyr Arg Pro Thr Thr Gly Ala Leu Leu Leu Leu Thr
            515                 520                 525

Ala Leu Gln Leu Cys Asp Gln Val Ser Ala Tyr Gly Phe Ile Thr Glu
            530                 535                 540

Gly His Glu Arg Phe Ser Asp His Tyr Tyr Asp Thr Ser Trp Lys Arg
545                 550                 555                 560

Leu Ile Phe Tyr Ile Asn His Asp Phe Lys Leu Glu Arg Glu Val Trp
                565                 570                 575

Lys Arg Leu His Asp Glu Gly Ile Ile Arg Leu Tyr Gln Arg Pro Gly
            580                 585                 590

Pro Gly Thr Ala Lys Ala Lys Asn
        595                 600

<210> SEQ ID NO 60
<211> LENGTH: 600
<212> TYPE: PRT
<213> ORGANISM: Homo sapiens
<220> FEATURE:
<223> OTHER INFORMATION: N-acetylgalactosamine-alpha2,6-
      sialyltransferase I (ST6GalNAcI)

<400> SEQUENCE: 60

-continued

```
Met Arg Ser Cys Leu Trp Arg Cys Arg His Leu Ser Gln Gly Val Gln
  1               5                  10                  15

Trp Ser Leu Leu Leu Ala Val Leu Val Phe Phe Leu Phe Ala Leu Pro
             20                  25                  30

Ser Phe Ile Lys Glu Pro Gln Thr Lys Pro Ser Arg His Gln Arg Thr
         35                  40                  45

Glu Asn Ile Lys Glu Arg Ser Leu Gln Ser Leu Ala Lys Pro Lys Ser
     50                  55                  60

Gln Ala Pro Thr Arg Ala Arg Arg Thr Thr Ile Tyr Ala Glu Pro Val
 65                  70                  75                  80

Pro Glu Asn Asn Ala Leu Asn Thr Gln Thr Gln Pro Lys Ala His Thr
                 85                  90                  95

Thr Gly Asp Arg Gly Lys Glu Ala Asn Gln Ala Pro Glu Glu Gln
                100                 105                 110

Asp Lys Val Pro His Thr Ala Gln Arg Ala Ala Trp Lys Ser Pro Glu
            115                 120                 125

Lys Glu Lys Thr Met Val Asn Thr Leu Ser Pro Arg Gly Gln Asp Ala
        130                 135                 140

Gly Met Ala Ser Gly Arg Thr Glu Ala Gln Ser Trp Lys Ser Gln Asp
145                 150                 155                 160

Thr Lys Thr Thr Lys Gly Asn Gly Gly Gln Thr Arg Lys Leu Thr Ala
                165                 170                 175

Ser Arg Thr Val Ser Glu Lys His Gln Gly Lys Ala Ala Thr Thr Ala
            180                 185                 190

Lys Thr Leu Ile Pro Lys Ser Gln His Arg Met Leu Ala Pro Thr Gly
        195                 200                 205

Ala Val Ser Thr Arg Thr Arg Gln Lys Gly Val Thr Thr Ala Val Ile
    210                 215                 220

Pro Pro Lys Glu Lys Lys Pro Gln Ala Thr Pro Pro Ala Pro Phe
225                 230                 235                 240

Gln Ser Pro Thr Thr Gln Arg Asn Gln Arg Leu Lys Ala Ala Asn Phe
                245                 250                 255

Lys Ser Glu Pro Arg Trp Asp Phe Glu Glu Lys Tyr Ser Phe Glu Ile
            260                 265                 270

Gly Gly Leu Gln Thr Thr Cys Pro Asp Ser Val Lys Ile Lys Ala Ser
        275                 280                 285

Lys Ser Leu Trp Leu Gln Lys Leu Phe Leu Pro Asn Leu Thr Leu Phe
    290                 295                 300

Leu Asp Ser Arg His Phe Asn Gln Ser Glu Trp Asp Arg Leu Glu His
305                 310                 315                 320

Phe Ala Pro Pro Phe Gly Phe Met Glu Leu Asn Tyr Ser Leu Val Gln
                325                 330                 335

Lys Val Val Thr Arg Phe Pro Pro Val Pro Gln Gln Gln Leu Leu Leu
            340                 345                 350

Ala Ser Leu Pro Ala Gly Ser Leu Arg Cys Ile Thr Cys Ala Val Val
        355                 360                 365

Gly Asn Gly Gly Ile Leu Asn Asn Ser His Ile Gly Gln Glu Ile Asp
    370                 375                 380

Ser His Asp Tyr Val Phe Arg Leu Ser Gly Ala Leu Ile Lys Gly Tyr
385                 390                 395                 400

Glu Gln Asp Val Gly Thr Arg Thr Ser Phe Tyr Gly Phe Thr Ala Phe
                405                 410                 415

Ser Leu Thr Gln Ser Leu Leu Ile Leu Gly Asn Arg Gly Phe Lys Asn
```

```
                420              425              430
Val Pro Leu Gly Lys Asp Val Arg Tyr Leu His Phe Leu Glu Gly Thr
            435              440              445

Arg Asp Tyr Glu Trp Leu Glu Ala Leu Leu Met Asn Gln Thr Val Met
450              455              460

Ser Lys Asn Leu Phe Trp Phe Arg His Arg Pro Gln Glu Ala Phe Arg
465              470              475              480

Glu Ala Leu His Met Asp Arg Tyr Leu Leu His Pro Asp Phe Leu
                485              490              495

Arg Tyr Met Lys Asn Arg Phe Leu Arg Ser Lys Thr Leu Asp Gly Ala
            500              505              510

His Trp Arg Ile Tyr Arg Pro Thr Thr Gly Ala Leu Leu Leu Thr
            515              520              525

Ala Leu Gln Leu Cys Asp Gln Val Ser Ala Tyr Gly Phe Ile Thr Glu
            530              535              540

Gly His Glu Arg Phe Ser Asp His Tyr Tyr Asp Thr Ser Trp Lys Arg
545              550              555              560

Leu Ile Phe Tyr Ile Asn His Asp Phe Lys Leu Glu Arg Glu Val Trp
                565              570              575

Lys Arg Leu His Asp Glu Gly Ile Ile Arg Leu Tyr Gln Arg Pro Gly
            580              585              590

Pro Gly Thr Ala Lys Ala Lys Asn
            595              600

<210> SEQ ID NO 61
<211> LENGTH: 526
<212> TYPE: PRT
<213> ORGANISM: Mus musculus
<220> FEATURE:
<223> OTHER INFORMATION: alpha-N-acetylgalactosaminide
      alpha-2,6-sialyltransferase I (ST6GalNAc-1)
<220> FEATURE:
<221> NAME/KEY: MISC_FEATURE
<222> LOCATION: (441)...(441)
<223> OTHER INFORMATION: Xaa can be any amino acid

<400> SEQUENCE: 61

Met Thr Arg Tyr Cys Arg Gly Leu Ser Gln Arg Gln Ala Phe Leu Leu
1               5                   10                  15

Leu Thr Val Leu Ala Leu Leu Phe Ile Leu Phe Val Val Lys Asp
            20                  25                  30

Pro Arg Ala Lys Asp Ser Arg Arg Gln Phe Ile Leu Asn Asn Asp Ser
            35                  40                  45

Ser Ala Gln Glu Ile Leu Gln Lys Ala Glu Pro Gln Gly Pro Ile Met
50                  55                  60

Thr Leu Ser Pro Arg Val His Asn Lys Glu Ala Thr Ser Val Ser Ser
65                  70                  75                  80

Lys Asp Leu Lys Lys Gln Glu Arg Glu Ala Val Gln Gly Glu Gln Ala
                85                  90                  95

Glu Gly Lys Glu Lys Arg Lys Leu Glu Thr Ile Arg Pro Ala Pro Glu
            100                 105                 110

Asn Pro Gln Ser Lys Ala Glu Pro Ala Ala Lys Thr Pro Val Ser Glu
            115                 120                 125

His Leu Asp Lys Val Pro Arg Thr Pro Gly Ala Leu Ser Thr Arg Lys
        130                 135                 140

Thr Pro Met Ala Thr Gly Ala Val Pro Ala Lys Lys Val Val Gln
145                 150                 155                 160
```

```
Ala Thr Lys Ser Pro Ala Ser Ser Pro His Pro Thr Thr Arg Arg Arg
            165                 170                 175

Gln Arg Leu Lys Ala Ser Glu Phe Lys Ser Glu Pro Arg Trp Asp Phe
        180                 185                 190

Glu Glu Glu Tyr Ser Leu Asp Met Ser Ser Leu Gln Thr Asn Cys Ser
            195                 200                 205

Ala Ser Val Lys Ile Lys Ala Ser Lys Ser Pro Trp Leu Gln Asn Ile
210                 215                 220

Phe Leu Pro Asn Ile Thr Leu Phe Leu Asp Ser Gly Arg Phe Thr Gln
225                 230                 235                 240

Ser Glu Trp Asn Arg Leu Glu His Phe Ala Pro Pro Phe Gly Phe Met
                245                 250                 255

Glu Leu Asn Gln Ser Leu Val Gln Lys Val Val Thr Arg Phe Pro Pro
            260                 265                 270

Val Arg Gln Gln Gln Leu Leu Leu Ala Ser Leu Pro Thr Gly Tyr Ser
            275                 280                 285

Lys Cys Ile Thr Cys Ala Val Val Gly Asn Gly Gly Ile Leu Asn Asp
        290                 295                 300

Ser Arg Val Gly Arg Glu Ile Asp Ser His Asp Tyr Val Phe Arg Leu
305                 310                 315                 320

Ser Gly Ala Val Ile Lys Gly Tyr Glu Gln Asp Val Gly Thr Arg Thr
                325                 330                 335

Ser Phe Tyr Gly Phe Thr Ala Phe Ser Leu Thr Gln Ser Ile Leu Ile
            340                 345                 350

Leu Gly Arg Arg Gly Phe Gln His Val Pro Leu Gly Lys Asp Val Arg
        355                 360                 365

Tyr Leu His Phe Leu Glu Gly Thr Arg Asn Tyr Glu Trp Leu Glu Ala
370                 375                 380

Met Phe Leu Asn Gln Thr Leu Ala Lys Thr His Leu Ser Trp Phe Arg
385                 390                 395                 400

His Arg Pro Gln Glu Ala Phe Arg Asn Ala Leu Asp Leu Asp Arg Tyr
                405                 410                 415

Leu Leu Leu His Pro Asp Phe Leu Arg Tyr Met Lys Asn Arg Phe Leu
            420                 425                 430

Arg Ser Lys Thr Leu Asp Thr Ala Xaa Trp Arg Ile Tyr Arg Pro Thr
        435                 440                 445

Thr Gly Ala Leu Leu Leu Leu Thr Ala Leu His Leu Cys Asp Lys Val
450                 455                 460

Ser Ala Tyr Gly Phe Ile Thr Glu Gly His Glu Arg Phe Ser Asp His
465                 470                 475                 480

Tyr Tyr Asp Thr Ser Trp Lys Arg Leu Ile Phe Tyr Ile Asn His Asp
                485                 490                 495

Phe Arg Leu Glu Arg Met Val Trp Lys Arg Leu His Asp Glu Gly Ile
            500                 505                 510

Ile Trp Leu Tyr Gln Arg Pro Gln Ser Asp Lys Ala Lys Asn
        515                 520                 525

<210> SEQ ID NO 62
<211> LENGTH: 566
<212> TYPE: PRT
<213> ORGANISM: Gallus gallus
<220> FEATURE:
<223> OTHER INFORMATION: alpha-N-acetylgalactosaminide
      alpha-2,6-sialyltransferase I (ST6GalNAc-1)

<400> SEQUENCE: 62
```

```
Met Gly Phe Leu Ile Arg Arg Leu Pro Lys Asp Ser Arg Ile Phe Arg
 1               5                  10                  15
Trp Leu Leu Ile Leu Thr Val Phe Ser Phe Ile Ile Thr Ser Phe Ser
            20                  25                  30
Ala Leu Phe Gly Met Glu Lys Ser Ile Phe Arg Gln Leu Lys Ile Tyr
        35                  40                  45
Gln Ser Ile Ala His Met Leu Gln Val Asp Thr Gln Asp Gln Gln Gly
50                  55                  60
Ser Asn Tyr Ser Ala Asn Gly Arg Ile Ser Lys Val Gly Leu Glu Arg
65                  70                  75                  80
Asp Ile Ala Trp Leu Glu Leu Asn Thr Ala Val Ser Thr Pro Ser Gly
                85                  90                  95
Glu Gly Lys Glu Gln Lys Lys Thr Val Lys Pro Val Ala Lys Val
            100                 105                 110
Glu Glu Ala Lys Glu Lys Val Thr Val Lys Pro Phe Pro Glu Val Met
        115                 120                 125
Gly Ile Thr Asn Thr Thr Ala Ser Thr Ala Ser Val Val Glu Arg Thr
    130                 135                 140
Lys Glu Lys Thr Thr Ala Arg Pro Val Pro Gly Val Gly Glu Ala Asp
145                 150                 155                 160
Gly Lys Arg Thr Thr Ile Ala Leu Pro Ser Met Lys Glu Asp Lys Glu
                165                 170                 175
Lys Ala Thr Val Lys Pro Ser Phe Gly Met Lys Val Ala His Ala Asn
            180                 185                 190
Ser Thr Ser Lys Asp Lys Pro Lys Ala Glu Pro Pro Ala Ser Val
        195                 200                 205
Lys Ala Ile Arg Pro Val Thr Gln Ala Ala Thr Val Thr Glu Lys Lys
210                 215                 220
Lys Leu Arg Ala Ala Asp Phe Lys Thr Glu Pro Gln Trp Asp Phe Asp
225                 230                 235                 240
Asp Glu Tyr Ile Leu Asp Ser Ser Pro Val Ser Thr Cys Ser Glu
                245                 250                 255
Ser Val Arg Ala Lys Ala Ala Lys Ser Asp Trp Leu Arg Asp Leu Phe
            260                 265                 270
Leu Pro Asn Ile Thr Leu Phe Ile Asp Lys Ser Tyr Phe Asn Val Ser
        275                 280                 285
Glu Trp Asp Arg Leu Glu His Phe Ala Pro Pro Tyr Gly Phe Met Glu
    290                 295                 300
Leu Asn Tyr Ser Leu Val Glu Glu Val Met Ser Arg Leu Pro Pro Asn
305                 310                 315                 320
Pro His Gln Gln Leu Leu Leu Ala Asn Ser Ser Ser Asn Val Ser Thr
                325                 330                 335
Cys Ile Ser Cys Ala Val Val Gly Asn Gly Gly Ile Leu Asn Asn Ser
            340                 345                 350
Gly Met Gly Gln Glu Ile Asp Ser His Asp Tyr Val Phe Arg Val Ser
        355                 360                 365
Gly Ala Val Ile Lys Gly Tyr Glu Lys Asp Val Gly Thr Lys Thr Ser
    370                 375                 380
Phe Tyr Gly Phe Thr Ala Tyr Ser Leu Val Ser Ser Leu Gln Asn Leu
385                 390                 395                 400
Gly His Lys Gly Phe Lys Lys Ile Pro Gln Gly Lys His Ile Arg Tyr
                405                 410                 415
Ile His Phe Leu Glu Ala Val Arg Asp Tyr Glu Trp Leu Lys Ala Leu
            420                 425                 430
```

```
Leu Leu Asp Lys Asp Ile Arg Lys Gly Phe Leu Asn Tyr Tyr Gly Arg
            435                 440                 445

Arg Pro Arg Glu Arg Phe Asp Glu Asp Phe Thr Met Asn Lys Tyr Leu
            450                 455                 460

Val Ala His Pro Asp Phe Leu Arg Tyr Leu Lys Asn Arg Phe Leu Lys
465                 470                 475                 480

Ser Lys Asn Leu Gln Lys Pro Tyr Trp Arg Leu Tyr Arg Pro Thr Thr
            485                 490                 495

Gly Ala Leu Leu Leu Leu Thr Ala Leu His Leu Cys Asp Arg Val Ser
            500                 505                 510

Ala Tyr Gly Tyr Ile Thr Glu Gly His Gln Lys Tyr Ser Asp His Tyr
            515                 520                 525

Tyr Asp Lys Glu Trp Lys Arg Leu Val Phe Tyr Val Asn His Asp Phe
            530                 535                 540

Asn Leu Glu Lys Gln Val Trp Lys Arg Leu His Asp Glu Asn Ile Met
545                 550                 555                 560

Lys Leu Tyr Gln Arg Ser
            565

<210> SEQ ID NO 63
<211> LENGTH: 519
<212> TYPE: PRT
<213> ORGANISM: Rattus norvegicus
<220> FEATURE:
<223> OTHER INFORMATION: alpha-N-acetylgalactosaminide
      alpha-2,6-sialyltransferase I (ST6GalNAc-1)

<400> SEQUENCE: 63

Met Glu Asn Arg Cys Arg Gly Leu Ser Gln Gly Gln Thr Phe Leu Leu
 1               5                  10                  15

Leu Thr Gly Leu Met Leu Leu Phe Ile Leu Pro Ser Val Val Lys Glu
            20                  25                  30

Pro Ser Thr Arg Val Ser Arg Gln Phe Ile Glu Asp Asn Glu Ser Ser
            35                  40                  45

Leu Gln Gly Val Pro Gln Lys Pro Ala Pro Gln Gly Pro Ile Val Thr
        50                  55                  60

Leu Thr Pro Thr Val His Asn Lys Lys Thr Thr Ser Val Arg Thr Lys
65                  70                  75                  80

Trp Val Glu Leu Gln Lys Gln Asp Arg Ala Thr Ala Arg Gly Glu Arg
            85                  90                  95

Gly Glu Gly Val Glu Lys Lys Leu Gln Ala Ile Arg Leu Ala Pro Glu
            100                 105                 110

Asn Pro Lys Gly Lys Ala Glu Pro Glu Val Lys Thr Pro Ala Ser Lys
            115                 120                 125

His Leu Asp Lys Leu Pro Arg Ala Thr Gly Ala Leu Ser Thr Arg Lys
        130                 135                 140

Thr Gln Met Ala Thr Gly Ala Ala Pro Ala Lys Lys Val Val Gln
145                 150                 155                 160

Pro Thr Pro Thr Pro Ala Ser Phe Pro His Leu Thr Thr Gln Arg Arg
            165                 170                 175

Gln Arg Leu Lys Ala Ser Asp Phe Lys Ser Glu Pro Arg Trp Asp Phe
            180                 185                 190

Glu Glu Glu Tyr Ser Leu Asp Gly Gly Ser Leu Gln Thr Leu Pro Trp
            195                 200                 205

Phe Leu Lys Ile Thr Val Ser His Ser Pro Trp Val Gln Asn Ile Phe
        210                 215                 220
```

```
Leu Pro Asn Ile Thr Leu Phe Leu Asp Ser Gly Arg Phe Asn Gln Ser
225                 230                 235                 240

Glu Trp Tyr Arg Leu Glu His Phe Thr Pro Pro Phe Gly Phe Met Glu
                245                 250                 255

Leu Asn Gln Ser Leu Val Gln Lys Val Ser Arg Phe Pro Pro Val
            260                 265                 270

Pro Gln Gln Gln Leu Leu Leu Ala Ser Leu Pro Thr Arg Asn Leu Thr
            275                 280                 285

Cys Ile Thr Cys Ala Val Val Gly Asn Gly Gly Ile Leu Asn Asn Ser
290                 295                 300

Arg Met Gly Gln Glu Ile Asp Ser His Asp Tyr Val Phe Arg Leu Ser
305                 310                 315                 320

Gly Thr Val Ile Lys Gly Tyr Glu Gln Asp Val Gly Thr Arg Thr Ser
                325                 330                 335

Phe Tyr Gly Phe Thr Ala Phe Ser Leu Gly Gln Ser Ile Leu Asn Leu
            340                 345                 350

Gly Ser Ser Arg Phe Ser Ala Cys Ala Phe Leu Gly Lys Asp Val Arg
        355                 360                 365

Tyr Leu His Phe Leu Glu Gly Thr Arg Asp Tyr Glu Trp Leu Glu Ala
370                 375                 380

Met Phe Leu Asn Arg Thr Met Ala Asn Thr Lys Leu Tyr Trp Phe Arg
385                 390                 395                 400

His Arg Pro Gln Glu Ala Phe Arg Glu Ala Leu Asp Leu Asp Arg Tyr
                405                 410                 415

Phe Leu Val His Pro Asp Phe Leu Arg Tyr Met Lys Asn Arg Phe Leu
            420                 425                 430

Arg Ser Lys Thr Leu Asp Thr Ala His Trp Arg Leu Tyr Arg Pro Thr
        435                 440                 445

Thr Gly Ala Leu Leu Leu Leu Thr Ala Leu His Leu Cys Asp Lys Val
450                 455                 460

Ser Ala Tyr Gly Phe Ile Thr Gln Gly His Glu Arg Phe Ser Asp His
465                 470                 475                 480

Tyr Tyr Asp Thr Ser Trp Lys Arg Leu Ile Phe Tyr Ile Asn His Asp
                485                 490                 495

Phe Ala Leu Glu Arg Thr Val Trp Lys Arg Leu His Asp Glu Gly Ile
            500                 505                 510

Ile Gln Leu Tyr Gln Arg Pro
        515

<210> SEQ ID NO 64
<211> LENGTH: 567
<212> TYPE: PRT
<213> ORGANISM: Pan troglodytes
<220> FEATURE:
<223> OTHER INFORMATION: alpha-N-acetylgalactosaminide
      alpha-2,6-sialyltransferase I (ST6GalNAc-1)

<400> SEQUENCE: 64

Met Arg Ser Cys Leu Trp Arg Cys Arg His Leu Ser Gln Gly Val Gln
 1               5                  10                  15

Trp Ser Leu Leu Leu Ala Val Leu Val Phe Leu Phe Ala Leu Pro
            20                  25                  30

Ser Phe Ile Lys Glu Pro Gln Thr Lys Pro Ser Arg Glu Pro Ala Pro
        35                  40                  45

Glu Asn Asn Ala Leu Asn Thr Gln Thr Gln Pro Lys Ala His Thr Ala
50                  55                  60
```

```
Gly Asp Arg Gly Lys Glu Ala Asn Gln Ala Pro Pro Glu Glu Gln Asp
 65                  70                  75                  80

Lys Val Pro His Thr Ala Gln Arg Ala Ala Trp Lys Ser Pro Glu Lys
                 85                  90                  95

Glu Lys Thr Met Val Asn Thr Leu Ser Pro Arg Gly Gln Asp Ala Gly
            100                 105                 110

Met Ala Ser Gly Arg Thr Gln Ala Gln Ser Trp Lys Ser Gln Asp Thr
        115                 120                 125

Lys Thr Thr Gln Gly Asn Gly Gly Gln Thr Arg Lys Leu Met Ala Ser
    130                 135                 140

Arg Thr Val Ser Glu Lys His Gln Gly Lys Ala Ala Thr Ala Lys
145                 150                 155                 160

Thr Leu Ile Pro Lys Ser Gln His Arg Met Leu Ala Pro Thr Gly Ala
                165                 170                 175

Val Ser Thr Arg Thr Arg Gln Lys Gly Val Thr Thr Ala Val Ile Pro
            180                 185                 190

Pro Lys Glu Lys Lys Pro Gln Ala Thr Pro Pro Ala Pro Phe Gln
        195                 200                 205

Ser Pro Thr Thr Gln Arg Asn Gln Arg Leu Lys Ala Ala Asn Phe Lys
    210                 215                 220

Ser Glu Pro Arg Trp Asp Phe Glu Glu Lys Tyr Ser Phe Glu Ile Gly
225                 230                 235                 240

Gly Leu Gln Thr Thr Cys Pro Asp Ser Val Lys Ile Lys Ala Ser Lys
                245                 250                 255

Ser Leu Trp Leu Gln Lys Leu Phe Leu Pro Asn Leu Thr Leu Phe Leu
            260                 265                 270

Asp Ser Arg His Phe Asn Gln Ser Glu Trp Asp Arg Leu Glu His Phe
        275                 280                 285

Ala Pro Pro Phe Gly Phe Met Glu Leu Asn Tyr Ser Leu Val Gln Lys
    290                 295                 300

Val Val Thr Arg Phe Pro Pro Val Pro Gln Gln Leu Leu Leu Ala
305                 310                 315                 320

Ser Leu Pro Ala Gly Ser Leu Arg Cys Ile Thr Cys Ala Val Val Gly
                325                 330                 335

Asn Gly Gly Ile Leu Asn Asn Ser His Met Gly Gln Glu Ile Asp Ser
            340                 345                 350

His Asp Tyr Val Phe Arg Leu Ser Gly Val Leu Ile Lys Gly Tyr Glu
        355                 360                 365

Gln Asp Ala Val Asp Arg Thr Ser Phe Tyr Gly Phe Thr Ala Phe Ser
    370                 375                 380

Leu Thr Gln Ser Leu Leu Ile Leu Gly Asn Arg Gly Phe Lys Asn Val
385                 390                 395                 400

Pro Leu Gly Lys Asp Val Arg Tyr Leu His Phe Leu Glu Gly Thr Arg
                405                 410                 415

Asp Tyr Glu Trp Leu Glu Ala Leu Leu Met Asn Gln Thr Val Met Ser
            420                 425                 430

Lys Asn Leu Phe Trp Phe Arg His Arg Pro Gln Glu Ala Phe Arg Glu
        435                 440                 445

Ala Leu His Met Asp Arg Tyr Leu Leu Leu His Pro Asp Phe Leu Arg
    450                 455                 460

Tyr Met Lys Asn Arg Phe Leu Arg Ser Lys Thr Leu Asp Gly Ala His
465                 470                 475                 480

Trp Arg Ile Tyr Arg Pro Thr Thr Gly Ala Leu Leu Leu Leu Thr Ala
```

```
                        485                 490                 495
Leu Gln Leu Cys Asp Gln Val Ser Ala Tyr Gly Phe Ile Thr Glu Gly
                500                 505                 510

His Glu Arg Phe Ser Asp His Tyr Tyr Asp Thr Ser Trp Lys Arg Leu
            515                 520                 525

Ile Phe Tyr Thr Asn His Asp Phe Lys Leu Glu Arg Glu Val Trp Lys
        530                 535                 540

Arg Leu His Asp Glu Gly Ile Ile Arg Leu Tyr Gln Arg Pro Gly Pro
545                 550                 555                 560

Gly Thr Ala Lys Ala Lys Asn
                565

<210> SEQ ID NO 65
<211> LENGTH: 662
<212> TYPE: PRT
<213> ORGANISM: Bos taurus
<220> FEATURE:
<223> OTHER INFORMATION: alpha-N-acetylgalactosaminide
      alpha-2,6-sialyltransferase I (ST6GalNAc-1)

<400> SEQUENCE: 65

Met Ala Thr Cys Pro Ala Cys Gly Arg Leu Arg Ser Leu Leu Arg Pro
1               5                   10                  15

Gly Ser Arg Lys Asn Glu His Gln Gln Asn Ile Lys Glu Arg Ser Pro
            20                  25                  30

Glu Leu Leu Gln Asn Ala Thr Ser Gln Ala Pro Thr Pro Arg Arg Arg
        35                  40                  45

Ala Thr Thr His Val Glu Ser Val Gln Gly Thr Arg Thr Arg Asp Thr
    50                  55                  60

His Pro Lys Ala Thr Thr Leu Thr Ala Asp Gln Arg Arg Arg Val Gln
65                  70                  75                  80

Thr Ser Lys Ala Arg Ala Glu Glu Pro Gly Arg Val Pro Thr Pro Ile
                85                  90                  95

Gly Lys Ala Ala Pro Gln Thr Gln Ala Ser Lys Asp Thr Arg Ala Asp
            100                 105                 110

Thr Leu Pro Pro Met Ala Gly Gly Gly Val Ala Ser Ser Arg Thr
        115                 120                 125

Glu Ala Pro Ser Leu Asn Ser Gln Asn Pro Arg Met Thr Lys Gly Ser
    130                 135                 140

Gly Asp Arg Lys Ala Arg Pro Thr Gly Pro Arg Ala Val Pro Thr Lys
145                 150                 155                 160

Leu Arg Asp Ser Pro Ser Pro Ala Thr Gln Arg Ser Gln Lys Leu Lys
                165                 170                 175

Ala Thr Asn Phe Lys Ser Glu Pro Gln Trp Asp Phe Glu Glu Glu Tyr
            180                 185                 190

Ser Leu Glu Val Gly Gly Leu Gln Thr Gly Thr Arg Thr Arg Asp Thr
        195                 200                 205

His Pro Lys Ala Thr Thr Leu Thr Ala Asp Gln Arg Arg Arg Val Gln
    210                 215                 220

Thr Ser Lys Ala Arg Ala Glu Glu Pro Gly Arg Val Pro Thr Pro Ile
225                 230                 235                 240

Gly Lys Ala Ala Pro Gln Thr Gln Ala Ser Lys Asp Thr Arg Ala Asp
                245                 250                 255

Thr Leu Pro Pro Met Ala Gly Gly Gly Val Ala Ser Ser Arg Thr
            260                 265                 270

Glu Ala Pro Ser Leu Asn Ser Gln Asn Pro Arg Met Thr Lys Gly Ser
```

```
                275                 280                 285
Gly Asp Arg Lys Asp Arg Ala Gln Pro Thr Arg Ser Ser Ala Pro Leu
290                 295                 300

Gln Ser Pro Ala Thr Gln Arg Ser Gln Lys Leu Lys Ala Thr Asn Phe
305                 310                 315                 320

Lys Ser Glu Pro Gln Trp Asp Phe Glu Asp Glu Tyr Ser Leu Glu Val
                325                 330                 335

Gly Gly Leu Gln Thr Thr Cys Pro Asp Ser Val Lys Ile Lys Ala Ser
            340                 345                 350

Lys Ser Pro Trp Leu Arg Thr Leu Phe Leu Pro Asn Leu Thr Leu Phe
        355                 360                 365

Leu Asp Ser Gly His Phe Asn Gln Ser Glu Trp Asp Arg Leu Glu His
    370                 375                 380

Phe Ala Pro Pro Phe Gly Phe Met Glu Leu Asn Phe Ser Leu Val Gln
385                 390                 395                 400

Lys Val Val Ala Arg Phe Pro Pro Val Pro Gln Gln Gln Leu Leu Leu
                405                 410                 415

Ala Ser Leu Pro Ala Gly Ser Ser Arg Cys Ile Ser Cys Ala Val Val
            420                 425                 430

Gly Asn Gly Gly Ile Leu Asn Asn Ser His Val Gly Pro Glu Ile Asp
        435                 440                 445

Ser His Asp Tyr Val Phe Arg Leu Ser Gly Ala Ile Ile Lys Gly Tyr
    450                 455                 460

Glu His Asp Val Gly Thr Arg Thr Ser Phe Tyr Gly Phe Thr Ala Phe
465                 470                 475                 480

Ser Leu Thr Gln Ser Leu Leu Ile Leu Gly Ser Arg Gly Phe Pro His
                485                 490                 495

Ala Pro Leu Gly Gln Asp Val Arg Tyr Leu His Phe Leu Glu Gly Thr
            500                 505                 510

Arg Asp Tyr Glu Trp Leu Glu Ala Leu Leu Asn Arg Thr Leu Thr
        515                 520                 525

Ser Arg Asn Leu Ser Trp Phe Arg Arg Pro Gln Glu Ala Phe Gln
    530                 535                 540

Glu Ala Leu Gln Leu Asp Arg Tyr Leu Leu His Pro Asp Leu Leu
545                 550                 555                 560

Arg Tyr Met Lys Asn Arg Phe Leu Arg Ser Lys Thr Leu Asn Thr Ala
                565                 570                 575

His Trp Arg Ile Tyr Arg Pro Thr Thr Gly Ala Leu Leu Leu Leu Thr
            580                 585                 590

Ala Leu Gln Leu Cys Asp Gln Val Ser Ala Tyr Gly Phe Ile Thr Glu
        595                 600                 605

Gly His Glu Arg Phe Ser Asp His Tyr Tyr Asp Lys Ser Trp Lys Arg
    610                 615                 620

Thr Ile Phe Tyr Thr Asn His Asp Phe Lys Leu Glu Arg Ala Leu Trp
625                 630                 635                 640

Lys Arg Leu His Asp Glu Gly Ile Ile Arg Leu Tyr Gln Arg Pro Ile
                645                 650                 655

Thr Ser Lys Pro Thr Ile
            660

<210> SEQ ID NO 66
<211> LENGTH: 1018
<212> TYPE: PRT
<213> ORGANISM: Canis familiaris
<220> FEATURE:
```

-continued

<223> OTHER INFORMATION: alpha-N-acetylgalactosaminide
      alpha-2,6-sialyltransferase I (ST6GalNAc-1)

<400> SEQUENCE: 66

```
Met Lys Ile Arg Leu Cys Arg Leu Ser His Leu Asp Gln Thr Thr Gln
 1               5                  10                  15

Trp Phe Leu Leu Ser Ala Val Leu Thr Phe Val Phe Ile Leu Pro
             20                  25                  30

Ser Phe Val Lys Glu Pro Asn Thr Lys Pro Phe Arg His Gln His Ile
             35                  40                  45

Arg Asn Glu Glu Arg Ser Pro Glu Ser Leu His Glu Val Thr Gly Gln
 50                  55                  60

Ala Pro Thr Ala Gly Asp Arg Thr Met Ala Pro Ala Val Ala Ser Ala
 65                  70                  75                  80

Gln Glu Lys Ser Val Trp Ala Pro Gln Ala Leu Ala Thr Ala Tyr Ala
                 85                  90                  95

Ala Gln Glu Asp Thr Arg Ala Gly Ala Leu Glu Ala Thr Ser Ala Gln
                100                 105                 110

Pro Thr Ser Met Arg Gly Gln Glu Arg Lys Asp Thr Met Pro Asp Thr
            115                 120                 125

Leu Pro Pro Arg Ala Gln Asp Lys Gly Val Ala Ser Asp Arg Thr Gly
130                 135                 140

Leu Pro Ser Val Met Ser Gln Asp Thr Arg Thr Ile Lys Gly Arg Arg
145                 150                 155                 160

Asp Gln Lys Glu Glu Pro Thr Ala Thr Arg Lys Val Thr Pro Gly Pro
                165                 170                 175

Gln Ser Lys Ala Arg Thr Thr Arg Arg Thr Pro Val Pro Glu Ser Gln
            180                 185                 190

Ala Lys Ala Leu Thr Thr Pro Gly Ala Gly Pro Met Gly Arg Thr Arg
        195                 200                 205

Lys Gly Ala Thr Thr Ala Ala Ala Pro His Arg Asp Thr Ala Arg Ala
210                 215                 220

Thr Pro Pro Ser Thr Ser Ser Gln Gly Arg Thr Thr Arg Arg Ser Pro
225                 230                 235                 240

Ser Leu Arg Ala Ala Asn Phe Lys Ser Glu Pro Arg Trp Asp Phe Glu
                245                 250                 255

Glu Gln Tyr Ser Phe Asp Thr Glu Ala Leu Gln Pro Thr Cys Pro Asp
            260                 265                 270

Ser Val Lys Val Lys Ala Ser Lys Ser Pro Trp Leu Gln Asn Leu Phe
        275                 280                 285

Leu Ala Asn Leu Thr Leu Phe Leu Asp Ser Ser Arg Phe Ser Gln Arg
290                 295                 300

Glu Trp Asp Arg Leu Glu His Phe Ala Pro Pro Phe Gly Phe Met Glu
305                 310                 315                 320

Leu Asn Gln Ser Leu Val Gln Lys Gly Val Thr Arg Phe Pro Pro Val
                325                 330                 335

Pro Gln Gln Gln Leu Leu Arg Ala Ser Leu Pro Ala Gly Ser Ser Gln
            340                 345                 350

Cys Ile Thr Cys Ala Val Val Gly Asn Gly Gly Ile Leu Asn Asp Ser
        355                 360                 365

Arg Val Gly Gln Glu Ile Asp Gly His Asp His Val Phe Arg Leu Ser
370                 375                 380

Gly Ala Val Thr Lys Gly Tyr Glu Gln Asp Val Gly Thr Arg Thr Ser
385                 390                 395                 400
```

-continued

Phe Tyr Gly Phe Thr Ala Phe Ser Ile Thr Gln Ser Leu Leu Ala Leu
                    405                 410                 415

Gly Gly Arg Gly Phe Pro His Val Pro Leu Gly Lys Asp Val Arg Tyr
                420                 425                 430

Leu His Phe Leu Glu Gly Thr Arg Asp Tyr Glu Trp Leu Glu Ala Leu
            435                 440                 445

Leu Leu Asn Gln Thr Leu Val Lys Ser Ser Leu Ser Trp Phe Arg Arg
        450                 455                 460

Arg Pro Gln Glu Ala Phe Arg Asp Thr Leu Gln Leu Asp Arg Tyr Leu
465                 470                 475                 480

Leu Leu His Pro Asp Phe Met Arg Tyr Met Lys Asn Arg Phe Leu Arg
                485                 490                 495

Ser Lys Thr Leu Asn Asn Ile His Trp Arg Ile Tyr Arg Pro Thr Thr
                500                 505                 510

Gly Ala Leu Leu Leu Leu Thr Ala Leu His Leu Cys Asp Gln Val Ser
            515                 520                 525

Ala Tyr Gly Phe Ile Thr Glu Gly His Glu Arg Phe Ser Asp His Tyr
        530                 535                 540

Tyr Asp Lys Ser Trp Lys Arg Thr Ile Phe Tyr Thr Asn His Asp Phe
545                 550                 555                 560

Pro Leu Glu Arg Thr Leu Trp Lys Arg Leu His Asp Glu Gly Ile Ile
                565                 570                 575

Arg Leu Tyr Gln Arg Pro Ile Ile Ser Lys Pro Lys Met Val Gln Thr
                580                 585                 590

Arg Pro Gln Ala Pro Pro Asp Ser Pro Gly Asp Thr Gly Thr Lys Glu
            595                 600                 605

Glu Asn Pro His Cys Arg Arg Pro Leu Asp Leu Ala Ile Gln Arg His
        610                 615                 620

Pro His Phe Arg Ala Leu Phe Asp Leu Ser Thr Pro Val Leu Leu Ser
625                 630                 635                 640

Gly Ser Leu Phe Thr Gln Glu Leu Trp Asp Ser Leu Ser Gln His Lys
                645                 650                 655

Ala Pro Tyr Gly Trp Gln Gly Leu Ser His Gln Ala Ile Asn Ser Thr
                660                 665                 670

Leu Ser Leu Leu Asn Gly Ser Glu Ser Ser Gln Leu Phe Ala Thr Ser
            675                 680                 685

Arg Lys Pro Leu Ser Ser Cys Ile Arg Cys Ala Val Val Gly Asn Gly
690                 695                 700

Gly Ile Leu Asn Gly Ser Arg Gln Gly Leu Asn Ile Asp Ala His Asp
705                 710                 715                 720

Tyr Val Phe Arg Gln Thr Leu Lys Thr Glu Arg Gly Gly Arg Val Pro
                725                 730                 735

Ala Arg Arg Gly Pro Pro Gly Arg Met Ser Pro Glu Val Arg Arg Cys
                740                 745                 750

Gly Asp Gly Leu Asp Gly Asp Ser Gly Arg Gly Gln His Ser Tyr
            755                 760                 765

Pro Phe Pro Asp Gly Asn Val Ser Val Gln Gly His Pro Ala Ala Lys
            770                 775                 780

Ile Ile Lys Val Gln Pro Leu Thr Thr Pro Ala Leu Gly Leu Pro
785                 790                 795                 800

Pro Pro Ser Leu Ser Cys Leu Pro Asp Asp Leu Arg Tyr Ile Phe Ile
                805                 810                 815

Pro Ser Asp Ile Arg Asp Tyr Val Met Leu Arg Ser Ala Ile Leu Gly
                820                 825                 830

-continued

Val Pro Val Pro Glu Gly Pro Asp Lys Gly Asp Arg Ser Pro Ser His
            835                 840                 845

Ser Pro Ala Thr Ser Ala Ser Tyr Ile Gly Pro Val Arg Gly Ile Pro
    850                 855                 860

Ser Tyr Ile Ala Pro Tyr Val Pro Arg Phe Leu Lys Glu Pro Pro Phe
865                 870                 875                 880

Phe Gln Pro Pro Thr Val Leu Val Gly Gly Lys Pro His Val Val Pro
                885                 890                 895

Thr Val Leu Ala Ala Thr Phe Tyr Thr Pro Phe Phe Arg Tyr Tyr Ala
            900                 905                 910

Gln Pro Trp Pro Tyr Arg Pro His Arg Lys Arg Pro Ser Leu Ser Gly
            915                 920                 925

Ala Arg Ser Ser Arg Gly Leu Val Trp Val Glu Pro Asn Leu Ile Trp
            930                 935                 940

Asp Asn Pro Tyr Lys Gly Pro Gly Ser Arg Leu Asp Leu Glu Leu Gly
945                 950                 955                 960

Leu Tyr Pro Val Ser Ala Tyr Gly Phe Ile Thr Ser Asn Tyr Trp Lys
                965                 970                 975

Phe Ser Asp His Tyr Phe Glu Arg Val Lys Lys Pro Leu Ile Phe Tyr
            980                 985                 990

Val Asn His Asp Leu Ser Leu Glu Ala Ser Leu Trp Arg Asp Leu His
            995                 1000                1005

Lys Ala Gly Ile Leu Gln Leu Tyr Gln Arg
    1010                1015

<210> SEQ ID NO 67
<211> LENGTH: 523
<212> TYPE: PRT
<213> ORGANISM: Danio rerio
<220> FEATURE:
<223> OTHER INFORMATION: alpha-N-acetylgalactosaminide
      alpha-2,6-sialyltransferase I (ST6GalNAc-1)

<400> SEQUENCE: 67

Met Asp Tyr Phe Leu Trp Pro Ser Val Leu Phe Thr Leu Leu Ala Gly
1               5                   10                  15

Ile Val Ala Ala Phe Val Leu Val Lys Asn Lys Pro Ala His His Gln
            20                  25                  30

Ser Ser Val Val Val Glu Glu Glu Lys Lys Ala Asp Ala Gly Val Ser
        35                  40                  45

Ser Gln Glu Gln His Cys Glu His Trp Asp Glu Ser Cys Gln Leu Lys
    50                  55                  60

Thr Val Glu Lys Arg Leu Gln Thr Glu Asp Lys Thr Leu Glu Lys Ala
65                  70                  75                  80

Lys Asp Leu Asn Arg Asp Asp Leu Glu Glu Asp Ala Leu Val Gln Pro
                85                  90                  95

Thr Ala Arg Glu Glu Glu Pro Gly Ile Arg Ser Ala Leu Arg Glu Tyr
            100                 105                 110

Ala Phe Ser Pro Asp Ala Glu Ser Lys Pro Leu Lys Tyr Met Ala Gly
        115                 120                 125

Met Leu Arg Thr Cys Gln Leu Glu Lys Met Met Thr Lys Glu Glu Leu
    130                 135                 140

Glu Glu Glu Gln Ser Lys Thr Ile Ile Ser Ser Leu Ile Leu Ser
145                 150                 155                 160

Pro Leu Gly Asn Thr Asn Leu Phe Lys Thr Gln Lys His Leu Asn Val
                165                 170                 175

Glu Arg Lys Val Asn Ile Thr Pro Ile Pro Val Leu Tyr Lys Lys Asn
            180                 185                 190

Phe Thr Lys Leu Pro Val Trp Asp Phe Glu Asp Val Tyr Leu Arg Asp
        195                 200                 205

Ser Asn Ala Arg Lys Pro Thr Cys Pro Lys Ser Leu His Asn Thr Glu
210                 215                 220

Asp Pro Glu Phe Lys Glu Ser Val Leu Pro Asp Ile Gln Leu Trp Leu
225                 230                 235                 240

Tyr Lys Gly Gln Leu Asn Met Ser Glu Trp Asn Arg Leu Ala His Phe
                245                 250                 255

Asn Asn Pro Phe Gly Phe Met Glu Tyr Asn Tyr Asn Glu Ile Lys Arg
            260                 265                 270

Ala Val Asp Leu Ile Pro Lys Pro Arg Ser Ser Ile Leu Leu Pro Val
        275                 280                 285

Pro Lys Gly Ser Lys Asp Gly Cys Ile Arg Cys Ala Val Val Gly Ala
290                 295                 300

Gly Gly Ile Leu Asn Asn Ser Lys Met Gly Arg Glu Ile Asp Ser His
305                 310                 315                 320

Asp Tyr Val Phe Arg Val Asn Gly Ala Val Thr Lys Gly Tyr Glu Glu
                325                 330                 335

Asp Val Gly Asn Arg Thr Ser Val Tyr Val His Thr Ala Phe Ser Leu
            340                 345                 350

Tyr Ala Thr Ile Leu Thr Leu Lys Lys Tyr Gly Phe His Asn Ile Pro
        355                 360                 365

Gln Asp Glu Gly Ile Lys Tyr Val Met Ile Pro Glu Gly Leu Arg Asp
370                 375                 380

Phe Glu Trp Leu Gln Gly Leu Gln Gly Lys Ala Ala Asn Gly Ser
385                 390                 395                 400

Phe Lys Gly Val Arg Pro Leu Asn Phe Asn Gly His Phe Asn Glu
                405                 410                 415

Ser Arg Phe Asn Val Leu His Pro Asp Phe Leu Arg Tyr Ile Arg Asn
            420                 425                 430

Arg Phe Met Pro Ser Lys Gln Met Gln Gly Asn Tyr Trp Ala Met Tyr
        435                 440                 445

Arg Pro Thr Asn Gly Ala Phe Ala Leu Phe Leu Ala Ile His Thr Cys
450                 455                 460

Asp Met Val Asn Ala Tyr Gly Phe Ile Thr Glu Asp His His Lys Tyr
465                 470                 475                 480

Ser Asn Tyr Tyr Tyr Glu Lys Phe Lys Lys Thr Ser Val Ile Phe Tyr
                485                 490                 495

Ile Asn His Asp Tyr Gly Leu Glu Ile Lys Thr Trp Lys Lys Leu His
            500                 505                 510

Asp Ser Gly Ile Ile Arg Leu Phe Gln Arg His
        515                 520

<210> SEQ ID NO 68
<211> LENGTH: 427
<212> TYPE: PRT
<213> ORGANISM: Danio rerio
<220> FEATURE:
<223> OTHER INFORMATION: alpha-N-acetylgalactosaminide
    alpha-2,6-sialyltransferase I (ST6GalNAc-1)

<400> SEQUENCE: 68

Met Phe Leu Leu Arg Ile Phe Leu Val Thr Thr Phe Ile Ala Ser Leu
1               5                   10                  15

```
Pro Leu Phe Ile Phe Val Thr Phe Tyr Asn Gly Thr Ser Thr Leu Gln
            20                  25                  30

Ile Lys Trp Arg Gln Tyr Tyr Trp Leu Asn Gln Gly Gln Val Ala
        35                  40                  45

Gly Ser Leu Leu Thr Ile Val Glu Pro Glu Pro Thr Asn Ser Ser Ala
 50                  55                  60

Leu Thr Asp Ile Leu Ala Asn Thr Thr Thr Met Arg Leu Asp Pro Phe
 65                  70                  75                  80

Glu Thr Leu Ser Thr Pro Leu Pro Ile Met Asp Lys His Lys Phe Thr
                85                  90                  95

Ser Leu Pro His Trp Lys Phe Asp Asp Leu Tyr Arg Leu Asp Pro His
            100                 105                 110

Phe Lys Pro Ser Glu Cys Ala Thr Ser Leu Gln Asn Ser Ser Asn Pro
            115                 120                 125

Thr Phe Lys Lys Lys Phe Ile Pro Asn Ile Gln Leu Phe Leu Gln Ser
            130                 135                 140

Asp His Leu Asn Met Ser Glu Trp Asn Arg Leu Tyr His Phe Asn Asn
145                 150                 155                 160

Pro Phe Gly Tyr Met Gly Leu Asn Tyr Thr Ala Ile Lys Ala Ala Val
                165                 170                 175

Glu Thr Ile His Lys Pro Ala Ser Ser Gln Leu Leu Gln Val His Pro
            180                 185                 190

Gly Val Lys Asp Gly Cys Ile Arg Cys Ala Val Val Gly Ala Ser Gly
            195                 200                 205

Ile Leu Asn Gly Ser Lys Leu Gly Lys Glu Ile Asp Ser Ser Asp Tyr
        210                 215                 220

Val Phe Arg Met Asn Ala Ala Ile Ile Ala Gly His Glu Glu Asp Val
225                 230                 235                 240

Gly Lys Arg Thr Ser Val Tyr Val His Thr Ala His Ser Ile Ile Gln
            245                 250                 255

Ser Leu Met Ile His Lys Lys Arg Gly Phe Lys Gln Ile Pro Thr Asp
                260                 265                 270

Lys Asp Ile Lys Tyr Val Leu Ile Pro Glu Gly Pro Arg Asp Tyr Asn
            275                 280                 285

Phe Leu Glu Ser Leu Met Lys Asn Arg Lys Ile Pro Ser Gly Ala Tyr
        290                 295                 300

Arg Gly Arg Thr Pro Arg Lys Tyr Tyr Ser Gly His Phe Asn Glu Ser
305                 310                 315                 320

Ser Tyr Tyr Ile Leu His Pro Asp Phe Leu Arg Tyr Val Arg Asn Arg
                325                 330                 335

Phe Leu Arg Ala Lys Gln Leu Lys Thr Lys Arg Trp Trp Val Val Arg
            340                 345                 350

Pro Thr Asn Gly Ala Phe Thr Leu Leu Leu Ala Met His Thr Cys Asp
            355                 360                 365

Ile Val Arg Val Tyr Gly Phe Cys Thr Ala Asp Tyr Arg Lys Tyr Pro
            370                 375                 380

Ser Tyr Tyr Tyr Asp Thr Lys His Thr Lys Leu Val Phe Tyr Gly Asn
385                 390                 395                 400

His Asp Tyr Arg Leu Glu Met Leu Thr Trp Lys Lys Phe His Asp Asp
                405                 410                 415

Lys Leu Ile Trp Met Tyr Leu Gly Lys Ser Asn
            420                 425
```

-continued

```
<210> SEQ ID NO 69
<211> LENGTH: 388
<212> TYPE: PRT
<213> ORGANISM: Xenopus tropicalis
<220> FEATURE:
<223> OTHER INFORMATION: alpha-N-acetylgalactosaminide
      alpha-2,6-sialyltransferase I (ST6GalNAc-1)

<400> SEQUENCE: 69
```

| | | | | | | | | | | | | | | | |
|---|---|---|---|---|---|---|---|---|---|---|---|---|---|---|---|
| Met | Arg | Pro | Arg | Trp | Leu | Arg | Ala | Val | Gly | Ile | Thr | Ile | Gly | Ala | Leu |
| 1 | | | | 5 | | | | | 10 | | | | | 15 | |
| Thr | Val | Cys | Ser | Leu | Phe | Tyr | Gly | His | Tyr | Tyr | Ser | Ser | Leu | Val | Ser |
| | | | 20 | | | | | 25 | | | | | 30 | | |
| Val | Ala | Arg | Ser | Pro | Gln | Gly | Gly | Val | Gly | Tyr | Asp | Leu | Pro | Ser | Lys |
| | | 35 | | | | | 40 | | | | | 45 | | | |
| Gly | Leu | Glu | Trp | Ile | Pro | Ala | Val | Pro | His | Gly | Arg | Glu | Arg | Asn | Arg |
| | 50 | | | | | 55 | | | | | 60 | | | | |
| Glu | Leu | Ala | Glu | Thr | Leu | Arg | Val | Gln | Arg | Pro | Ser | Lys | Val | Pro | Gly |
| 65 | | | | | 70 | | | | | 75 | | | | | 80 |
| Thr | Cys | Pro | Thr | Ser | Leu | Gln | Leu | Arg | Val | Lys | Asn | Asp | Ser | Tyr | Phe |
| | | | | 85 | | | | | 90 | | | | | 95 | |
| Lys | Thr | Ile | Phe | Asn | Phe | Glu | Val | Pro | Leu | Leu | Leu | Trp | Asn | Ser | His |
| | | | 100 | | | | | 105 | | | | | 110 | | |
| Leu | Thr | Glu | Asn | Asn | Trp | Asp | Thr | Leu | Ser | Lys | Arg | Pro | Val | Pro | Tyr |
| | | | 115 | | | | | 120 | | | | | 125 | | |
| Gly | Trp | Lys | Asp | Leu | Pro | Arg | Glu | Asp | Val | Ala | Ser | Ala | Leu | Lys | Leu |
| | 130 | | | | | 135 | | | | | 140 | | | | |
| Leu | Asn | Asp | Ser | Ala | Asn | Lys | Ala | Met | Phe | Glu | Arg | Gln | Gly | Pro | Gln |
| 145 | | | | | 150 | | | | | 155 | | | | | 160 |
| Lys | Cys | Ile | Arg | Cys | Ala | Val | Val | Gly | Asn | Gly | Gly | Ile | Leu | Asn | Gly |
| | | | | 165 | | | | | 170 | | | | | 175 | |
| Ser | Lys | Lys | Gly | Lys | Glu | Ile | Asp | Gly | His | Asp | Tyr | Val | Phe | Arg | Leu |
| | | | 180 | | | | | 185 | | | | | 190 | | |
| Asn | Gly | Ala | Val | Ile | Lys | Gly | Phe | Glu | Lys | Asp | Val | Gly | Thr | Lys | Thr |
| | | | 195 | | | | | 200 | | | | | 205 | | |
| Ser | Phe | Tyr | Gly | Phe | Thr | Val | Asn | Thr | Met | Lys | Asn | Ser | Leu | Ile | Ser |
| | 210 | | | | | 215 | | | | | 220 | | | | |
| Tyr | Gln | Glu | His | Gly | Phe | Thr | Glu | Thr | Pro | Lys | Gly | Lys | Asp | Leu | His |
| 225 | | | | | 230 | | | | | 235 | | | | | 240 |
| Tyr | Ile | Phe | Ile | Pro | Ser | Asp | Leu | Arg | Asp | Tyr | Val | Met | Leu | Arg | Ser |
| | | | | 245 | | | | | 250 | | | | | 255 | |
| Gly | Ile | Leu | Gly | Val | Lys | Val | Pro | Ser | Gly | Tyr | Asp | Glu | Gly | Asp | Lys |
| | | | 260 | | | | | 265 | | | | | 270 | | |
| Pro | Ser | Glu | Tyr | Phe | Gly | Pro | Lys | Pro | Ser | Pro | Lys | Lys | Phe | Lys | Met |
| | | | 275 | | | | | 280 | | | | | 285 | | |
| Leu | His | Pro | Asp | Phe | Leu | Leu | Tyr | Thr | Arg | Asp | Arg | Phe | Leu | Lys | Ser |
| | 290 | | | | | 295 | | | | | 300 | | | | |
| Asp | Ile | Leu | Asn | Thr | Glu | Tyr | Ala | Ser | Leu | Tyr | Met | Pro | Ser | Thr | Gly |
| 305 | | | | | 310 | | | | | 315 | | | | | 320 |
| Gly | Leu | Met | Leu | Leu | Thr | Ala | Leu | His | Ser | Cys | Asp | Gln | Val | Ser | Ala |
| | | | | 325 | | | | | 330 | | | | | 335 | |
| Tyr | Gly | Phe | Ile | Thr | Pro | Asp | Tyr | Asn | Arg | Tyr | Ser | Asp | His | Tyr | Tyr |
| | | | 340 | | | | | 345 | | | | | 350 | | |
| Glu | Arg | Gln | Lys | Val | Pro | Leu | Glu | Val | Asp | Ala | Asn | His | Asp | Met | Leu |
| | | | 355 | | | | | 360 | | | | | 365 | | |
| Met | Glu | Met | Gln | Leu | Trp | Gly | Arg | Leu | His | Asp | Arg | Gly | Ile | Ile | Lys |

Leu Tyr Lys Arg
385

<210> SEQ ID NO 70
<211> LENGTH: 411
<212> TYPE: PRT
<213> ORGANISM: Takifugu rubripes
<220> FEATURE:
<223> OTHER INFORMATION: alpha-N-acetylgalactosaminide
    alpha-2,6-sialyltransferase I (ST6GalNAc-1)

<400> SEQUENCE: 70

Ser Ser Gly Ser Leu Glu Ser Met Lys Leu Ser Asp Gln Gln Ile Lys
1               5                   10                  15

Val Asp Ser Arg Thr Thr Ala Thr Pro Ala Tyr Val Lys Ser Ser Gly
            20                  25                  30

Pro Arg Gln His Thr Glu His Arg Ala Arg Glu Gln Glu Ile Gln Asn
        35                  40                  45

Val Ser Arg Ser Thr Pro Arg Ser Arg Gly Ala Asn Gln Thr Arg Ile
    50                  55                  60

Glu Val Pro Val Lys Lys Pro Gln Gln Pro Thr Gln Glu Thr Arg Thr
65                  70                  75                  80

Thr Asp Pro Pro Phe Ile Gly Asp Thr Tyr Met Ser Glu Glu Ile Pro
                85                  90                  95

Pro Gln Thr Thr Cys Pro Asp Gly Ile Arg Thr Arg Arg Thr Asn Thr
            100                 105                 110

Glu Phe Ser Gly Asn Phe Leu Asn Asn Val Pro Val Leu Gln Trp Ala
        115                 120                 125

Arg His Ala Thr His Glu Glu Tyr Gly Arg Leu Ser Gln His Arg Gly
    130                 135                 140

Ala His Gly Trp Gly Gly Val Asp Tyr Asn Thr Leu Val Asp Ala Leu
145                 150                 155                 160

Ser Val Leu Asn Ser Ser Ala Asn Trp Gln Met Leu Asp Asp Trp Lys
                165                 170                 175

Asp Arg Ser Asn Asn Ser Glu Cys Ile Arg Cys Ala Val Val Gly Asn
            180                 185                 190

Gly Gly Ile Leu Lys Asp Ser Lys Arg Gly Ala Glu Ile Asp Ser His
        195                 200                 205

His Tyr Val Phe Arg Thr Asn Gly Ala Val Ile Lys Gly Phe Glu Lys
    210                 215                 220

Asp Val Gly Ser Arg Thr Thr His Tyr Thr Phe Ser Ala Thr Thr Leu
225                 230                 235                 240

Met Asn Ser Ile Arg Ala Tyr Ala Gly Val Gly Phe Lys Ala Pro Pro
                245                 250                 255

Val Ser Lys Glu Thr Arg Tyr Ile Phe Leu Pro Glu Asn Asp Arg Asp
            260                 265                 270

Tyr Leu Leu Val Lys Ala Ala Thr His Thr Leu Val Glu Arg Gly
        275                 280                 285

Pro Gln Arg Asn Gln Lys Pro Ala Ser Phe Phe Gly Lys Asp Val Ser
    290                 295                 300

Ala Glu Lys Val Lys Met Tyr His Pro Asp Phe Val Arg Tyr Leu Arg
305                 310                 315                 320

Asn Arg Phe Leu Arg Ser Ala Thr Leu Lys Thr Lys Tyr Lys Asp Ile
                325                 330                 335

Tyr Arg Pro Ser Thr Gly Ala Val Met Leu Leu Val Ala Leu His Thr

```
                        340                 345                 350
Cys Asp Lys Val Ser Ala Tyr Gly Phe Met Thr Pro Asp Tyr Met Lys
            355                 360                 365

Tyr Ser Asp His Tyr Asp Lys Lys Gln Lys Ser Val Val Phe Phe
370                 375                 380

Lys Asn His Asp Leu Arg Met Glu Met Ala Leu Trp Gln Arg Leu His
385                 390                 395                 400

Gln Ala Gly Leu Ile Gln Leu Tyr Met Arg Gln
                405                 410

<210> SEQ ID NO 71
<211> LENGTH: 454
<212> TYPE: PRT
<213> ORGANISM: Strongylocentrotus purpuratus
<220> FEATURE:
<223> OTHER INFORMATION: alpha-N-acetylgalactosaminide
      alpha-2,6-sialyltransferase I (ST6GalNAc-1)

<400> SEQUENCE: 71

Met Arg Leu Trp Arg Lys Leu Thr Ser Cys Lys Thr Arg Ser Arg Phe
1               5                   10                  15

Val Leu Leu Ala Phe Trp Tyr Thr Met Ile Ala Leu Ser Val Ser Leu
            20                  25                  30

Leu Tyr Ser Leu Arg Gly Thr His His Ser Gln Asp Asp Ser Gly Thr
        35                  40                  45

Thr Ser Arg Arg Ser Arg Phe Tyr Asn Ser Leu Phe Pro Phe Ser Arg
50                  55                  60

Asn Asp Val Ala Asp Tyr Ala Thr Leu Thr Gln His Asp Val Ala Asp
65                  70                  75                  80

Asp Ile Val Ala Pro Pro His Val Gly Ala Thr Gly Glu Ile Gly Pro
                85                  90                  95

Glu Lys Asn Val Ala Ile Asp Asp Asn Lys Gln Ile Gln His Leu Ile
            100                 105                 110

Arg Arg Asn Ser Gly Gly Ile Ala Gly Gln Ser Gly Asn Leu Ile Gly
        115                 120                 125

Asp Met Leu Asn Asp Glu Glu Gln Arg Thr Phe Glu Val Val Glu Glu
    130                 135                 140

Glu Val Ala Glu Gln Glu Glu Ile Glu Val Val Asn Glu Phe Arg Asp
145                 150                 155                 160

Leu Asn Gly Lys Arg Pro Ser Gly Asp Asp Pro Arg Ala Pro Val Thr
                165                 170                 175

Ser Thr Ile Asp Val Thr Ser Ile His Phe Val Asn Ala Thr Val Lys
            180                 185                 190

Pro Thr Pro Pro Pro Glu Val Gln Gly Tyr Tyr Asn Val Gln Thr Lys
        195                 200                 205

Asp Lys Leu Arg Met Arg Cys Ser Gln Cys Ala Leu Val Ser Ser Ser
    210                 215                 220

Gly His Leu Val Asn Thr Ser Ala Gly Ala Glu Ile Asp Ser Tyr Pro
225                 230                 235                 240

Cys Val Leu Arg Met Asn Ser Ala Pro Val Arg Gly Tyr Glu Val Asp
                245                 250                 255

Val Gly Arg Arg Thr Thr Ile Arg Ile Met Gly His Val Asn Leu Lys
            260                 265                 270

Val Leu Asn Ala Ser Asn Glu Leu Gln Asp Glu Ile Leu Ile Asn Ser
        275                 280                 285

Thr Thr Arg Ala Glu Lys Ile Ile Val Pro Trp Leu Tyr Asn Val Lys
```

```
                290                 295                 300
Val Asn Gln Ala Thr Asp Met Tyr Tyr Lys Ser Ala Arg Asn Leu Ser
305                 310                 315                 320

Ser Leu Tyr Pro His Val Glu Phe Tyr Leu Leu Thr Pro Asp Lys Met
                325                 330                 335

Lys Ile Ala Glu Ser Leu Phe Gln Thr Glu Thr Gly Leu Thr Arg Gln
                340                 345                 350

Glu Thr Arg Thr Trp Leu Ser Thr Gly Trp Met Asn Met Leu Tyr Ala
                355                 360                 365

Val Asp Val Cys Asp Lys Val Asp Ile Phe Gly Leu Val Pro Glu Asn
370                 375                 380

Tyr Cys Leu Lys Asn Pro Asn Ser Ser Val Leu Tyr His Tyr Tyr Glu
385                 390                 395                 400

Ser Asp Gly Leu Lys Glu Cys Asp Tyr Tyr Thr Ile Ser Glu Glu Arg
                405                 410                 415

Leu Thr Ser Gly His Lys Phe Ile Thr Glu Lys Ala Val Phe Ala Arg
                420                 425                 430

Trp Ala Thr Lys Phe Asn Met Val Ile Pro Pro Thr Ser Leu Glu Pro
                435                 440                 445

His Gly Arg Cys Pro Tyr
    450

<210> SEQ ID NO 72
<211> LENGTH: 565
<212> TYPE: PRT
<213> ORGANISM: Artificial Sequence
<220> FEATURE:
<223> OTHER INFORMATION: Truncated human alpha-N-acetylgalactosaminide
      alpha-2,6-sialyltransferase I (ST6GalNAc-1
      delta 35)

<400> SEQUENCE: 72

Lys Glu Pro Gln Thr Lys Pro Ser Arg His Gln Arg Thr Glu Asn Ile
1               5                   10                  15

Lys Glu Arg Ser Leu Gln Ser Leu Ala Lys Pro Lys Ser Gln Ala Pro
                20                  25                  30

Thr Arg Ala Arg Arg Thr Thr Ile Tyr Ala Glu Pro Val Pro Glu Asn
                35                  40                  45

Asn Ala Leu Asn Thr Gln Thr Gln Pro Lys Ala His Thr Thr Gly Asp
            50                  55                  60

Arg Gly Lys Glu Ala Asn Gln Ala Pro Glu Glu Gln Asp Lys Val
65                  70                  75                  80

Pro His Thr Ala Gln Arg Ala Ala Trp Lys Ser Pro Glu Lys Glu Lys
                85                  90                  95

Thr Met Val Asn Thr Leu Ser Pro Arg Gly Gln Asp Ala Gly Met Ala
                100                 105                 110

Ser Gly Arg Thr Glu Ala Gln Ser Trp Lys Ser Gln Asp Thr Lys Thr
            115                 120                 125

Thr Gln Gly Asn Gly Gly Gln Thr Arg Lys Leu Thr Ala Ser Arg Thr
        130                 135                 140

Val Ser Glu Lys His Gln Gly Lys Ala Ala Thr Thr Ala Lys Thr Leu
145                 150                 155                 160

Ile Pro Lys Ser Gln His Arg Met Leu Ala Pro Thr Gly Ala Val Ser
                165                 170                 175

Thr Arg Thr Arg Gln Lys Gly Val Thr Thr Ala Val Ile Pro Pro Lys
                180                 185                 190
```

```
Glu Lys Lys Pro Gln Ala Thr Pro Pro Ala Pro Phe Gln Ser Pro
    195                 200                 205
Thr Thr Gln Arg Asn Gln Arg Leu Lys Ala Ala Asn Phe Lys Ser Glu
    210                 215                 220
Pro Arg Trp Asp Phe Glu Glu Lys Tyr Ser Phe Glu Ile Gly Gly Leu
225                 230                 235                 240
Gln Thr Thr Cys Pro Asp Ser Val Lys Ile Lys Ala Ser Lys Ser Leu
                245                 250                 255
Trp Leu Gln Lys Leu Phe Leu Pro Asn Leu Thr Leu Phe Leu Asp Ser
            260                 265                 270
Arg His Phe Asn Gln Ser Glu Trp Asp Arg Leu Glu His Phe Ala Pro
        275                 280                 285
Pro Phe Gly Phe Met Glu Leu Asn Tyr Ser Leu Val Gln Lys Val Val
    290                 295                 300
Thr Arg Phe Pro Pro Val Pro Gln Gln Leu Leu Leu Ala Ser Leu
305                 310                 315                 320
Pro Ala Gly Ser Leu Arg Cys Ile Thr Cys Ala Val Val Gly Asn Gly
                325                 330                 335
Gly Ile Leu Asn Asn Ser His Met Gly Gln Glu Ile Asp Ser His Asp
            340                 345                 350
Tyr Val Phe Arg Leu Ser Gly Ala Leu Ile Lys Gly Tyr Glu Gln Asp
        355                 360                 365
Val Gly Thr Arg Thr Ser Phe Tyr Gly Phe Thr Ala Phe Ser Leu Thr
    370                 375                 380
Gln Ser Leu Leu Ile Leu Gly Asn Arg Gly Phe Lys Asn Val Pro Leu
385                 390                 395                 400
Gly Lys Asp Val Arg Tyr Leu His Phe Leu Glu Gly Thr Arg Asp Tyr
                405                 410                 415
Glu Trp Leu Glu Ala Leu Leu Met Asn Gln Thr Val Met Ser Lys Asn
            420                 425                 430
Leu Phe Trp Phe Arg His Arg Pro Gln Glu Ala Phe Arg Glu Ala Leu
        435                 440                 445
His Met Asp Arg Tyr Leu Leu Leu His Pro Asp Phe Leu Arg Tyr Met
    450                 455                 460
Lys Asn Arg Phe Leu Arg Ser Lys Thr Leu Asp Gly Ala His Trp Arg
465                 470                 475                 480
Ile Tyr Arg Pro Thr Thr Gly Ala Leu Leu Leu Leu Thr Ala Leu Gln
                485                 490                 495
Leu Cys Asp Gln Val Ser Ala Tyr Gly Phe Ile Thr Glu Gly His Glu
            500                 505                 510
Arg Phe Ser Asp His Tyr Tyr Asp Thr Ser Trp Lys Arg Leu Ile Phe
        515                 520                 525
Tyr Ile Asn His Asp Phe Lys Leu Glu Arg Glu Val Trp Lys Arg Leu
    530                 535                 540
His Asp Glu Gly Ile Ile Arg Leu Tyr Gln Arg Pro Gly Pro Gly Thr
545                 550                 555                 560
Ala Lys Ala Lys Asn
                565
```

<210> SEQ ID NO 73
<211> LENGTH: 958
<212> TYPE: PRT
<213> ORGANISM: Artificial Sequence
<220> FEATURE:
<223> OTHER INFORMATION: maltose binding protein-tagged truncated human
      alpha-N-acetylgalactosaminide alpha-2,6-sialyltransferase I (MBP-ST6GalNAc-1 delta 35)

<400> SEQUENCE: 73

```
Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
370                 375                 380

Glu Gly Arg Ile Ser Glu Phe Gly Ser Lys Glu Pro Gln Thr Lys Pro
385                 390                 395                 400
```

-continued

Ser Arg His Gln Arg Thr Glu Asn Ile Lys Glu Arg Ser Leu Gln Ser
            405                 410                 415

Leu Ala Lys Pro Lys Ser Gln Ala Pro Thr Arg Ala Arg Thr Thr
        420                 425                 430

Ile Tyr Ala Glu Pro Val Pro Glu Asn Asn Ala Leu Asn Thr Gln Thr
        435                 440                 445

Gln Pro Lys Ala His Thr Thr Gly Asp Arg Gly Lys Glu Ala Asn Gln
    450                 455                 460

Ala Pro Pro Glu Glu Gln Asp Lys Val Pro His Thr Ala Gln Arg Ala
465                 470                 475                 480

Ala Trp Lys Ser Pro Glu Lys Glu Lys Thr Met Val Asn Thr Leu Ser
                485                 490                 495

Pro Arg Gly Gln Asp Ala Gly Met Ala Ser Gly Arg Thr Glu Ala Gln
            500                 505                 510

Ser Trp Lys Ser Gln Asp Thr Lys Thr Thr Gln Gly Asn Gly Gly Gln
        515                 520                 525

Thr Arg Lys Leu Thr Ala Ser Arg Thr Val Ser Glu Lys His Gln Gly
    530                 535                 540

Lys Ala Thr Thr Ala Lys Thr Leu Ile Pro Lys Ser Gln His Arg
545                 550                 555                 560

Met Leu Ala Pro Thr Gly Ala Val Ser Thr Arg Thr Arg Gln Lys Gly
                565                 570                 575

Val Thr Thr Ala Val Ile Pro Pro Lys Glu Lys Pro Gln Ala Thr
            580                 585                 590

Pro Pro Pro Ala Pro Phe Gln Ser Pro Thr Thr Gln Arg Asn Gln Arg
        595                 600                 605

Leu Lys Ala Ala Asn Phe Lys Ser Glu Pro Arg Trp Asp Phe Glu Glu
    610                 615                 620

Lys Tyr Ser Phe Glu Ile Gly Gly Leu Gln Thr Thr Cys Pro Asp Ser
625                 630                 635                 640

Val Lys Ile Lys Ala Ser Lys Ser Leu Trp Leu Gln Lys Leu Phe Leu
                645                 650                 655

Pro Asn Leu Thr Leu Phe Leu Asp Ser Arg His Phe Asn Gln Ser Glu
            660                 665                 670

Trp Asp Arg Leu Glu His Phe Ala Pro Pro Phe Gly Phe Met Glu Leu
        675                 680                 685

Asn Tyr Ser Leu Val Gln Lys Val Val Thr Arg Phe Pro Pro Val Pro
    690                 695                 700

Gln Gln Gln Leu Leu Leu Ala Ser Leu Pro Ala Gly Ser Leu Arg Cys
705                 710                 715                 720

Ile Thr Cys Ala Val Val Gly Asn Gly Gly Ile Leu Asn Asn Ser His
                725                 730                 735

Met Gly Gln Glu Ile Asp Ser His Asp Tyr Val Phe Arg Leu Ser Gly
            740                 745                 750

Ala Leu Ile Lys Gly Tyr Glu Gln Asp Val Gly Thr Arg Thr Ser Phe
        755                 760                 765

Tyr Gly Phe Thr Ala Phe Ser Leu Thr Gln Ser Leu Leu Ile Leu Gly
    770                 775                 780

Asn Arg Gly Phe Lys Asn Val Pro Leu Gly Lys Asp Val Arg Tyr Leu
785                 790                 795                 800

His Phe Leu Glu Gly Thr Arg Asp Tyr Glu Trp Leu Glu Ala Leu Leu
                805                 810                 815

Met Asn Gln Thr Val Met Ser Lys Asn Leu Phe Trp Phe Arg His Arg
            820                 825                 830

```
Pro Gln Glu Ala Phe Arg Glu Ala Leu His Met Asp Arg Tyr Leu Leu
            835                 840                 845

Leu His Pro Asp Phe Leu Arg Tyr Met Lys Asn Arg Phe Leu Arg Ser
        850                 855                 860

Lys Thr Leu Asp Gly Ala His Trp Arg Ile Tyr Arg Pro Thr Thr Gly
865                 870                 875                 880

Ala Leu Leu Leu Leu Thr Ala Leu Gln Leu Cys Asp Gln Val Ser Ala
                885                 890                 895

Tyr Gly Phe Ile Thr Glu Gly His Glu Arg Phe Ser Asp His Tyr Tyr
                900                 905                 910

Asp Thr Ser Trp Lys Arg Leu Ile Phe Tyr Ile Asn His Asp Phe Lys
            915                 920                 925

Leu Glu Arg Glu Val Trp Lys Arg Leu His Asp Glu Gly Ile Ile Arg
        930                 935                 940

Leu Tyr Gln Arg Pro Gly Pro Gly Thr Ala Lys Ala Lys Asn
945                 950                 955
```

<210> SEQ ID NO 74
<211> LENGTH: 335
<212> TYPE: PRT
<213> ORGANISM: Artificial Sequence
<220> FEATURE:
<223> OTHER INFORMATION: Truncated chicken
    N-acetylgalactosamine-alpha2,6-sialyltransferase I
    (ST6GalNAc-1 delta 231)

<400> SEQUENCE: 74

```
Lys Thr Glu Pro Gln Trp Asp Phe Asp Asp Glu Tyr Ile Leu Asp Ser
1               5                   10                  15

Ser Ser Pro Val Ser Thr Cys Ser Glu Ser Val Arg Ala Lys Ala Ala
            20                  25                  30

Lys Ser Asp Trp Leu Arg Asp Leu Phe Leu Pro Asn Ile Thr Leu Phe
        35                  40                  45

Ile Asp Lys Ser Tyr Phe Asn Val Ser Glu Trp Asp Arg Leu Glu His
    50                  55                  60

Phe Ala Pro Pro Tyr Gly Phe Met Glu Leu Asn Tyr Ser Leu Val Glu
65                  70                  75                  80

Glu Val Met Ser Arg Leu Pro Pro Asn Pro His Gln Gln Leu Leu Leu
                85                  90                  95

Ala Asn Ser Ser Ser Asn Val Ser Thr Cys Ile Ser Cys Ala Val Val
            100                 105                 110

Gly Asn Gly Gly Ile Leu Asn Asn Ser Gly Met Gly Gln Glu Ile Asp
        115                 120                 125

Ser His Asp Tyr Val Phe Arg Val Ser Gly Ala Val Ile Lys Gly Tyr
    130                 135                 140

Glu Lys Asp Val Gly Thr Lys Thr Ser Phe Tyr Gly Phe Thr Ala Tyr
145                 150                 155                 160

Ser Leu Val Ser Ser Leu Gln Asn Leu Gly His Lys Gly Phe Lys Lys
                165                 170                 175

Ile Pro Gln Gly Lys His Ile Arg Tyr Ile His Phe Leu Glu Ala Val
            180                 185                 190

Arg Asp Tyr Glu Trp Leu Lys Ala Leu Leu Asp Lys Asp Ile Arg
        195                 200                 205

Lys Gly Phe Leu Asn Tyr Tyr Gly Arg Arg Pro Arg Glu Arg Phe Asp
    210                 215                 220

Glu Asp Phe Thr Met Asn Lys Tyr Leu Val Ala His Pro Asp Phe Leu
```

```
                225                 230                 235                 240
Arg Tyr Leu Lys Asn Arg Phe Leu Lys Ser Lys Asn Leu Gln Lys Pro
                    245                 250                 255

Tyr Trp Arg Leu Tyr Arg Pro Thr Thr Gly Ala Leu Leu Leu Leu Thr
            260                 265                 270

Ala Leu His Leu Cys Asp Arg Val Ser Ala Tyr Gly Tyr Ile Thr Glu
                275                 280                 285

Gly His Gln Lys Tyr Ser Asp His Tyr Tyr Asp Lys Glu Trp Lys Arg
            290                 295                 300

Leu Val Phe Tyr Val Asn His Asp Phe Asn Leu Glu Lys Gln Val Trp
305                 310                 315                 320

Lys Arg Leu His Asp Glu Asn Ile Met Lys Leu Tyr Gln Arg Ser
                325                 330                 335

<210> SEQ ID NO 75
<211> LENGTH: 375
<212> TYPE: PRT
<213> ORGANISM: Homo sapiens
<220> FEATURE:
<223> OTHER INFORMATION: Gal beta-1,3-GalNAc alpha-2,3-sialyltransferase
      III (ST3Gal3)

<400> SEQUENCE: 75

Met Gly Leu Leu Val Phe Val Arg Asn Leu Leu Leu Ala Leu Cys Leu
1               5                   10                  15

Phe Leu Val Leu Gly Phe Leu Tyr Tyr Ser Ala Trp Lys Leu His Leu
            20                  25                  30

Leu Gln Trp Glu Glu Asp Ser Asn Ser Val Val Leu Ser Phe Asp Ser
        35                  40                  45

Ala Gly Gln Thr Leu Gly Ser Glu Tyr Asp Arg Leu Gly Phe Leu Leu
    50                  55                  60

Asn Leu Asp Ser Lys Leu Pro Ala Glu Leu Ala Thr Lys Tyr Ala Asn
65                  70                  75                  80

Phe Ser Glu Gly Ala Cys Lys Pro Gly Tyr Ala Ser Ala Leu Met Thr
                85                  90                  95

Ala Ile Phe Pro Arg Phe Ser Lys Pro Ala Pro Met Phe Leu Asp Asp
            100                 105                 110

Ser Phe Arg Lys Trp Ala Arg Ile Arg Glu Phe Val Pro Pro Phe Gly
        115                 120                 125

Ile Lys Gly Gln Asp Asn Leu Ile Lys Ala Ile Leu Ser Val Thr Lys
    130                 135                 140

Glu Tyr Arg Leu Thr Pro Ala Leu Asp Ser Leu Arg Cys Arg Arg Cys
145                 150                 155                 160

Ile Ile Val Gly Asn Gly Gly Val Leu Ala Asn Lys Ser Leu Gly Ser
                165                 170                 175

Arg Ile Asp Asp Tyr Asp Ile Val Val Arg Leu Asn Ser Ala Pro Val
            180                 185                 190

Lys Gly Phe Glu Lys Asp Val Gly Ser Lys Thr Thr Leu Arg Ile Thr
        195                 200                 205

Tyr Pro Glu Gly Ala Met Gln Arg Pro Glu Gln Tyr Glu Arg Asp Ser
    210                 215                 220

Leu Phe Val Leu Ala Gly Phe Lys Trp Gln Asp Phe Lys Trp Leu Lys
225                 230                 235                 240

Tyr Ile Val Tyr Lys Glu Arg Val Ser Ala Ser Asp Gly Phe Trp Lys
                245                 250                 255

Ser Val Ala Thr Arg Val Pro Lys Glu Pro Pro Glu Ile Arg Ile Leu
```

```
                         260                 265                 270
Asn Pro Tyr Phe Ile Gln Glu Ala Ala Phe Thr Leu Ile Gly Leu Pro
                275                 280                 285

Phe Asn Asn Gly Leu Met Gly Arg Gly Asn Ile Pro Thr Leu Gly Ser
            290                 295                 300

Val Ala Val Thr Met Ala Leu His Gly Cys Asp Glu Val Ala Val Ala
305                 310                 315                 320

Gly Phe Gly Tyr Asp Met Ser Thr Pro Asn Ala Pro Leu His Tyr Tyr
                325                 330                 335

Glu Thr Val Arg Met Ala Ala Ile Lys Glu Ser Trp Thr His Asn Ile
            340                 345                 350

Gln Arg Glu Lys Glu Phe Leu Arg Lys Leu Val Lys Ala Arg Val Ile
        355                 360                 365

Thr Asp Leu Ser Ser Gly Ile
        370                 375

<210> SEQ ID NO 76
<211> LENGTH: 374
<212> TYPE: PRT
<213> ORGANISM: Rattus norvegicus
<220> FEATURE:
<223> OTHER INFORMATION: Gal beta-1,3-GalNAc alpha-2,3-sialyltransferase
      III (ST3Gal3)

<400> SEQUENCE: 76

Met Gly Leu Leu Val Phe Val Arg Asn Leu Leu Leu Ala Leu Cys Leu
1               5                   10                  15

Phe Leu Val Leu Gly Phe Leu Tyr Tyr Ser Ala Trp Lys Leu His Leu
            20                  25                  30

Leu Gln Trp Glu Asp Ser Asn Ser Leu Ile Leu Ser Leu Asp Ser Ala
        35                  40                  45

Gly Gln Thr Leu Gly Thr Glu Tyr Asp Arg Leu Gly Phe Leu Leu Lys
    50                  55                  60

Leu Asp Ser Lys Leu Pro Ala Glu Leu Ala Thr Lys Tyr Ala Asn Phe
65                  70                  75                  80

Ser Glu Gly Ala Cys Lys Pro Gly Tyr Ala Ser Ala Met Met Thr Ala
                85                  90                  95

Ile Phe Pro Arg Phe Ser Lys Pro Ala Pro Met Phe Leu Asp Asp Ser
            100                 105                 110

Phe Arg Lys Trp Ala Arg Ile Arg Glu Phe Val Pro Pro Phe Gly Ile
        115                 120                 125

Lys Gly Gln Asp Asn Leu Ile Lys Ala Ile Leu Ser Val Thr Lys Glu
    130                 135                 140

Tyr Arg Leu Thr Pro Ala Leu Asp Ser Leu His Cys Arg Arg Cys Ile
145                 150                 155                 160

Ile Val Gly Asn Gly Gly Val Leu Ala Asn Lys Ser Leu Gly Ser Arg
                165                 170                 175

Ile Asp Asp Tyr Asp Ile Val Ile Arg Leu Asn Ser Ala Pro Val Lys
            180                 185                 190

Gly Phe Glu Lys Asp Val Gly Ser Lys Thr Thr Leu Arg Ile Thr Tyr
        195                 200                 205

Pro Glu Gly Ala Met Gln Arg Pro Glu Gln Tyr Glu Arg Asp Ser Leu
    210                 215                 220

Phe Val Leu Ala Gly Phe Lys Trp Gln Asp Phe Lys Trp Leu Lys Tyr
225                 230                 235                 240

Ile Val Tyr Lys Glu Arg Val Ser Ala Ser Asp Gly Phe Trp Lys Ser
```

```
                    245                 250                 255
Val Ala Thr Arg Val Pro Lys Glu Pro Pro Glu Ile Arg Ile Leu Asn
                260                 265                 270

Pro Tyr Phe Ile Gln Glu Ala Ala Phe Thr Leu Ile Gly Leu Pro Phe
            275                 280                 285

Asn Asn Gly Leu Met Gly Arg Gly Asn Ile Pro Thr Leu Gly Ser Val
        290                 295                 300

Ala Val Thr Met Ala Leu Asp Gly Cys Asp Glu Val Ala Val Ala Gly
    305                 310                 315                 320

Phe Gly Tyr Asp Met Asn Thr Pro Asn Ala Pro Leu His Tyr Tyr Glu
                325                 330                 335

Thr Val Arg Met Ala Ala Ile Lys Glu Ser Trp Thr His Asn Ile Gln
                340                 345                 350

Arg Glu Lys Glu Phe Leu Arg Lys Leu Val Lys Ala Arg Val Ile Thr
            355                 360                 365

Asp Leu Ser Ser Gly Ile
            370

<210> SEQ ID NO 77
<211> LENGTH: 302
<212> TYPE: PRT
<213> ORGANISM: Artificial Sequence
<220> FEATURE:
<223> OTHER INFORMATION: Truncated rat Gal beta-1,3-GalNAc
      alpha-2,3-sialyltransferase III (ST3Gal3 delta 72)
      V162I D311H mutant

<400> SEQUENCE: 77

Leu Ala Thr Lys Tyr Ala Asn Phe Ser Glu Gly Ala Cys Lys Pro Gly
1               5                   10                  15

Tyr Ala Ser Ala Met Met Thr Ala Ile Phe Pro Arg Phe Ser Lys Pro
            20                  25                  30

Ala Pro Met Phe Leu Asp Asp Ser Phe Arg Lys Trp Ala Arg Ile Arg
        35                  40                  45

Gln Phe Val Pro Pro Phe Gly Ile Lys Gly Gln Asp Asn Leu Ile Lys
    50                  55                  60

Ala Ile Leu Ser Val Thr Lys Glu Tyr Arg Leu Thr Pro Ala Leu Asp
65                  70                  75                  80

Ser Leu His Cys Arg Arg Cys Ile Ile Ile Gly Asn Gly Gly Val Leu
                85                  90                  95

Ala Asn Lys Ser Leu Gly Ser Arg Ile Asp Asp Tyr Asp Ile Val Ile
            100                 105                 110

Arg Leu Asn Ser Ala Pro Val Lys Gly Phe Glu Lys Asp Val Gly Ser
        115                 120                 125

Lys Thr Thr Leu Arg Ile Thr Tyr Pro Glu Gly Ala Met Gln Arg Pro
    130                 135                 140

Glu Gln Tyr Glu Arg Asp Ser Leu Phe Val Leu Ala Gly Phe Lys Trp
145                 150                 155                 160

Gln Asp Phe Lys Trp Leu Lys Tyr Ile Val Tyr Lys Glu Arg Val Ser
                165                 170                 175

Ala Ser Asp Gly Phe Trp Lys Ser Val Ala Thr Arg Val Pro Lys Glu
            180                 185                 190

Pro Pro Glu Ile Arg Ile Leu Asn Pro Tyr Phe Ile Gln Glu Ala Ala
        195                 200                 205

Phe Thr Leu Ile Gly Leu Pro Phe Asn Asn Gly Leu Met Gly Arg Gly
    210                 215                 220
```

```
Asn Ile Pro Thr Leu Gly Ser Val Ala Val Thr Met Ala Leu His Gly
225                 230                 235                 240

Cys Asp Glu Val Ala Val Ala Gly Phe Gly Tyr Asp Met Asn Thr Pro
            245                 250                 255

Asn Ala Pro Leu His Tyr Tyr Glu Thr Val Arg Met Ala Ala Ile Lys
        260                 265                 270

Glu Ser Trp Thr His Asn Ile Gln Arg Glu Lys Glu Phe Leu Arg Lys
    275                 280                 285

Leu Val Lys Ala Arg Val Ile Thr Asp Leu Ser Ser Gly Ile
290                 295                 300
```

<210> SEQ ID NO 78
<211> LENGTH: 695
<212> TYPE: PRT
<213> ORGANISM: Artificial Sequence
<220> FEATURE:
<223> OTHER INFORMATION: MBP-tagged truncated rat Gal beta-1,3-GalNAc
    alpha-2,3-sialyltransferase III (ST3Gal3 delta 72)
    V162I D311H mutant

<400> SEQUENCE: 78

```
Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285
```

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
                355                 360                 365

Ser Ser Ser Asn Asn Asn Asn Asn Asn Asn Asn Asn Leu Gly Ile
        370                 375                 380

Glu Gly Arg Ile Ser Glu Phe Gly Ser Leu Ala Thr Lys Tyr Ala Asn
385                 390                 395                 400

Phe Ser Glu Gly Ala Cys Lys Pro Gly Tyr Ala Ser Ala Met Met Thr
                405                 410                 415

Ala Ile Phe Pro Arg Phe Ser Lys Pro Ala Pro Met Phe Leu Asp Asp
                420                 425                 430

Ser Phe Arg Lys Trp Ala Arg Ile Arg Glu Phe Val Pro Pro Phe Gly
                435                 440                 445

Ile Lys Gly Gln Asp Asn Leu Ile Lys Ala Ile Leu Ser Val Thr Lys
                450                 455                 460

Glu Tyr Arg Leu Thr Pro Ala Leu Asp Ser Leu His Cys Arg Arg Cys
465                 470                 475                 480

Ile Ile Ile Gly Asn Gly Gly Val Leu Ala Asn Lys Ser Leu Gly Ser
                485                 490                 495

Arg Ile Asp Asp Tyr Asp Ile Val Ile Arg Leu Asn Ser Ala Pro Val
                500                 505                 510

Lys Gly Phe Glu Lys Asp Val Gly Ser Lys Thr Thr Leu Arg Ile Thr
                515                 520                 525

Tyr Pro Glu Gly Ala Met Gln Arg Pro Glu Gln Tyr Glu Arg Asp Ser
                530                 535                 540

Leu Phe Val Leu Ala Gly Phe Lys Trp Gln Asp Phe Lys Trp Leu Lys
545                 550                 555                 560

Tyr Ile Val Tyr Lys Glu Arg Val Ser Ala Ser Asp Gly Phe Trp Lys
                565                 570                 575

Ser Val Ala Thr Arg Val Pro Lys Glu Pro Glu Ile Arg Ile Leu
                580                 585                 590

Asn Pro Tyr Phe Ile Gln Glu Ala Ala Phe Thr Leu Ile Gly Leu Pro
                595                 600                 605

Phe Asn Asn Gly Leu Met Gly Arg Gly Asn Ile Pro Thr Leu Gly Ser
                610                 615                 620

Val Ala Val Thr Met Ala Leu His Gly Cys Asp Glu Val Ala Val Ala
625                 630                 635                 640

Gly Phe Gly Tyr Asp Met Asn Thr Pro Asn Ala Pro Leu His Tyr Tyr
                645                 650                 655

Glu Thr Val Arg Met Ala Ala Ile Lys Glu Ser Trp Thr His Asn Ile
                660                 665                 670

Gln Arg Glu Lys Glu Phe Leu Arg Lys Leu Val Lys Ala Arg Val Ile
                675                 680                 685

Thr Asp Leu Ser Ser Gly Ile
                690                 695

```
<210> SEQ ID NO 79
<211> LENGTH: 348
<212> TYPE: PRT
<213> ORGANISM: Rattus norvegicus
<220> FEATURE:
<223> OTHER INFORMATION: GalE

<400> SEQUENCE: 79
```

| | | | | | | | | | | | | | | | |
|---|---|---|---|---|---|---|---|---|---|---|---|---|---|---|---|
|Met|Glu|Glu|Lys|Val|Leu|Val|Thr|Gly|Gly|Ala|Gly|Tyr|Ile|Gly|Ser|
|1| | | |5| | | | |10| | | | |15| |
|His|Thr|Val|Leu|Glu|Leu|Leu|Glu|Ala|Gly|Tyr|Ser|Pro|Val|Val|Ile|
| | | |20| | | | |25| | | | |30| | |
|Asp|Asn|Phe|His|Asn|Ser|Ile|Arg|Gly|Glu|Asp|Ser|Met|Pro|Glu|Ser|
| | |35| | | | |40| | | | |45| | | |
|Leu|Arg|Arg|Val|Gln|Glu|Leu|Thr|Gly|Arg|Ser|Val|Glu|Phe|Glu|Glu|
| |50| | | | |55| | | | |60| | | | |
|Met|Asp|Ile|Leu|Asp|Gln|Ala|Ala|Leu|Gln|His|Leu|Phe|Lys|Lys|His|
|65| | | | |70| | | | |75| | | | |80|
|Asn|Phe|Lys|Ala|Val|Ile|His|Phe|Ala|Gly|Leu|Lys|Ala|Val|Gly|Glu|
| | | | |85| | | | |90| | | | |95| |
|Ser|Val|Gln|Lys|Pro|Leu|Asp|Tyr|Tyr|Arg|Val|Asn|Leu|Thr|Gly|Thr|
| | | |100| | | | |105| | | | |110| | |
|Ile|Gln|Leu|Leu|Glu|Ile|Met|Arg|Ala|His|Gly|Val|Lys|Ser|Leu|Val|
| | |115| | | | |120| | | | |125| | | |
|Phe|Ser|Ser|Ser|Ala|Thr|Val|Tyr|Gly|Asn|Pro|Gln|Tyr|Leu|Pro|Leu|
| |130| | | | |135| | | | |140| | | | |
|Asp|Glu|Ala|His|Pro|Thr|Gly|Gly|Cys|Thr|Asn|Pro|Tyr|Gly|Lys|Ser|
|145| | | | |150| | | | |155| | | | |160|
|Lys|Phe|Phe|Ile|Glu|Glu|Met|Ile|Gln|Asp|Leu|Cys|Arg|Ala|Asp|Thr|
| | | | |165| | | | |170| | | | |175| |
|Ala|Trp|Asn|Ala|Val|Leu|Leu|Arg|Tyr|Phe|Asn|Pro|Ile|Gly|Ala|His|
| | | |180| | | | |185| | | | |190| | |
|Ala|Ser|Gly|Arg|Ile|Gly|Glu|Asp|Pro|Gln|Gly|Ile|Pro|Asn|Asn|Leu|
| | |195| | | | |200| | | | |205| | | |
|Met|Pro|Tyr|Val|Ser|Gln|Val|Ala|Ile|Gly|Arg|Arg|Glu|Ala|Leu|Asn|
| |210| | | | |215| | | | |220| | | | |
|Val|Phe|Gly|Asp|Asp|Tyr|Ala|Thr|Glu|Asp|Gly|Thr|Gly|Val|Arg|Asp|
|225| | | | |230| | | | |235| | | | |240|
|Tyr|Ile|His|Val|Val|Asp|Leu|Ala|Lys|Gly|His|Ile|Ala|Ala|Leu|Lys|
| | | | |245| | | | |250| | | | |255| |
|Lys|Leu|Lys|Glu|Gln|Cys|Gly|Cys|Arg|Ile|Tyr|Asn|Leu|Gly|Thr|Gly|
| | | |260| | | | |265| | | | |270| | |
|Thr|Gly|Tyr|Ser|Val|Leu|Gln|Met|Val|Gln|Ala|Met|Glu|Lys|Ala|Ser|
| | |275| | | | |280| | | | |285| | | |
|Gly|Lys|Lys|Ile|Pro|Tyr|Lys|Val|Val|Ala|Arg|Arg|Glu|Gly|Asp|Val|
| |290| | | | |295| | | | |300| | | | |
|Ala|Ala|Cys|Tyr|Ala|Asn|Pro|Ser|Leu|Ala|His|Glu|Glu|Leu|Gly|Trp|
|305| | | | |310| | | | |315| | | | |320|
|Thr|Ala|Ala|Leu|Gly|Leu|Asp|Arg|Met|Cys|Glu|Asp|Leu|Trp|Arg|Trp|
| | | | |325| | | | |330| | | | |335| |
|Gln|Lys|Gln|Asn|Pro|Ser|Gly|Phe|Gly|Ala|His|Gly| | | | |
| | | |340| | | | |345| | | | | | | |

```
<210> SEQ ID NO 80
<211> LENGTH: 328
<212> TYPE: PRT
<213> ORGANISM: Campylobacter jejuni
```

<220> FEATURE:
<223> OTHER INFORMATION: GNE

<400> SEQUENCE: 80

Met Lys Ile Leu Ile Ser Gly Gly Ala Gly Tyr Ile Gly Ser His Thr
1               5                   10                  15

Leu Arg Gln Phe Leu Lys Thr Asp His Glu Ile Cys Val Leu Asp Asn
            20                  25                  30

Leu Ser Lys Gly Ser Lys Ile Ala Ile Glu Asp Leu Gln Lys Thr Arg
        35                  40                  45

Ala Phe Lys Phe Phe Glu Gln Asp Leu Ser Asp Phe Gln Gly Val Lys
    50                  55                  60

Ala Leu Phe Glu Arg Glu Lys Phe Asp Ala Ile Val His Phe Ala Ala
65              70                  75                  80

Ser Ile Glu Val Phe Glu Ser Met Gln Asn Pro Leu Lys Tyr Tyr Met
                85                  90                  95

Asn Asn Thr Val Asn Thr Thr Asn Leu Ile Glu Thr Cys Leu Gln Thr
            100                 105                 110

Gly Val Asn Lys Phe Ile Phe Ser Ser Thr Ala Ala Thr Tyr Gly Glu
        115                 120                 125

Pro Gln Thr Pro Val Val Ser Glu Thr Ser Pro Leu Ala Pro Ile Asn
    130                 135                 140

Pro Tyr Gly Arg Ser Lys Leu Met Ser Glu Glu Val Leu Arg Asp Ala
145                 150                 155                 160

Ser Met Ala Asn Pro Glu Phe Lys His Cys Ile Leu Arg Tyr Phe Asn
                165                 170                 175

Val Ala Gly Ala Cys Met Asp Tyr Thr Leu Gly Gln Arg Tyr Pro Lys
            180                 185                 190

Ala Thr Leu Leu Ile Lys Val Ala Ala Glu Cys Ala Ala Gly Lys Arg
        195                 200                 205

Asp Lys Leu Phe Ile Phe Gly Asp Asp Tyr Asp Thr Lys Asp Gly Thr
    210                 215                 220

Cys Ile Arg Asp Phe Ile His Val Asp Asp Ile Ser Ser Ala His Leu
225                 230                 235                 240

Ala Ala Leu Asp Tyr Leu Lys Glu Asn Glu Ser Asn Val Phe Asn Val
                245                 250                 255

Gly Tyr Gly His Gly Phe Ser Val Lys Glu Val Ile Glu Ala Met Lys
            260                 265                 270

Lys Val Ser Gly Val Asp Phe Lys Val Glu Leu Ala Pro Arg Arg Ala
        275                 280                 285

Gly Asp Pro Ser Val Leu Ile Ser Asp Ala Ser Lys Ile Arg Asn Leu
    290                 295                 300

Thr Ser Trp Gln Pro Lys Tyr Asp Asp Leu Glu Leu Ile Cys Lys Ser
305                 310                 315                 320

Ala Phe Asp Trp Glu Lys Gln Cys
                325

<210> SEQ ID NO 81
<211> LENGTH: 175
<212> TYPE: PRT
<213> ORGANISM: Artificial Sequence
<220> FEATURE:
<223> OTHER INFORMATION: Human G-CSF 174 aa form

<400> SEQUENCE: 81

Met Thr Pro Leu Gly Pro Ala Ser Ser Leu Pro Gln Ser Phe Leu Leu
1               5                   10                  15

```
Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
        130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 82
<211> LENGTH: 8
<212> TYPE: PRT
<213> ORGANISM: Artificial Sequence
<220> FEATURE:
<223> OTHER INFORMATION: FLAG tag

<400> SEQUENCE: 82

Asp Tyr Lys Asp Asp Asp Asp Lys
1               5

<210> SEQ ID NO 83
<211> LENGTH: 5
<212> TYPE: PRT
<213> ORGANISM: Artificial Sequence
<220> FEATURE:
<223> OTHER INFORMATION: EC5

<400> SEQUENCE: 83

Asp Asp Asp Asp Lys
1               5

<210> SEQ ID NO 84
<211> LENGTH: 6
<212> TYPE: PRT
<213> ORGANISM: Artificial Sequence
<220> FEATURE:
<223> OTHER INFORMATION: EYMPME 6 residue peptide tag

<400> SEQUENCE: 84

Glu Tyr Met Pro Met Glu
1               5

<210> SEQ ID NO 85
<211> LENGTH: 6
<212> TYPE: PRT
<213> ORGANISM: Artificial Sequence
<220> FEATURE:
<223> OTHER INFORMATION: 6 histidine residues
```

```
<400> SEQUENCE: 85

His His His His His His
 1               5
```